(12) United States Patent
Bruhlmann

(10) Patent No.: US 11,447,800 B2
(45) Date of Patent: Sep. 20, 2022

(54) METHOD FOR PRODUCING VANILLIN

(71) Applicant: FIRMENICH SA, Satigny (CH)

(72) Inventor: Fredi Bruhlmann, Satigny (CH)

(73) Assignee: FIRMENICH SA, Satigny (CH)

( * ) Notice: Subject to any disclaimer, the term of this patent is extended or adjusted under 35 U.S.C. 154(b) by 78 days.

(21) Appl. No.: 17/041,906

(22) PCT Filed: Mar. 29, 2019

(86) PCT No.: PCT/EP2019/058101
§ 371 (c)(1),
(2) Date: Sep. 25, 2020

(87) PCT Pub. No.: WO2019/185926
PCT Pub. Date: Oct. 3, 2019

(65) Prior Publication Data
US 2021/0139936 A1 May 13, 2021

(30) Foreign Application Priority Data

Mar. 29, 2018 (EP) ..................................... 18165125

(51) Int. Cl.
*C12P 7/24* (2006.01)
*C12N 9/04* (2006.01)
*C12N 1/21* (2006.01)

(52) U.S. Cl.
CPC .............. *C12P 7/24* (2013.01); *C12N 9/0006* (2013.01); *C12Y 101/01319* (2015.07)

(58) Field of Classification Search
None
See application file for complete search history.

(56) References Cited

U.S. PATENT DOCUMENTS

| 6,068,991 A * | 5/2000 | Liu ........................ C12N 15/72 |
|---|---|---|
| | | 435/320.1 |
| 2014/0178954 A1 * | 6/2014 | Hitz ........................ C12P 7/18 |
| | | 435/254.2 |

FOREIGN PATENT DOCUMENTS

| CN | 106754802 A | * | 5/2017 | ........... C12N 9/0006 |
|---|---|---|---|---|
| WO | 03057897 A2 | | 7/2003 | |

OTHER PUBLICATIONS

Yamada et al., Purification, characterization and gene cloning of isoeugenol-degrading enzyme from Pseudomonas putida IE27, Arch. Microbiol. 187, 2007, 511-17. (Year: 2007).*
Genbank, Accession No. AB291707.1, 2007, www.ncbi.nlm.nih.gov. (Year: 2007).*

(Continued)

*Primary Examiner* — Robert B Mondesi
*Assistant Examiner* — Todd M Epstein
(74) *Attorney, Agent, or Firm* — Armstrong Teasdale LLP

(57) ABSTRACT

The present disclosure relates to a novel method of producing vanillin and/or derivatives thereof by applying improved biocatalysts. Also provided herein are expression systems for preparing said improved biocatalysts. Moreover provided herewith are novel enzyme mutants, corresponding coding sequences and vectors applicable in the biochemical production of vanillin. The present disclosure further provides recombinant host cells or organisms genetically modified for improved functional expression of biocatalysts, as well as recombinant host cells or organisms useful to produce vanillin.

17 Claims, 9 Drawing Sheets

Specification includes a Sequence Listing.

(56) References Cited

OTHER PUBLICATIONS

Furuya et al., A Coenzyme-Independent Decarboxylase/Oxygenase Cascade for the Efficient Synthesis of Vanillin, ChemBioChem 15, 2014, 2248-54. (Year: 2014).*
Ryu et al., Isoeugenol monooxygenase and its putative regulatory gene are located in the eugenol metabolic gene cluster in Pseudomonas nitroreducens Jin1, Arch. Mircobiol. 192, 2010, 201-09. (Year: 2010).*
Genbank, Accession No. FJ851547.1, 2010, www.ncbi.nlm.nih.gov. (Year: 2010).*
Zhao et al., Efficient biotransformation of isoeugenol to vanillin in recombinant strains of *Escherichia coli* by using engineered isoeugenol monooxygenase and sol-gel chitosan membrane, Process Biochem. 71, 2018, 76-81. (Year: 2018).*
Genbank, Accession No. MF669473.1, 2018, www.ncbi.nlm.nih.gov. (Year: 2018).*
International Search Report and Written Opinion for corresponding PCT/EP2019/058101 dated Jun. 18, 2019, 17 pages.
Ryu et al., "Transcriptional Control of the Isoeugenol Monooxygenase of Pseudomonas nitroreducens Jin1 in *Escherichia coli*", Bioscience, Biotechnology, and Biochemistry, May 22, 2014, vol. 76, No. 10, pp. 1891-1896.
Yamada et al., "Vanillin production using *Escherichia coli* cells over-expressing isoeugenol monooxygenase of Pseudomonas putida", Biotechnology Letters, Nov. 27, 2007, vol. 30, pp. 665-670.

\* cited by examiner

Feature Map pIEM2_C154_T222_A1318

| Name | Start | End |
|---|---|---|
| IEM_C154_T222_A1318 | 1528 | 2997 |
| Ori_p15a | 1 | 827 |
| Term_rpoC | 1009 | 1128 |
| Term_bla | 1129 | 1429 |
| P_T7_Inducible | 1456 | 1497 |
| LacO1 | 1477 | 1497 |
| Term_T7 | 3002 | 3049 |
| P_Amp | 3322 | 3439 |
| Kanamycin-r | 3450 | 4259 |
| P_lacI | 4260 | 4341 |
| lacI | 4342 | 5424 |

METHOD FOR PRODUCING VANILLIN

CROSS-REFERENCE TO RELATED APPLICATIONS

This application is a U.S. National Phase Application of PCT/EP2019/058101, filed on Mar. 29, 2019, which claims the benefit of priority to European Patent Application Number 18165125.8, filed Mar. 29, 2018, the entire contents of which are hereby incorporated by reference herein.

REFERENCE TO AN ELECTRONIC SEQUENCE LISTING

The contents of the electronic sequence listing (Filename: 36803-247 ST25.txt; Date of Creation: Sep. 25, 2020; and Size: 81,321 bytes) are herein incorporated by reference in their entirety.

TECHNICAL FIELD

Provided herein are biochemical methods of producing vanillin and related compounds and derivatives, which method comprises the use of a novel combination of polypeptides. Moreover provided herewith are novel enzyme mutants applicable in the biochemical production of vanillin.

BACKGROUND

Vanillin is an important compound globally for use in foods, beverages, and pharmaceuticals. Only a small portion of the world's production is derived naturally through extraction from vanilla pods; however, the availability of these natural plant sources is low and the production methods are laborious and slow. Whereas complex extracts derived from the pods of the orchids *V. planifolia*, or *V. tahitensis* offer unique and complex mixtures and olfactory qualities at high costs, the majority of vanillin (>99% i.e. 16'000 tons per year) is produced from petrochemical feed stocks, with a minor fraction still obtained from lignin waste of the paper industry. However, there is a small but growing market for natural 'vanillin not from the bean' (NFB), which mainly serves North America and Europe. The regulatory requirements for claiming natural status are different for these two markets.

Different starting materials including ferulic acid, curcumin, eugenol, or isoeugenol can be converted into vanillin using different biochemistries. Biotechnical methods for producing vanillin have been reviewed [Gallage N J, Wøller B L. 2015. Mol Plant 8, 40-57; Kaur, B, Chakraborty, D. 2013. Appl Biochem Biotechnol 169, 1353-1372; Walton N J, Mayer M J, Narbad A. 2003. Phytochem 63, 505-515].

More recently, microorganisms have been engineered that can convert simple carbon sources such as sugars like glucose into vanillin [Hansen E H, Lindberg Møller B, Kock G R, Bünner C M, C Kristensen, Jensen O R, Okkels F T, Olsen C E, Motawia M S, Hansen J. 2009. Appl Environ Microbiol 75, 2765-2774; Ni J, Tao F, Du H, Xu P. 2015. Sci Rep 5, 1-11]

Isoeugenol is a phenyl propenoid found in many plants. However, it seems less abundant than eugenol, from which it has been traditionally obtained by isomerization under heat in presence of a strong base. That method is no longer compatible with the European legislation for natural flavoring substances. However, botanicals rich in isoeugenol could be identified.

Isoeugenol can be converted into vanillin via an array of different biochemical methods. For example non-heme iron containing enzymes such as lipoxygenases, or iron-porphyrin containing enzymes (e.g. horse radish peroxidase) have been used for oxidatively cleaving isoeugenol into vanillin Recently, it was found that purified hemin alone was as good as non-specific, heme containing enzymes for such biotransformation [Mutti F G. 2012. Bioorg Chem Appl 2012, 1-13; Li Y-H, Sun Z-H, Zhao L-Q, Xu Y. 2005. Appl Biochem Biotechnol 125, 1-10; Mutti F G, Lara M, Kroutil M, Kroutil W. 2010. Chem Eur J 16, 14142-14148]. However, these methods are prone to formation of side products.

Interestingly, isoeugenol oxidizing enzymes of microbial origin including but not limited to isoeugenol monooxygenases have been described for converting isoeugenol into vanillin [Ryu J-Y, J Seo, S Park, J-H Ahn, Y Chong, M J Sadowsky, H-G Hur. 2013. Biosci Biotechnol Biochem 77, 289-294; Yamada M, Y Okada, T Yoshida, T Nagasawa. 2007. Appl Microbiol Biotechnol 73, 1025-1030; Yamada M, Y Okada, T Yoshida, T Nagasawa 2008. Biotechnol Lett 30, 665-670]. Oxidation of isoeugenol with such enzymes showed formation of vanillin and acetaldehyde as main products [Yamada M, Y Okada, T Yoshida, T Nagasawa. 2007. Arch Microbiol 187, 511-517; Ryu J-Y, J Seo, S Park, J-H Ahn, Y Chong, M J Sadowsky, H-G Hur. 2013. Biosci Biotechnol Biochem 77, 289-294]. The approaches described therein are, however, not directed to an industrial scale production of vanillin.

For an industrial process it is often necessary to overproduce one or several functional enzymes in a recombinant bacterium such as *E. coli*. The overproduction of an enzyme in a suitable bacterium provides a secure and economic source of that enzyme. Overproduction of key enzymes also helps to minimize side activities caused by endogenous enzyme activities of the host organism (e.g. enzymes that could reduce or oxidize vanillin into vanillyl alcohol, or vanillic acid, respectively).

The correct folding of an enzyme in the host organism is critical for catalytic activity. Non-correctly folded enzymes have reduced or no catalytic activity as they are prone to aggregation (e.g. inclusion bodies) or degradation in the host. Different strategies can be applied to ensure correctly folded enzyme in the host organism. For example reducing the expression level in a recombinant host organism by low gene dosage, low transcript level by low inducer concentration (in case of an inducible system) or low promotor strength can be beneficial. Low temperature during enzyme synthesis can also help to improve folding of a recombinant protein. Alternatively, a non-correctly folded enzyme can sometimes get unfolded by strong denaturing chemicals, followed by refolding under physiological conditions. However, such procedure is time consuming and expensive.

In molecular biology, the large class of molecular chaperones represents proteins that assist the covalent folding or unfolding and the assembly or disassembly of other macromolecular structures. The group of chaperonin proteins belongs to said large class of chaperon molecules. The structure of these chaperonins resembles two donut-like structures stacked on top of one another to create a barrel. Each ring is composed of either 7, 8 or 9 subunits depending on the organism in which the chaperonin is found.

Group I chaperonins are found in bacteria as well as organelles of endosymbiotic origin: chloroplasts and mitochondria. Group II chaperonins, as found in the eukaryotic cytosol and in archaea, are more poorly characterized. The GroEL/GroES complex is a Group I chaperonin. Group II chaperonins are not thought to utilize a GroES-type cofactor to fold their substrates.

As mentioned, the chaperonin system GroES/GroEL forms a barrel like structure with a cavity that allows the up-take of misfolded proteins for refolding at the expense of ATP [Gragerov A, E Nudler, N Komissarova, G A Gaitanaris, M E Gottesman, V Nikiforov. 1992. Proc Nat Acad Sci 89, 10341-10344; Keskin O, Bahar I, Flatow D, Covell D G, Jernigan R L. 2002. Biochem 41, 491-501].

The applicability of any member of the large class of chaperons for recombinant production of monooxygenases, in particular of isoeugenol monooxygenases for the enzymatic synthesis of vanillin, has so far not been investigated.

Although there have been several reports of natural vanillin production through bio-engineering (for example, WO2013/022881, KR101163542 (B1)), there still remains a need for the discovery of simpler, efficient and cost/or effective processes for production of natural vanillin. In particular, higher specific activity of the enzyme would allow lower catalyst loading for improved process performance and economics. Moreover, there is a need of further improved enzymes applicable in the biochemical production of vanillin, in particular from isoeugenol as starting material.

SUMMARY

The present invention addresses the above-mentioned drawbacks associated with the known systems so far applied for the biochemical production of vanillin.

The present inventors surprisingly observed that certain helper polypeptides may be successfully used in the large scale production of certain known and even of certain novel isoeugenol oxidizing enzymes of high functional activity. In particular, it was surprisingly found by the present inventors, that the coexpression with chaperonins GroES and GroEL significantly improved the amount of catalytically active isoeugenol monooxygenase enzymes produced in the bacterium $E.$ $coli.$ Moreover, the present inventors surprisingly were able to genetically modify a microbial oxidase enzyme from a microorganism of the species $Pseudomonas$ $putida,$ so that it is applicable for the first time in the conversion of isoeugenol, in particular (E)-isoeugenol, to vanillin in the presence of molecular oxygen.

Thus the present inventors could surprisingly improve the biochemical approach of production of vanillin via isoeugenol by applying the isoeugenol oxidizing enzymes produced and/or genetically modified as herein below described in more detail.

Figure 1:
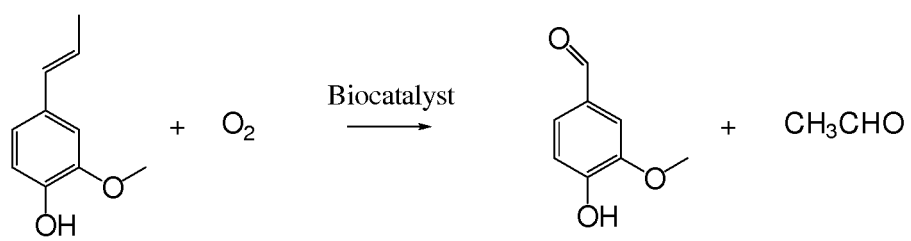
FIG. 1: One step conversion of isoeugenol into vanillin and acetaldehyde.

ABBREVIATIONS USED bp base pair
kb kilo base
DNA deoxyribonucleic acid
cDNA complementary DNA
DTT dithiothreitol
GC gas chromatograph
IPTG isopropyl-D-thiogalacto-pyranoside
IEM isoeugenol monooxygenase
LB lysogeny broth
MS mass spectrometer/mass spectrometry
PCR polymerase chain reaction
RBS ribosomal binding site
RNA ribonucleic acid
mRNA messenger ribonucleic acid
miRNA micro RNA
siRNA small interfering RNA
rRNA ribosomal RNA
tRNA transfer RNA
P. Pseudomonas Specific Definitions The term "isoeugenol" relates 2-methoxy-4-(prop-1-en-1-yl)phenol (CAS Registry Number: 97-54-1) and to any isomer mixture of trans- and cis-isoeugenol, or (E)- and (Z)-isoeugenol, respectively.

The terms "isoeugenol monooxygenase" or "polypeptide having isoeugenol monooxygenase activity" or "isoeugenol monooxygenase protein" or "isoeugenol oxidizing enzyme" or "polypeptide having isoeugenol oxidizing activity" or "isoeugenol oxidizing protein" or "IEM" relate to a polypeptide capable of catalyzing the synthesis of vanillin, starting from an isoeugenol, in the presence of molecular oxygen under formation of acetaldehyde, without being limited to any particular molecular mechanism of action of said enzyme. Preferably said enzyme converts stereospecifically the (E)- or trans-isomer of isoeugenol. Vanillin preferably is obtained as the main product.

"Isoeugenol oxidizing activity" is determined under "standard conditions" as described herein below in more detail in the examples: They can be determined using recombinant IEM expressing cells, disrupted IEM expressing cells, fractions of these or enriched or purified IEM enzyme, in a reaction medium, preferably buffered, having a pH in the range of 8.5 to 11, preferably 9 to 10, in the presence of molecular oxygen, at a temperature in the range of about 20 to 30° C. and in the presence of a reference substrate, here isoeugenol, in particular trans-isoeugenol, at an initial concentration in the range of 1 to 40 mg/ml, preferably 1 to 10 mg/ml more preferably 3 to 7 mg/ml.

The terms "biological function," "function," "biological activity" or "activity" refer to the ability of the isoeugenol oxidizing enzyme to catalyze the formation of vanillin from isoeugenol.

As used herein, the term "host cell" or "transformed cell" refers to a cell (or organism) altered to harbor at least one nucleic acid molecule, for instance, a recombinant gene encoding a desired protein or nucleic acid sequence which upon transcription yields a polypeptide for use as described herein. The host cell is particularly a bacterial cell, a fungal cell or a plant cell. The host cell may contain a recombinant gene which has been integrated into the nuclear or organelle genomes of the host cell. Alternatively, the host may contain the recombinant gene extra-chromosomally.

"Homologous" sequences include orthologous or paralogous sequences. Methods of identifying orthologs or paralogs including phylogenetic methods, sequence similarity and hybridization methods are known in the art and are described herein.

"Paralogs" or paralogous sequences result from gene duplication that gives rise to two or more genes with similar sequences and similar functions. Paralogs typically cluster together and are formed by duplications of genes within related plant species. Paralogs are found in groups of similar genes using pair-wise Blast analysis or during phylogenetic analysis of gene families using programs such as CLUSTAL. In paralogs, consensus sequences can be identified characteristic to sequences within related genes and having similar functions of the genes.

"Orthologs", or orthologous sequences, are sequences similar to each other because they are found in species that descended from a common ancestor. For instance, plant species that have common ancestors are known to contain many enzymes that have similar sequences and functions. The skilled artisan can identify orthologous sequences and predict the functions of the orthologs, for example, by constructing a polygenic tree for a gene family of one species using CLUSTAL or BLAST programs. A method for identifying or confirming similar functions among homologous sequences is by comparing of the transcript profiles in host cells or organisms, such as plants or microorganisms, overexpressing or lacking (in knockouts/knockdowns) related polypeptides. The skilled person will understand that genes having similar transcript profiles, with greater than 50% regulated transcripts in common, or with greater than 70% regulated transcripts in common, or greater than 90% regulated transcripts in common will have similar functions. Homologs, paralogs, orthologs and any other variants of the sequences herein are expected to function in a similar manner by making the host cells, organism such as plants or microorganisms producing isoeugenol monooxygenase.

The term "plant" is used interchangeably to include plant cells including plant protoplasts, plant tissues, plant cell tissue cultures giving rise to regenerated plants, or parts of plants, or plant organs such as roots, stems, leaves, flowers, pollen, ovules, embryos, fruits and the like. Any plant can be used to carry out the methods of an embodiment herein.

A particular organism or cell is meant to be "capable of producing vanillin" when it produces vanillin naturally or when it does not produce vanillin naturally but is transformed to produce vanillin, either prior to the transformation with a nucleic acid as described herein or together with said nucleic acid. Organisms or cells transformed to produce a higher amount of vanillin than the naturally occurring organism or cell are also encompassed by the "organisms or cells capable of producing vanillin"

The terms "purified," "substantially purified," and "isolated" as used herein refer to the state of being free of other, dissimilar compounds with which a compound of the invention is normally associated in its natural state, so that the "purified," "substantially purified," and "isolated" subject comprises at least 0.5%, 1%, 5%, 10%, or 20%, or at least 50% or 75% of the mass, by weight, of a given sample. In one embodiment, these terms refer to the compound of the invention comprising at least 95, 96, 97, 98, 99 or 100%, of the mass, by weight, of a given sample. As used herein, the terms "purified," "substantially purified," and "isolated" when referring to a nucleic acid or protein, of nucleic acids or proteins, also refers to a state of purification or concentration different than that which occurs naturally, for example in an prokaryotic or eukaryotic environment, like, for example in a bacterial or fungal cell, or in the mammalian organism, especially human body. Any degree of purification or concentration greater than that which occurs naturally, including (1) the purification from other associated structures or compounds or (2) the association with structures or compounds to which it is not normally associated in said prokaryotic or eukaryotic environment, are within the meaning of "isolated". The nucleic acid or protein or classes of nucleic acids or proteins, described herein, may be isolated, or otherwise associated with structures or compounds to which they are not normally associated in nature, according to a variety of methods and processes known to those of skill in the art.

In the context of the descriptions provided herein and of the appended claims, the use of "or" means "and/or" unless stated otherwise.

Similarly, "comprise," "comprises," "comprising", "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

The term "about" indicates a potential variation of ±25% of the stated value, in particular ±15%, ±10%, more particularly ±5%, ±2% or ±1%.

The term "substantially" describes a range of values of from about 80 to 100%, such as, for example, 85-99.9%, in particular 90 to 99.9%, more particularly 95 to 99.9%, or 98 to 99.9% and especially 99 to 99.9%.

"Predominantly" refers to a proportion in the range of above 50%, as for example in the range of 51 to 100%, particularly in the range of 75 to 99.9%; more particularly 85 to 98.5%, like 95 to 99%.

A "main product" in the context of the present invention designates a single compound or a group of at least 2 compounds, like 2, 3, 4, 5 or more, particularly 2 or 3 compounds, which single compound or group of compounds is "predominantly" prepared by a reaction as described herein, and is contained in said reaction in a predominant proportion based on the total amount of the constituents of the product formed by said reaction. Said proportion may be a molar proportion, a weight proportion or, preferably based on chromatographic analytics, an area proportion calculated from the corresponding chromatogram of the reaction products.

A "side product" in the context of the present invention designates a single compound or a group of at least 2 compounds, like 2, 3, 4, 5 or more, particularly 2 or 3 compounds, which single compound or group of compounds is not "predominantly" prepared by a reaction as described herein.

Because of the reversibility of enzymatic reactions, the present invention relates, unless otherwise stated, to the enzymatic or biocatalytic reactions described herein in both directions of reaction.

"Functional mutants" of herein described polypeptides include the "functional equivalents" of such polypeptides as defined below.

The term "stereoisomers" includes in particular conformational isomers.

Included in general are, according to the invention, all "stereoisomeric forms" of the compounds described herein, such as constitutional isomers and, in particular, stereoisomers and mixtures thereof, e.g. optical isomers, or geometric isomers, such as E- and Z-isomers, and combinations thereof. If several asymmetric centers are present in one molecule, the invention encompasses all combinations of different conformations of these asymmetry centers, e.g. enantiomeric pairs "Stereoselectivity" describes the ability to produce a particular stereoisomer of a compound in a stereoisomerically pure form or to specifically convert a particular stereoisomer in an enzyme catalyzed method as described herein out of a plurality of stereoisomers. More specifically, this means that a product of the invention is enriched with respect to a specific stereoisomer, or an educt may be depleted with respect to a particular stereoisomer. This may be quantified via the purity % ee-parameter calculated according to the formula:

$$\% \ ee = [X_A - X_B]/[X_A + X_B]*100,$$

wherein $X_A$ and $X_B$ represent the molar ratio (Molenbruch) of the stereoisomers A and B.

"Yield" and/or the "conversion rate" of a reaction according to the invention is determined over a defined period of, for example, 4, 6, 8, 10, 12, 16, 20, 24, 36 or 48 hours, in which the reaction takes place. In particular, the reaction is carried out under precisely defined conditions, for example at "standard conditions" as herein defined.

The different yield parameters ("Yield" or $Y_{P/S}$; "Specific Productivity Yield"; or Space-Time-Yield (STY)) are well known in the art and are determined as described in the literature.

"Yield" and "$Y_{P/S}$" (each expressed in mass of product produced/mass of material consumed) are herein used as synonyms.

The specific productivity-yield describes the amount of a product, like Vanillin, that is produced per h and L fermentation broth per g of biomass. The amount of wet cell weight stated as WCW describes the quantity of biologically active microorganism in a biochemical reaction. The value is given as g product per g WCW per h (i.e. $g/gWCW^{-1} \ h^{-1}$). Alternatively, the quantity of biomass can also be expressed as the amount of dry cell weight stated as DCW. Furthermore, the biomass concentration can be more easily determined by measuring the optical density at 600 nm ($OD_{600}$) and by using an experimentally determined correlation factor for estimating the corresponding wet cell or dry cell weight, respectively.

The term "fermentative production" or "fermentation" refers to the ability of a microorganism (assisted by enzyme activity contained in or generated by said microorganism) to produce a chemical compound in cell culture utilizing at least one carbon source added to the incubation.

The term "fermentation broth" is understood to mean a liquid, particularly aqueous or aqueous/organic solution which is based on a fermentative process and has not been worked up or has been worked up, for example, as described herein.

An "enzymatically catalyzed" or "biocatalytic" method means that said method is performed under the catalytic action of an enzyme, including enzyme mutants, as herein defined. Thus the method can either be performed in the presence of said enzyme in isolated (purified, enriched) or crude form or in the presence of a cellular system, in particular, natural or recombinant microbial cells containing said enzyme in active form, and having the ability to catalyze the conversion reaction as disclosed herein.

The terms "selectively converting" or "increasing the selectivity" in general means that a particular stereoisomeric form as for example the E-form, of an unsaturated hydrocarbon, is converted in a higher proportion or amount (compared on a molar basis) than the corresponding Z-form, either during the entire course of said reaction (i.e. between initiation and termination of the reaction), at a certain point of time of said reaction, or during an "interval" of said reaction. In particular, said selectivity may be observed during an "interval" corresponding 1 to 99%, 2 to 95%, 3 to 90%, 5 to 85%, 10 to 80%, 15 to 75%, 20 to 70%, 25 to 65%, 30 to 60, or 40 to 50% conversion of the initial amount of the substrate. Said higher proportion or amount may, for example, be expressed in terms of:

a higher maximum yield of an isomer observed during the entire course of the reaction or said interval thereof;
a higher relative amount of an isomer at a defined % degree of conversion value of the substrate; and/or
an identical relative amount of an isomer at a higher % degree of conversion value;
each of which preferably being observed relative to a reference method, said reference method being performed under otherwise identical condition with known chemical obr biochemical means.

"E-stereoselectivity" or "E-selectivity" describes the ability to produce an E-Isomer of a particular C=C-double bond in an E-isomerically pure or essentially pure or enriched form or to specifically or essentially specifically convert an E-isomer in an enzymatically catalyzed method as described herein out of a plurality of other isomers or a mixture of E- and Z-isomers at said particular position of the double-bond.

Generally also comprised in accordance with the invention are all "isomeric forms" of the compounds described herein, such as constitutional isomers and in particular stereoisomers and mixtures of these, such as, for example, optical isomers or geometric isomers, such as E- and Z-isomers, and combinations of these. If several centers of asymmetry are present in a molecule, then the invention comprises all combinations of different conformations of these centers of asymmetry, such as, for example, pairs of enantiomers, or any mixtures of stereoisomeric forms.

If the present disclosure refers to features, parameters and ranges thereof of different degree of preference (including general, not explicitly preferred features, parameters and ranges thereof) then, unless otherwise stated, any combination of two or more of such features, parameters and ranges thereof, irrespective of their respective degree of preference, is encompassed by the disclosure of the present description.

"Polycistronic" refers to nucleic acid molecules, in particular mRNAs or corresponding cDNAs that can encode more than one polypeptide separately within the same nucleic acid molecule.

"Derived from" a "polycistronic" construct or nucleic acid molecule means that molecule may be modified by introducing one or more identical or different regulatory sequences at appropriate position, like promotors, RBS and/or terminators, in order to influence or modulate the transcription and/or translation of at least one coding sequence contained in said nucleic acid molecule.

DETAILED DESCRIPTION a. Particular Embodiments of the Invention

The present invention particularly refers to the following embodiments:

1. An expression system for the recombinant expression of a polypeptide having isoeugenol oxidizing activity, which expression system comprises a combination of at least two different nucleic acid sequences contained in at least one recombinant nucleic acid construct; wherein said expression system comprises:
   a. a nucleotide sequence (A) encoding a polypeptide having enzymatic isoeugenol oxidizing activity, particularly catalyzing in the presence of oxygen, in particular molecular oxygen, the formation of vanillin and acetaldehyde from isoeugenol, and
   b. at least one nucleotide sequence (B) encoding at least one, like 1, 2, or 3, preferably 2, helper polypeptide which alone or, preferably in cooperation assist in the functional expression of the polypeptide, in particular the correct folding of said expressed polypeptide, encoded by said nucleotide sequence (A);
   wherein said expression system provides for the co-expression of said nucleotide sequences (A) and (B).

2. The expression system of embodiment 1, which is selected from
   a. a combination of at least two, preferably independently of each other acting or working nucleic acid constructs carrying said nucleic acid sequence (A) and said at least one nucleic acid (B), respectively; and
   b. a single nucleic acid construct carrying said nucleic acid sequence (A) and said at least one nucleic acid (B), which may be for example a nucleic acid construct or vector carrying multiple cloning sites or may more preferably be a polycistronic nucleic acid construct, which is ultimately transcribed in a single mRNA molecule containing the coding sequences (A) for the polypeptide having enzymatic isoeugenol oxidizing activity and (B) for the helper polypeptide(s). Said single nucleic acid construct carrying said nucleic acid sequence (A) and said at least one nucleic acid (B), may also be derived from a polycistronic nucleic acid construct. It may be derived therefrom, for example, by introducing one or more identical or different regulatory sequences at appropriate position, like promotors, RBS and/or terminators, in order to influence or modulate the transcription and/or translation of at least one coding sequence of (A) and (B) contained in said nucleic acid molecule, as further exemplified in the experimental section.

3. The expression system of one of the preceding embodiments, wherein said nucleotide sequence (A) encodes
   a. a polypeptide having isoeugenol oxidizing activity and comprises an amino acid sequence having at least 70%, 75%, 80%, 85%, 90%, 95%, 96%, 97%, 98%, 99% or 100% sequence identity to SEQ ID NO:2 (i.e. IEM1, as originally isolated from *Pseudomonas nitroreducens* Jin 1); or
   b. a polypeptide having isoeugenol oxidizing activity and comprises an amino acid sequence having at least 70%, 75%, 80%, 85%, 90%, 95%, 96%, 97%, 98%, 99% or 100% sequence identity to SEQ ID NO: 4 (i.e. IEM2, as originally isolated from *Pseudomonas putida* 1E27), wherein the amino acid sequence having at least 70%, 75%, 80%, 85%, 90%, 95%, 96%, 97%, 98%, 99% or 100% identity to SEQ ID NO: 4 comprises at least one mutation in an amino acid sequence position selected from T52, Q74, D440, and optionally at least one, like 1, 2, 3, 4 or 5, further mutation in an amino acid sequence position selected from N120, T121, F281, M298, and L470, in particular selected from N120I, T121P, F281Q, M298K, and L470S.

4. The expression system of embodiment 3, wherein the polypeptide having isoeugenol oxidizing activity and comprises an amino acid sequence having at least 70%, 75%, 80%, 85%, 90%, 95%, 96%, 97%, 98%, 99% or 100% sequence identity to SEQ ID NO: 4 is a mutant polypeptide comprising at least one mutation in an amino acid sequence position selected from T52, Q74 and D440.

5. The expression system of embodiment 4, wherein said mutant is selected from the following IEM 2 mutants:
   a. the single mutants (T52$X_1$), (Q74$X_2$) and (D440$X_3$)
   b. the double mutants (T52$X_1$,Q74$X_2$), (T52$X_1$,D440$X_3$) and (Q74$X_2$,D440$X_3$) and
   c. the triple mutant (T52$X_1$,Q74$X_2$,D440$X_3$) wherein
      $X_1$ is P, K or M or any other natural or non-natural, in particular natural amino acid substitution resulting in a functional, vanillin producing enzyme mutant; preferably $X_1$ is P or M, and most preferably P;
      $X_2$ is H or A or any other natural or non-natural, in particular natural amino acid substitution resulting in a functional, vanillin producing enzyme mutant; most preferably $X_2$ is H; and;
      $X_3$ is N, A, C, E, F, G, H, I, K, L, M, Q, R, S, T, V, W or Y or any other natural or non-natural, in particular natural amino acid substitution resulting in a functional, vanillin producing enzyme mutant; preferably $X_3$ is N, A, C, E, F, G, H, K, L, M, Q, R, S, T, V, or Y; and most preferably N As non-limiting examples of such double-mutants to be expressed by such expression system there may be mentioned:
(T52$X_1$,Q74$X_2$):
   wherein $X_1$ is P, and $X_2$ is H or A; or
   wherein $X_1$ is K, and $X_2$ is H or A; or
   wherein $X_1$ is M, and $X_2$ is H or A.
(T52$X_1$,D440$X_3$)
   wherein $X_1$ is P, and $X_3$ is N, A, C, E, F, G, H, I, K, L, M, Q, R, S, T, V, W or Y; or
   wherein $X_1$ is K, and $X_3$ is N, A, C, E, F, G, H, I, K, L, M, Q, R, S, T, V, W or Y; or
   wherein $X_1$ is M, and $X_3$ is N, A, C, E, F, G, H, I, K, L, M, Q, R, S, T, V, W or Y.
(Q74$X_2$,D440$X_3$)
   wherein $X_2$ is H, and $X_3$ is N, A, C, E, F, G, H, I, K, L, M, Q, R, S, T, V, W or Y; or
   wherein $X_2$ is A, and $X_3$ is N, A, C, E, F, G, H, I, K, L, M, Q, R, S, T, V, W or Y.

Preferred double mutants are:
(T52P,Q74H);
(T52P,D440$X_3$) wherein $X_3$ is N, A, C, E, F, G, H, K, L, M, Q, R, S, T, V or Y
(Q74H,D440$X_3$) wherein $X_3$ is N, A, C, E, F, G, H, K, L, M, Q, R, S, T, V or Y As non-limiting examples of such triple-mutants to be expressed by such expression system there may be mentioned:

(T52$X_1$,Q74$X_2$,D440$X_3$)
   wherein $X_1$ is P, $X_2$ is H and $X_3$ is N, A, C, E, F, G, H, I, K, L, M, Q, R, S, T, V, W or Y;
   wherein $X_1$ is K, $X_2$ is H and $X_3$ is N, A, C, E, F, G, H, I, K, L, M, Q, R, S, T, V, W or Y;
   wherein $X_1$ is M, $X_2$ is H and $X_3$ is N, A, C, E, F, G, H, I, K, L, M, Q, R, S, T, V, W or Y;
   wherein $X_1$ is P, $X_2$ is A and $X_3$ is N, A, C, E, F, G, H, I, K, L, M, Q, R, S, T, V, W or Y;
   wherein $X_1$ is K, $X_2$ is A and $X_3$ is N, A, C, E, F, G, H, I, K, L, M, Q, R, S, T, V, W or Y;
   wherein $X_1$ is M, $X_2$ is A and $X_3$ is N, A, C, E, F, G, H, I, K, L, M, Q, R, S, T, V, W or Y.

Preferred triple mutants are:
(T52P,Q74H,D440$X_3$) wherein $X_3$ is N, A, C, E, F, G, H, K, L, M, Q, R, S, T, V or Y Said above-mentioned single, double or triple mutant may optionally be further modified by at least one, like 1, 2, 3, 4 or 5, preferably 1, 2 or 3, most preferably 1 further mutation in an amino acid sequence position of SEQ ID NO: 4 selected from N120, T121, F281, M298, and L470, in particular selected from the mutations N120I, T121P, F281Q, M298K, and L470S.

6. The expression system of one of the preceding embodiments, wherein said at least nucleotide sequence (B) comprises nucleotide sequences (B1) and (B2), wherein
   a. (B1) encodes a polypeptide having chaperonin activity comprising an amino acid sequence having at least 70%, 75%, 80%, 85%, 90%, 95%, 96%, 97%, 98%, 99% or 100% sequence identity to SEQ ID NO:8 (GroEL); and
   b. (B2) encodes a polypeptide having chaperonin activity comprising an amino acid sequence having at least 70%, 75%, 80%, 85%, 90%, 95%, 96%, 97%, 98%, 99% or 100% sequence identity to SEQ ID NO:10 (GroES).

Non-limiting examples of preferred expression systems of the invention are IEM1-expressing systems, that comprise a nucleotide sequence having at least 70%, 75%, 80%, 85%, 90%, 95%, 96%, 97%, 98%, 99% or 100% sequence identity to a sequence selected from SEQ ID NO: 11 (PC1); SEQ ID NO: 12 (PC2); SEQ ID NO: 13 (PC3); SEQ ID NO: 14 (PC4); SEQ ID NO: 15 (PC5); which are applicable according to the invention for expressing a functional polypeptide having isoeugenol oxidizing activity and comprises an amino acid sequence having at least 70%, 75%, 80%, 85%, 90%, 95%, 96%, 97%, 98%, 99% or 100% sequence identity to SEQ ID NO:2 (IEM1);

Further non limiting examples of preferred expression systems may be derived from such IEM-1 expressing systems of SEQ ID NO: 11, 12, 13, 14, or 15 by replacing the coding sequence of IEM1 by a nucleotide sequence encoding a functional IEM 2 mutant derived from SEQ ID NO:4 as described above for embodiment 5. Such IEM2-expressing systems are also preferred.

7. A polypeptide having isoeugenol oxidizing activity and being obtainable by recombinant expression utilizing an expression system as defined in anyone of the preceding embodiments.

8. A polypeptide having isoeugenol oxidizing activity and comprises an amino acid sequence having at least 70%, 75%, 80%, 85%, 90%, 95%, 96%, 97%, 98%, 99% or 100% sequence identity to SEQ ID NO: 4 (i.e. IEM2), wherein the amino acid sequence having at least 70%, 75%, 80%, 85%, 90%, 95%, 96%, 97%, 98%, 99% or 100% identity to SEQ ID NO: 4 comprises at least one mutation in an amino acid sequence position selected from T52, Q74, D440 optionally at least one, like 1, 2, 3, 4 or 5, further mutation in an amino acid sequence position selected from N120, T121, F281, M298, and L470, in particular selected from N120I, T121P, F281Q, M298K, and L470S.

9. The polypeptide of embodiment 8, which is a mutant polypeptide comprising at least one mutation in an amino acid sequence position selected from T52, Q74 and D440 of SEQ ID NO: 4.

10. The polypeptide of embodiment 9, wherein said mutant is selected from
   a. the single mutants $(T52X_1)$, $(Q74X_2)$ and $(D440X_3)$
   b. the double mutants $(T52X_1,Q74X_2)$, $(T52X_1,D440X_3)$ and $(Q74X_2,D440X_3)$ and
   c. the triple mutant $(T52X_1,Q74X_2,D440X_3)$ wherein
      $X_1$ is P, K or M or any other natural or non-natural, in particular natural amino acid substitution resulting in a functional, vanillin producing enzyme mutant, preferably $X_1$ is P or M, and most preferably P;
      $X_2$ is H or A or any other natural or non-natural, in particular natural amino acid substitution resulting in a functional, vanillin producing enzyme mutant, most preferably $X_2$ is H; and
      $X_3$ is N, A, C, E, F, G, H, I, K, L, M, Q, R, S, T, V, W Y or any other natural or non-natural, in particular natural amino acid substitution resulting in a functional, vanillin producing enzyme mutant; preferably $X_3$ is N, A, C, E, F, G, H, K, L, M, Q, R, S, T, V, or Y; and most preferably N.

As regards non-limiting examples of such double-mutants and triple mutants of the invention reference is made to embodiment 5 above.

Said single, double or triple mutant may optionally be further modified by at least one, like 1, 2, 3, 4 or 5, preferably 1, 2 or 3, most preferably 1 further mutation in an amino acid sequence position of SEQ ID NO: 4 selected from N120, T121, F281, M298, and L470, in particular selected from N120I, T121P, F281Q, M298K, and L470S.

11. A recombinant nucleic acid comprising a nucleotide sequence encoding a polypeptide of anyone of the embodiments 8 to 10.

12. A recombinant nucleic acid comprising a nucleotide sequence having at least 70%, 75%, 80%, 85%, 90%, 95%, 96%, 97%, 98%, 99% or 100%, or less than 100% like 99.9% sequence identity to SEQ ID NO:1, 3 or 5 or the reverse complement thereof.

A related embodiment provides a nucleic acid sequence which is complementary to the nucleic acid sequence according to SEQ ID NO:1, 3 or 5, or nucleic acid sequence which hybridizes under stringent conditions to at least part of the nucleotide sequence according to SEQ ID NO: 1, 3 or 5.

Particular examples of recombinant nucleic acids are those comprising a nucleotide sequence having at least 70%, 75%, 80%, 85%, 90%, 95%, 96%, 97%, 98%, 99% or 100%, or less than 100%, like 99.9% sequence identity to SEQ ID NO: 3 or 5 and which encodes an IEM 2 mutant as described above for embodiment 5; or the reverse complement thereof.

Such recombinant nucleic acids may be included in monocistronic or polycistronic expression vectors as further described herein.

13. A recombinant nucleic acid construct comprising the recombinant nucleic acid of embodiment 11 or embodiment 12 or the reverse complement thereof.

14. An expression vector comprising
   a. the recombinant expression system of anyone of the embodiments 1 to 6 or one of said partial nucleic acid constructs or the reverse complement thereof; or
   b. a nucleic acid as defined in embodiments 11 or 12; or
   c. a construct of embodiment 13.

15. The expression vector of embodiment 14, wherein the vector is a prokaryotic vector, viral vector, a eukaryotic vector, or one or more plasmids.

The above mentioned nucleic acid molecules or vectors may be such that monocistronic mRNAs or in particular a polycistronic mRNA, encoding an isoeugenol oxidizing enzyme of the invention and one or more helper polypeptides as described herein is transcribed upon expression.

16. A non-human host organism or host cell comprising, optionally stably integrated into its genome,
   a. the recombinant expression system of anyone of the embodiments 1 to 6 or one of said partial nucleic acid constructs; or
   b. a nucleic acid as defined in embodiments 11 or 12 or the reverse complement thereof; or
   c. the construct of embodiment 13; or
   d. the vector of embodiment 14 or 15.

17. The non-human host organism or host cell of embodiment 16, selected from a prokaryotic or eukaryotic microorganism, a plant, or a cell derived therefrom.

18. The non-human host organism or host cell of embodiment 17, wherein the microorganism is a bacterium or a fungus, in particular yeast.

19. The non-human host organism or host cell of embodiment 18, wherein said bacterium is selected from the genus *Escherichia*, in particular from the species *E. coli* and said yeast is selected from the genus *Saccharomyces* or *Pichia*, in particular from the species *Saccharomyces cerevisiae* or *Pichia pastoris*.

20. A method for producing an isolated catalytically active polypeptide having isoeugenol oxidizing activity, which method comprises the co-expression, like for example the substantially simultaneous, and in particular the simultaneous expression of said polypeptide having isoeugenol oxidizing activity and of at least one helper polypeptide each encoded by an expression system as defined in anyone of the embodiments 1 to 6 in a host cell system; and optionally isolating said polypeptide having isoeugenol oxidizing activity.

"Co-expression" or "co-expressing should be understood broadly as long as it is performed in a manner which results in a cooperative action of the helper polypeptide assisting the functional expression of the polypeptide having isoeugenol oxidizing activity (IEM), in particular the correct folding of said expressed IEM polypeptide. A simultaneous or substantially simultaneous co-expression of both polypeptides represents one non-limiting alternative among others. Another non-limiting alternative might be seen in the timely sequential expression of both polypeptides starting with expression of the helper polypeptide followed by the IEM polypeptide expression. Another non-limiting alternative might be seen a timely overlapping co-expression of both polypeptides, wherein in the initial phase merely the helper polypeptide is expressed and in the overlapping phase both polypeptides are expressed. Other alternatives may be developed by a skilled reader without inventive effort.
21. The method of embodiment 20, wherein an isoeugenol oxidizing enzyme as defined in anyone of the embodiments 7 to 10 is prepared.
22. The method of embodiment 20 or 21, wherein a non-human host organism or host cell as defined in anyone of the embodiments 16 to 19 is applied for expression.
23. A method of producing vanillin comprising
   a. contacting isoeugenol with a polypeptide having isoeugenol oxidizing activity as defined in anyone of the embodiments 7 to 10, or a polypeptide having isoeugenol oxidizing activity as prepared by a method of anyone of the embodiments 20 to 22 in the presence of oxygen, in particular molecular oxygen, to produce vanillin and acetaldehyde; and
   b. optionally isolating the vanillin produced in step a.
   In preferred embodiment vanillin is isolated.
   In another preferred embodiment vanillin (and acetaldehyde) is obtained as the main product of the isoeugenol oxigenation process.
   The vanillin produced in any of the method described herein can be converted to derivatives such as, but not limited to hydrocarbons, esters, amides, glycosides, ethers, epoxides, aldehydes, ketons, alcohols, diols, acetals or ketals.
   The vanillin derivatives can be obtained by a chemical method such as, but not limited to oxidation, reduction, alkylation, acylation and/or rearrangement.
   Alternatively, the vanillin derivatives can be obtained using a biochemical method by contacting vanillin with an enzyme such as, but not limited to an oxidoreductase, a monooxygenase, a dioxygenase, a transferase. The biochemical conversion can be performed in-vitro using isolated enzymes, enzymes from lysed cells or in-vivo using whole cells.
24. The method of embodiment 23, comprising transforming a non-human host organism or host cell with an expression system as defined in anyone of the embodiments 1 to 6, expressing the coding nucleotide sequences (A) and (B) thereof.
25. The method of any one of embodiments 23 or 24, wherein the isoeugenol is contacted with a host cell, with a cell lysate of the host cell, or a culture medium containing said host cell and/or with the polypeptide having isoeugenol oxidizing activity as defined in anyone of the embodiments 7 to 10, isolated from the host cell, cell lysate or culture medium.
   The isoeugenol substrate may either be added to reaction medium applied or, in an alternative embodiment, a non-human host organism or a host cell already capable of producing isoeugenol is transformed with an expression system as defined in anyone of the embodiments 1 to 6 to express at least one polypeptide having isoeugenol monooxygenase activity, and is cultivated under conditions conducive to the production of vanillin.
26. The method of embodiment 25, wherein vanillin is fermentatively produced by said non-human host organism or host cell.
27. The method of embodiment 25, wherein vanillin is enzymatically produced by the conversion of isoeugenol with an isolated polypeptide having isoeugenol oxidizing activity as defined in anyone of the embodiments 7 to 10, in the presence of oxygen, and optionally further adjuvants.
28. The method of anyone of the embodiments 23 to 27, which method further comprises in advance of step a. the step of chemical or biochemical isomerization of eugenol to isoeugenol, and optionally isolating isoeugenol from the reaction medium.
29. A method for preparing a mutant polypeptide having isoeugenol oxidizing activity comprising the steps of:
   a. selecting a nucleic acid according to any one of the embodiments 11 and 12;
   b. modifying the selected nucleic acid to obtain at least one mutant nucleic acid;
   c. providing host cells or unicellular organisms with the mutant nucleic acid sequence to express a polypeptide encoded by the mutant nucleic acid sequence;
   d. screening for at least one mutant polypeptide with activity in oxidizing isoeugenol;
   e. optionally, if the mutated polypeptide has no desired activity, repeating the process steps a. to d. until a polypeptide with a desired activity is obtained; and,
   f. optionally, if a mutant polypeptide having a desired activity was identified in step d. or e., isolating the corresponding mutant nucleic acid.

Further aspects and embodiments of the present invention as described above by reference to particular, preferred embodiments are described in the subsequent sections.

b. Polypeptides Applicable According to the Invention

In this context the following definitions apply:

The generic terms "polypeptide" or "peptide", which may be used interchangeably, refer to a natural or synthetic, linear chain or sequence of consecutive, peptidically linked amino acid residues, comprising about 10 up to more than 1.000 residues. Short chain polypeptides with up to 30 residues are also designated as "oligopeptides".

The term "protein" refers to a macromolecular structure consisting of one or more polypeptides. The amino acid sequence of its polypeptide(s) represents the "primary structure" of the protein. The amino acid sequence also predetermines the "secondary structure" of the protein by the formation of special structural elements, such as alpha-helical and beta-sheet structures formed within a polypeptide chain. The arrangement of a plurality of such secondary structural elements defines the "tertiary structure" or spatial arrangement of the protein. If a protein comprises more than one polypeptide chains said chains are spatially arranged forming the "quaternary structure" of the protein. A correct spacial arrangement or "folding" of the protein is prerequisite of protein function. Denaturation or unfolding destroys protein function. If such destruction is reversible, protein function may be restored by refolding.

A typical protein function referred to herein is an "enzyme function", i.e. the protein acts as biocatalyst on a substrate, for example a chemical compound, and catalyzes the conversion of said substrate to a product. An enzyme may show a high or low degree of substrate and/or product specificity.

A "polypeptide" referred to herein as having a particular "activity" thus implicitly refers to a correctly folded protein showing the indicated activity, as for example a specific enzyme activity.

Thus, unless otherwise indicated the term "polypeptide" also encompasses the terms "protein" and "enzyme".

Similarly, the term "polypeptide fragment" encompasses the terms "protein fragment" and "enzyme fragment".

The term "isolated polypeptide" refers to an amino acid sequence that is removed from its natural environment by any method or combination of methods known in the art and includes recombinant, biochemical and synthetic methods.

"Target peptide" refers to an amino acid sequence which targets a protein, or polypeptide to intracellular organelles, i.e., mitochondria, or plastids, or to the extracellular space (secretion signal peptide). A nucleic acid sequence encoding a target peptide may be fused to the nucleic acid sequence encoding the amino terminal end, e.g., N-terminal end, of the protein or polypeptide, or may be used to replace a native targeting polypeptide.

The present invention also relates to "functional equivalents" (also designated as "analogs" or "functional mutations") of the polypeptides specifically described herein.

For example, "functional equivalents" refer to polypeptides which, in a test used for determining enzymatic isoeugenol oxidizing activity or, more particularly IEM activity, display at least a 1 to 10%, or at least 20%, or at least 50%, or at least 75%, or at least 90% higher or lower IEM activity, as that of the respective polypeptide specifically defined herein.

"Functional equivalents" may also be derived from helper polypeptides as described therein which assist in the functional expression of another, preferably enzymatically active, polypeptide, in particular the correct folding of said expressed polypeptide, as for example of a polypeptide with isoeugenol oxidizing activity or, more particularly IEM activity. Such modified helper polypeptide may still be regarded as functional, as long as it improves the correct expression or folding said enzymatically active polypeptide relative the expression of the same enzymatically active polypeptide under otherwise identical conditions but in the absence of such helper polypeptide.

"Functional equivalents", according to the invention, also cover particular mutants, which, in at least one sequence position of an amino acid sequences stated herein, have an amino acid that is different from that concretely stated one, but nevertheless possess one of the aforementioned biological activities, as for example enzyme activity. "Functional equivalents" thus comprise mutants obtainable by one or more, like 1 to 20, in particular 1 to 15 or 5 to 10 amino acid additions, substitutions, in particular conservative substitutions, deletions and/or inversions, where the stated changes can occur in any sequence position, provided they lead to a mutant with the profile of properties according to the invention. Functional equivalence is in particular also provided if the activity patterns coincide qualitatively between the mutant and the unchanged polypeptide, i.e. if, for example, interaction with the same agonist or antagonist or substrate, however at a different rate, (i.e. expressed by a $EC_{50}$ or $IC_{50}$ value or any other parameter suitable in the present technical field) is observed. Examples of suitable (conservative) amino acid substitutions are shown in the following table:

| Original residue | Examples of substitution |
| --- | --- |
| Ala | Ser |
| Arg | Lys |
| Asn | Gln; His |
| Asp | Glu |
| Cys | Ser |
| Gln | Asn |
| Glu | Asp |
| Gly | Pro |
| His | Asn; Gln |
| Ile | Leu; Val |
| Leu | Ile; Val |
| Lys | Arg; Gln; Glu |
| Met | Leu; Ile |

-continued

| Original residue | Examples of substitution |
| --- | --- |
| Phe | Met; Leu; Tyr |
| Ser | Thr |
| Thr | Ser |
| Trp | Tyr |
| Tyr | Trp; Phe |
| Val | Ile; Leu |

"Functional equivalents" in the above sense are also "precursors" of the polypeptides described herein, as well as "functional derivatives" and "salts" of the polypeptides.

"Precursors" are in that case natural or synthetic precursors of the polypeptides with or without the desired biological activity.

The expression "salts" means salts of carboxyl groups as well as salts of acid addition of amino groups of the protein molecules according to the invention. Salts of carboxyl groups can be produced in a known way and comprise inorganic salts, for example sodium, calcium, ammonium, iron and zinc salts, and salts with organic bases, for example amines, such as triethanolamine, arginine, lysine, piperidine and the like. Salts of acid addition, for example salts with inorganic acids, such as hydrochloric acid or sulfuric acid and salts with organic acids, such as acetic acid and oxalic acid, are also covered by the invention.

"Functional derivatives" of polypeptides according to the invention can also be produced on functional amino acid side groups or at their N-terminal or C-terminal end using known techniques. Such derivatives comprise for example aliphatic esters of carboxylic acid groups, amides of carboxylic acid groups, obtainable by reaction with ammonia or with a primary or secondary amine; N-acyl derivatives of free amino groups, produced by reaction with acyl groups; or O-acyl derivatives of free hydroxyl groups, produced by reaction with acyl groups.

"Functional equivalents" naturally also comprise polypeptides that can be obtained from other organisms, as well as naturally occurring variants. For example, areas of homologous sequence regions can be established by sequence comparison, and equivalent polypeptides can be determined on the basis of the concrete parameters of the invention.

"Functional equivalents" also comprise "fragments", like individual domains or sequence motifs, of the polypeptides according to the invention, or N- and or C-terminally truncated forms, which may or may not display the desired biological function. Preferably such "fragments" retain the desired biological function at least qualitatively.

"Functional equivalents" are, moreover, fusion proteins, which have one of the polypeptide sequences stated herein or functional equivalents derived there from and at least one further, functionally different, heterologous sequence in functional N-terminal or C-terminal association (i.e. without substantial mutual functional impairment of the fusion protein parts). Non-limiting examples of these heterologous sequences are e.g. signal peptides, histidine anchors or enzymes.

"Functional equivalents" which are also comprised in accordance with the invention are homologs to the specifically disclosed polypeptides. These have at least 60%, preferably at least 75%, in particular at least 80 or 85%, such as, for example, 90, 91, 92, 93, 94, 95, 96, 97, 98 or 99%, homology (or identity) to one of the specifically disclosed amino acid sequences, calculated by the algorithm of Pearson and Lipman, Proc. Natl. Acad, Sci. (USA) 85(8), 1988, 2444-2448. A homology or identity, expressed as a percentage, of a homologous polypeptide according to the invention means in particular an identity, expressed as a percentage, of the amino acid residues based on the total length of one of the amino acid sequences described specifically herein.

The identity data, expressed as a percentage, may also be determined with the aid of BLAST alignments, algorithm blastp (protein-protein BLAST), or by applying the Clustal settings specified herein below.

In the case of a possible protein glycosylation, "functional equivalents" according to the invention comprise polypeptides as described herein in deglycosylated or glycosylated form as well as modified forms that can be obtained by altering the glycosylation pattern.

Functional equivalents or homologues of the polypeptides according to the invention can be produced by mutagenesis, e.g. by point mutation, lengthening or shortening of the protein or as described in more detail below.

Functional equivalents or homologs of the polypeptides according to the invention can be identified by screening combinatorial databases of mutants, for example shortening mutants. For example, a variegated database of protein variants can be produced by combinatorial mutagenesis at the nucleic acid level, e.g. by enzymatic ligation of a mixture of synthetic oligonucleotides. There are a great many methods that can be used for the production of databases of potential homologues from a degenerated oligonucleotide sequence. Chemical synthesis of a degenerated gene sequence can be carried out in an automatic DNA synthesizer, and the synthetic gene can then be ligated in a suitable expression vector. The use of a degenerated genome makes it possible to supply all sequences in a mixture, which code for the desired set of potential protein sequences. Methods of synthesis of degenerated oligonucleotides are known to a person skilled in the art.

Several techniques are known for the screening of gene products of combinatorial databases, which were produced by point mutations or shortening, and for the screening of cDNA libraries for gene products with a selected property. These techniques can be adapted for the rapid screening of the gene banks that were produced by combinatorial mutagenesis of homologues according to the invention. The techniques most frequently used for the screening of large gene banks, which are based on a high-throughput analysis, comprise cloning of the gene bank in expression vectors that can be replicated, transformation of the suitable cells with the resultant vector database and expression of the combinatorial genes in conditions in which detection of the desired activity facilitates isolation of the vector that codes for the gene whose product was detected. Recursive Ensemble Mutagenesis (REM), a technique that increases the frequency of functional mutants in the databases, can be used in combination with the screening tests, in order to identify homologues.

An embodiment provided herein provides orthologs and paralogs of polypeptides disclosed herein as well as methods for identifying and isolating such orthologs and paralogs.

c. Coding Nucleic Acid Sequences Applicable According to the Invention

In this context the following definitions apply:

The terms "nucleic acid sequence," "nucleic acid," "nucleic acid molecule" and "polynucleotide" are used interchangeably meaning a sequence of nucleotides. A nucleic acid sequence may be a single-stranded or double-stranded deoxyribonucleotide, or ribonucleotide of any length, and include coding and non-coding sequences of a gene, exons, introns, sense and anti-sense complimentary sequences, genomic DNA, cDNA, miRNA, siRNA, mRNA, rRNA, tRNA, recombinant nucleic acid sequences, isolated and purified naturally occurring DNA and/or RNA sequences, synthetic DNA and RNA sequences, fragments, primers and nucleic acid probes. The skilled artisan is aware that the nucleic acid sequences of RNA are identical to the DNA sequences with the difference of thymine (T) being replaced by uracil (U). The term "nucleotide sequence" should also be understood as comprising a polynucleotide molecule or an oligonucleotide molecule in the form of a separate fragment or as a component of a larger nucleic acid.

An "isolated nucleic acid" or "isolated nucleic acid sequence" relates to a nucleic acid or nucleic acid sequence that is in an environment different from that in which the nucleic acid or nucleic acid sequence naturally occurs and can include those that are substantially free from contaminating endogenous material. The term "naturally-occurring" as used herein as applied to a nucleic acid refers to a nucleic acid that is found in a cell of an organism in nature and which has not been intentionally modified by a human in the laboratory.

A "fragment" of a polynucleotide or nucleic acid sequence refers to contiguous nucleotides that is particularly at least 15 bp, at least 30 bp, at least 40 bp, at least 50 bp and/or at least 60 bp in length of the polynucleotide of an embodiment herein. Particularly the fragment of a polynucleotide comprises at least 25, more particularly at least 50, more particularly at least 75, more particularly at least 100, more particularly at least 150, more particularly at least 200, more particularly at least 300, more particularly at least 400, more particularly at least 500, more particularly at least 600, more particularly at least 700, more particularly at least 800, more particularly at least 900, more particularly at least 1000 contiguous nucleotides of the polynucleotide of an embodiment herein. Without being limited, the fragment of the polynucleotides herein may be used as a PCR primer, and/or as a probe, or for anti-sense gene silencing or RNAi.

As used herein, the term "hybridization" or hybridizes under certain conditions is intended to describe conditions for hybridization and washes under which nucleotide sequences that are significantly identical or homologous to each other remain bound to each other. The conditions may be such that sequences, which are at least about 70%, such as at least about 80%, and such as at least about 85%, 90%, or 95% identical, remain bound to each other. Definitions of low stringency, moderate, and high stringency hybridization conditions are provided herein below. Appropriate hybridization conditions can also be selected by those skilled in the art with minimal experimentation as exemplified in Ausubel et al. (1995, *Current Protocols in Molecular Biology*, John Wiley & Sons, sections 2, 4, and 6). Additionally, stringency conditions are described in Sambrook et al. (1989, *Molecular Cloning: A Laboratory Manual*, 2nd ed., Cold Spring Harbor Press, chapters 7, 9, and 11).

"Recombinant nucleic acid sequences" are nucleic acid sequences that result from the use of laboratory methods (for example, molecular cloning) to bring together genetic material from more than on source, creating or modifying a nucleic acid sequence that does not occur naturally and would not be otherwise found in biological organisms.

"Recombinant DNA technology" refers to molecular biology procedures to prepare a recombinant nucleic acid sequence as described, for instance, in Laboratory Manuals edited by Weigel and Glazebrook, 2002, Cold Spring Harbor Lab Press; and Sambrook et al., 1989, Cold Spring Harbor, N.Y., Cold Spring Harbor Laboratory Press.

The term "gene" means a DNA sequence comprising a region, which is transcribed into a RNA molecule, e.g., an mRNA in a cell, operably linked to suitable regulatory regions, e.g., a promoter. A gene may thus comprise several operably linked sequences, such as a promoter, a 5' leader sequence comprising, e.g., sequences involved in translation initiation, a coding region of cDNA or genomic DNA, introns, exons, and/or a 3'non-translated sequence comprising, e.g., transcription termination sites.

"Polycistronic" refers to nucleic acid molecules, in particular mRNAs or corresponding cDNAs that can encode more than one polypeptide separately within the same nucleic acid molecule. A polycistronic gene allows for the translation initiation at two or more sites on one single sequence.

A "chimeric gene" refers to any gene which is not normally found in nature in a species, in particular, a gene in which one or more parts of the nucleic acid sequence are present that are not associated with each other in nature. For example the promoter is not associated in nature with part or all of the transcribed region or with another regulatory region. The term "chimeric gene" is understood to include expression constructs in which a promoter or transcription regulatory sequence is operably linked to one or more coding sequences or to an antisense, i.e., reverse complement of the sense strand, or inverted repeat sequence (sense and antisense, whereby the RNA transcript forms double stranded RNA upon transcription). The term "chimeric gene" also includes genes obtained through the combination of portions of one or more coding sequences to produce a new gene.

A "3' UTR" or "3' non-translated sequence" (also referred to as "3' untranslated region," or "3'end") refers to the nucleic acid sequence found downstream of the coding sequence of a gene, which comprises, for example, a transcription termination site and (in most, but not all eukaryotic mRNAs) a polyadenylation signal such as AAUAAA or variants thereof. After termination of transcription, the mRNA transcript may be cleaved downstream of the polyadenylation signal and a poly(A) tail may be added, which is involved in the transport of the mRNA to the site of translation, e.g., cytoplasm.

The term "primer" refers to a short nucleic acid sequence that is hybridized to a template nucleic acid sequence and is used for polymerization of a nucleic acid sequence complementary to the template.

The term "selectable marker" refers to any gene which upon expression may be used to select a cell or cells that include the selectable marker. Examples of selectable markers are described below. The skilled artisan will know that different antibiotic, fungicide, auxotrophic or herbicide selectable markers are applicable to different target species.

The invention also relates to nucleic acid sequences that code for polypeptides as defined herein.

In particular, the invention also relates to nucleic acid sequences (single-stranded and double-stranded DNA and RNA sequences, e.g. cDNA, genomic DNA and mRNA), coding for one of the above polypeptides and their functional equivalents, which can be obtained for example using artificial nucleotide analogs.

The invention relates both to isolated nucleic acid molecules, which code for polypeptides according to the invention or biologically active segments thereof, and to nucleic acid fragments, which can be used for example as hybridization probes or primers for identifying or amplifying coding nucleic acids according to the invention.

The present invention also relates to nucleic acids with a certain degree of "identity" to the sequences specifically disclosed herein. "Identity" between two nucleic acids means identity of the nucleotides, in each case over the entire length of the nucleic acid.

The "identity" between two nucleotide sequences (the same applies to peptide or amino acid sequences) is a function of the number of nucleotide residues (or amino acid residues) or that are identical in the two sequences when an alignment of these two sequences has been generated. Identical residues are defined as residues that are the same in the two sequences in a given position of the alignment. The percentage of sequence identity, as used herein, is calculated from the optimal alignment by taking the number of residues identical between two sequences dividing it by the total number of residues in the shortest sequence and multiplying by 100. The optimal alignment is the alignment in which the percentage of identity is the highest possible. Gaps may be introduced into one or both sequences in one or more positions of the alignment to obtain the optimal alignment. These gaps are then taken into account as non-identical residues for the calculation of the percentage of sequence identity. Alignment for the purpose of determining the percentage of amino acid or nucleic acid sequence identity can be achieved in various ways using computer programs and for instance publicly available computer programs available on the world wide web.

Particularly, the BLAST program (Tatiana et al, *FEMS Microbiol Lett.*, 1999, 174:247-250, 1999) set to the default parameters, available from the National Center for Biotechnology Information (NCBI) website at ncbi.nlm.nih.gov/BLAST/b12seq/wblast2.cgi, can be used to obtain an optimal alignment of protein or nucleic acid sequences and to calculate the percentage of sequence identity.

In another example the identity may be calculated by means of the Vector NTI Suite 7.1 program of the company Informax (USA) employing the Clustal Method (Higgins D G, Sharp P M. ((1989))) with the following settings:

Multiple alignment parameter:

| | |
|---|---|
| Gap opening penalty | 10 |
| Gap extension penalty | 10 |
| Gap separation penalty range | 8 |
| Gap separation penalty | off |
| % identity for alignment delay | 40 |
| Residue specific gaps | off |
| Hydrophilic residue gap | off |
| Transition weighing | 0 |

Pairwise alignment parameter:

| | |
|---|---|
| FAST algorithm | on |
| K-tuple size | 1 |
| Gap penalty | 3 |
| Window size | 5 |
| Number of best diagonals | 5 |

Alternatively the identity may be determined according to Chenna, et al. (2003), the web page: http://www.ebi.ac.uk/Tools/clustalw/index.html# and the following settings

| | |
|---|---|
| DNA Gap Open Penalty | 15.0 |
| DNA Gap Extension Penalty | 6.66 |

| | |
|---|---|
| DNA Matrix | Identity |
| Protein Gap Open Penalty | 10.0 |
| Protein Gap Extension Penalty | 0.2 |
| Protein matrix | Gonnet |
| Protein/DNA ENDGAP | −1 |
| Protein/DNA GAPDIST | 4 |

All the nucleic acid sequences mentioned herein (single-stranded and double-stranded DNA and RNA sequences, for example cDNA and mRNA) can be produced in a known way by chemical synthesis from the nucleotide building blocks, e.g. by fragment condensation of individual overlapping, complementary nucleic acid building blocks of the double helix. Chemical synthesis of oligonucleotides can, for example, be performed in a known way, by the phosphoamidite method (Voet, Voet, 2nd edition, Wiley Press, New York, pages 896-897). The accumulation of synthetic oligonucleotides and filling of gaps by means of the Klenow fragment of DNA polymerase and ligation reactions as well as general cloning techniques are described in Sambrook et al. (1989), see below.

The nucleic acid molecules according to the invention can in addition contain non-translated sequences from the 3' and/or 5' end of the coding genetic region.

The invention further relates to the nucleic acid molecules that are complementary to the concretely described nucleotide sequences or a segment thereof.

The nucleotide sequences according to the invention make possible the production of probes and primers that can be used for the identification and/or cloning of homologous sequences in other cellular types and organisms. Such probes or primers generally comprise a nucleotide sequence region which hybridizes under "stringent" conditions (as defined herein elsewhere) on at least about 12, preferably at least about 25, for example about 40, 50 or 75 successive nucleotides of a sense strand of a nucleic acid sequence according to the invention or of a corresponding antisense strand.

An "isolated" nucleic acid molecule is separated from other nucleic acid molecules that are present in the natural source of the nucleic acid and can moreover be substantially free from other cellular material or culture medium, if it is being produced by recombinant techniques, or can be free from chemical precursors or other chemicals, if it is being synthesized chemically.

A nucleic acid molecule according to the invention can be isolated by means of standard techniques of molecular biology and the sequence information supplied according to the invention. For example, cDNA can be isolated from a suitable cDNA library, using one of the concretely disclosed complete sequences or a segment thereof as hybridization probe and standard hybridization techniques (as described for example in Sambrook, (1989)).

In addition, a nucleic acid molecule comprising one of the disclosed sequences or a segment thereof, can be isolated by the polymerase chain reaction, using the oligonucleotide primers that were constructed on the basis of this sequence. The nucleic acid amplified in this way can be cloned in a suitable vector and can be characterized by DNA sequencing. The oligonucleotides according to the invention can also be produced by standard methods of synthesis, e.g. using an automatic DNA synthesizer.

Nucleic acid sequences according to the invention or derivatives thereof, homologues or parts of these sequences, can for example be isolated by usual hybridization techniques or the PCR technique from other bacteria, e.g. via genomic or cDNA libraries. These DNA sequences hybridize in standard conditions with the sequences ac-cording to the invention.

"Hybridize" means the ability of a polynucleotide or oligonucleotide to bind to an almost complementary sequence in standard conditions, whereas nonspecific binding does not occur between non-complementary partners in these conditions. For this, the sequences can be 90-100% complementary. The property of complementary sequences of being able to bind specifically to one another is utilized for example in Northern Blotting or Southern Blotting or in primer binding in PCR or RT-PCR.

Short oligonucleotides of the conserved regions are used advantageously for hybridization. However, it is also possible to use longer fragments of the nucleic acids according to the invention or the complete sequences for the hybridization. These "standard conditions" vary depending on the nucleic acid used (oligonucleotide, longer fragment or complete sequence) or depending on which type of nucleic acid—DNA or RNA—is used for hybridization. For example, the melting temperatures for DNA:DNA hybrids are approx. 10° C. lower than those of DNA:RNA hybrids of the same length.

For example, depending on the particular nucleic acid, standard conditions mean temperatures between 42 and 58° C. in an aqueous buffer solution with a concentration between 0.1 to 5×SSC (1×SSC=0.15 M NaCl, 15 mM sodium citrate, pH 7.2) or additionally in the presence of 50% formamide, for example 42° C. in 5×SSC, 50% formamide. Advantageously, the hybridization conditions for DNA:DNA hybrids are 0.1×SSC and temperatures between about 20° C. to 45° C., preferably between about 30° C. to 45° C. For DNA:RNA hybrids the hybridization conditions are advantageously 0.1×SSC and temperatures between about 30° C. to 55° C., preferably between about 45° C. to 55° C. These stated temperatures for hybridization are examples of calculated melting temperature values for a nucleic acid with a length of approx. 100 nucleotides and a G+C content of 50% in the absence of formamide. The experimental conditions for DNA hybridization are described in relevant genetics textbooks, for example Sambrook et al., 1989, and can be calculated using formulae that are known by a person skilled in the art, for example depending on the length of the nucleic acids, the type of hybrids or the G+C content. A person skilled in the art can obtain further information on hybridization from the following textbooks: Ausubel et al. (eds), (1985), Brown (ed) (1991).

"Hybridization" can in particular be carried out under stringent conditions. Such hybridization conditions are for example described in Sambrook (1989), or in Current Protocols in Molecular Biology, John Wiley & Sons, N.Y. (1989), 6.3.1-6.3.6.

As used herein, the term hybridization or hybridizes under certain conditions is intended to describe conditions for hybridization and washes under which nucleotide sequences that are significantly identical or homologous to each other remain bound to each other. The conditions may be such that sequences, which are at least about 70%, such as at least about 80%, and such as at least about 85%, 90%, or 95% identical, remain bound to each other. Definitions of low stringency, moderate, and high stringency hybridization conditions are provided herein.

Appropriate hybridization conditions can be selected by those skilled in the art with minimal experimentation as exemplified in Ausubel et al. (1995, *Current Protocols in*

*Molecular Biology*, John Wiley & Sons, sections 2, 4, and 6). Additionally, stringency conditions are described in Sambrook et al. (1989, *Molecular Cloning: A Laboratory Manual*, 2nd ed., Cold Spring Harbor Press, chapters 7, 9, and 11).

As used herein, defined conditions of low stringency are as follows. Filters containing DNA are pretreated for 6 h at 40° C. in a solution containing 35% formamide, 5×SSC, 50 mM Tris-HCl (pH 7.5), 5 mM EDTA, 0.1% PVP, 0.1% Ficoll, 1% BSA, and 500 µg/ml denatured salmon sperm DNA. Hybridizations are carried out in the same solution with the following modifications: 0.02% PVP, 0.02% Ficoll, 0.2% BSA, 100 µg/ml salmon sperm DNA, 10% (wt/vol) dextran sulfate, and 5-20×106 32P-labeled probe is used. Filters are incubated in hybridization mixture for 18-20 h at 40° C., and then washed for 1.5 h at 55° C. In a solution containing 2×SSC, 25 mM Tris-HCl (pH 7.4), 5 mM EDTA, and 0.1% SDS. The wash solution is replaced with fresh solution and incubated an additional 1.5 h at 60° C. Filters are blotted dry and exposed for autoradiography.

As used herein, defined conditions of moderate stringency are as follows. Filters containing DNA are pretreated for 7 h at 50° C. in a solution containing 35% formamide, 5×SSC, 50 mM Tris-HCl (pH 7.5), 5 mM EDTA, 0.1% PVP, 0.1% Ficoll, 1% BSA, and 500 µg/ml denatured salmon sperm DNA. Hybridizations are carried out in the same solution with the following modifications: 0.02% PVP, 0.02% Ficoll, 0.2% BSA, 100 µg/ml salmon sperm DNA, 10% (wt/vol) dextran sulfate, and 5-20×106 32P-labeled probe is used. Filters are incubated in hybridization mixture for 30 h at 50° C., and then washed for 1.5 h at 55° C. In a solution containing 2×SSC, 25 mM Tris-HCl (pH 7.4), 5 mM EDTA, and 0.1% SDS. The wash solution is replaced with fresh solution and incubated an additional 1.5 h at 60° C. Filters are blotted dry and exposed for autoradiography.

As used herein, defined conditions of high stringency are as follows. Prehybridization of filters containing DNA is carried out for 8 h to overnight at 65° C. in buffer composed of 6×SSC, 50 mM Tris-HCl (pH 7.5), 1 mM EDTA, 0.02% PVP, 0.02% Ficoll, 0.02% BSA, and 500 µg/ml denatured salmon sperm DNA. Filters are hybridized for 48 h at 65° C. in the prehybridization mixture containing 100 µg/ml denatured salmon sperm DNA and 5-20×106 cpm of 32P-labeled probe. Washing of filters is done at 37° C. for 1 h in a solution containing 2×SSC, 0.01% PVP, 0.01% Ficoll, and 0.01% BSA. This is followed by a wash in 0.1×SSC at 50° C. for 45 minutes.

Other conditions of low, moderate, and high stringency well known in the art (e.g., as employed for cross-species hybridizations) may be used if the above conditions are inappropriate (e.g., as employed for cross-species hybridizations).

A detection kit for nucleic acid sequences encoding a polypeptide of the invention may include primers and/or probes specific for nucleic acid sequences encoding the polypeptide, and an associated protocol to use the primers and/or probes to detect nucleic acid sequences encoding the polypeptide in a sample. Such detection kits may be used to determine whether a plant, organism, microorganism or cell has been modified, i.e., transformed with a sequence encoding the polypeptide.

To test a function of variant DNA sequences according to an embodiment herein, the sequence of interest is operably linked to a selectable or screenable marker gene and expression of said reporter gene is tested in transient expression assays, for example, with microorganisms or with protoplasts or in stably transformed plants.

The invention also relates to derivatives of the concretely disclosed or derivable nucleic acid sequences.

Thus, further nucleic acid sequences according to the invention can be derived from the sequences specifically disclosed herein and can differ from it by one or more, like 1 to 20, in particular 1 to 15 or 5 to 10 additions, substitutions, insertions or deletions of one or several (like for example 1 to 10) nucleotides, and furthermore code for polypeptides with the desired profile of properties.

The invention also encompasses nucleic acid sequences that comprise so-called silent mutations or have been altered, in comparison with a concretely stated sequence, according to the codon usage of a special original or host organism.

According to a particular embodiment of the invention variant nucleic acids may be prepared in order to adapt its nucleotide sequence to a specific expression system. For example, bacterial expression systems are known to more efficiently express polypeptides if amino acids are encoded by particular codons. Due to the degeneracy of the genetic code, more than one codon may encode the same amino acid sequence, multiple nucleic acid sequences can code for the same protein or polypeptide, all these DNA sequences being encompassed by an embodiment herein. Where appropriate, the nucleic acid sequences encoding the polypetides described herein may be optimized for increased expression in the host cell. For example, nucleic acids of an embodiment herein may be synthesized using codons particular to a host for improved expression.

The invention also encompasses naturally occurring variants, e.g. splicing variants or allelic variants, of the sequences described therein.

Allelic variants may have at least 60% homology at the level of the derived amino acid, preferably at least 80% homology, quite especially preferably at least 90% homology over the entire sequence range (regarding homology at the amino acid level, reference should be made to the details given above for the polypeptides). Advantageously, the homologies can be higher over partial regions of the sequences.

The invention also relates to sequences that can be obtained by conservative nucleotide substitutions (i.e. as a result thereof the amino acid in question is replaced by an amino acid of the same charge, size, polarity and/or solubility).

The invention also relates to the molecules derived from the concretely disclosed nucleic acids by sequence polymorphisms. Such genetic polymorphisms may exist in cells from different populations or within a population due to natural allelic variation. Allelic variants may also include functional equivalents. These natural variations usually produce a variance of 1 to 5% in the nucleotide sequence of a gene. Said polymorphisms may lead to changes in the amino acid sequence of the polypeptides disclosed herein. Allelic variants may also include functional equivalents.

Furthermore, derivatives are also to be understood to be homologs of the nucleic acid sequences according to the invention, for example animal, plant, fungal or bacterial homologs, shortened sequences, single-stranded DNA or RNA of the coding and noncoding DNA sequence. For example, homologs have, at the DNA level, a homology of at least 40%, preferably of at least 60%, especially preferably of at least 70%, quite especially preferably of at least 80% over the entire DNA region given in a sequence specifically disclosed herein.

Moreover, derivatives are to be understood to be, for example, fusions with promoters. The promoters that are added to the stated nucleotide sequences can be modified by at least one nucleotide exchange, at least one insertion, inversion and/or deletion, though without impairing the functionality or efficacy of the promoters. Moreover, the efficacy of the promoters can be increased by altering their sequence or can be exchanged completely with more effective promoters even of organisms of a different genus.

d. Generation of Functional Polypeptide Mutants

Moreover, a person skilled in the art is familiar with methods for generating functional mutants, that is to say nucleotide sequences which code for a polypeptide with at least 80%, 81%, 82%, 83%, 84%, 85%, 86%, 87%, 88%, 89%, 90%, 91%, 92%, 93%, 94%, 95%, 96%, 97%, 98% or 99% sequence identity to anyone of amino acid related SEQ ID NOs as disclosed herein and/or encoded by a nucleic acid molecule comprising a nucleotide sequence having at least 70% sequence identity to anyone of the nucleotide related SEQ ID NOs as disclosed herein.

Depending on the technique used, a person skilled in the art can introduce entirely random or else more directed mutations into genes or else noncoding nucleic acid regions (which are for example important for regulating expression) and subsequently generate genetic libraries. The methods of molecular biology required for this purpose are known to the skilled worker and for example described in Sambrook and Russell, Molecular Cloning. 3rd Edition, Cold Spring Harbor Laboratory Press 2001.

Methods for modifying genes and thus for modifying the polypeptide encoded by them have been known to the skilled worker for a long time, such as, for example
- site-specific mutagenesis, where individual or several nucleotides of a gene are replaced in a directed fashion (Trower M K (Ed.) 1996; In vitro mutagenesis protocols. Humana Press, New Jersey),
- saturation mutagenesis, in which a codon for any amino acid can be exchanged or added at any point of a gene (Kegler-Ebo D M, Docktor C M, DiMaio D (1994) Nucleic Acids Res 22:1593; Barettino D, Feigenbutz M, Valcarel R, Stunnenberg H G (1994) Nucleic Acids Res 22:541; Barik S (1995) Mol Biotechnol 3:1),
- error-prone polymerase chain reaction, where nucleotide sequences are mutated by error-prone DNA polymerases (Eckert K A, Kunkel T A (1990) Nucleic Acids Res 18:3739);
- the SeSaM method (sequence saturation method), in which preferred exchanges are prevented by the polymerase. Schenk et al., Biospektrum, Vol. 3, 2006, 277-279
- the passaging of genes in mutator strains, in which, for example owing to defective DNA repair mechanisms, there is an increased mutation rate of nucleotide sequences (Greener A, Callahan M, Jerpseth B (1996) An efficient random mutagenesis technique using an E. coli mutator strain. In: Trower MK (Ed.) In vitro mutagenesis protocols. Humana Press, New Jersey), or
- DNA shuffling, in which a pool of closely related genes is formed and digested and the fragments are used as templates for a polymerase chain reaction in which, by repeated strand separation and reassociation, full-length mosaic genes are ultimately generated (Stemmer WPC (1994) Nature 370:389; Stemmer WPC (1994) Proc Natl Acad Sci USA 91:10747).

Using so-called directed evolution (described, inter alia, in Reetz M T and Jaeger K-E (1999), Topics Curr Chem 200:31; Zhao H, Moore J C, Volkov A A, Arnold F H (1999), Methods for optimizing industrial polypeptides by directed evolution, In: Demain A L, Davies J E (Ed.) Manual of industrial microbiology and biotechnology. American Society for Microbiology), a skilled worker can produce functional mutants in a directed manner and on a large scale. To this end, in a first step, gene libraries of the respective polypeptides are first produced, for example using the methods given above. The gene libraries are expressed in a suitable way, for example by bacteria or by phage display systems.

The relevant genes of host organisms which express functional mutants with properties that largely correspond to the desired properties can be submitted to another mutation cycle. The steps of the mutation and selection or screening can be repeated iteratively until the present functional mutants have the desired properties to a sufficient extent. Using this iterative procedure, a limited number of mutations, for example 1, 2, 3, 4 or 5 mutations, can be performed in stages and assessed and selected for their influence on the activity in question. The selected mutant can then be submitted to a further mutation step in the same way. In this way, the number of individual mutants to be investigated can be reduced significantly.

The results according to the invention also provide important information relating to structure and sequence of the relevant polypeptides, which is required for generating, in a targeted fashion, further polypeptides with desired modified properties. In particular, it is possible to define so-called "hot spots", i.e. sequence segments that are potentially suitable for modifying a property by introducing targeted mutations.

Information can also be deduced regarding amino acid sequence positions, in the region of which mutations can be effected that should probably have little effect on the activity, and can be designated as potential "silent mutations".

e. Constructs for Expressing Polypeptides of the Invention

In this context the following definitions apply:

"Expression of a gene" encompasses "heterologous expression" and "over-expression" and involves transcription of the gene and translation of the mRNA into a protein. Overexpression refers to the production of the gene product as measured by levels of mRNA, polypeptide and/or enzyme activity in transgenic cells or organisms that exceeds levels of production in non-transformed cells or organisms of a similar genetic background.

"Expression vector" as used herein means a nucleic acid molecule engineered using molecular biology methods and recombinant DNA technology for delivery of foreign or exogenous DNA into a host cell. The expression vector typically includes sequences required for proper transcription of the nucleotide sequence. The coding region usually codes for a protein of interest but may also code for an RNA, e.g., an antisense RNA, siRNA and the like.

An "expression vector" as used herein includes any linear or circular recombinant vector including but not limited to viral vectors, bacteriophages and plasmids. The skilled person is capable of selecting a suitable vector according to the expression system. In one embodiment, the expression vector includes the nucleic acid of an embodiment herein operably linked to at least one "regulatory sequence", which controls transcription, translation, initiation and termination, such as a transcriptional promoter, operator or enhancer, or an mRNA ribosomal binding site and, optionally, including at least one selection marker. Nucleotide sequences are "operably linked" when the regulatory sequence functionally relates to the nucleic acid of an embodiment herein.

An "expression system" as used herein encompasses any combination of nucleic acid molecules required for the expression of one, or the co-expression of two or more polypeptides either in vivo of a given expression host, or in vitro. The respective coding sequences may either be located on a single nucleic acid molecule or vector, as for example a vector containing multiple cloning sites, or on a polycistronic nucleic acid, or may be distributed over two or more physically distinct vectors.

As used herein, the terms "amplifying" and "amplification" refer to the use of any suitable amplification methodology for generating or detecting recombinant of naturally expressed nucleic acid, as described in detail, below. For example, the invention provides methods and reagents (e.g., specific degenerate oligonucleotide primer pairs, oligo dT primer) for amplifying (e.g., by polymerase chain reaction, PCR) naturally expressed (e.g., genomic DNA or mRNA) or recombinant (e.g., cDNA) nucleic acids of the invention in vivo, ex vivo or in vitro.

"Regulatory sequence" refers to a nucleic acid sequence that determines expression level of the nucleic acid sequences of an embodiment herein and is capable of regulating the rate of transcription of the nucleic acid sequence operably linked to the regulatory sequence. Regulatory sequences comprise promoters, enhancers, transcription factors, promoter elements and the like.

A "promoter", a "nucleic acid with promoter activity" or a "promoter sequence" is understood as meaning, in accordance with the invention, a nucleic acid which, when functionally linked to a nucleic acid to be transcribed, regulates the transcription of said nucleic acid. "Promoter" in particular refers to a nucleic acid sequence that controls the expression of a coding sequence by providing a binding site for RNA polymerase and other factors required for proper transcription including without limitation transcription factor binding sites, repressor and activator protein binding sites. The meaning of the term promoter also includes the term "promoter regulatory sequence". Promoter regulatory sequences may include upstream and downstream elements that may influences transcription, RNA processing or stability of the associated coding nucleic acid sequence. Promoters include naturally-derived and synthetic sequences. The coding nucleic acid sequences is usually located downstream of the promoter with respect to the direction of the transcription starting at the transcription initiation site.

In this context, a "functional" or "operative" linkage is understood as meaning for example the sequential arrangement of one of the nucleic acids with a regulatory sequence. For example the sequence with promoter activity and of a nucleic acid sequence to be transcribed and optionally further regulatory elements, for example nucleic acid sequences which ensure the transcription of nucleic acids, and for example a terminator, are linked in such a way that each of the regulatory elements can perform its function upon transcription of the nucleic acid sequence. This does not necessarily require a direct linkage in the chemical sense. Genetic control sequences, for example enhancer sequences, can even exert their function on the target sequence from more remote positions or even from other DNA molecules. Preferred arrangements are those in which the nucleic acid sequence to be transcribed is positioned behind (i.e. at the 3'-end of) the promoter sequence so that the two sequences are joined together covalently. The distance between the promoter sequence and the nucleic acid sequence to be expressed recombinantly can be smaller than 200 base pairs, or smaller than 100 base pairs or smaller than 50 base pairs.

In addition to promoters and terminator, the following may be mentioned as examples of other regulatory elements: targeting sequences, enhancers, polyadenylation signals, selectable markers, amplification signals, replication origins and the like. Suitable regulatory sequences are described, for example, in Goeddel, Gene Expression Technology: Methods in Enzymology 185, Academic Press, San Diego, Calif. (1990).

The term "constitutive promoter" refers to an unregulated promoter that allows for continual transcription of the nucleic acid sequence it is operably linked to.

As used herein, the term "operably linked" refers to a linkage of polynucleotide elements in a functional relationship. A nucleic acid is "operably linked" when it is placed into a functional relationship with another nucleic acid sequence. For instance, a promoter, or rather a transcription regulatory sequence, is operably linked to a coding sequence if it affects the transcription of the coding sequence. Operably linked means that the DNA sequences being linked are typically contiguous. The nucleotide sequence associated with the promoter sequence may be of homologous or heterologous origin with respect to the plant to be transformed. The sequence also may be entirely or partially synthetic. Regardless of the origin, the nucleic acid sequence associated with the promoter sequence will be expressed or silenced in accordance with promoter properties to which it is linked after binding to the polypeptide of an embodiment herein. The associated nucleic acid may code for a protein that is desired to be expressed or suppressed throughout the organism at all times or, alternatively, at a specific time or in specific tissues, cells, or cell compartment. Such nucleotide sequences particularly encode proteins conferring desirable phenotypic traits to the host cells or organism altered or transformed therewith. More particularly, the associated nucleotide sequence leads to the production of vanillin in the cell or organism. Particularly, the nucleotide sequence encodes an IEM.

The nucleotide sequence as described herein above may be part of an "expression cassette". The terms "expression cassette" and "expression construct" are used synonymously. The (preferably recombinant) expression construct contains a nucleotide sequence which encodes a polypeptide according to the invention and which is under genetic control of regulatory nucleic acid sequences.

In a process applied according to the invention, the expression cassette may be part of an "expression vector", in particular of a recombinant expression vector.

An "expression unit" is understood as meaning, in accordance with the invention, a nucleic acid with expression activity which comprises a promoter as defined herein and, after functional linkage with a nucleic acid to be expressed or a gene, regulates the expression, i.e. the transcription and the translation of said nucleic acid or said gene. It is therefore in this connection also referred to as a "regulatory nucleic acid sequence". In addition to the promoter, other regulatory elements, for example enhancers, can also be present.

An "expression cassette" or "expression construct" is understood as meaning, in accordance with the invention, an expression unit which is functionally linked to the nucleic acid to be expressed or the gene to be expressed. In contrast to an expression unit, an expression cassette therefore comprises not only nucleic acid sequences which regulate transcription and translation, but also the nucleic acid sequences that are to be expressed as protein as a result of transcription and translation.

The terms "expression" or "overexpression" describe, in the context of the invention, the production or increase in intracellular activity of one or more polypeptides in a microorganism, which are encoded by the corresponding DNA. To this end, it is possible for example to introduce a gene into an organism, replace an existing gene with another gene, increase the copy number of the gene(s), use a strong promoter or use a gene which encodes for a corresponding polypeptide with a high activity; optionally, these measures can be combined.

Preferably such constructs according to the invention comprise a promoter 5'-upstream of the respective coding sequence and a terminator sequence 3'-downstream and optionally other usual regulatory elements, in each case in operative linkage with the coding sequence.

Nucleic acid constructs according to the invention comprise in particular a sequence coding for a polypeptide for example derived from the amino acid related SEQ ID NOs as described therein or the reverse complement thereof, or derivatives and homologs thereof and which have been linked operatively or functionally with one or more regulatory signals, advantageously for controlling, for example increasing, gene expression.

In addition to these regulatory sequences, the natural regulation of these sequences may still be present before the actual structural genes and optionally may have been genetically modified so that the natural regulation has been switched off and expression of the genes has been enhanced. The nucleic acid construct may, however, also be of simpler construction, i.e. no additional regulatory signals have been inserted before the coding sequence and the natural promoter, with its regulation, has not been removed. Instead, the natural regulatory sequence is mutated such that regulation no longer takes place and the gene expression is increased.

A preferred nucleic acid construct advantageously also comprises one or more of the already mentioned "enhancer" sequences in functional linkage with the promoter, which sequences make possible an enhanced expression of the nucleic acid sequence. Additional advantageous sequences may also be inserted at the 3'-end of the DNA sequences, such as further regulatory elements or terminators. One or more copies of the nucleic acids according to the invention may be present in a construct. In the construct, other markers, such as genes which complement auxotrophisms or antibiotic resistances, may also optionally be present so as to select for the construct.

Examples of suitable regulatory sequences are present in promoters such as cos, tac, trp, tet, trp-tet, lpp, lac, lpp-lac, lad", T7, T5, T3, H9, H10, G6, C4, gal, trc, ara, rhaP (rhaP$_{BAD}$)SP6, lambda-P$_R$ or in the lambda-P$_L$ promoter, and these are advantageously employed in Gram-negative bacteria. Further advantageous regulatory sequences are present for example in the Gram-positive promoters amy and SPO2, in the yeast or fungal promoters ADC1, MFalpha, AC, P-60, CYC1, GAPDH, TEF, rp28, ADH. Artificial promoters may also be used for regulation. See for example also Jones et al. ePathOptimize: A Combinatorial Approach for Transcriptional Balancing of Metabolic Pathways. Sci. Rep. 2015, 5, 11301.

For expression in a host organism, the nucleic acid construct is inserted advantageously into a vector such as, for example, a plasmid or a phage, which makes possible optimal expression of the genes in the host. Vectors are also understood as meaning, in addition to plasmids and phages, all the other vectors which are known to the skilled worker, that is to say for example viruses such as SV40, CMV, baculovirus and adenovirus, transposons, IS elements, phasmids, cosmids and linear or circular DNA or artificial chromosomes. These vectors are capable of replicating autonomously in the host organism or else chromosomally. These vectors are a further development of the invention. Binary or cpo-integration vectors are also applicable.

Suitable plasmids are, for example, in *E. coli* pLG338, pACYC184, pBR322, pUC18, pUC19, pKC30, pRep4, pHS1, pKK223-3, pDHE19.2, pHS2, pPLc236, pMBL24, pLG200, pUR290, pIN-III$^{113}$-B1, λgt11 or pBdCI, in *Streptomyces* pIJ101, pIJ364, pIJ702 or pIJ361, in *Bacillus* pUB110, pC194 or pBD214, in *Corynebacterium* pSA77 or pAJ667, in fungi pALS1, pIL2 or pBB116, in yeasts 2alphaM, pAG-1, YEp6, YEp13 or pEMBLYe23 or in plants pLGV23, pGHlac$^+$, pBIN19, pAK2004 or pDH51. The abovementioned plasmids are a small selection of the plasmids which are possible. Further plasmids are well known to the skilled worker and can be found for example in the book Cloning Vectors (Eds. Pouwels P. H. et al. Elsevier, Amsterdam-New York-Oxford, 1985, ISBN 0 444 904018).

In a further development of the vector, the vector which comprises the nucleic acid construct according to the invention or the nucleic acid according to the invention can advantageously also be introduced into the microorganisms in the form of a linear DNA and integrated into the host organism's genome via heterologous or homologous recombination. This linear DNA can consist of a linearized vector such as a plasmid or only of the nucleic acid construct or the nucleic acid according to the invention.

For optimal expression of heterologous genes in organisms, it is advantageous to modify the nucleic acid sequences to match the specific "codon usage" used in the organism. The "codon usage" can be determined readily by computer evaluations of other, known genes of the organism in question.

An expression cassette according to the invention is generated by fusing a suitable promoter to a suitable coding nucleotide sequence and a terminator or polyadenylation signal. Customary recombination and cloning techniques are used for this purpose, as are described, for example, in T. Maniatis, E. F. Fritsch and J. Sambrook, Molecular Cloning: A Laboratory Manual, Cold Spring Harbor Laboratory, Cold Spring Harbor, N.Y. (1989) and in T. J. Silhavy, M. L. Berman and L. W. Enquist, Experiments with Gene Fusions, Cold Spring Harbor Laboratory, Cold Spring Harbor, N.Y. (1984) and in Ausubel, F. M. et al., Current Protocols in Molecular Biology, Greene Publishing Assoc. and Wiley Interscience (1987).

For expression in a suitable host organism, the recombinant nucleic acid construct or gene construct is advantageously inserted into a host-specific vector which makes possible optimal expression of the genes in the host. Vectors are well known to the skilled worker and can be found for example in "cloning vectors" (Pouwels P. H. et al., Ed., Elsevier, Amsterdam-New York-Oxford, 1985).

An alternative embodiment of an embodiment herein provides a method to "alter gene expression" in a host cell. For instance, the polynucleotide of an embodiment herein may be enhanced or overexpressed or induced in certain contexts (e.g. upon exposure to certain temperatures or culture conditions) in a host cell or host organism.

Alteration of expression of a polynucleotide provided herein may also result in ectopic expression which is a different expression pattern in an altered and in a control or wild-type organism. Alteration of expression occurs from interactions of polypeptide of an embodiment herein with exogenous or endogenous modulators, or as a result of chemical modification of the polypeptide. The term also refers to an altered expression pattern of the polynucleotide of an embodiment herein which is altered below the detection level or completely suppressed activity.

In one embodiment, provided herein is also an isolated, recombinant or synthetic polynucleotide encoding a polypeptide or variant polypeptide provided herein.

In one embodiment, several polypeptide encoding nucleic acid sequences are co-expressed in a single host, particularly under control of different promoters. In another embodiment, several polypeptide encoding nucleic acid sequences can be present on a single transformation vector or be co-transformed at the same time using separate vectors and selecting transformants comprising both chimeric genes. Similarly, one or polypeptide encoding genes may be expressed in a single plant, cell, microorganism or organism together with other chimeric genes.

f. Microorganisms to be Applied for the Present Invention

Depending on the context, the term "microorganism" can mean the wild-type microorganism or a genetically altered, recombinant microorganism or both.

In one embodiment, using the vectors according to the invention, recombinant microorganisms can be produced, which are for example transformed with at least one vector according to the invention and can be used for producing the polypeptides according to the invention. Advantageously, the recombinant constructs according to the invention, described above, are introduced into a suitable host system and expressed. Preferably common cloning and transfection methods, known by a person skilled in the art, are used, for example coprecipitation, protoplast fusion, electroporation, retroviral transfection and the like, for expressing the stated nucleic acids in the respective expression system. Suitable systems are described for example in Current Protocols in Molecular Biology, F. Ausubel et al., Ed., Wiley Interscience, New York 1997, or Sambrook et al. Molecular Cloning: A Laboratory Manual. 2nd edition, Cold Spring Harbor Laboratory, Cold Spring Harbor Laboratory Press, Cold Spring Harbor, N.Y., 1989.

In principle, all prokaryotic or eukaryotic organisms may be considered as recombinant host organisms for the nucleic acid according to the invention or the nucleic acid construct. Advantageously, microorganisms such as bacteria, fungi or yeasts are used as host organisms. Advantageously, gram-positive or gram-negative bacteria are used, preferably bacteria of the families Enterobacteriaceae, Pseudomonadaceae, Rhizobiaceae, Streptomycetaceae or Nocardiaceae, especially preferably bacteria of the genera *Escherichia, Pseudomonas, Streptomyces, Nocardia, Burkholderia, Salmonella, Agrobacterium, Clostridium* or *Rhodococcus*. The genus and species *Escherichia coli* is quite especially preferred. Furthermore, other advantageous bacteria are to be found in the group of alpha-Proteobacteria, beta-Proteobacteria or gamma-Proteobacteria.

Depending on the host organism, the organisms used in the method according to the invention are grown or cultured in a manner known by a person skilled in the art. Culture can be batchwise, semi-batchwise or continuous. Nutrients can be present at the beginning of fermentation or can be supplied later, semicontinuously or continuously. This is also described in more detail below.

g. Recombinant Production of Polypeptides According to the Invention

The invention further relates to methods for recombinant production of polypeptides according to the invention or functional, biologically active fragments thereof, wherein a polypeptide-producing microorganism is cultured, optionally the expression of the polypeptides is induced by applying at least one inducer inducing gene expression and the expressed polypeptides are isolated from the culture. The polypeptides can also be produced in this way on an industrial scale, if desired.

The microorganisms produced according to the invention can be cultured continuously or discontinuously in the batch method or in the fed-batch method or repeated fed-batch method. A summary of known cultivation methods can be found in the textbook by Chmiel (Bioprozesstechnik 1. Einflihrung in die Bioverfahrenstechnik [Bioprocess technology 1. Introduction to bioprocess technology] (Gustav Fischer Verlag, Stuttgart, 1991)) or in the textbook by Storhas (Bioreaktoren and periphere Einrichtungen [Bioreactors and peripheral equipment] (Vieweg Verlag, Braunschweig/Wiesbaden, 1994)).

The culture medium to be used must suitably meet the requirements of the respective strains. Descriptions of culture media for various microorganisms are given in the manual "Manual of Methods for General Bacteriology" of the American Society for Bacteriology (Washington D. C., USA, 1981).

These media usable according to the invention usually comprise one or more carbon sources, nitrogen sources, inorganic salts, vitamins and/or trace elements.

Preferred carbon sources are sugars, such as mono-, di- or polysaccharides. Very good carbon sources are for example glucose, fructose, mannose, galactose, ribose, sorbose, ribulose, lactose, maltose, sucrose, raffinose, starch or cellulose. Sugars can also be added to the media via complex compounds, such as molasses, or other by-products of sugar refining. It can also be advantageous to add mixtures of different carbon sources. Other possible carbon sources are oils and fats, for example soybean oil, sunflower oil, peanut oil and coconut oil, fatty acids, for example palmitic acid, stearic acid or linoleic acid, alcohols, for example glycerol, methanol or ethanol and organic acids, for example acetic acid or lactic acid.

Nitrogen sources are usually organic or inorganic nitrogen compounds or materials that contain these compounds. Examples of nitrogen sources comprise ammonia gas or ammonium salts, such as ammonium sulfate, ammonium chloride, ammonium phosphate, ammonium carbonate or ammonium nitrate, nitrates, urea, amino acids or complex nitrogen sources, such as corn-steep liquor, soya flour, soya protein, yeast extract, meat extract and others. The nitrogen sources can be used alone or as a mixture.

Inorganic salt compounds that can be present in the media comprise the chloride, phosphorus or sulfate salts of calcium, magnesium, sodium, cobalt, molybdenum, potassium, manganese, zinc, copper and iron.

Inorganic sulfur-containing compounds, for example sulfates, sulfites, dithionites, tetrathionates, thiosulfates, sulfides, as well as organic sulfur compounds, such as mercaptans and thiols, can be used as the sulfur source.

Phosphoric acid, potassium dihydrogen phosphate or dipotassium hydrogen phosphate or the corresponding sodium-containing salts can be used as the phosphorus source.

Chelating agents can be added to the medium, in order to keep the metal ions in solution. Especially suitable chelating agents comprise dihydroxyphenols, such as catechol or protocatechuate, or organic acids, such as citric acid.

The fermentation media used according to the invention usually also contain other growth factors, such as vitamins or growth promoters, which include for example biotin, riboflavin, thiamine, folic acid, nicotinic acid, pantothenate and pyridoxine. Growth factors and salts often originate from the components of complex media, such as yeast extract, molasses, corn-steep liquor and the like. Moreover, suitable precursors can be added to the culture medium. The exact composition of the compounds in the medium is strongly dependent on the respective experiment and is decided for each specific case individually. Information on media optimization can be found in the textbook "Applied Microbiol. Physiology, A Practical Approach" (Ed. P. M. Rhodes, P. F. Stanbury, IRL Press (1997) p. 53-73, ISBN 0 19 963577 3). Growth media can also be obtained from commercial suppliers, such as Standard 1 (Merck) or BHI (brain heart infusion, DIFCO) and the like.

All components of the medium are sterilized, either by heat (20 min at 1.5 bar and 121° C.) or by sterile filtration. The components can either be sterilized together, or separately if necessary. All components of the medium can be present at the start of culture or can be added either continuously or batchwise.

The culture temperature is normally between 15° C. and 45° C., preferably 25° C. to 40° C. and can be varied or kept constant during the experiment. The pH of the medium should be in the range from 5 to 8.5, preferably around 7.0. The pH for growing can be controlled during growing by adding basic compounds such as sodium hydroxide, potassium hydroxide, ammonia or ammonia water or acid compounds such as phosphoric acid or sulfuric acid. Antifoaming agents, for example fatty acid polyglycol esters, can be used for controlling foaming. To maintain the stability of plasmids, suitable selective substances, for example antibiotics, can be added to the medium. To maintain aerobic conditions, oxygen or oxygen-containing gas mixtures, for example ambient air, are fed into the culture. The temperature of the culture is normally in the range from 20° C. to 45° C. The culture is continued until a maximum of the desired product has formed. This target is normally reached within 10 hours to 160 hours.

The fermentation broth is then processed further. Depending on requirements, the biomass can be removed from the fermentation broth completely or partially by separation techniques, for example centrifugation, filtration, decanting or a combination of these methods or can be left in it completely.

If the polypeptides are not secreted in the culture medium, the cells can also be lysed and the product can be obtained from the lysate by known methods for isolation of proteins. The cells can optionally be disrupted with high-frequency ultrasound, high pressure, for example in a French press, by osmolysis, by the action of detergents, lytic enzymes or organic solvents, by means of homogenizers or by a combination of several of the aforementioned methods.

The polypeptides can be purified by known chromatographic techniques, such as molecular sieve chromatography (gel filtration), such as Q-sepharose chromatography, ion exchange chromatography and hydrophobic chromatography, and with other usual techniques such as ultrafiltration, crystallization, salting-out, dialysis and native gel electrophoresis. Suitable methods are described for example in Cooper, T. G., Biochemische Arbeitsmethoden [Biochemical processes], Verlag Walter de Gruyter, Berlin, N.Y. or in Scopes, R., Protein Purification, Springer Verlag, New York, Heidelberg, Berlin.

For isolating the recombinant protein, it can be advantageous to use vector systems or oligonucleotides, which lengthen the cDNA by defined nucleotide sequences and therefore code for altered polypeptides or fusion proteins, which for example serve for easier purification. Suitable modifications of this type are for example so-called "tags" functioning as anchors, for example the modification known as hexa-histidine anchor or epitopes that can be recognized as antigens of antibodies (described for example in Harlow, E. and Lane, D., 1988, Antibodies: A Laboratory Manual. Cold Spring Harbor (N.Y.) Press). These anchors can serve for attaching the proteins to a solid carrier, for example a polymer matrix, which can for example be used as packing in a chromatography column, or can be used on a microtiter plate or on some other carrier.

At the same time these anchors can also be used for recognition of the proteins. For recognition of the proteins, it is moreover also possible to use usual markers, such as fluorescent dyes, enzyme markers, which form a detectable reaction product after reaction with a substrate, or radioactive markers, alone or in combination with the anchors for derivatization of the proteins.

For the expression of mutants according to the invention, reference may be made to the description of expression of the wild-type enzyme EbN1 and the expression systems usable for this in WO2005/108590 and WO2006/094945, to which reference is hereby expressly made.

h. Polypeptide Immobilization

The enzymes or polypetides according to the invention can be used free or immobilized in the method described herein. An immobilized enzyme is an enzyme that is fixed to an inert carrier. Suitable carrier materials and the enzymes immobilized thereon are known from EP-A-1149849, EP-A-1 069 183 and DE-OS 100193773 and from the references cited therein. Reference is made in this respect to the disclosure of these documents in their entirety. Suitable carrier materials include for example clays, clay minerals, such as kaolinite, diatomaceous earth, perlite, silica, aluminum oxide, sodium carbonate, calcium carbonate, cellulose powder, anion exchanger materials, synthetic polymers, such as polystyrene, acrylic resins, phenol formaldehyde resins, polyurethanes and polyolefins, such as polyethylene and polypropylene. For making the supported enzymes, the carrier materials are usually employed in a finely-divided, particulate form, porous forms being preferred. The particle size of the carrier material is usually not more than 5 mm, in particular not more than 2 mm (particle-size distribution curve). Similarly, when using dehydrogenase as whole-cell catalyst, a free or immobilized form can be selected. Carrier materials are e.g. Ca-alginate, and carrageenan. Enzymes as well as cells can also be crosslinked directly with glutaraldehyde (cross-linking to CLEAs). Corresponding and other immobilization techniques are described for example in J. Lalonde and A. Margolin "Immobilization of Enzymes" in K. Drauz and H. Waldmann, Enzyme Catalysis in Organic Synthesis 2002, Vol. III, 991-1032, Wiley-VCH, Weinheim. Further information on biotransformations and bioreactors for carrying out methods according to the invention are also given for example in Rehm et al. (Ed.) Biotechnology, 2nd Edn, Vol 3, Chapter 17, VCH, Weinheim.

i. Reaction Conditions for Biocatalytic Production Methods of the Invention

The at least one polypeptide/enzyme which is present during a method of the invention or an individual step of a multistep-method as defined herein above, can be present in living cells naturally or recombinantly producing the enzyme or enzymes, in harvested cells, in dead cells, in permeabilized cells, in crude cell extracts, in purified extracts, or in essentially pure or completely pure form. The at least one enzyme may be present in solution or as an enzyme immobilized on a carrier. One or several enzymes may simultaneously be present in soluble and/or immobilised form.

The methods according to the invention can be performed in common reactors, which are known to those skilled in the art, and in different ranges of scale, e.g. from a laboratory scale (few millilitres to dozens of litres of reaction volume) to an industrial scale (several litres to thousands of cubic meters of reaction volume). If the polypeptide is used in a form encapsulated by non-living, optionally permeabilized cells, in the form of a more or less purified cell extract or in purified form, a chemical reactor can be used. The chemical reactor usually allows controlling the amount of the at least one enzyme, the amount of the at least one substrate, the pH, the temperature and the circulation of the reaction medium. When the at least one polypeptide/enzyme is present in living cells, the process will be a fermentation. In this case the biocatalytic production will take place in a bioreactor (fermenter), where parameters necessary for suitable living conditions for the living cells (e.g. culture medium with nutrients, temperature, aeration, presence or absence of oxygen or other gases, antibiotics, and the like) can be controlled. Those skilled in the art are familiar with chemical reactors or bioreactors, e.g. with procedures for up-scaling chemical or biotechnological methods from laboratory scale to industrial scale, or for optimizing process parameters, which are also extensively described in the literature (for biotechnological methods see e.g. Crueger and Crueger, Biotechnologie—Lehrbuch der angewandten Mikrobiologie, 2. Ed., R. Oldenbourg Verlag, München, Wien, 1984).

Cells containing the at least one enzyme can be permeabilized by physical or mechanical means, such as ultrasound or radiofrequency pulses, French presses, or chemical means, such as hypotonic media, lytic enzymes and detergents present in the medium, or combination of such methods. Examples for detergents are digitonin, n-dodecylmaltoside, octylglycoside, Triton® X-100, Tween® 20, deoxycholate, CHAPS (3-[(3-Cholamidopropyl)dimethylammonio]-1-propansulfonate), Nonidet® P40 (Ethylphenolpoly(ethyleneglycolether), and the like.

Instead of living cells, biomass of non-living cells containing the required biocatalyst(s) may be applied to the biotransformation reactions of the invention as well.

If the at least one enzyme is immobilised, it is attached to an inert carrier as described above.

The conversion reaction can be carried out batch wise, semi-batch wise or continuously. Reactants (and optionally nutrients) can be supplied at the start of reaction or can be supplied subsequently, either semi-continuously or continuously.

The reaction of the invention, depending on the particular reaction type, may be performed in an aqueous, aqueous-organic or non-aqueous reaction medium.

An aqueous or aqueous-organic medium may contain a suitable buffer in order to adjust the pH to a value in the range of 5 to 11, like 6 to 10.

In an aqueous-organic medium an organic solvent miscible, partly miscible or immiscible with water may be applied. Non-limiting examples of suitable organic solvents are listed below. Further examples are mono- or polyhydric, aromatic or aliphatic alcohols, in particular polyhydric aliphatic alcohols like glycerol.

The non-aqueous medium may contain is substantially free of water, i.e. will contain less that about 1 wt.-% or 0.5 wt.-% of water.

Biocatalytic methods may also be performed in an organic non-aqueous medium. As suitable organic solvents there may be mentioned aliphatic hydrocarbons having for example 5 to 8 carbon atoms, like pentane, cyclopentane, hexane, cyclohexane, heptane, octane or cyclooctane; aromatic carbohydrates, like benzene, toluene, xylenes, chlorobenzene or dichlorobenzene, aliphatic acyclic and ethers, like diethylether, methyl-tert.-butylether, ethyl-tert.-butylether, dipropylether, diisopropylether, dibutylether; or mixtures thereof.

The concentration of the reactants/substrates may be adapted to the optimum reaction conditions, which may depend on the specific enzyme applied. For example, the initial substrate concentration may be in the 0.1 to 0.5 M, as for example 10 to 100 mM.

The reaction temperature may be adapted to the optimum reaction conditions, which may depend on the specific enzyme applied. For example, the reaction may be performed at a temperature in a range of from 0 to 70° C., as for example 20 to 50 or 25 to 40° C. Examples for reaction temperatures are about 30° C., about 35° C., about 37° C., about 40° C., about 45° C., about 50° C., about 55° C. and about 60° C.

The process may proceed until equilibrium between the substrate and then product(s) is achieved, but may be stopped earlier. Usual process times are in the range from 1 minute to 25 hours, in particular 10 min to 6 hours, as for example in the range from 1 hour to 4 hours, in particular 1.5 hours to 3.5 hours. These parameters are non-limiting examples of suitable process conditions.

If the host is a transgenic plant, optimal growth conditions can be provided, such as optimal light, water and nutrient conditions, for example.

k. Product Isolation

The methodology of the present invention can further include a step of recovering an end or intermediate product, optionally in stereoisomerically or enantiomerically substantially pure form. The term "recovering" includes extracting, harvesting, isolating or purifying the compound from culture or reaction media. Recovering the compound can be performed according to any conventional isolation or purification methodology known in the art including, but not limited to, treatment with a conventional resin (e.g., anion or cation exchange resin, non-ionic adsorption resin, etc.), treatment with a conventional adsorbent (e.g., activated charcoal, silicic acid, silica gel, cellulose, alumina, etc.), alteration of pH, solvent extraction (e.g., with a conventional solvent such as an alcohol, ethyl acetate, hexane and the like), distillation, dialysis, filtration, concentration, crystallization, recrystallization, pH adjustment, lyophilization and the like.

Identity and purity of the isolated product may be determined by known techniques, like High Performance Liquid Chromatography (HPLC), gas chromatography (GC), Spektroskopy (like IR, UV, NMR), Colouring methods, TLC, NIRS, enzymatic or microbial assays. (see for example: Patek et al. (1994) Appl. Environ. Microbiol. 60:133-140; Malakhova et al. (1996) Biotekhnologiya 11 27-32; und Schmidt et al. (1998) Bioprocess Engineer. 19:67-70. Ullmann's Encyclopedia of Industrial Chemistry (1996) Bd. A27, VCH: Weinheim, S. 89-90, S. 521-540, S. 540-547, S. 559-566, 575-581 und S. 581-587; Michal, G (1999) Biochemical Pathways: An Atlas of Biochemistry and Molecular Biology, John Wiley and Sons; Fallon, A. et al. (1987) Applications of HPLC in Biochemistry in: Laboratory Techniques in Biochemistry and Molecular Biology, Bd. 17.)

l. Fermentative Production of Vanillin

The invention also relates to methods for the fermentative production of vanillin.

A fermentation as used according to the present invention can, for example, be performed in stirred fermenters, bubble columns and loop reactors. A comprehensive overview of the possible method types including stirrer types and geometric designs can be found in "Chmiel: Bioprozesstechnik: Einfuhrung in die Bioverfahrenstechnik, Band 1". In the process of the invention, typical variants available are the following variants known to those skilled in the art or explained, for example, in "Chmiel, Hammes and Bailey: Biochemical Engineering", such as batch, fed-batch, repeated fed-batch or else continuous fermentation with and without recycling of the biomass. Depending on the production strain, sparging with air, oxygen, carbon dioxide, hydrogen, nitrogen or appropriate gas mixtures may be effected in order to achieve good yield (YP/S).

The culture medium that is to be used must satisfy the requirements of the particular strains in an appropriate manner Descriptions of culture media for various microorganisms are given in the handbook "Manual of Methods for General Bacteriology" of the American Society for Bacteriology (Washington D. C., USA, 1981).

These media that can be used according to the invention may comprise one or more sources of carbon, sources of nitrogen, inorganic salts, vitamins and/or trace elements.

Preferred sources of carbon are sugars, such as mono-, di- or polysaccharides. Very good sources of carbon are for example glucose, fructose, mannose, galactose, ribose, sorbose, ribulose, lactose, maltose, sucrose, raffinose, starch or cellulose. Sugars can also be added to the media via complex compounds, such as molasses, or other by-products from sugar refining. It may also be advantageous to add mixtures of various sources of carbon. Other possible sources of carbon are oils and fats such as soybean oil, sunflower oil, peanut oil and coconut oil, fatty acids such as palmitic acid, stearic acid or linoleic acid, alcohols such as glycerol, methanol or ethanol and organic acids such as acetic acid or lactic acid.

Sources of nitrogen are usually organic or inorganic nitrogen compounds or materials containing these compounds. Examples of sources of nitrogen include ammonia gas or ammonium salts, such as ammonium sulfate, ammonium chloride, ammonium phosphate, ammonium carbonate or ammonium nitrate, nitrates, urea, amino acids or complex sources of nitrogen, such as corn-steep liquor, soybean flour, soy-bean protein, yeast extract, meat extract and others. The sources of nitrogen can be used separately or as a mixture.

Inorganic salt compounds that may be present in the media comprise the chloride, phosphate or sulfate salts of calcium, magnesium, sodium, cobalt, molybdenum, potassium, manganese, zinc, copper and iron.

Inorganic sulfur-containing compounds, for example sulfates, sulfites, di-thionites, tetrathionates, thiosulfates, sulfides, but also organic sulfur compounds, such as mercaptans and thiols, can be used as sources of sulfur.

Phosphoric acid, potassium dihydrogenphosphate or dipotassium hydrogenphosphate or the corresponding sodium-containing salts can be used as sources of phosphorus.

Chelating agents can be added to the medium, in order to keep the metal ions in solution. Especially suitable chelating agents comprise dihydroxyphenols, such as catechol or protocatechuate, or organic acids, such as citric acid.

The fermentation media used according to the invention may also contain other growth factors, such as vitamins or growth promoters, which include for example biotin, riboflavin, thiamine, folic acid, nicotinic acid, pantothenate and pyridoxine. Growth factors and salts often come from complex components of the media, such as yeast extract, molasses, corn-steep liquor and the like. In addition, suitable precursors can be added to the culture medium. The precise composition of the compounds in the medium is strongly dependent on the particular experiment and must be decided individually for each specific case. Information on media optimization can be found in the textbook "Applied Microbiol. Physiology, A Practical Approach" (1997) Growing media can also be obtained from commercial suppliers, such as Standard 1 (Merck) or BHI (Brain heart infusion, DIFCO) etc.

All components of the medium are sterilized, either by heating (20 min at 1.5 bar and 121° C.) or by sterile filtration. The components can be sterilized either together, or if necessary separately. All the components of the medium can be present at the start of growing, or optionally can be added continuously or by batch feed.

The temperature of the culture is normally between 15° C. and 45° C., preferably 25° C. to 40° C. and can be kept constant or can be varied during the experiment. The pH value of the medium should be in the range from 5 to 8.5, preferably around 7.0. The pH value for growing can be controlled during growing by adding basic compounds such as sodium hydroxide, potassium hydroxide, ammonia or ammonia water or acid compounds such as phosphoric acid or sulfuric acid. Antifoaming agents, e.g. fatty acid polyglycol esters, can be used for controlling foaming. To maintain the stability of plasmids, suitable substances with selective action, e.g. antibiotics, can be added to the medium. Oxygen or oxygen-containing gas mixtures, e.g. the ambient air, are fed into the culture in order to maintain aerobic conditions. The temperature of the culture is normally from 20° C. to 45° C. Culture is continued until a maximum of the desired product has formed. This is normally achieved within 1 hour to 160 hours.

The methodology of the present invention can further include a step of recovering Vanillin The term "recovering" includes extracting, harvesting, isolating or purifying the compound from culture media. Recovering the compound can be performed according to any conventional isolation or purification methodology known in the art including, but not limited to, treatment with a conventional resin (e.g., anion or cation exchange resin, non-ionic adsorption resin, etc.), treatment with a conventional adsorbent (e.g., activated charcoal, silicic acid, silica gel, cellulose, alumina, etc.), alteration of pH, solvent extraction (e.g., with a conventional solvent such as an alcohol, ethyl acetate, hexane and the like), distillation, dialysis, filtration, concentration, crystallization, recrystallization, pH adjustment, lyophilization and the like.

Before the intended isolation the biomass of the broth can be removed. Processes for removing the biomass are known to those skilled in the art, for example filtration, sedimentation and flotation. Consequently, the biomass can be removed, for example, with centrifuges, separators, decanters, filters or in flotation apparatus. For maximum recovery of the product of value, washing of the biomass is often advisable, for example in the form of a diafiltration. The selection of the method is dependent upon the biomass content in the fermenter broth and the properties of the biomass, and also the interaction of the biomass with the product of value.

In one embodiment, the fermentation broth can be sterilized or pasteurized. In a further embodiment, the fermentation broth is concentrated. Depending on the requirement, this concentration can be done batch wise or continuously. The pressure and temperature range should be selected such that firstly no product damage occurs, and secondly minimal use of apparatus and energy is necessary. The skilful selection of pressure and temperature levels for a multistage evaporation in particular enables saving of energy.

The following examples are illustrative only and are not meant to limit the scope of invention as set forth in the Summary, Description or in the Claims.

The numerous possible variations that will become immediately evident to a person skilled in the art after heaving considered the disclosure provided herein also fall within the scope of the invention.

EXAMPLES

Materials:

Unless otherwise stated, all chemical and biochemical materials and microorganisms or cells employed herein are commercially available products.

Unless otherwise specified, recombinant proteins are cloned and expressed by standard methods, such as, for example, as described by Sambrook, J., Fritsch, E. F. and Maniatis, T., Molecular cloning: A Laboratory Manual, $2^{nd}$ Edition, Cold Spring Harbor Laboratory, Cold Spring Harbor Laboratory Press, Cold Spring Harbor, N.Y., 1989.

Methods:

In a typical isoeugenol monooxygenase assay reactions were centrifuged and extracted with MTBE as described in the following examples prior to the analysis by gas chromatography.

Gas chromatography was carried out with Agilent Technologies' 6850 equipped with an FID detector and a DB-WAX column (30 m, 250 microM, 0.25 microM) using the following program: 100° C. (1 min), 245° C. at 20° C. $min^{-1}$, 245° C. (10 min). Carrier gas: Hydrogen, 75 cm $sec^{-1}$, split=50, injection volume=1 µL.

Example 1: Preparation and Testing of $1^{st}$ Generation Isoeugenol Monooxygenase (IEM1)

The following $1^{st}$ generation biocatalyst was used:

| E. coli strain | Plasmid construct |
|---|---|
| BL21(DE3): pIEM1 | Codon modified isoeugenol monooxygenase of P. nitroreducens Jin1 in pJ414 (T7, $amp^R$, high copy, strong RBS). The wild type sequence originated from Genbank #FJ851547 |

A freshly grown colony of strain BL21(DE3):pIEM1 was picked from an LB agar plate and transferred into 20 mL of LB medium containing 100 mg/L of ampicillin Cultivation was under shaking at 225 rpm at 37° C. for 20 h. 1 mL of that culture was taken to inoculate 200 mL of sterile LB medium with 100 mg $L^{-1}$ of ampicillin using a 1 L Erlenmeyer flask. Growth was under shaking at 220 rpm and at 37° C. till an $OD_{600}$ of 0.4 was reached. Temperature was reduced to 20° C. while the culture continued to grow till an $OD_{600}$ of 0.6 was reached. The culture was induced with 1 mM IPTG and grown for another 18 h. Typically an $OD_{600}$ of 5.5 to 7 was reached after an overnight incubation.

Figure 3:
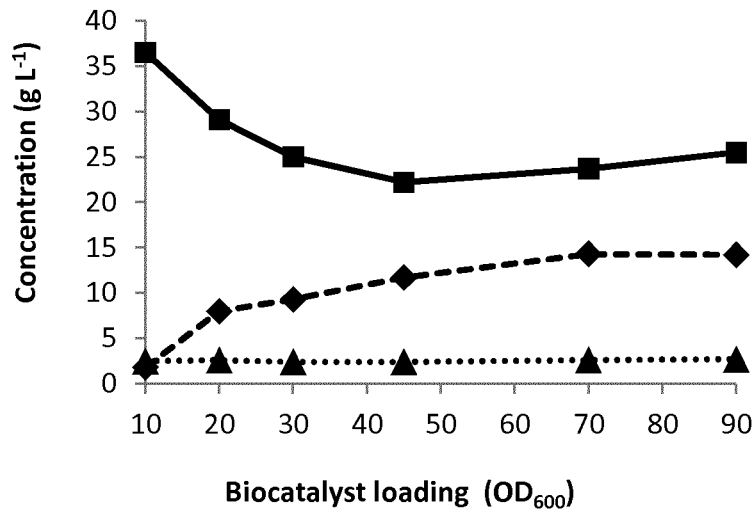
FIG. 3: $1^{st}$ generation catalyst based on IEM1: Product titers at different biocatalyst loadings under non-limiting substrate concentrations at pH 10.5. Symbols: Vanillin (♦), remaining trans-isoeugenol (■), remaining (Z)-isoeugenol (▲). Averaged data of two experiments are shown.

Cells were centrifuged at 9000 g and at 4° C. for 20 minutes. The supernatant was discarded and cells were resuspended in 100 mM glycine-NaOH buffer pH 10.5 containing 10 v/v % DMSO (the optimum pH was later found to be around pH 9 for the isoeugenol monooxygenase of P. nitroreducens Jin 1). Suspensions of different cell densities were prepared corresponding to an $OD_{600}$ of 10 to 90. Into a 20 mL vial were added: 2 mL cell suspension of a defined optical density, 75 mg of isoeugenol (Sigma Aldrich #I17206). Reactions were stirred at 500 rpm at room temperature (24° C.) for 20 hours using vial closures made with a punctured membrane of aluminum for oxygenation. Reactions were acidified with 6 drops of 15% HCl and extracted with 10 mL of MTBE containing 1 g $L^{-1}$ of tridecane as the internal standard prior to analysis by gas chromatography. A negative control was carried out the same way with empty cells. The time curve for the formation of vanillin is shown in FIG. 3.

Example 2: Vanillin Production by $1^{st}$ Generation Isoeugenol Monooxygenase (IEM1)

Vanillin was prepared as follows: Cells of E. coli expressing the isoeugenol monooxygenase of P. nitroreducens Jin1 (see Example 1) were transferred from an ampicillin containing LB agar plate into 50 mL of an ampicillin containing mineral salt medium with 15 g $L^{-1}$ of glucose as the carbon source and grown under shaking at 225 rpm and at 37° C. for 20 h. The mineral salt medium was composed of 15 g $L^{-1}$ of glucose 5 g $L^{-1}$ of $(NH_4)_2HPO_4$, 16 g $L^{-1}$ of $K_2HPO_4$, 2 g $L^{-1}$ of citric acid, 1 g $L^{-1}$ of $MgSO_4$, and 30 mg $L^{-1}$ of $CaCl_2$ besides trace elements, vitamins and 100 mg $L^{-1}$ of ampicillin. Then 0.4 mL of this culture was taken to inoculate 200 mL of mineral salt medium of the same composition using a 1-L-flask. Several flasks were run in parallel. The culture was grown under shaking at 37° C., 180 rpm till an $OD_{600}$ of 2.5 was reached. The temperature was lowered to 20° C. The culture was induced with 1 mM IPTG at $OD_{600}$ of 3 and grown under shaking at 20° C. and at 180 rpm for another 17 h. An $OD_{600}$ of 24 was observed at the end of cultivation. The culture was centrifuged at 4000 g at 4° C. for 50 min. Cells were re-suspended in 100 mM glycine-NaOH buffer pH 9 to give a final $OD_{600}$ of 45.

Into a 2 L reaction flasks were added 1.3 L of the cell suspension of an $OD_{600}$ of 45 and 19.5 g of isoeugenol. The reaction was stirred at room temperature for 20 h. Analysis of the reaction by gas chromatography showed 7.3 g L$^{-1}$ of vanillin, 1.2 g L$^{-1}$ of (Z)-isoeugenol, and 4.1 g L$^{-1}$ of remaining (E)-isoeugenol. The temperature of the reaction broth was lowered to 12° C. and the pH was adjusted to pH 12.5 prior to extraction with distilled ethyl acetate (1 L). After phase separation and removal of the organic phase the water phase was again adjusted to 12° C. and pH 12.5. A second extraction with 700 mL of ethyl acetate was carried out and the organic phase was discarded. The pH of the water phase was then adjusted to pH 7 with 15% of HCl. The water phase was extracted twice with 1 L of distilled ethyl acetate. These combined extracts contained 7.7 g of vanillin based on GC analysis. The combined organic extract was then washed with 600 mL of water before evaporation under vacuum. A yellow residue of 7.7 g was obtained. Efforts to remove the yellow color by another extraction with ethyl acetate at 10° C. and pH 12.5 failed. About 0.8 g of vanillin was lost in this effort leaving a remaining 6.9 g of a slightly yellow, solid residue. The residue was dissolved in 153 mL of hot water at 55° C. Once all crude vanillin was dissolved the solution was left at room temperature for 1 h. The temperature was lowered to 4° C. and kept at this temperature for 3 h. Finally, the solution was cooled in an ice-water bath for 18 h. The solution with the precipitated vanillin was passed through a precooled paper filter. The crystals were washed with ice cold water (30 mL). The crystals were then dried in a desiccator under vacuum at room temperature for 6 h. A slightly yellowish solid residue of 5.4 g was recovered containing 99.7% of vanillin by GC based on the internal standard. The chemical identity was verified by GC-MS, 1H-NMR and 13C-NMR. Some losses during purification occurred. Ethyl acetate was not well suited for alkaline extraction and could be replaced by a more stable solvent such as MTBE.

Example 3: Preparation of 2$^{nd}$ Generation Isoeugenol Monooxygenases

The following 2$^{nd}$ generation biocatalysts (IEM and helper polypeptides located on two different plasmids) were tested:

| E. coli strain | Plasmid constructs |
| --- | --- |
| BL21(DE3): pIEM1_pG-KJE8 | pIEM1: codon modified isoeugenol monooxygenase of P. nitroreducens Jin1 in pJ414 (T7, amp$^R$, high copy, provider Atum, Newark, CA). pG-KJE8 (araB, pACYC ori, Pzt-1, cm$^R$, dnak, dnaj, grpE, groES, groEL). |
| BL21(DE3): pIEM1_pGro7 | pIEM1: codon modified isoeugenol monooxygenase of P. nitroreducens Jin1 in pJ414 (T7, amp$^R$, high copy). pGro7 (araB, pACYC ori, cm$^R$, groES, groEL. |
| BL21(DE3): pIEM1_pKJE7 | pIEM1: codon modified isoeugenol monooxygenase of P. nitroreducens Jin1 in pJ414 (T7, amp$^R$, high copy). pKJE7 (araB, pACYC ori, cm$^R$, dnak, dnaj, grpE). |
| BL21(DE3): pIEM1_pG-Tf2 | pIEM1: codon modified isoeugenol monooxygenase of P. nitroreducens Jin1 in pJ414 (T7, amp$^R$, high copy). pG-Tf2 (pACYC ori, Pzt-1, cm$^R$, tet$^r$, groES, groEL, tig). |
| BL21(DE3): pIEM1_pTf16 | pIEM1: codon modified isoeugenol monooxygenase of P. nitroreducens Jin1 in pJ414 (T7, amp$^R$, high copy). pTf16 (araB, pACYC ori, cm$^R$, tig). |

Figure 4:
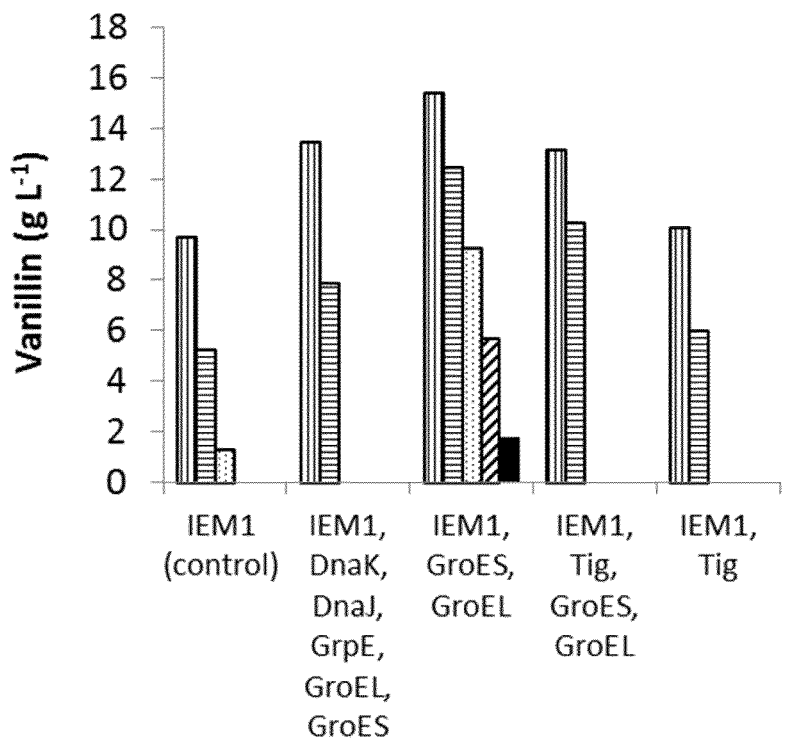
FIG. 4: $2^{nd}$ generation catalysts: Product titers at different catalyst loadings expressed as different optical cell densities: $OD_{600}=18$ (vertical stripes), $OD_{600}=10$ (horizontal stripes), $OD_{600}=5$ (dotted), $OD_{600}=2$ (diagonal stripes), $OD_{600}=1$ (black). The biocatalyst was previously grown in LB medium. IEM1: Isoeugenol monooxygenase of $P.$ $nitroreducens$ Jin1. Co-expressed chaperones are also indicated. IEM1 (control) designates the activity of a wildtype isoeugenol monooxygenase of $P.$ $nitroreducens$ Jin1 expressed in the absence of any chaperons according to Example 1. Values reflect averaged endpoint measurements within 10% variation.

Freshly grown cells were isolated from an agar plate, grown in 2 mL LB medium containing ampicillin and chloramphenicol under shaking at 37° C. till an optical density OD$_{600}$=1 was reached. 1 mL of this culture was taken to inoculate 200 mL of LB medium containing 100 mg L$^{-1}$ ampicillin and 30 mg L$^{-1}$ chloramphenicol, supplemented with 5 mg L$^{-1}$ of FeCl$_3$ placed in a 1000-mL-flask. Induction of chaperones was at the beginning of the cultivation with 2 mg mL$^{-1}$ of arabinose and if necessary with 5 ng mL$^{-1}$ of tetracycline according to the protocol of the manufacturer (Takara Bio Inc.). Cultivation was at 37° C. under shaking at 180 rpm till an OD$_{600}$ of 0.4 was reached. Temperature was lowered to 20° C. prior to induction with 1 mM of IPTG at OD$_{600}$=0.6. Cells were harvested after an overnight cultivation by centrifugation at 3600 g, re-suspended in cold buffer of 0.1 M glycine NaOH pH 9.5 to the desired optical density. Catalytic activities were tested as described under Example 1. The catalytic activities observed with different constructs are shown in FIG. 4. Higher specific activities were obtained with most of the 2$^{nd}$ generation catalysts than with the 1$^{st}$ generation catalyst (control). Cells co-expressing the isoeugenol monooxygenase of P. nitroreducens Jin1 and the chaperonins GroES and GroEL were most active. Cells harboring the plasmid pKJE7 showed very weak growth and were not tested for activity.

Example 4: Fed-Batch Cultivation of a 2$^{nd}$ Generation Isoeugenol Monooxygenases The strain BL21(DE3):pIEM1_pGro7 was tested under fed-batch culture conditions. Fed-batch cultivation was carried out in a reactor with 3.7 L of working volume (Bioengineering, Switzerland) using a glucose feeding based on dissolved oxygen. A mineral salt medium as described containing 5 g L$^{-1}$ of yeast extract and supplemented with carbenicillin and chloramphenicol at pH 7 served as the growth medium using glycerol instead of glucose as the carbon source. Cultivation was at 37° C. At an OD$_{600}$ of 48, the temperature was lowered to 25° C., and the culture was induced with 1.5 g L$^{-1}$ of arabinose at an OD$_{600}$ of 51. At an OD$_{600}$ of 59, the culture was induced with 1 mM of IPTG. The feeding solution contained 70% sterile, aqueous glycerol. The pH control was with aqueous NH$_3$. The fermentation lasted for 43 h and reached a final OD$_{600}$ of 163. Plasmid stability was determined using agar plates with and without the appropriate antibiotics for selection. Bacterial cells were harvested by centrifugation as previously described, resuspended in 100 mM glycine-NaOH buffer pH 9 and tested for activity. Up to 3.7 g L$^{-1}$ of vanillin were observed by gas chromatography in a reaction carried out as described under Example 1 with a catalyst loading corresponding to an OD$_{600}$ of 5.

Example 5: Preparation of 3$^{rd}$ Generation Isoeugenol Monooxygenases

The following 3$^{rd}$ generation biocatalysts (IEM and helper polypeptides located on one single polycistronic construct) were prepared and tested:

| E. coli strain | Plasmid construct |
| --- | --- |
| BL21(DE3)T1: pPC1 | Polycistronic construct containing the codon modified isoeugenol monooxygenase of P. nitroreducens Jin1, groEL and groES under the T7 promotor in pJ431 (T7, kan$^R$, low copy; provider Atum, Newark, CA). T1 phage resistance. Sequence elements: Strong RBS-IEM1-strong RBS-groES-native RBS-groEL. |
| BL21(DE3)T1: pPC2 | Polycistronic construct containing the codon modified isoeugenol monooxygenase of P. nitroreducens Jin1, groEL and groES under the T7 promotor in pJ431 (T7, kan$^R$, low copy). T1 phage resistance. Sequence elements: Strong RBS-IEM1-spacer-strong RBS-groES-native RBS-groEL. |
| BL21(DE3)T1: pPC3 | Polycistronic construct containing the codon modified isoeugenol monooxygenase of P. nitroreducens Jin1, groEL and groES under the T7 promotor in pJ431 (T7, kan$^R$, low copy). T1 phage resistance. Sequence elements: Strong RBS-IEM1-medium RBS-groES-native RBS-groEL |
| BL21(DE3)T1: pPC4 | Polycistronic construct containing the codon modified isoeugenol monooxygenase of P. nitroreducens Jin1, groEL and groES under the T7 promotor in pJ431 (T7, kan$^R$, low copy). T1 phage resistance. Sequence elements: Strong RBS-IEM1-strong RBS-groES-strong RBS-groEL |
| BL21(DE3)T1: pPC5 | Polycistronic construct containing the codon modified isoeugenol monooxygenase of P. nitroreducens Jin1, groEL and groES under the T7 promotor in pJ431 (T7, kan$^R$, low copy). T1 phage resistance. Sequence elements: Strong RBS-IEM1- weak RBS-groES- native RBS-groEL |

Figure 2:
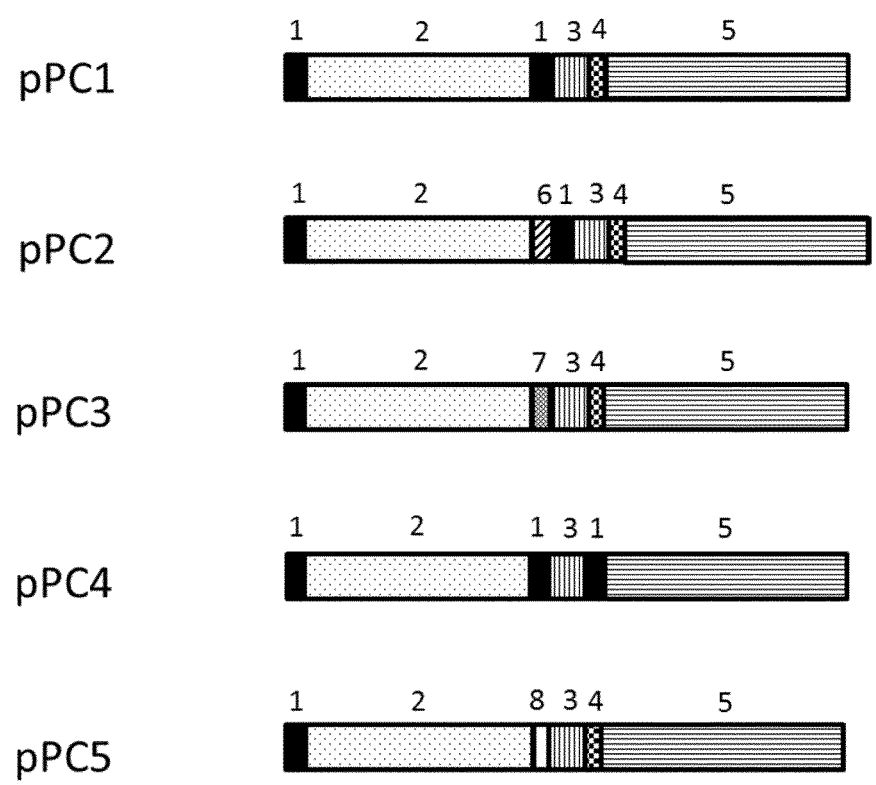
FIG. 2: Polycistronic constructs for co-expressing the isoeugenol monooxygenase (IEM1) of $P.$ $nitroreducens$ Jin1 with chaperonins GroES and GroEL using low and high copy plasmids. The plasmid name of the low copy number construct is indicated to the left of each construct. Numbers above the horizontal bar refer to the following elements: 1: RBS (strong); 2: IEM1; 3: GroES; 4: native RBS; 5: GroEL; 6: spacer; 7: RBS (medium); 8: RBS (weak).
Figure 5:
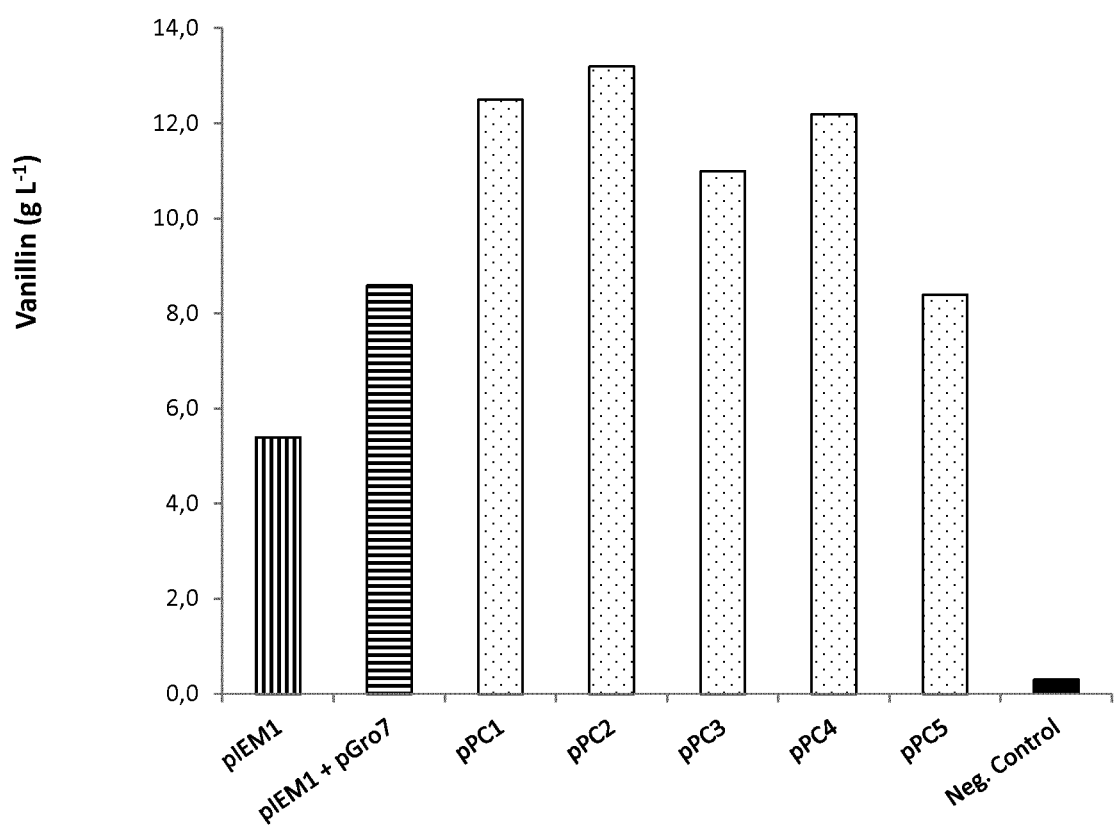
FIG. 5: Product titers from small scale reactions at catalyst loading of $OD_{600}=5$ using one of the $1^{st}$ generation catalysts (vertical stripes), $2^{nd}$ generation catalyst (horizontal stripes), and $3^{rd}$ generation catalysts (dotted). The negative control was obtained with empty cells (filled black). Averaged endpoint concentrations of a double experiment (max 10% variation) are shown.

A schematic representation of the different polycistronic constructs is also given (FIG. 2). Cultivation, induction and activity testes were carried out as described in Example 1. Comparative activity tests with a catalyst loading of an OD$_{600}$ of 5 showed that cells of E. coli expressing one of the polycistronic constructs (3$^{rd}$ generation catalyst) exhibited higher specific catalytic activities compared to the 1$^{st}$ and 2$^{nd}$ generation catalysts (FIG. 5).

Example 6: Generation of Mutants of the Isoeugenol Monooxygenase of P. putida IE27

Artificial mutants of the isoeugenol monooxygenase of P. putida IE27 (IEM2) were inserted into the plasmid pJ431 (T7, kan$^R$, low copy; provider Atum, Newark, Calif.) for expression in E. coli BL21(DE3)T1. Alternatively, cells of E. coli producing one of the mutants of P. putida IE27 were co-transformed with the plasmid pGro7 for co-producing the chaperonins GroES and GroEL.

The following mutants were tested:

| Plasmid | | Mutant |
| --- | --- | --- |
| pIEM2c8g | c8g | Thr3Arg |
| pIEM2a13 a | g13a | Asp5Asn |
| pIEM2a67g | a67g | Asn23Asp |
| pIEM2t106t | g106t | Ala36Ser |
| pIEM2t125a | t125a | Phe42Tyr |
| pIEM2a154c | a154c | Thr52Pro |
| pIEM2g222t | g222t | Gln74His |
| pIEM2c253g | c253g | Pro85Ala |
| pIEM2t314a | t314a | Phe105Tyr |
| pIEM2c325a | c325a | Pro109Thr |
| pIEM2g334a | g334a | Glu112Lys |
| pIEM2a434g | a434g | Glnl45Arg |
| pIEM2a458t | a458t | Tyr153Phe |
| pIEM2t486a | t486a | His162Gln |
| pIEM2t509a | t509a | Phe170Tyr |
| pIEM2c517g | c517g | Gln173Glu |
| pIEM2t569c | t569c | Leu190Pro |
| pIEM2t598c | t598c | Tyr200His |
| pIEM2a628g | a628g | Lys210Glu |
| pIEM2g761t | g761t | Arg254Leu |
| pIEM2a866t | a866t | Glu289Val |
| pIEM2a947c | a947c | Asp316Ala |
| pIEM2a994g | a994g | Asn332Asp |
| pIEM2a1025g | a1025g | Gln342Arg |

| Plasmid | Mutant | |
| --- | --- | --- |
| pIEM2a1037T | a1037t | Tyr346Phe |
| pIEM2c1084a | c1084a | His362Asn |
| pIEM2c1094g | c1094g | Ala365Gly |
| pIEM2a1097t | a1097t | Tyr366Phe |
| pIEM2t1211a | t1211a | Phe404Tyr |
| pIEM2a1219g | a1219g | Lys407Glu |
| pIEM2g1318a | g1318a | Asp440Asn |
| pIEM2g1360t | g1360t | Ala454Ser |
| pIEM2t1426c | t1426c | Ser476Pro |
| pIEM2c154_t222 | a154c, g222t | Thr52Pro, Gln74His |
| PIEM2c154_t222 + pGro7 | a154c, g222t | Thr52Pro, Gln74His, GroES, GroEL |
| pIEM2_c154_a1318 | a154c, g1318a | Thr52Pro, Asp440Asn |
| pIEM2_c154_a1318 + pGro7 | a154c, g1318a | Thr52Pro, Asp440Asn, GroES, GroEL |
| pIEM2_t222_a1318 | g222t, g1318a | Gln74His, Asp440Asn |
| pIEM2_t222_a1318 + pGro7 | g222t, g1318a | Gln74His, Asp440Asn, GroES, GroEL |
| pIEM2_c154_t222_a1318 | a154c, g222t, g1318a | Thr52Pro, Gln74His, Asp440Asn |
| pIEM2_c154_t222_a1318 + pGro7 | a154c, g222t, g1318a | Thr52Pro, Gln74His, Asp440Asn, GroES, GroEL |
| pIEM2 'reference' | wt | Wild type iem of *P. putida* IE27 in pJ411 |

Figure 6:
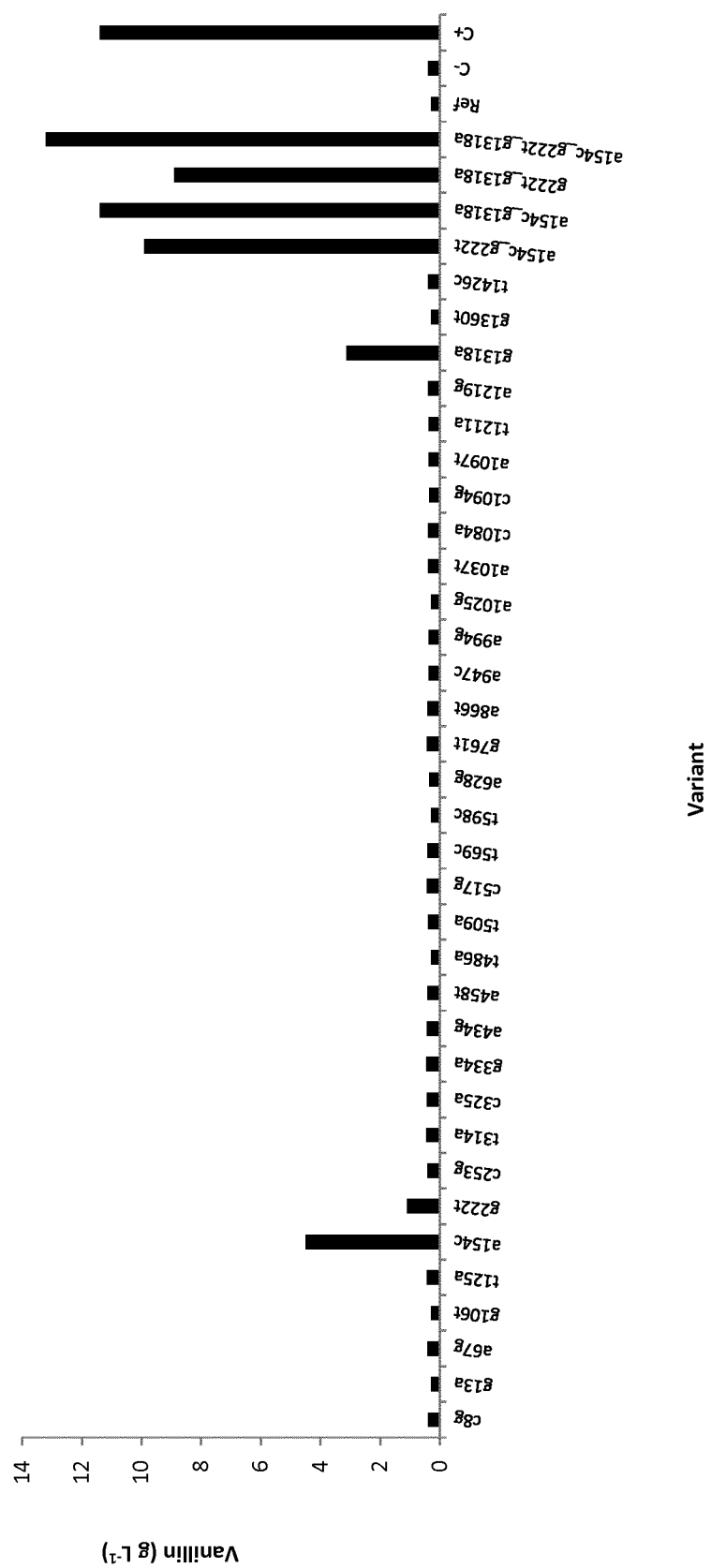
FIG. 6: Vanillin titers obtained with single, double and triple mutants of the isoeugenol monooxygenase of $P.$ $putida$ IE27 (IEM2). 'Ref' relates to the (inactive) isoeugenol monooxygenase of $P.$ $putida$ IE27 used as reference. Cells producing the isoeugenol monooxygenase of $P.$ $nitroreducens$ Jin1 (IEM1) served as positive control (C+). Cells containing the empty vector served as negative control (C−). Data points were averaged from a double experiment.
Figure 10:
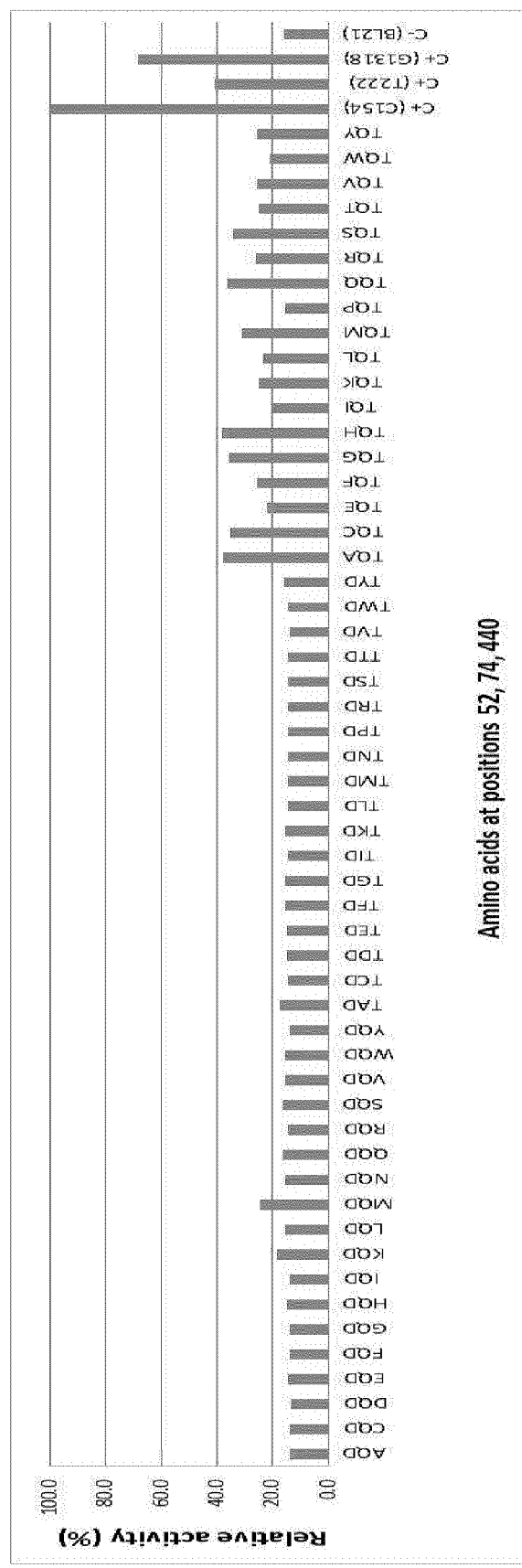
FIG. 10: Relative activity of mutants of the isoeugenol monooxygenase of $P.$ $putida$ IE27 obtained by individual saturation mutagenesis at amino acid positions T52, or Q74 or D440. The corresponding amino acids at these positions are indicated on the horizontal axe. The relative activity of each mutant is expressed as the fraction of the averaged vanillin titers obtained with the mutant "C154" (i.e. mutant a154c; corresponding to PQD) under standard assay conditions. For comparison the previously identified mutant "T222" (i.e. mutant g222t, corresponding to THD) and G1318 (i.e. mutant g1318a; corresponding to TQN) are also shown. Empty cells served as the negative control (C−).

A freshly grown colony of *E. coli* harboring the plasmid encoded mutant was picked from an LB agar plate and grown in 2 mL LB liquid culture with 30 mg $L^{-1}$ of kanamycin at 220 rpm and at 37° C. over night (16 h). 150 µL were then transferred to a flask with 50 mL LB medium containing the required antibiotic and grown at 37° C. under shaking at 200 rpm for about 2 h till an $OD_{600}$ of 0.45 was reached. The temperature was lowered to 20° C. while the culture continued to grow to an $OD_{600}$ of 0.6. After induction with 0.5 mM of IPTG, the culture was grown for another 16 hours under the same conditions. Cells of *E. coli* containing the mutant isoeugenol monooxygenases of *P. putida* 1E27 were harvested by centrifugation and re-suspended in ice cold 0.1 M glycine buffer pH 9.5 containing 10 v/v % of DMSO to reach a final $OD_{600}$ of 45. In case of *E. coli* cells containing the isoeugenol monooxygenase of *P. nitroreducens* Jin1 (used as positive control) the same procedure was applied using 0.1 M glycine buffer, pH 9.0. Into a 20 mL vial were added: 80 mg of isoeugenol, 2 mL of the cell suspension of $OD_{600}$=45. The vial was closed with a punctured aluminum membrane for air circulation. The reaction was stirred with a magnet at 450 rpm at room temperature (23° C.) for 17 h. The reaction was acidified with 3 drops of 15% HCl and extracted with 10 mL of MTBE containing 1 g $L^{-1}$ of tridecane as the internal standard for analysis by GC. The vanillin concentration obtained with the individual mutants and controls is shown in FIG. 6. Further mutants of the isoeugenol monooxygenase of *P. putida* IE27 (IEM) were obtained by individual saturation mutagenesis experiments at amino acid positions T52, or Q74 or D440 performed by a commercial manufacturer. These additional mutants were tested in analogy to the above identified mutants. The relative activity of each mutant as shown in FIG. 10, and is expressed as the fraction of the averaged vanillin titers obtained with the mutant "C154" (i.e. mutant a154c; corresponding to PQD) under standard assay conditions.

Figure 7:
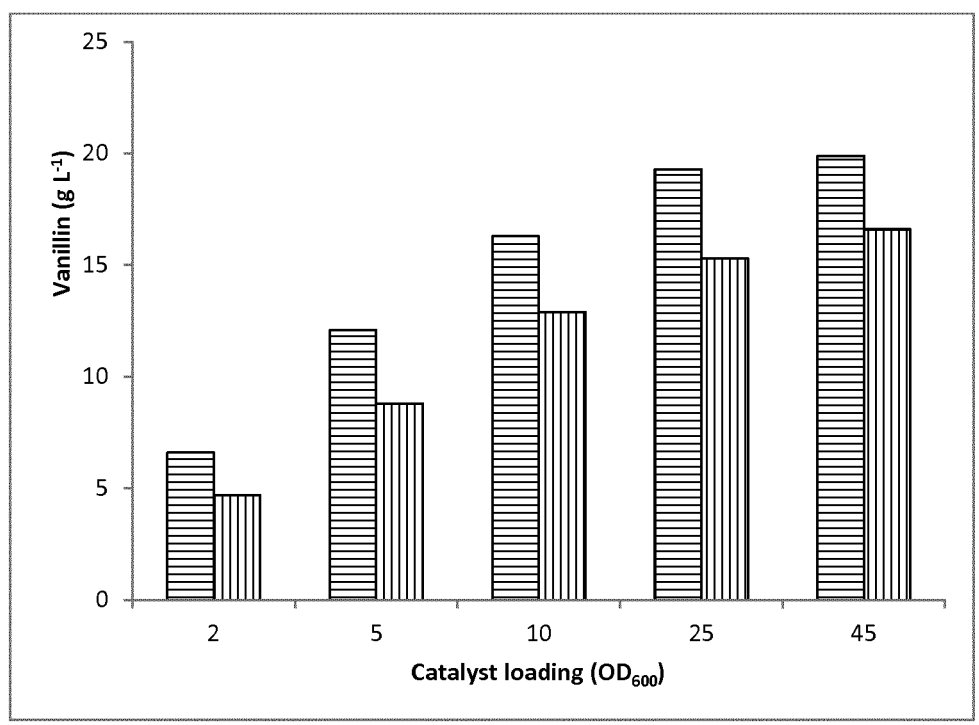
FIG. 7: Biotransformation of isoeugenol into vanillin at different catalyst loading shown for the triple codon mutant of the isoeugenol monooxygenase of $P.$ $putida$ IE27 (IEM2) (horizontal stripes), and for the isoeugenol monooxygenase of $P.$ $nitroreducens$ Jin1 (IEM1) (vertical stripes). Cells of $E.$ $coli$ harboring the two-plasmid-system for co-expressing the isoeugenol monooxygenase and the chaperonins GroES and GroEL served as the catalyst. The isoeugenol monooxygenase of $P.$ $nitroreducens$ Jin1 was produced with a high copy construct, while the triple mutant of $P.$ $putida$ IE27 was produced with a low copy construct. Averaged product titers of two experiments with variations within less than 10% are shown.
Figure 8:
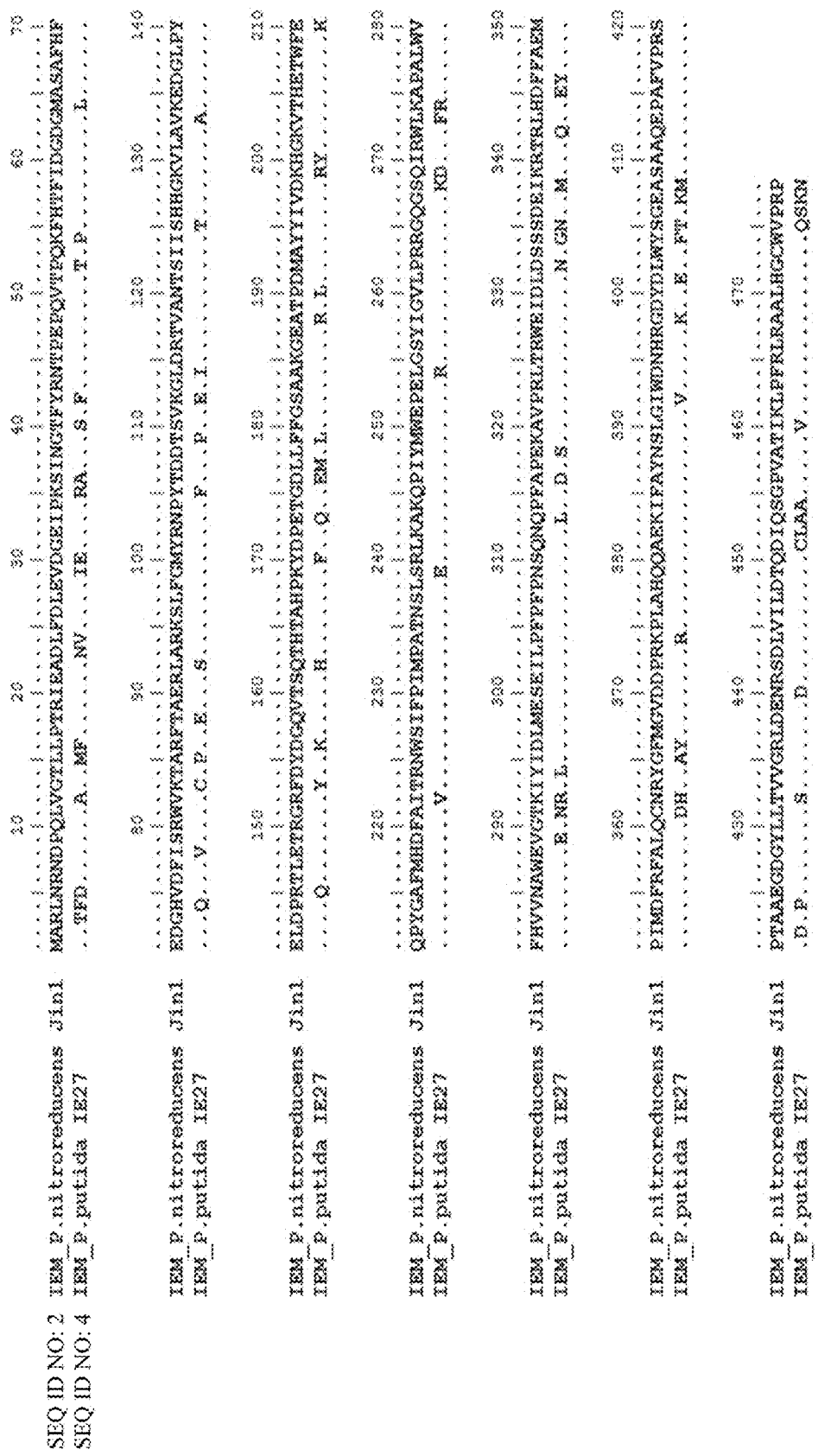
FIG. 8: Amino acid sequence alignment of IEM 1 of $Pseudomonas$ $nitroreducens$ Jin 1 and IEM 2 of $Pseudomonas$ $putida$ IE27.
Figure 9:
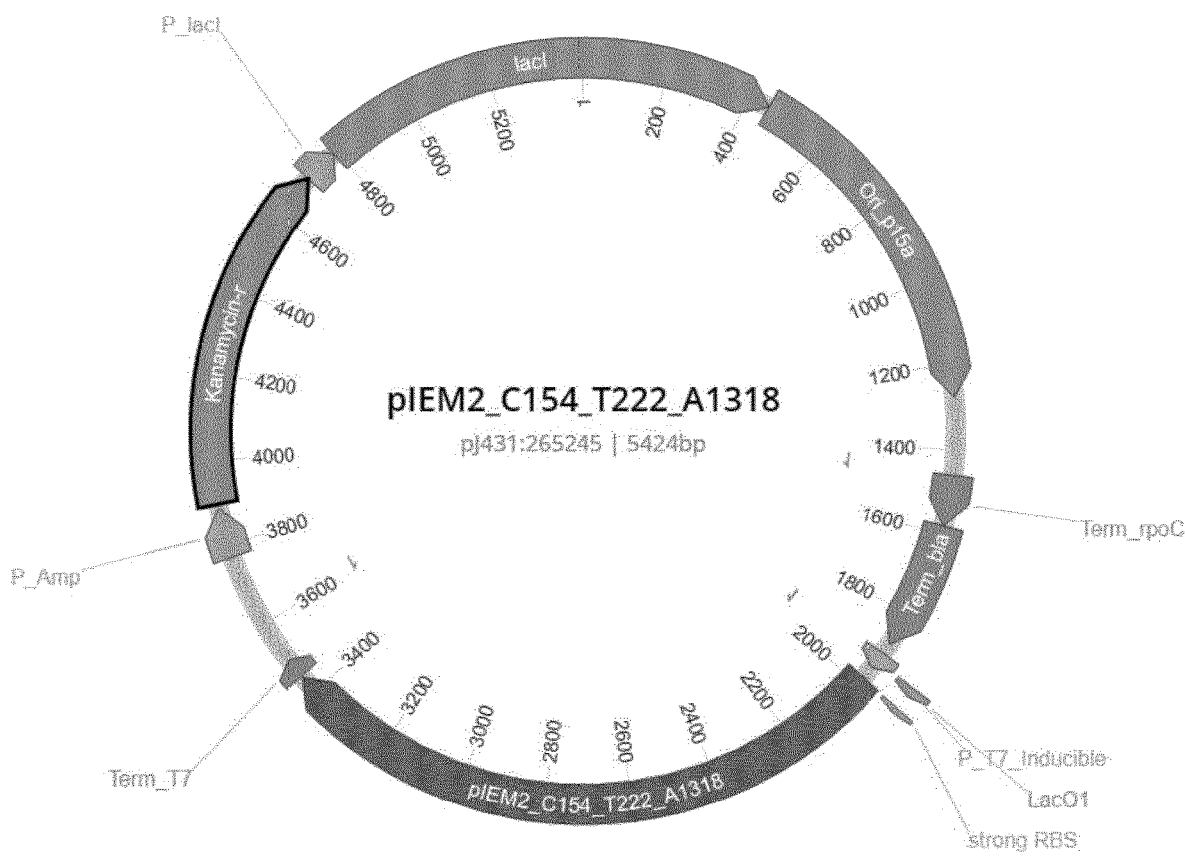
FIG. 9: Annotation of plasmid pIEM2_C154_T222_A1318 for expressing a triple mutant of IEM 2 of $Pseudomonas$ $putida$ IE27 and corresponding plasmid map.

Example 7: Triple Mutant of the Isoeugenol Monooxygenase of *P. putida* IE27 Co-Expressed with GroES and GroEL A colony of *E. coli* BL21(DE3)T1 harboring the plasmids pIEM2_c154_t222_a1318 (see plasmid map and annotation of FIG. 8 as well as SEQ ID NO:16) and pGro7 was isolated from the agar plate and added to 2 mL of LB medium containing 30 mg/L of kanamycin and 30 mg/L of chloramphenicol. The culture was grown at 37° C. under shaking at 220 rpm for 16 h. 150 µL were transferred to 50 mL of fresh LB medium containing the same antibiotics. Cells were grown at 37° C. under shaking at 220 rpm till an $OD_{600}$ of 0.45 was reached. The culture was induced with 1.5 g/L of arabinose and the temperature lowered to 20° C. for growth under shaking till an $OD_{600}$ of 0.6 was reached. The culture was induced with 0.5 mM of IPTG and grown at 20° C. under shaking at 220 rpm for another 16 h. Cells were harvested by centrifugation and re-suspended in ice cold 0.1 M glycine buffer pH 9.5. Different cell dilutions were prepared corresponding to and $OD_{600}$ of 2 to 45. Into an open 20 mL reaction vial were added 80 mg of isoeugenol, 2 mL of the cell suspension of different optical densities. The reaction was stirred with a magnetic bar at 500 rpm at room temperature for 17 h. Reactions were acidified with 3 drops of 15% HCl and extracted with 10 mL of MTBE containing 1 g/L of tridecane as the internal standard for analysis by GC. The vanillin concentration observed in reactions containing different cell densities is shown in FIG. 7.

Example 8: Triple Mutant of the Isoeugenol Monooxygenase of *P. putida* IE27 Co-Expressed with GroES and GroEL from Different Expression Constructs Derived from the Polycistronic Construct PC1 Triple (SEQ ID NO:25; Containing the Triple Mutant of IEM IE27)

Figure 11:
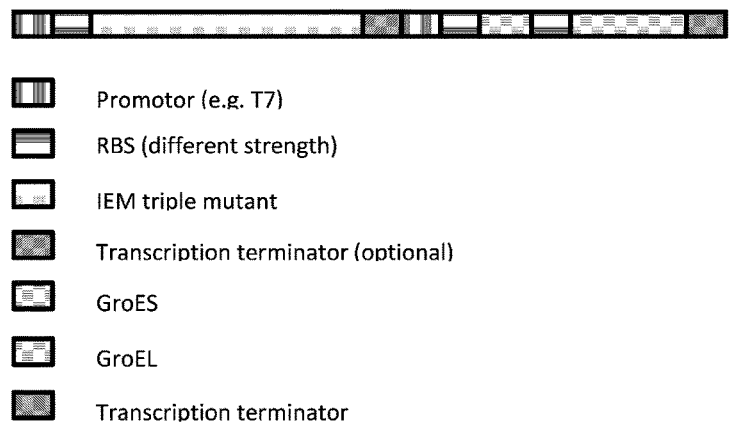
FIG. 11: General scheme of modified insert architectures for expressing an IEM, like the triple mutant of the isoeugenol monooxygenase IE27 as described herein, and the chaperonins GroES and GroEL.

Colonies of *E. coli* cells BL21(DE3)T1 harboring different plasmid constructs (construed according to the general scheme of FIG. 11, and having a nucleotide sequence selected from SEQ ID NO:17 to 24 and corresponding constructs wherein the transcription terminator of the IEM coding sequence was absent) for expressing the triple mutant of the isoeugenol monooxygenase IE27 together with the chaperonins GroES and GroEL were picked from kanamycyin containing agar plates and inoculated into 2 mL of a mineral salt medium. The mineral salt medium contained 30 g/L of glycerol, 5 g $L^{-1}$ of $(NH_4)_2HPO_4$, 16 g $L^{-1}$ of K$_2$HPO$_4$, 2 g L$^{-1}$ of citric acid, 1 g L$^{-1}$ of MgSO$_4$, 30 mg L$^{-1}$ of CaCl$_2$, 5 g/L of yeast extract, trace elements and 50 mg/L of kanamycin.

The cultures were shaken at 37° C. at 230 rpm for 16 hours. 0.25 mL of the culture was transferred to a flask containing 50 mL of the same medium and cultivated at 37° C. at 230 rpm till and optical density OD$_{600}$ of 2.5 was reached. The temperature was lowered to 23° C. and the cultivation continued at 220 rpm till an OD$_{600}$ of 3 was reached. The culture was induced with 0.5 mM of IPTG and kept under the same conditions over night.

At the end of the cultivation samples were taken for determining the optical density at 600 nm, for estimating the cell dry weight using a standard gravimetrical method, and for activity testing. For the activity testing 15 mL of the culture were centrifuged at 3500 g at 4° C. for 35 min and the supernatant was discarded. The cell pellet was frozen for a few hours at −80° C. The frozen pellet was thawn on ice and resuspended in ice-cold 0.1 M of glycine buffer pH 9.5 to a final OD$_{600}$ of 20.

Into a 20 mL flask were added 80 mg of isoeugenol, 1800 µL of ice-cold 0.1 M glycine buffer pH 9.5. Under magnetic stirring were added 200 µL of the cell resuspension (OD$_{600}$=20) to reach a final OD$_{600}$ of 2. The reaction was agitated with a magnetic stirrer at 23° C. at 450 rpm for 16 hours.

Figure 12:
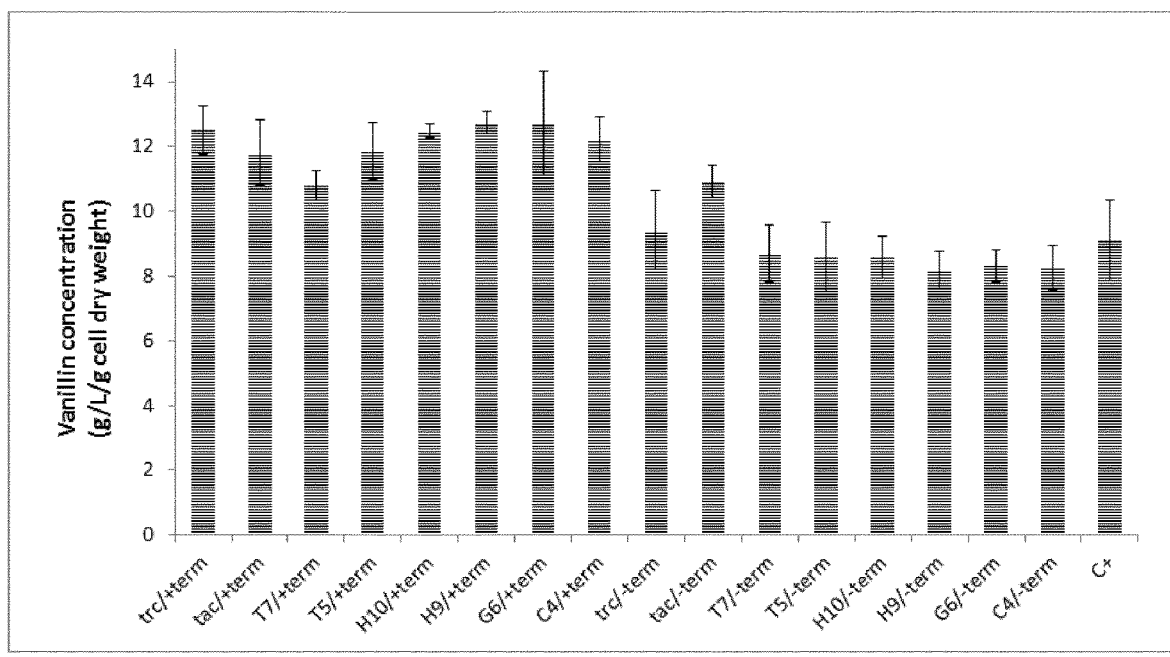
FIG. 12: Normalized product titers of vanillin obtained under standard assay conditions with strains of $E.$ $coli$ containing different plasmid constructs, prepared by following the general scheme of FIG. 11, for expressing the triple mutant of the isoeugenol monooxygenase 1E27 together with the chaperonins GroES and GroEL. The plasmid constructs varied in the promotor sequences for expressing the chaperonins and contained optionally a transcription terminator after the ORF of the isoeugenol monooxygenase indicated as +term, or −term, respectively. The polycistronic construct PC1_triple is shown as reference C+.

The reaction was acidified with 8 drops (80 µL) of 85% of phosphoric acid prior to extraction with 10 mL of MTBE containing 1 g L$^{-1}$ of tridecane as the internal standard. The vanillin concentration was determined with a gas chromatograph as described. The vanillin concentrations obtained with the different plasmid constructs were normalized with regard to cell dry weight of the cell suspension used in the reaction. The results are shown in FIG. 12.

The content of the documents cross-referenced is incorporated by reference.

Sequences as herein referred to are:

| SEQ ID NO | Name | Source | Type |
|---|---|---|---|
| 1 | IMG1 codon modified | *P. nitroreducens* Jin1 | NA |
| 2 | IMG1 | *P. nitroreducens* Jin1 | AA |
| 3 | IMG2 wild type | *P. putida* IE27 | NA |
| 4 | IMG2 wild type | *P. putida* IE27 | AA |
| 5 | IMG2 codon modified | *P. putida* IE27 | NA |
| 6 | IMG2 | *P. putida* IE27 | AA |
| 7 | GroEL | *E. coli* | NA |
| 8 | GroEL | *E. coli* | AA |
| 9 | GroES | *E. coli* | NA |
| 10 | GroES | *E. coli* | AA |
| 11 | PC1 | expression construct | NA |
| 12 | PC2 | expression construct | NA |
| 13 | PC3 | expression construct | NA |
| 14 | PC4 | expression construct | NA |
| 15 | PC5 | expression construct | NA |
| 16 | pIEM2__c154__t222__a1318 | expression plasmid | NA |
| 17 | trc/+term | expression construct | NA |
| 18 | tac/+term | expression construct | NA |
| 19 | T7/+term | expression construct | NA |
| 20 | T5/+term | expression construct | NA |
| 21 | H10/+term | expression construct | NA |
| 22 | H9/+term | expression construct | NA |
| 23 | G6/+term | expression construct | NA |
| 24 | C4/+term | expression construct | NA |
| 25 | PC1_triple | expression construct | NA |

NA = Nucleic Acid
AA = Amino Acid

```
Sequence Listing
SEQ ID NO: 1-isoeugenol monooxygenase of P. nitroreducens Jin1 (codon modified)
ATGGCACGTCTGAACCGTAATGATCCGCAACTCGTCGGCACCCTGTTACCAACCCGTATTGAGGCTGACCTGTT

CGACCTGGAAGTGGACGGCGAAATTCCGAAGTCCATCAACGGTACCTTCTACCGTAACACGCCGGAGCCTCA

GGTGACGCCGCAGAAATTCCACACCTTCATCGATGGTGACGGCATGGCGTCTGCATTTCATTTTGAAGATGGC

CACGTGGACTTCATCAGCCGCTGGGTTAAAACCGCGCGTTTCACGGCGGAGAGACTGGCACGTAAAAGCCTG

TTCGGTATGTACCGTAATCCGTACACCGATGACACGTCTGTGAAGGGTCTGGATCGTACCGTTGCCAACACGA

GCATCATCAGCCATCACGGTAAGGTTCTGGCGGTGAAAGAAGATGGCTTGCCGTACGAGCTGGACCCACGCA

CTCTGGAAACCCGTGGTCGCTTTGACTATGATGGCCAAGTCACCAGCCAGACGCACACCGCGCATCCGAAGTA

TGACCCGGAAACCGGTGACCTGTTGTTCTTTGGCTCCGCAGCCAAGGGTGAGGCAACGCCTGATATGGCCTAT

TACATCGTTGATAAACATGGTAAGGTAACGCATGAGACTTGGTTCGAGCAACCGTATGGCGCCTTTATGCATG

ATTTTGCTATTACCCGCAATTGGAGCATCTTCCCGATCATGCCGGCTACCAATTCGTTGAGCCGCCTGAAAGCG

AAGCAGCCGATTTACATGTGGGAGCCGGAACTGGGTTCCTATATTGGTGTTCTGCCGCGTCGCGGTCAAGGTA

GCCAGATCCGCTGGCTGAAAGCACCAGCGCTGTGGGTCTTTCACGTCGTCAACGCCTGGGAAGTGGGCACCA

AAATCTACATTGACCTTATGGAGAGCGAAATTCTGCCATTCCCGTTCCCGAATAGCCAAAATCAGCCGTTCGCT

CCTGAGAAAGCAGTGCCGCGTCTGACCCGTTGGGAGATTGATCTGGATAGCAGCAGCGATGAGATTAAGCGT

ACGCGTCTGCACGACTTCTTTGCAGAGATGCCGATCATGGATTTTCGTTTTGCGCTGCAGTGCAACCGCTACG

GTTTTATGGGTGTCGATGACCCGCGCAAGCCGCTGGCGCACCAACAAGCGGAGAAGATTTTTGCGTACAATA

GCCTGGGTATCTGGGACAACCACCGTGGTGATTATGATTTGTGGTACAGCGGCGAAGCCTCAGCGGCGCAAG

AACCGGCTTTCGTTCCGCGTTCTCCGACTGCAGCGGAAGGCGACGGTTATCTGCTGACCGTTGTGGGCCGTTT

GGACGAGAACCGCAGCGACCTGGTCATTCTGGACACGCAGGACATCCAGAGCGGTCCGGTTGCGACCATTAA
```

-continued

ACTGCCGTTTCGCCTGCGTGCGGCCCTGCACGGCTGTTGGGTTCCGCGTCCGTAA

SEQ ID NO: 2-Isoeugenol monooxygenase of P. nitroreducens Jin1 protein
MARLNRNDPQLVGTLLPTRIEADLFDLEVDGEIPKSINGTFYRNTPEPQVTPQKFHTFIDGDGMASAFHFEDGH

VDFISRWVKTARFTAERLARKSLFGMYRNPYTDDTSVKGLDRTVANTSIISHHGKVLAVKEDGLPYELDPRTLE

TRGRFDYDGQVTSQTHTAHPKYDPETGDLLFFGSAAKGEATPDMAYYIVDKHGKVTHETWFEQPYGAFMHDFAI

TRNWSIFPIMPATNSLSRLKAKQPIYMWEPELGSYIGVLPRRGQGSQJRWLKAPALWVFHVVNAWEVGTKIYID

LMESEILPFPFPNSQNQPFAPEKAVPRLTRWEIDLDSSSDEIKRTRLHDFFAEMPIMDFRFALQCNRYGFMGVD

DPRKPLAHQQAEKIFAYNSLGIWDNHRGDYDLWYSGEASAAQEPAFVPRSPTAAEGDGYLLTVVGRLDENRSDL

VILDTQDIQSGPVATIKLPFRLRAALHGCWVPRP

SEQ ID NO: 3-Isoeugenol monooxygenase of P. putida IE27 (GenBank
Accession AB291707)
ATGGCAACGTTTGACCGCAATGATCCGCAGTTGGCAGGAACGATGTTCCCCACCCGAATAGAGGCGAATGTC

TTTGACCTTGAAATTGAGGGCGAGATCCCACGTGCAATCAACGGGAGCTTCTTCCGCAACACCCCCGAACCTC

AGGTCACCACGCAACCTTTCCACACCTTCATCGATGGGGATGGTTTGGCGTCTGCTTTTCATTTCGAAGATGGC

CAGGTCGACTTTGTCAGCCGTTGGGTATGTACTCCTCGCTTTGAAGCTGAGCGGTCGGCTCGTAAATCACTCTT

CGGTATGTACCGCAATCCGTTCACTGATGATCCATCGGTAGAAGGTATTGATCGTACAGTCGCCAACACCAGT

ATCATCACTCATCACGGGAAAGTACTGGCCGCAAAGGAAGATGGACTACCTTATGAGCTTGACCCCCAAACCC

TGGAAACCCGAGGTCGTTATGATTACAAGGGGCAGGTAACCAGCCATACACATACAGCGCACCCTAAGTTCG

ACCCCCAGACAGGTGAAATGTTACTCTTCGGCTCCGCTGCTAAAGGCGAACGAACGCTTGATATGGCGTACTA

TATTGTTGATCGCTACGGCAAGGTGACACATGAGACCTGGTTTAAGCAGCCTTACGGTGCATTCATGCACGAC

TTTGCTGTCACGCGCAACTGGTCAATCTTTCCGATCATGCCTGCGACAAATAGCCTTGAGCGTCTTAAAGCAA

GACAGCCCATTTACATGTGGGAGCCTGAGCGAGGAAGCTATATAGGAGTACTTCCTCGTCGTGGTCAGGGCAA

GGACATTCGTTGGTTCCGTGCCCCGGCGTTGTGGGTTTTCCATGTCGTGAATGCTTGGGAGGAAGGGAATAGA

ATTCTGATTGACTTGATGGAAAGTGAGATTTTGCCGTTCCCATTCCCGAACTCGCAGAACCTTCCATTTGATC

CCTCCAAGGCTGTTCCGCGTCTAACCCGTTGGGAAATTGATCTCAATAGTGGTAACGATGAGATGAAACGTAC

GCAGCTACACGAATATTTTGCAGAAATGCCTATCATGGATTTCCGTTTTGCGCTCCAGGATCATCGCTACGCC

TACATGGGGGTTGACGATCCTCGTCGCCCCTTAGCTCATCAGCAAGCTGAAAAAATCTTTGCCTACAATTCGT

TAGGGGTTTGGGACAACCATCGTAAAGATTATGAACTTTGGTTTACGGGAAAAATGTCTGCAGCGCAGGAACC

GGCGTTTGTTCCTAGAAGCCCAGATGCGCCTGAGGGCGATGGCTACCTACTCAGTGTAGTAGGGCGGCTCGAT

GAAGATCGTAGCGATCTAGTTATCCTTGATACGCAATGTTTGGCAGCTGGGCCTGTGGCCACTGTCAAGCTTC

CCTTCCGTCTCCGAGCAGCGTTGCACGGTTGTTGGCAGTCTAAGAACTGA

SEQ ID NO: 4 or 6-Isoeugenol monooxygenase of P. putida IE27 protein
MATFDRNDPQLAGTMFPTRIEANVFDLEIEGEIPRAINGSFFRNTPEPQVTTQPFHTFIDGDGLASAFHFEDGQV

DFVSRWVCTPRFEAERSARKSLFGMYRNPFTDDPSVEGIDRTVANTSIITHHGKVLAAKEDGLPYELDPQTLETR

GRYDYKGQVTSHTHTAHPKFDPQTGEMLLFGSAAKGERTLDMAYYIVDRYGKVTHETWFKQPYGAFMHDFAVTRN

WSIFPIMPATNSLERLKAKQPIYMWEPERGSYIGVLPRRGQGKDIRWFRAPALWVFHWNAWEEGNRILIDLMESE

ILPFPFPNSQNLPFDPSKAVPRLTRWEIDLNSGNDEMKRTQLHEYFAEMPIMDFRFALQDHRYAYMGVDDPRRPL

AHQQAEKIFAYNSLGVWDNHRKDYELWFTGKMSAAQEPAFVPRSPDAPEGDGYLLSVVGRLDEDRSDLVILDTQ

CLAAGPVATVKLPFRLRAALHGCWQSKN

SEQ ID NO: 5-Isoeugenol monooxygenase of P. putida IE27 (codon modified)
ATGGCCACTTTTGACCGCAATGACCCGCAACTGGCAGGCACCATGTTCCCGACGCGCATCGAAGCGAATGTTT

TTGATCTGGAGATTGAAGGTGAGATTCCGCGTGCGATCAACGGTAGCTTTTTCCGCAACACGCCAGAGCCGCA

AGTCACCACGCAGCCGTTTCATACTTTCATCGACGGCGACGGCCTGGCGTCAGCGTTCCACTTCGAAGATGGC

-continued

```
CAGGTCGACTTTGTGAGCCGCTGGGTCTGCACCCCGCGTTTCGAGGCAGAGCGCAGCGCGCGTAAAAGCCTGT

TTGGTATGTATCGCAATCCGTTTACGGATGACCCGAGCGTTGAAGGCATTGACCGTACCGTGGCGAATACCT

CGATCATTACCCACCACGGTAAGGTCCTGGCAGCAAAAGAAGATGGCTTGCCGTACGAGTTAGATCCGCAGA

CCCTGGAAACGCGTGGTCGCTATGACTACAAGGGCCAGGTTACCAGCCATACCCACACGGCTCACCCTAAGT

TTGATCCGCAAACGGGTGAGATGCTGCTGTTCGGCAGCGCGGCAAAGGGTGAGCGTACCCTGGACATGGCGT

ACTATATCGTTGACCGTTACGGTAAAGTGACCCATGAAACCTGGTTCAAGCAACCGTACGGCGCCTTTATGC

ACGACTTCGCAGTCACGCGCAACTGGTCTATCTTTCCGATTATGCCGGCCACCAATAGCCTGGAGCGTCTGA

AAGCTAAGCAACCGATTTACATGTGGGAACCGGAGCGTGGTTCCTACATCGGCGTGCTGCCGCGTCGTGGTC

AGGGTAAAGATATCCGCTGGTTCCGTGCGCCTGCCCTCTGGGTGTTCCACGTTGTGAACGCATGGGAAGAGG

GCAATCGTATTCTGATCGATCTGATGGAGAGCGAAATCCTGCCATTCCCGTTTCCGAACTCTCAGAATCTGC

CGTTCGATCCGAGCAAAGCCGTACCGCGCTTGACCCGTTGGGAGATTGATTTGAACAGCGGTAATGACGAGA

TGAAGCGTACTCAGCTGCACGAATACTTCGCTGAGATGCCGATTATGGACTTTCGTTTCGCGCTGCAAGATC

ACCGTTACGCGTATATGGGTGTTGATGATCCACGCCGTCCATTGGCGCATCAACAAGCGGAAAAGATTTTTG

CGTATAACAGCCTGGGTGTTTGGGACAACCATCGTAAAGACTATGAGCTGTGGTTTACGGGTAAAATGTCCG

CGGCTCAGGAACCGGCCTTCGTGCCGCGCAGCCCGGACGCCCCTGAGGGTGATGGTTATTTGCTGTCCGTCG

TGGGTCGCCTGGATGAAGATCGTAGCGACCTGGTTATCCTGGACACCCAGTGCCTTGCGGCAGGCCCGGTTG

CGACCGTCAAGCTGCCGTTCCGTCTGCGTGCAGCTCTGCATGGTTGTTGGCAGAGCAAAAACTAA
```

SEQ ID NO: 7-chaperonin GroEL (GenBank Accession CP009685.1, region 3964433 ... 3966079)

```
ATGGCAGCTAAAGACGTAAAATTCGGTAACGACGCTCGTGTGAAAATGCTGCGCGGCGTAAACGTACTGGCA

GATGCAGTGAAAGTTACCCTCGGTCCAAAAGGCCGTAACGTAGTTCTGGATAAATCTTTCGGTGCACCGACCA

TCACCAAAGATGGTGTTTCCGTTGCTCGTGAAATCGAACTGGAAGACAAGTTCGAAAATATGGGTGCGCAGA

TGGTGAAAGAAGTTGCCTCTAAAGCAAACGACGCTGCAGGCGACGGTACCACCACTGCAACCGTACTGGCTC

AGGCTATCATCACTGAAGGTCTGAAAGCTGTTGCTGCGGGCATGAACCCGATGGACCTGAAACGTGGTATCG

ACAAAGCGGTTACCGCTGCAGTTGAAGAACTGAAAGCGCTGTCCGTACCATGCTCTGACTCTAAAGCGATTGC

TCAGGTTGGTACCATCTCCGCTAACTCCGACGAAACCGTAGGTAAACTGATCGCTGAAGCGATGGACAAAGTC

GGTAAAGAAGGCGTTATCACCGTTGAAGACGGTACCGGTCTGCAGGACGAACTGGACGTGGTTGAAGGTATGC

AGTTCGACCGTGGCTACCTGTCTCCTTACTTCATCAACAAGCCGGAAACTGGCGCAGTAGAACTGGAAAGCCC

GTTCATCCTGCTGGCTGACAAGAAAATCTCCAACATCCGCGAAATGCTGCCGGTTCTGGAAGCTGTTGCCA

AAGCAGGCAAACCGCTGCTGATCATCGCTGAAGATGTAGAAGGCGAAGCGCTGGCAACTCTGGTTGTTAACA

CCATGCGTGGCATCGTGAAAGTCGCTGCGGTTAAAGCACCGGGCTTCGGCGATCGTCGTAAAGCTATGCTGC

AGGATATCGCAACCCTGACTGGCGGTACCGTGATCTCTGAAGAGATCGGTATGGAGCTGGAAAAAGCAACCC

TGGAAGACCTGGGTCAGGCTAAACGTGTTGTGATCAACAAAGACACCACCACTATCATCGATGGCGTGGGTG

AAGAAGCTGCAATCCAGGGCCGTGTTGCTCAGATCCGTCAGCAGATTGAAGAAGCAACTTCTGACTACGACC

GTGAAAAACTGCAGGAACGCGTAGCGAAACTGGCAGGCGGCGTTGCAGTTATCAAAGTGGGTGCTGCTACC

GAAGTTGAAATGAAAGAGAAAAAAGCACGCGTTGAAGATGCCCTGCACGCGACCCGTGCTGCGGTAGAAGA

AGGCGTGGTTGCTGGTGGTGGTGTTGCGCTGATCCGCGTAGCGTCTAAACTGGCTGACCTGCGTGGTCAGAA

CGAAGACCAGAACGTGGGTATCAAAGTTGCACTGCGTGCAATGGAAGCTCCGCTGCGTCAGATCGTATTGAA

CTGCGGCGAAGAACCGTCTGTTGTTGCTAACACCGTTAAAGGCGGCGACGGCAACTACGGTTACAACGCAGC

AACCGAAGAATACGGCAACATGATCGACATGGGTATCCTGGATCCAACCAAAGTAACTCGTTCTGCTCTGCAG

TACGCAGCTTCTGTGGCTGGCCTGATGATCACCACCGAATGCATGGTTACCGACCTGCCGAAAAACGATGCAG

CTGACTTAGGCGCTGCTGGCGGTATGGGCGGCATGGGTGGCATGGGCGGCATGATGTAA
```

SEQ ID NO: 8-chaperonin GroEL protein
MAAKDVKFGNDARVKMLRGVNVLADAVKVTLGPKGRNVVLDKSFGAPTITKDGVSVAREIELEDKFENMGAQMV

KEVASKANDAAGDGTTTATVLAQAIITEGLKAVAAGMNPMDLKRGIDKAVTAAVEELKALSVPCSDSKAIAQVG

TISANSDETVGKLIAEAMDKVGKEGVITVEDGTGLQDELDVVEGMQFDRGYLSPYFINKPETGAVELESPFILL

ADKKISNIREMLPVLEAVAKAGKPLLIIAEDVEGEALATLVVNTMRGIVKVAAVKAPGFGDRRKAMLQDIATLT

GGTVISEEIGMELEKATLEDLGQAKRVVINKDTTTIIDGVGEEAAIQGRVAQIRQQIEEATSDYDREKLQERVA

KLAGGVAVIKVGAATEVEMKEKKARVEDALHATRAAVEEGVVAGGGVALIRVASKLADLRGQNEDQNVGIKVAL

RAMEAPLRQIVLNCGEEPSVVANTVKGGDGNYGYNAATEEYGNMIDMGILDPTKVTRSALQYAASVAGLMITTE

CMVTDLPKNDAADLGAAGGMGGMGGMGGMM

SEQ ID NO: 9-chaperonin GroES (GenBank Accession CP009685.1,
region 3966123 ... 3966416)
ATGAATATTCGTCCATTGCATGATCGCGTGATCGTCAAGCGTAAAGAAGTTGAAACTAAATCTGCTGGCGGCA

TCGTTCTGACCGGCTCTGCAGCGGCTAAATCCACCCGCGGCGAAGTGCTGGCTGTCGGCAATGGCCGTATCCT

TGAAAATGGCGAAGTGAAGCCGCTGGATGTGAAAGTTGGCGACATCGTTATTTTCAACGATGGCTACGGTGT

GAAATCTGAGAAGATCGACAATGAAGAAGTGTTGATCATGTCCGAAAGCGACATTCTGGCAATTGTTGAAGC

GTAA

SEQ ID NO: 10-chaperonin GroES protein
MNIRPLHDRVIVKRKEVETKSAGGIVLTGSAAAKSTRGEVLAVGNGRILENGEVKPLDVKVGDIVIFNDGYG

VKSEKIDNEEVLIMSESDILAIVEA

SEQ ID NO: 11-PC1 (polycistroncic construct containing codon modified
isoeugenol monooxygenase of P. nitroreducens Jin 1, groES, groEL)
GAAGGAGATATACATATGGCACGTCTGAACCGTAATGATCCGCAACTCGTCGGCACCCTGTTACCAACCCGTA

TTGAGGCTGACCTGTTCGACCTGGAAGTGGACGGCGAAATTCCGAAGTCCATCAACGGTACCTTCTACCGTAA

CACGCCGGAGCCTCAGGTGACGCCGCAGAAATTCCACACCTTCATCGATGGTGACGGCATGGCGTCTGCATTT

CATTTTGAAGATGGCCACGTGGACTTCATCAGCCGCTGGGTTAAAACCGCGCGTTTCACGGCGGAGAGACTG

GCACGTAAAAGCCTGTTCGGTATGTACCGTAATCCGTACACCGATGACACGTCTGTGAAGGGTCTGGATCGTA

CCGTTGCCAACACGAGCATCATCAGCCATCACGGTAAGGTTCTGGCGGTGAAAGAAGATGGCTTGCCGTACG

AGCTGGACCCACGCACTCTGGAAACCCGTGGTCGCTTTGACTATGATGGCCAAGTCACCAGCCAGACGCACAC

CGCGCATCCGAAGTATGACCCGGAAACCGGTGACCTGTTGTTCTTTGGCTCCGCAGCCAAGGGTGAGGCAAC

GCCTGATATGGCCTATTACATCGTTGATAAACATGGTAAGGTAACGCATGAGACTTGGTTCGAGCAACCGTAT

GGCGCCTTTATGCATGATTTTGCTATTACCCGCAATTGGAGCATCTTCCCGATCATGCCGGCTACCAATTCGT

TGAGCCGCCTGAAAGCGAAGCAGCCGATTTACATGTGGGAGCGGAACTGGGTTCCTATATTGTGTTCTGCC

GCGTCGCGGTCAAGGTAGCCAGATCCGCTGGCTGAAAGCACCAGCGCTGTGGGTCTTTCACGTCGTCAACGC

CTGGGAAGTGGGCACCAAAATCTACATTGACCTTATGGAGAGCGAAATTCTGCCATTCCCGTTCCCGAATAGC

CAAAATCAGCCGTTCGCTCCTGAGAAAGCAGTGCCGCGTCTGACCCGTTGGGAGATTGATCTGGATAGCAGC

AGCGATGAGATTAAGCGTACGCGTCTGCACGACTTCTTTGCAGAGATGCCGATCATGGATTTTCGTTTTGCGC

TGCAGTGCAACCGCTACGGTTTTATGGGTGTCGATGACCCGCGCAAGCCGCTGGCGCACCAACAAGCGGAGA

AGATTTTTGCGTACAATAGCCTGGGTATCTGGGACAACCACCGTGGTGATTATGATTTGTGGTACAGCGGCGA

AGCCTCAGCGGCGCAAGAACCGGCTTTCGTTCCGCGTTCTCCGACTGCAGCGGAAGGCGACGGTTATCTGCTG

ACCGTTGTGGGCCGTTTGGACGAGAACCGCAGCGACCTGGTCATTCTGGACACGCAGGACATCCAGAGCGGT

CCGGTTGCGACCATTAAACTGCCGTTTCGCCTGCGTGCGGCCCTGCACGGCTGTTGGGTTCCGCGTCCGTAAG

AAGGAGATATACATATGAATATTCGTCCATTGCATGATCGCGTGATCGTCAAGCGTAAAGAAGTTGAAACTAA

ATCTGCTGGCGGCATCGTTCTGACCGGCTCTGCAGCGGCTAAATCCACCCGCGGCGAAGTGCTGGCTGTCGG

```
CAATGGCCGTATCCTTGAAAATGGCGAAGTGAAGCCGCTGGATGTGAAAGTTGGCGACATCGTTATTTTCAAC

GATGGCTACGGTGTGAAATCTGAGAAGATCGACAATGAAGAAGTGTTGATCATGTCCGAAAGCGACATTCTG

GCAATTGTTGAAGCGTAATCCGCGCACGACACTGAACATACGAATTTAAGGAATAAAGATAATGGCAGCTAA

AGACGTAAAATTCGGTAACGACGCTCGTGTGAAAATGCTGCGCGGCGTAAACGTACTGGCAGATGCAGTGAA

AGTTACCCTCGGTCCAAAAGGCCGTAACGTAGTTCTGGATAAATCTTTCGGTGCACCGACCATCACCAAAGAT

GGTGTTTCCGTTGCTCGTGAAATCGAACTGGAAGACAAGTTCGAAAATATGGGTGCGCAGATGGTGAAAGAA

GTTGCCTCTAAAGCAAACGACGCTGCAGGCGACGGTACCACCACTGCAACCGTACTGGCTCAGGCTATCATCA

CTGAAGGTCTGAAAGCTGTTGCTGCGGGCATGAACCCGATGGACCTGAAACGTGGTATCGACAAAGCGGTTA

CCGCTGCAGTTGAAGAACTGAAAGCGCTGTCCGTACCATGCTCTGACTCTAAAGCGATTGCTCAGGTTGGTAC

CATCTCCGCTAACTCCGACGAAACCGTAGGTAAACTGATCGCTGAAGCGATGGACAAAGTCGGTAAAGAAGG

CGTTATCACCGTTGAAGACGGTACCGGTCTGCAGGACGAACTGGACGTGGTTGAAGGTATGCAGTTCGACCG

TGGCTACCTGTCTCCTTACTTCATCAACAAGCCGGAAACTGGCGCAGTAGAACTGGAAAGCCCGTTCATCCTG

CTGGCTGACAAGAAAATCTCCAACATCCGCGAAATGCTGCCGGTTCTGGAAGCTGTTGCCAAAGCAGGCAAA

CCGCTGCTGATCATCGCTGAAGATGTAGAAGGCGAAGCGCTGGCAACTCTGGTTGTTAACACCATGCGTGGC

ATCGTGAAAGTCGCTGCGGTTAAAGCACCGGGCTTCGGCGATCGTCGTAAAGCTATGCTGCAGGATATCGCA

ACCCTGACTGGCGGTACCGTGATCTCTGAAGAGATCGGTATGGAGCTGGAAAAAGCAACCCTGGAAGACCTG

GGTCAGGCTAAACGTGTTGTGATCAACAAAGACACCACCACTATCATCGATGGCGTGGGTGAAGAAGCTGCA

ATCCAGGGCCGTGTTGCTCAGATCCGTCAGCAGATTGAAGAAGCAACTTCTGACTACGACCGTGAAAAACTGC

AGGAACGCGTAGCGAAACTGGCAGGCGGCGTTGCAGTTATCAAAGTGGGTGCTGCTACCGAAGTTGAAATG

AAAGAGAAAAAAGCACGCGTTGAAGATGCCCTGCACGCGACCCGTGCTGCGGTAGAAGAAGGCGTGGTTGC

TGGTGGTGGTGTTGCGCTGATCCGCGTAGCGTCTAAACTGGCTGACCTGCGTGGTCAGAACGAAGACCAGAA

CGTGGGTATCAAAGTTGCACTGCGTGCAATGGAAGCTCCGCTGCGTCAGATCGTATTGAACTGCGGCGAAGA

ACCGTCTGTTGTTGCTAACACCGTTAAAGGCGGCGACGGCAACTACGGTTACAACGCAGCAACCGAAGAATA

CGGCAACATGATCGACATGGGTATCCTGGATCCAACCAAAGTAACTCGTTCTGCTCTGCAGTACGCAGCTTCT

GTGGCTGGCCTGATGATCACCACCGAATGCATGGTTACCGACCTGCCGAAAAACGATGCAGCTGACTTAGGC

GCTGCTGGCGGTATGGGCGGCATGGGTGGCATGGGCGGCATGATGTAA

SEQ ID NO: 12-PC2 (polycistroncic construct containing codon modified
isoeugenol monooxygenase of P. nitroreducens Jin 1, groES, groEL)
GAAGGAGATATACATATGGCACGTCTGAACCGTAATGATCCGCAACTCGTCGGCACCCTGTTACCAACCCGTA

TTGAGGCTGACCTGTTCGACCTGGAAGTGGACGGCGAAATTCCGAAGTCCATCAACGGTACCTTCTACCGTAA

CACGCCGGAGCCTCAGGTGACGCCGCAGAAATTCCACACCTTCATCGATGGTGACGGCATGGCGTCTGCATTT

CATTTTGAAGATGGCCACGTGGACTTCATCAGCCGCTGGGTTAAAACCGCGCGTTTCACGGCGGAGAGACTG

GCACGTAAAAGCCTGTTCGGTATGTACCGTAATCCGTACACCGATGACACGTCTGTGAAGGGTCTGGATCGTA

CCGTTGCCAACACGAGCATCATCAGCCATCACGGTAAGGTTCTGGCGGTGAAAGAAGATGGCTTGCCGTACG

AGCTGGACCCACGCACTCTGGAAACCCGTGGTCGCTTTGACTATGATGGCCAAGTCACCAGCCAGACGCACAC

CGCGCATCCGAAGTATGACCCGGAAACCGGTGACCTGTTGTTCTTTGGCTCCGCAGCCAAGGGTGAGGCAAC

GCCTGATATGGCCTATTACATCGTTGATAAACATGGTAAGGTAACGCATGAGACTTGGTTCGAGCAACCGTAT

GGCGCCTTTATGCATGATTTTGCTATTACCCGCAATTGGAGCATCTTCCCGATCATGCCGGCTACCAATTCGTT

GAGCCGCCTGAAAGCGAAGCAGCCGATTTACATGTGGGAGCCGGAACTGGGTTCCTATATTGGTGTTCTGCC

GCGTCGCGGTCAAGGTAGCCAGATCCGCTGGCTGAAAGCACCAGCGCTGTGGGTCTTTCACGTCGTCAACGC

CTGGGAAGTGGGCACCAAAATCTACATTGACCTTATGGAGAGCGAAATTCTGCCATTCCCGTTCCCGAATAGC

CAAAATCAGCCGTTCGCTCCTGAGAAAGCAGTGCCGCGTCTGACCCGTTGGGAGATTGATCTGGATAGCAGC
```

-continued

```
AGCGATGAGATTAAGCGTACGCGTCTGCACGACTTCTTTGCAGAGATGCCGATCATGGATTTTCGTTTTGCGC
TGCAGTGCAACCGCTACGGTTTTATGGGTGTCGATGACCCGCGCAAGCCGCTGGCGCACCAACAAGCGGAGA
AGATTTTTGCGTACAATAGCCTGGGTATCTGGGACAACCACCGTGGTGATTATGATTTGTGGTACAGCGGCGA
AGCCTCAGCGGCGCAAGAACCGGCTTTCGTTCCGCGTTCTCCGACTGCAGCGGAAGGCGACGGTTATCTGCTG
ACCGTTGTGGGCCGTTTGGACGAGAACCGCAGCGACCTGGTCATTCTGGACACGCAGGACATCCAGAGCGGT
CCGGTTGCGACCATTAAACTGCCGTTTCGCCTGCGTGCGGCCCTGCACGGCTGTTGGGTTCCGCGTCCGTAAT
CCGCGCACGACACTGAACATACGGAAGGAGATATACATATGAATATTCGTCCATTGCATGATCGCGTGATCGT
CAAGCGTAAAGAAGTTGAAACTAAATCTGCTGGCGGCATCGTTCTGACCGGCTCTGCAGCGGCTAAATCCACC
CGCGGCGAAGTGCTGGCTGTCGGCAATGGCCGTATCCTTGAAAATGGCGAAGTGAAGCCGCTGGATGTGAA
AGTTGGCGACATCGTTATTTTCAACGATGGCTACGGTGTGAAATCTGAGAAGATCGACAATGAAGAAGTGTT
GATCATGTCCGAAAGCGACATTCTGGCAATTGTTGAAGCGTAATCCGCGCACGACACTGAACATACGAATTTA
AGGAATAAAGATAATGGCAGCTAAAGACGTAAAATTCGGTAACGACGCTCGTGTGAAAATGCTGCGCGGCGT
AAACGTACTGGCAGATGCAGTGAAAGTTACCCTCGGTCCAAAAGGCCGTAACGTAGTTCTGGATAAATCTTTC
GGTGCACCGACCATCACCAAAGATGGTGTTTCCGTTGCTCGTGAAATCGAACTGGAAGACAAGTTCGAAAATA
TGGGTGCGCAGATGGTGAAAGAAGTTGCCTCTAAAGCAAACGACGCTGCAGGCGACGGTACCACCACTGCAA
CCGTACTGGCTCAGGCTATCATCACTGAAGGTCTGAAAGCTGTTGCTGCGGGCATGAACCCGATGGACCTGAA
ACGTGGTATCGACAAAGCGGTTACCGCTGCAGTTGAAGAACTGAAAGCGCTGTCCGTACCATGCTCTGACTCT
AAAGCGATTGCTCAGGTTGGTACCATCTCCGCTAACTCCGACGAAACCGTAGGTAAACTGATCGCTGAAGCGA
TGGACAAAGTCGGTAAAGAAGGCGTTATCACCGTTGAAGACGGTACCGGTCTGCAGGACGAACTGGACGTG
GTTGAAGGTATGCAGTTCGACCGTGGCTACCTGTCTCCTTACTTCATCAACAAGCCGGAAACTGGCGCAGTAG
AACTGGAAAGCCCGTTCATCCTGCTGGCTGACAAGAAAATCTCCAACATCCGCGAAATGCTGCCGGTTCTGGA
AGCTGTTGCCAAAGCAGGCAAACCGCTGCTGATCATCGCTGAAGATGTAGAAGGCGAAGCGCTGGCAACTCT
GGTTGTTAACACCATGCGTGGCATCGTGAAAGTCGCTGCGGTTAAAGCACCGGGCTTCGGCGATCGTCGTAA
AGCTATGCTGCAGGATATCGCAACCCTGACTGGCGGTACCGTGATCTCTGAAGAGATCGGTATGGAGCTGGA
AAAAGCAACCCTGGAAGACCTGGGTCAGGCTAAACGTGTTGTGATCAACAAAGACACCACCACTATCATCGAT
GGCGTGGGTGAAGAAGCTGCAATCCAGGGCCGTGTTGCTCAGATCCGTCAGCAGATTGAAGAAGCAACTTCT
GACTACGACCGTGAAAAACTGCAGGAACGCGTAGCGAAACTGGCAGGCGGCGTTGCAGTTATCAAAGTGGG
TGCTGCTACCGAAGTTGAAATGAAAGAGAAAAAAGCACGCGTTGAAGATGCCCTGCACGCGACCCGTGCTGC
GGTAGAAGAAGGCGTGGTTGCTGGTGGTGGTGTTGCGCTGATCCGCGTAGCGTCTAAACTGGCTGACCTGCG
TGGTCAGAACGAAGACCAGAACGTGGGTATCAAAGTTGCACTGCGTGCAATGGAAGCTCCGCTGCGTCAGAT
CGTATTGAACTGCGGCGAAGAACCGTCGTTGTTGCTAACACCGTTAAAGGCGGCGACGGCAACTACGGTTA
CAACGCAGCAACCGAAGAATACGGCAACATGATCGACATGGGTATCCTGGATCCAACCAAAGTAACTCGTTCT
GCTCTGCAGTACGCAGCTTCTGTGGCTGGCCTGATGATCACCACCGAATGCATGGTTACCGACCTGCCGAAAA
ACGATGCAGCTGACTTAGGCGCTGCTGGCGGTATGGGCGGCATGGGTGGCATGGGCGGCATGATGTAA
```

SEQ ID NO: 13-PC3 (polycistroncic construct containing codon modified isoeugenol monooxygenase of *P. nitroreducens* Jin 1, groES, groEL)

```
GAAGGAGATATACATATGGCACGTCTGAACCGTAATGATCCGCAACTCGTCGGCACCCTGTTACCAACCCGTA
TTGAGGCTGACCTGTTCGACCTGGAAGTGGACGGCGAAATTCCGAAGTCCATCAACGGTACCTTCTACCGTAA
CACGCCGGAGCCTCAGGTGACGCCGCAGAAATTCCACACCTTCATCGATGGTGACGGCATGGCGTCTGCATTT
CATTTTGAAGATGGCCACGTGGACTTCATCAGCCGCTGGGTTAAAACCGCGCGTTTCACGGCGGAGAGACTG
GCACGTAAAAGCCTGTTCGGTATGTACCGTAATCCGTACACCGATGACACGTCTGTGAAGGGTCTGGATCGTA
```

-continued

```
CCGTTGCCAACACGAGCATCATCAGCCATCACGGTAAGGTTCTGGCGGTGAAAGAAGATGGCTTGCCGTACG

AGCTGGACCCACGCACTCTGGAAACCCGTGGTCGCTTTGACTATGATGGCCAAGTCACCAGCCAGACGCACAC

CGCGCATCCGAAGTATGACCCGGAAACCGGTGACCTGTTGTTCTTTGGCTCCGCAGCCAAGGGTGAGGCAAC

GCCTGATATGGCCTATTACATCGTTGATAAACATGGTAAGGTAACGCATGAGACTTGGTTCGAGCAACCGTAT

GGCGCCTTTATGCATGATTTTGCTATTACCCGCAATTGGAGCATCTTCCCGATCATGCCGGCTACCAATTCGTT

GAGCCGCCTGAAAGCGAAGCAGCCGATTTACATGTGGGAGCCGGAACTGGGTTCCTATATTGGTGTTCTGCC

GCGTCGCGGTCAAGGTAGCCAGATCCGCTGGCTGAAAGCACCAGCGCTGTGGGTCTTTCACGTCGTCAACGC

CTGGGAAGTGGGCACCAAAATCTACATTGACCTTATGGAGAGCGAAATTCTGCCATTCCCGTTCCCGAATAGC

CAAAATCAGCCGTTCGCTCCTGAGAAAGCAGTGCCGCGTCTGACCCGTTGGGAGATTGATCTGGATAGCAGC

AGCGATGAGATTAAGCGTACGCGTCTGCACGACTTCTTTGCAGAGATGCCGATCATGGATTTTCGTTTTGCGC

TGCAGTGCAACCGCTACGGTTTTATGGGTGTCGATGACCCGCGCAAGCCGCTGGCGCACCAACAAGCGGAGA

AGATTTTTGCGTACAATAGCCTGGGTATCTGGGACAACCACCGTGGTGATTATGATTTGTGGTACAGCGGCGA

AGCCTCAGCGGCGCAAGAACCGGCTTTCGTTCCGCGTTCTCCGACTGCAGCGGAAGGCGACGGTTATCTGCTG

ACCGTTGTGGGCCGTTTGGACGAGAACCGCAGCGACCTGGTCATTCTGGACACGCAGGACATCCAGAGCGGT

CCGGTTGCGACCATTAAACTGCCGTTTCGCCTGCGTGCGGCCCTGCACGGCTGTTGGGTTCCGCGTCCGTAAA

ATTAGGTAAAAAATAAAAAATGAATATTCGTCCATTGCATGATCGCGTGATCGTCAAGCGTAAAGAAGTTGAA

ACTAAATCTGCTGGCGGCATCGTTCTGACCGGCTCTGCAGCGGCTAAATCCACCCGCGGCGAAGTGCTGGCTG

TCGGCAATGGCCGTATCCTTGAAAATGGCGAAGTGAAGCCGCTGGATGTGAAAGTTGGCGACATCGTTATTTT

CAACGATGGCTACGGTGTGAAATCTGAGAAGATCGACAATGAAGAAGTGTTGATCATGTCCGAAAGCGACAT

TCTGGCAATTGTTGAAGCGTAATCCGCGCACGACACTGAACATACGAATTTAAGGAATAAAGATAATGGCAGC

TAAAGACGTAAAATTCGGTAACGACGCTCGTGTGAAAATGCTGCGCGGCGTAAACGTACTGGCAGATGCAGT

GAAAGTTACCCTCGGTCCAAAAGGCCGTAACGTAGTTCTGGATAAATCTTTCGGTGCACCGACCATCACCAAA

GATGGTGTTTCCGTTGCTCGTGAAATCGAACTGGAAGACAAGTTCGAAAATATGGGTGCGCAGATGGTGAAA

GAAGTTGCCTCTAAAGCAAACGACGCTGCAGGCGACGGTACCACCACTGCAACCGTACTGGCTCAGGCTATC

ATCACTGAAGGTCTGAAAGCTGTTGCTGCGGGCATGAACCCGATGGACCTGAAACGTGGTATCGACAAAGCG

GTTACCGCTGCAGTTGAAGAACTGAAAGCGCTGTCCGTACCATGCTCTGACTCTAAAGCGATTGCTCAGGTTG

GTACCATCTCCGCTAACTCCGACGAAACCGTAGGTAAACTGATCGCTGAAGCGATGGACAAAGTCGGTAAAG

AAGGCGTTATCACCGTTGAAGACGGTACCGGTCTGCAGGACGAACTGGACGTGGTTGAAGGTATGCAGTTCG

ACCGTGGCTACCTGTCTCCTTACTTCATCAACAAGCCGGAAACTGGCGCAGTAGAACTGGAAAGCCCGTTCAT

CCTGCTGGCTGACAAGAAAATCTCCAACATCCGCGAAATGCTGCCGGTTCTGGAAGCTGTTGCCAAAGCAGGC

AAACCGCTGCTGATCATCGCTGAAGATGTAGAAGGCGAAGCGCTGGCAACTCTGGTTGTTAACACCATGCGT

GGCATCGTGAAAGTCGCTGCGGTTAAAGCACCGGGCTTCGGCGATCGTCGTAAAGCTATGCTGCAGGATATC

GCAACCCTGACTGGCGGTACCGTGATCTCTGAAGAGATCGGTATGGAGCTGGAAAAAGCAACCCTGGAAGAC

CTGGGTCAGGCTAAACGTGTTGTGATCAACAAAGACACCACCACTATCATCGATGGCGTGGGTGAAGAAGCT

GCAATCCAGGGCCGTGTTGCTCAGATCCGTCAGCAGATTGAAGAAGCAACTTCTGACTACGACCGTGAAAAA

CTGCAGGAACGCGTAGCGAAACTGGCAGGCGGCGTTGCAGTTATCAAAGTGGGTGCTGCTACCGAAGTTGAA

ATGAAAGAGAAAAAAGCACGCGTTGAAGATGCCCTGCACGCGACCCGTGCTGCGGTAGAAGAAGGCGTGGT

TGCTGGTGGTGGTGTTGCGCTGATCCGCGTAGCGTCTAAACTGGCTGACCTGCGTGGTCAGAACGAAGACCA

GAACGTGGGTATCAAAGTTGCACTGCGTGCAATGGAAGCTCCGCTGCGTCAGATCGTATTGAACTGCGGCGA

AGAACCGTCTGTTGTTGCTAACACCGTTAAAGGCGGCGACGGCAACTACGGTTACAACGCAGCAACCGAAGA

ATACGGCAACATGATCGACATGGGTATCCTGGATCCAACCAAAGTAACTCGTTCTGCTCTGCAGTACGCAGCT
```

-continued

TCTGTGGCTGGCCTGATGATCACCACCGAATGCATGGTTACCGACCTGCCGAAAAACGATGCAGCTGACTTAG

GCGCTGCTGGCGGTATGGGCGGCATGGGTGGCATGGGCGGCATGATGTAA

SEQ ID NO: 14-PC4 (polycistroncic construct containing codon modified
isoeugenol monooxygenase of *P. nitroreducens* Jin 1, groES, groEL)
GAAGGAGATATACATATGGCACGTCTGAACCGTAATGATCCGCAACTCGTCGGCACCCTGTTACCAACCCGTA

TTGAGGCTGACCTGTTCGACCTGGAAGTGGACGGCGAAATTCCGAAGTCCATCAACGGTACCTTCTACCGTAA

CACGCCGGAGCCTCAGGTGACGCCGCAGAAATTCCACACCTTCATCGATGGTGACGGCATGGCGTCTGCATTT

CATTTTGAAGATGGCCACGTGGACTTCATCAGCCGCTGGGTTAAAACCGCGCGTTTCACGGCGGAGAGACTG

GCACGTAAAAGCCTGTTCGGTATGTACCGTAATCCGTACACCGATGACACGTCTGTGAAGGGTCTGGATCGTA

CCGTTGCCAACACGAGCATCATCAGCCATCACGGTAAGGTTCTGGCGGTGAAAGAAGATGGCTTGCCGTACG

AGCTGGACCCACGCACTCTGGAAACCCGTGGTCGCTTTGACTATGATGGCCAAGTCACCAGCCAGACGCACAC

CGCGCATCCGAAGTATGACCCGGAAACCGGTGACCTGTTGTTCTTTGGCTCCGCAGCCAAGGGTGAGGCAAC

GCCTGATATGGCCTATTACATCGTTGATAAACATGGTAAGGTAACGCATGAGACTTGGTTCGAGCAACCGTAT

GGCGCCTTTATGCATGATTTTGCTATTACCCGCAATTGGAGCATCTTCCCGATCATGCCGGCTACCAATTCGTT

GAGCCGCCTGAAAGCGAAGCAGCCGATTTACATGTGGGAGCCGGAACTGGGTTCCTATATTGGTGTTCTGCC

GCGTCGCGGTCAAGGTAGCCAGATCCGCTGGCTGAAAGCACCAGCGCTGTGGGTCTTTCACGTCGTCAACGC

CTGGGAAGTGGGCACCAAAATCTACATTGACCTTATGGAGAGCGAAATTCTGCCATTCCCGTTCCCGAATAGC

CAAAATCAGCCGTTCGCTCCTGAGAAAGCAGTGCCGCGTCTGACCCGTTGGGAGATTGATCTGGATAGCAGC

AGCGATGAGATTAAGCGTACGCGTCTGCACGACTTCTTTGCAGAGATGCCGATCATGGATTTTCGTTTTGCGC

TGCAGTGCAACCGCTACGGTTTTATGGGTGTCGATGACCCGCGCAAGCCGCTGGCGCACCAACAAGCGGAGA

AGATTTTTGCGTACAATAGCCTGGGTATCTGGGACAACCACCGTGGTGATTATGATTTGTGGTACAGCGGCGA

AGCCTCAGCGGCGCAAGAACCGGCTTTCGTTCCGCGTTCTCCGACTGCAGCGGAAGGCGACGGTTATCTGCTG

ACCGTTGTGGGCCGTTTGGACGAGAACCGCAGCGACCTGGTCATTCTGGACACGCAGGACATCCAGAGCGGT

CCGGTTGCGACCATTAAACTGCCGTTTCGCCTGCGTGCGGCCCTGCACGGCTGTTGGGTTCCGCGTCCGTAAG

AAGGAGATATACATATGAATATTCGTCCATTGCATGATCGCGTGATCGTCAAGCGTAAAGAAGTTGAAACTAA

ATCTGCTGGCGGCATCGTTCTGACCGGCTCTGCAGCGGCTAAATCCACCCGCGGCGAAGTGCTGGCTGTCGG

CAATGGCCGTATCCTTGAAAATGGCGAAGTGAAGCCGCTGGATGTGAAAGTTGGCGACATCGTTATTTTCAAC

GATGGCTACGGTGTGAAATCTGAGAAGATCGACAATGAAGAAGTGTTGATCATGTCCGAAAGCGACATTCTG

GCAATTGTTGAAGCGTAAGAAGGAGATATACATATGGCAGCTAAAGACGTAAAATTCGGTAACGACGCTCGT

GTGAAAATGCTGCGCGGCGTAAACGTACTGGCAGATGCAGTGAAAGTTACCCTCGGTCCAAAAGGCCGTAAC

GTAGTTCTGGATAAATCTTTCGGTGCACCGACCATCACCAAAGATGGTGTTTCCGTTGCTCGTGAAATCGAACT

GGAAGACAAGTTCGAAAATATGGGTGCGCAGATGGTGAAAGAAGTTGCCTCTAAAGCAAACGACGCTGCAG

GCGACGGTACCACCACTGCAACCGTACTGGCTCAGGCTATCATCACTGAAGGTCTGAAAGCTGTTGCTGCGGG

CATGAACCCGATGGACCTGAAACGTGGTATCGACAAAGCGGTTACCGCTGCAGTTGAAGAACTGAAAGCGCT

GTCCGTACCATGCTCTGACTCTAAAGCGATTGCTCAGGTTGGTACCATCTCCGCTAACTCCGACGAAACCGTAG

GTAAACTGATCGCTGAAGCGATGGACAAAGTCGGTAAAGAAGGCGTTATCACCGTTGAAGACGGTACCGGTC

TGCAGGACGAACTGGACGTGGTTGAAGGTATGCAGTTCGACCGTGGCTACCTGTCTCCTTACTTCATCAACAA

GCCGGAAACTGGCGCAGTAGAACTGGAAAGCCCGTTCATCCTGCTGGCTGACAAGAAAATCTCCAACATCCG

CGAAATGCTGCCGGTTCTGGAAGCTGTTGCCAAAGCAGGCAAACCGCTGCTGATCATCGCTGAAGATGTAGA

AGGCGAAGCGCTGGCAACTCTGGTTGTTAACACCATGCGCTGGCATCGTGAAAGTCGCTGCGGTTAAAGCACC

GGGCTTCGGCGATCGTCGTAAAGCTATGCTGCAGGATATCGCAACCCTGACTGGCGGTACCGTGATCTCTGAA

-continued

GAGATCGGTATGGAGCTGGAAAAAGCAACCCTGGAAGACCTGGGTCAGGCTAAACGTGTTGTGATCAACAA

AGACACCACCACTATCATCGATGGCGTGGGTGAAGAAGCTGCAATCCAGGGCCGTGTTGCTCAGATCCGTCA

GCAGATTGAAGAAGCAACTTCTGACTACGACCGTGAAAAACTGCAGGAACGCGTAGCGAAACTGGCAGGCG

GCGTTGCAGTTATCAAAGTGGGTGCTGCTACCGAAGTTGAAATGAAAGAGAAAAAAGCACGCGTTGAAGATG

CCCTGCACGCGACCCGTGCTGCGGTAGAAGAAGGCGTGGTTGCTGGTGGTGGTGTTGCGCTGATCCGCGTAG

CGTCTAAACTGGCTGACCTGCGTGGTCAGAACGAAGACCAGAACGTGGGTATCAAAGTTGCACTGCGTGCAA

TGGAAGCTCCGCTGCGTCAGATCGTATTGAACTGCGGCGAAGAACCGTCTGTTGTTGCTAACACCGTTAAAGG

CGGCGACGGCAACTACGGTTACAACGCAGCAACCGAAGAATACGGCAACATGATCGACATGGGTATCCTGGA

TCCAACCAAAGTAACTCGTTCTGCTCTGCAGTACGCAGCTTCTGTGGCTGGCCTGATGATCACCACCGAATGCA

TGGTTACCGACCTGCCGAAAAACGATGCAGCTGACTTAGGCGCTGCTGGCGGTATGGGCGGCATGGGTGGCA

TGGGCGGCATGATGTAA

SEQ ID NO: 15-PC5 (polycistroncic construct containing codon modified
isoeugenol monooxygenase of P. nitroreducens Jin 1, groES, groEL)
GAAGGAGATATACATATGGCACGTCTGAACCGTAATGATCCGCAACTCGTCGGCACCCTGTTACCAACCCGTA

TTGAGGCTGACCTGTTCGACCTGGAAGTGGACGGCGAAATTCCGAAGTCCATCAACGGTACCTTCTACCGTAA

CACGCCGGAGCCTCAGGTGACGCCGCAGAAATTCCACACCTTCATCGATGGTGACGGCATGGCGTCTGCATTT

CATTTTGAAGATGGCCACGTGGACTTCATCAGCCGCTGGGTTAAAACCGCGCGTTTCACGGCGGAGAGACTG

GCACGTAAAAGCCTGTTCGGTATGTACCGTAATCCGTACACCGATGACACGTCTGTGAAGGGTCTGGATCGTA

CCGTTGCCAACACGAGCATCATCAGCCATCACGGTAAGGTTCTGGCGGTGAAAGAAGATGGCTTGCCGTACG

AGCTGGACCCACGCACTCTGGAAACCCGTGGTCGCTTTGACTATGATGGCCAAGTCACCAGCCAGACGCACAC

CGCGCATCCGAAGTATGACCCGGAAACCGGTGACCTGTTGTTCTTTGGCTCCGCAGCCAAGGGTGAGGCAAC

GCCTGATATGGCCTATTACATCGTTGATAAACATGGTAAGGTAACGCATGAGACTTGGTTCGAGCAACCGTAT

GGCGCCTTTATGCATGATTTTGCTATTACCCGCAATTGGAGCATCTTCCCGATCATGCCGGCTACCAATTCGTT

GAGCCGCCTGAAAGCGAAGCAGCCGATTTACATGTGGGAGCCGGAACTGGGTTCCTATATTGGTGTTCTGCC

GCGTCGCGGTCAAGGTAGCCAGATCCGCTGGCTGAAAGCACCAGCGCTGTGGGTCTTTCACGTCGTCAACGC

CTGGGAAGTGGGCACCAAAATCTACATTGACCTTATGGAGAGCGAAATTCTGCCATTCCCGTTCCCGAATAGC

CAAAATCAGCCGTTCGCTCCTGAGAAAGCAGTGCCGCGTCTGACCCGTTGGGAGATTGATCTGGATAGCAGC

AGCGATGAGATTAAGCGTACGCGTCTGCACGACTTCTTTGCAGAGATGCCGATCATGGATTTTCGTTTTGCGC

TGCAGTGCAACCGCTACGGTTTTATGGGTGTCGATGACCCGCGCAAGCCGCTGGCGCACCAACAAGCGGAGA

AGATTTTTGCGTACAATAGCCTGGGTATCTGGGACAACCACCGTGGTGATTATGATTTGTGGTACAGCGGCGA

AGCCTCAGCGGCGCAAGAACCGGCTTTCGTTCCGCGTTCTCCGACTGCAGCGGAAGGCGACGGTTATCTGCTG

ACCGTTGTGGGCCGTTTGGACGAGAACCGCAGCGACCTGGTCATTCTGGACACGCAGGACATCCAGAGCGGT

CCGGTTGCGACCATTAAACTGCCGTTTCGCCTGCGTGCGGCCCTGCACGGCTGTTGGGTTCCGCGTCCGTAAA

AGATAGCAAAAAATAAAAAATGAATATTCGTCCATTGCATGATCGCGTGATCGTCAAGCGTAAAGAAGTTGAA

ACTAAATCTGCTGGCGGCATCGTTCTGACCGGCTCTGCAGCGGCTAAATCCACCCGCGGCGAAGTGCTGGCTG

TCGGCAATGGCCGTATCCTTGAAAATGGCGAAGTGAAGCCGCTGGATGTGAAAGTTGGCGACATCGTTATTTT

CAACGATGGCTACGGTGTGAAATCTGAGAAGATCGACAATGAAGAAGTGTTGATCATGTCCGAAAGCGACAT

TCTGGCAATTGTTGAAGCGTAATCCGCGCACGACACTGAACATACGAATTTAAGGAATAAAGATAATGGCAGC

TAAAGACGTAAAATTCGGTAACGACGCTCGTGTGAAAATGCTGCGCGGCGTAAACGTACTGGCAGATGCAGT

GAAAGTTACCCTCGGTCCAAAAGGCCGTAACGTAGTTCTGGATAAATCTTTCGGTGCACCGACCATCACCAAA

GATGGTGTTTCCGTTGCTCGTGAAATCGAACTGGAAGACAAGTTCGAAAATATGGGTGCGCAGATGGTGAAA

GAAGTTGCCTCTAAAGCAAACGACGCTGCAGGCGACGGTACCACCACTGCAACCGTACTGGCTCAGGCTATC

-continued

```
ATCACTGAAGGTCTGAAAGCTGTTGCTGCGGGCATGAACCCGATGGACCTGAAACGTGGTATCGACAAAGCG
GTTACCGCTGCAGTTGAAGAACTGAAAGCGCTGTCCGTACCATGCTCTGACTCTAAAGCGATTGCTCAGGTTG
GTACCATCTCCGCTAACTCCGACGAAACCGTAGGTAAACTGATCGCTGAAGCGATGGACAAAGTCGGTAAAG
AAGGCGTTATCACCGTTGAAGACGGTACCGGTCTGCAGGACGAACTGGACGTGGTTGAAGGTATGCAGTTCG
ACCGTGGCTACCTGTCTCCTTACTTCATCAACAAGCCGGAAACTGGCGCAGTAGAACTGGAAAGCCCGTTCAT
CCTGCTGGCTGACAAGAAAATCTCCAACATCCGCGAAATGCTGCCGGTTCTGGAAGCTGTTGCCAAAGCAGGC
AAACCGCTGCTGATCATCGCTGAAGATGTAGAAGGCGAAGCGCTGGCAACTCTGGTTGTTAACACCATGCGT
GGCATCGTGAAAGTCGCTGCGGTTAAAGCACCGGGCTTCGGCGATCGTCGTAAAGCTATGCTGCAGGATATC
GCAACCCTGACTGGCGGTACCGTGATCTCTGAAGAGATCGGTATGGAGCTGGAAAAAGCAACCCTGGAAGAC
CTGGGTCAGGCTAAACGTGTTGTGATCAACAAAGACACCACCACTATCATCGATGGCGTGGGTGAAGAAGCT
GCAATCCAGGGCCGTGTTGCTCAGATCCGTCAGCAGATTGAAGAAGCAACTTCTGACTACGACCGTGAAAAA
CTGCAGGAACGCGTAGCGAAACTGGCAGGCGGCGTTGCAGTTATCAAAGTGGGTGCTGCTACCGAAGTTGAA
ATGAAAGAGAAAAAAGCACGCGTTGAAGATGCCCTGCACGCGACCCGTGCTGCGGTAGAAGAAGGCGTGGT
TGCTGGTGGTGGTGTTGCGCTGATCCGCGTAGCGTCTAAACTGGCTGACCTGCGTGGTCAGAACGAAGACCA
GAACGTGGGTATCAAAGTTGCACTGCGTGCAATGGAAGCTCCGCTGCGTCAGATCGTATTGAACTGCGGCGA
AGAACCGTCTGTTGTTGCTAACACCGTTAAAGGCGGCGACGGCAACTACGGTTACAACGCAGCAACCGAAGA
ATACGGCAACATGATCGACATGGGTATCCTGGATCCAACCAAAGTAACTCGTTCTGCTCTGCAGTACGCAGCT
TCTGTGGCTGGCCTGATGATCACCACCGAATGCATGGTTACCGACCTGCCGAAAAACGATGCAGCTGACTTAG
GCGCTGCTGGCGGTATGGGCGGCATGGGTGGCATGGGCGGCATGATGTAA
```

SEQ ID NO: 16 pIEM2_C154_T222_A1318
```
ttaataagat gatcttcttg agatcgtttt ggtctgcgcg taatctcttg ctctgaaaac    60
gaaaaaccg  ccttgcaggg cggttttcg  aaggttctct gagctaccaa ctctttgaac   120
cgaggtaact ggcttggagg agcgcagtca ccaaaacttg tcctttcagt ttagccttaa   180
ccggcgcatg acttcaagac taactcctct aaatcaatta ccagtggctg ctgccagtgg   240
tgcttttgca tgtctttccg ggttggactc aagacgatag ttaccggata aggcgcagcg   300
gtcggactga acgggggtt  cgtgcataca gtccagcttg gagcgaactg cctacccgga   360
actgagtgtc aggcgtggaa tgagacaaac gcggccataa cagcggaatg acaccggtaa   420
accgaaaggc aggaacagga gagcgcacga gggagccgcc aggggaaac  gcctggtatc   480
tttatagtcc tgtcgggttt cgccaccact gatttgagcg tcagatttcg tgatgcttgt   540
caggggggcg gagcctatgg aaaaacggct ttgccgcggc cctctcactt ccctgttaag   600
tatcttcctg gcatcttcca ggaaatctcc gccccgttcg taagccattt ccgctcgccg   660
cagtcgaacg accgagcgta gcgagtcagt gagcgaggaa gcggaatata tcctgtatca   720
catattctgc tgacgcaccg gtgcagcctt ttttctcctg ccacatgaag cacttcactg   780
acaccctcat cagtgccaac atagtaagcc agtatacact ccgctagcgc tgaggtcccg   840
cagccgaacg accgagcgca gcgagtcagt gagcgaggaa gcggaaggcg agagtaggga   900
actgccaggc atcaaactaa gcagaaggcc cctgacggat ggccttttg  cgtttctaca   960
aactcttct  gtgttgtaaa acgacggcca gtcttaagct cgggcccct  gggcggttct  1020
gataacgagt aatcgttaat ccgcaaataa cgtaaaaacc cgcttcggcg gtttttttta  1080
tgggggagt  ttagggaaag agcatttgtc agaatattta agggcgcctg tcactttgct  1140
tgatatatga gaattattta acctataaa  tgagaaaaaa gcaacgcact ttaaataaga  1200
tacgttgctt tttcgattga tgaacaccta taattaaact attcatctat tatttatgat  1260
```

```
ttttgtata  tacaatattt  ctagtttgtt  aaagagaatt  aagaaaataa  atctcgaaaa  1320
taataaaggg  aaaatcagtt  tttgatatca  aaattataca  tgtcaacgat  aatacaaaat  1380
ataatacaaa  ctataagatg  ttatcagtat  ttattatgca  tttagaataa  attttgtgtc  1440
gcccttccgc  gaaattaata  cgactcacta  taggggaatt  gtgagcggat  aacaattccc  1500
ctctagaaat  aattttgttt  aacttttgaa  ggagatatac  atatggcaac  gtttgaccgc  1560
aatgatccgc  agttggcagg  aacgatgttc  cccacccgaa  tagaggcgaa  tgtctttgac  1620
cttgaaattg  agggcgagat  cccacgtgca  atcaacggga  gcttcttccg  caacaccccc  1680
gaacctcagg  tcaccccgca  acctttccac  accttcatcg  atggggatgg  tttggcgtct  1740
gcttttcatt  tcgaagatgg  ccatgtcgac  tttgtcagcc  gttgggtatg  tactcctcgc  1800
tttgaagctg  agcggtcggc  tcgtaaatca  ctcttcggta  tgtaccgcaa  tccgttcact  1860
gatgatccat  cggtagaagg  tattgatcgt  acagtcgcca  acaccagtat  catcactcat  1920
cacgggaaag  tactggccgc  aaaggaagat  ggactacctt  atgagcttga  ccccaaaccc  1980
ctggaaaccc  gaggtcgtta  tgattacaag  gggcaggtaa  ccagccatac  acatacagcg  2040
caccctaagt  tcgaccccca  gacaggtgaa  atgttactct  tcggctccgc  tgctaaaggc  2100
gaacgaacgc  ttgatatggc  gtactatatt  gttgatcgct  acggcaaggt  gacacatgag  2160
acctggttta  agcagcctta  cggtgcattc  atgcacgact  tgctgtcac  gcgcaactgg  2220 tcaatctttc  cgatcatgcc  tgcgacaaat  agccttgagc  gtcttaaagc  aaagcagccc  2280
atttacatgt  gggagcctga  gcgaggaagc  tatataggag  tacttcctcg  tcgtggtcag  2340
ggcaaggaca  ttcgttggtt  ccgtgccccg  gcgttgtggg  ttttccatgt  cgtgaatgct  2400
tgggaggaag  ggaatagaat  tctgattgac  ttgatggaaa  gtgagatttt  gccgttccca  2460
ttcccgaact  cgcagaacct  tccatttgat  ccctccaagg  ctgttccgcg  tctaacccgt  2520
tgggaaattg  atctcaatag  tggtaacgat  gagatgaaac  gtacgcagct  acacgaatat  2580
tttgcagaaa  tgcctatcat  ggatttccgt  tttgcgctcc  aggatcatcg  ctacgcctac  2640 atggggttg  acgatcctcg  tcgccccttta  gctcatcagc  aagctgaaaa  atctttgcc  2700 tacaattcgt  taggggtttg  gacaaccat  cgtaaagatt  atgaactttg  gtttacggga  2760
aaaatgtctg  cagcgcagga  accggcgttt  gttcctagaa  gcccagatgc  gcctgagggc  2820
gatggctacc  tactcagtgt  agtagggcgg  ctcgatgaaa  atcgtagcga  tctagttatc  2880
cttgatacgc  aatgtttggc  agctgggcct  gtggccactg  tcaagcttcc  cttccgtctc  2940
cgagcagcgt  tgcacggttg  ttggcagtct  aagaactgag  gatccgaatt  cgagctcccc  3000
cctagcataa  ccccttgggg  cctctaaacg  ggtcttgagg  ggttttttgc  ccctgagacg  3060
cgtcaatcga  gttcgtacct  aagggcgaca  ccccctaatt  agcccgggcg  aaaggcccag  3120
tctttcgact  gagcctttcg  ttttatttga  tgcctggcag  ttccctactc  tcgcatgggg  3180
agtccccaca  ctaccatcgg  cgctacggcg  tttcacttct  gagttcggca  tggggtcagg  3240
tgggaccacc  gcgctactgc  cgccaggcaa  acaagggtg  ttatgagcca  tattcaggta  3300
taaatgggct  cgcgataatg  ttcagaattg  gttaattggt  tgtaacactg  acccctattt  3360
gtttattttt  ctaaatacat  tcaaatatgt  atccgctcat  gagacaataa  ccctgataaa  3420
tgcttcaata  atattgaaaa  aggaagaata  tgagccatat  tcaacgggaa  acgtcgaggc  3480
cgcgattaaa  ttccaacatg  gatgctgatt  tatatgggta  taaatgggct  cgcgataatg  3540
tcgggcaatc  aggtgcgaca  atctatcgct  tgtatgggaa  gcccgatgcg  ccagagttgt  3600
ttctgaaaca  tggcaaaggt  agcgttgcca  atgatgttac  agatgagatg  gtcagactaa  3660
```

```
actggctgac ggaatttatg ccacttccga ccatcaagca ttttatccgt actcctgatg  3720
atgcatggtt actcaccact gcgatccccg gaaaaacagc gttccaggta ttagaagaat  3780
atcctgattc aggtgaaaat attgttgatg cgctggcagt gttcctgcgc cggttgcact  3840
cgattcctgt ttgtaattgt ccttttaaca gcgatcgcgt atttcgcctc gctcaggcgc  3900
aatcacgaat gaataacggt ttggttgatg cgagtgattt tgatgacgag cgtaatggct  3960
ggcctgttga acaagtctgg aaagaaatgc ataaacttt gccattctca ccggattcag   4020
tcgtcactca tggtgatttc tcacttgata accttattt tgacgagggg aaattaatag   4080
gttgtattga tgttggacga gtcggaatcg cagaccgata ccaggatctt gccatcctat  4140
ggaactgcct cggtgagttt tctccttcat tacagaaacg gcttttcaa aaatatggta   4200 ttgataatcc tgatatgaat aaattgcagt tcatttgat gctcgatgag ttttctaag    4260 cggcgcgcca tcgaatggcg caaaaccttt cgcggtatgg catgatagcg cccggaagag  4320
agtcaattca gggtggtgaa tatgaaacca gtaacgttat acgatgtcgc agagtatgcc  4380
ggtgtctctt atcagaccgt ttcccgcgtg gtgaaccagg ccagccacgt ttctgcgaaa  4440
acgcgggaaa aagtggaagc ggcgatggcg gagctgaatt acattcccaa ccgcgtggca  4500
caacaactgg cgggcaaaca gtcgttgctg attggcgttg ccacctccag tctgccctg   4560 cacgcgccgt cgcaaattgt cgcggcgatt aaatctcgcg ccgatcaact gggtgccagc  4620
gtggtggtgt cgatggtaga acgaagcggc gtcgaagcct gtaaagcggc ggtgcacaat  4680
cttctcgcgc aacgcgtcag tgggctgatc attaactatc gctggatga ccaggatgcc   4740 attgctgtgg aagctgcctg cactaatgtt ccggcgttat tcttgatgt ctctgaccag   4800 acacccatca acagtattat tttctcccat gaggacggta cgcgactggg cgtggagcat  4860
ctggtcgcat tgggtcacca gcaaatcgcg ctgttagcgg gcccattaag ttctgtctcg  4920
gcgcgtctgc gtctggctgg ctggcataaa tatctcactc gcaatcaaat tcagccgata  4980
gcggaacggg aaggcgactg gagtgccatg tccggttttc aacaaaccat gcaaatgctg  5040
aatgagggca tcgttcccac tgcgatgctg gttgccaacg atcagatggc gctgggcgca  5100
atgcgcgcca ttaccgagtc cgggctgcgc gttggtgcgg atatctcggt agtgggatac  5160
gacgataccg aagatagctc atgttatatc ccgccgttaa ccaccatcaa acaggatttt  5220
cgcctgctgg ggcaaaccag cgtggaccgc ttgctgcaac tctctcaggg ccaggcggtg  5280
aagggcaatc agctgttgcc agtctcactg gtgaaaagaa aaaccaccct ggcgcccaat  5340
acgcaaaccg cctctccccg cgcgttggcc gattcattaa tgcagctggc acgacaggtt  5400
tcccgactgg aaagcgggca gtga                                         5424
```

SEQ ID NO: 17: Plasmid construct trc/+term
```
TTAATAAGATGATCTTCTTGAGATCGTTTTGGTCTGCGCGTAATCTCTTGCTCTGAAAACGAAAAAACCGCCT

TGCAGGGCGGTTTTTCGAAGGTTCTCTGAGCTACCAACTCTTTGAACCGAGGTAACTGGCTTGGAGGAGCG

CAGTCACCAAAACTTGTCCTTTCAGTTTAGCCTTAACCGGCGCATGACTTCAAGACTAACTCCTCTAAATCAA

TTACCAGTGGCTGCTGCCAGTGGTGCTTTTGCATGTCTTTCCGGGTTGGACTCAAGACGATAGTTACCGGAT

AAGGCGCAGCGGTCGGACTGAACGGGGGGTTCGTGCATACAGTCCAGCTTGGAGCGAACTGCCTACCCGG

AACTGAGTGTCAGGCGTGGAATGAGACAAACGCGGCCATAACAGCGGAATGACACCGGTAAACCGAAAGG

CAGGAACAGGAGAGCGCACGAGGGAGCCGCCAGGGGGAAACGCCTGGTATCTTTATAGTCCTGTCGGGTT

TCGCCACCACTGATTTGAGCGTCAGATTTCGTGATGCTTGTCAGGGGGGCGGAGCCTATGGAAAAACGGCT

TTGCCGCGGCCCTCTCACTTCCCTGTTAAGTATCTTCCTGGCATCTTCCAGGAAATCTCCGCCCCGTTCGTA

AGCCATTTCCGCTCGCCGCAGTCGAACGACCGAGCGTAGCGAGTCAGTGAGCGAGGAAGCGGAATATATC
```

-continued

```
CTGTATCACATATTCTGCTGACGCACCGGTGCAGCCTTTTTTCTCCTGCCACATGAAGCACTTCACTGACAC

CCTCATCAGTGCCAACATAGTAAGCCAGTATACACTCCGCTAGCGCTGAGGTCCCGCAGCCGAACGACCGA

GCGCAGCGAGTCAGTGAGCGAGGAAGCGGAAGGCGAGAGTAGGGAACTGCCAGGCATCAAACTAAGCAGA

AGGCCCCTGACGGATGGCCTTTTTGCGTTTCTACAAACTCTTTCTGTGTTGTAAAACGACGGCCAGTCTTAA

GCTCGGGCCCCTGGGCGGTTCTGATAACGAGTAATCGTTAATCCGCAAATAACGTAAAAACCCGCTTCGGC

GGGTTTTTTATGGGGGGAGTTTAGGGAAAGAGCATTTGTCAGAATATTTAAGGGCGCCTGTCACTTTGCTT

GATATATGAGAATTATTTAACCTTATAAATGAGAAAAAAGCAACGCACTTTAAATAAGATACGTTGCTTTTC

GATTGATGAACACCTATAATTAAACTATTCATCTATTATTTATGATTTTTTGTATATACAATATTTCTAGTTTGT

TAAAGAGAATTAAGAAAATAAATCTCGAAAATAATAAAGGGAAAATCAGTTTTTGATATCAAAATTATACATGTC

AACGATAATACAAAATATAATACAAACTATAAGATGTTATCAGTATTTATTATGCATTTAGAATAAATTTTGTGT

CGCCCTTCCGCGAAATTAATACGACTCACTATAGGGGAATTGTGAGCGGATAACAATTCCCCTCTAGAAATA

ATTTTGTTTAACTTTTGAAGGAGATATACATATGGCAACGTTTGACCGCAATGATCCGCAGTTGGCAGGAACG

ATGTTCCCCACCCGAATAGAGGCGAATGTCTTTGACCTTGAAATTGAGGGCGAGATCCCACGTGCAATCAAC

GGGAGCTTCTTCCGCAACACCCCCGAACCTCAGGTCACCCCGCAACCTTTCCACACCTTCATCGATGGGGA

TGGTTTGGCGTCTGCTTTTCATTTCGAAGATGGCCATGTCGACTTTGTCAGCCGTTGGGTATGTACTCCTCG

CTTTGAAGCTGAGCGGTCGGCTCGTAAATCACTCTTCGGTATGTACCGCAATCCGTTCACTGATGATCCATC

GGTAGAAGGTATTGATCGTACAGTCGCCAACACCAGTATCATCACTCATCACGGGAAAGTACTGGCCGCAAA

GGAAGATGGACTACCTTATGAGCTTGACCCCCAAACCCTGGAAACCCGAGGTCGTTATGATTACAAGGGGC

AGGTAACCAGCCATACACATACAGCGCACCCTAAGTTCGACCCCCAGACAGGTGAAATGTTACTCTTCGGCT

CCGCTGCTAAAGGCGAACGAACGCTTGATATGGCGTACTATATTGTTGATCGCTACGGCAAGGTGACACAT

GAGACCTGGTTTAAGCAGCCTTACGGTGCATTCATGCACGACTTTGCTGTCACGCGCAACTGGTCAATCTTT

CCGATCATGCCTGCGACAAATAGCCTTGAGCGTCTTAAAGCAAAGCAGCCCATTTACATGTGGGAGCCTGA

GCGAGGAAGCTATATAGGAGTACTTCCTCGTCGTGGTCAGGGCAAGGACATTCGTTGGTTCCGTGCCCCGG

CGTTGTGGGTTTTCCATGTCGTGAATGCTTGGGAGGAAGGGAATAGAATTCTGATTGACTTGATGGAAAGTG

AGATTTTGCCGTTCCCATTCCCGAACTCGCAGAACCTTCCATTTGATCCCTCCAAGGCTGTTCCGCGTCTAA

CCCGTTGGGAAATTGATCTCAATAGTGGTAACGATGAGATGAAACGTACGCAGCTACACGAATATTTTGCAG

AAATGCCTATCATGGATTTCCGTTTTGCGCTCCAGGATCATCGCTACGCCTACATGGGGGTTGACGATCCTC

GTCGCCCCTTAGCTCATCAGCAAGCTGAAAAAATCTTTGCCTACAATTCGTTAGGGGTTTGGGACAACCATC

GTAAAGATTATGAACTTTGGTTTACGGGAAAAATGTCTGCAGCGCAGGAACCGGCGTTTGTTCCTAGAAGCC

CAGATGCGCCTGAGGGCGATGGCTACCTACTCAGTGTAGTAGGGCGGCTCGATGAAAATCGTAGCGATCTA

GTTATCCTTGATACGCAATGTTTGGCAGCTGGGCCTGTGGCCACTGTCAAGCTTCCCTTCCGTCTCCGAGCA

GCGTTGCACGGTTGTTGGCAGTCTAAGAACTGACTAGCATAACCCCTTGGGGCCTCTAAACGGGTCTTGAG

GGGTTTTTTGGCATCCTGTCCATGACTCGGTGACAATTAATTATCCGGCTCGTATAATGTGTGGAATTGTGAG

CGGATAACAATTCCCTCTAGAAATAATTTTGTTTAACTTTTAAAGGAGAGTTATCAATGAATATTCGTCCATT

GCATGATCGCGTGATCGTCAAGCGTAAAGAAGTTGAAACTAAATCTGCTGGCGGCATCGTTCTGACCGGCTCT

GCAGCGGCTAAATCCACCCGCGGCGAAGTGCTGGCTGTCGGCAATGGCCGTATCCTTGAAAATGGCGAAG

TGAAGCCGCTGGATGTGAAAGTTGGCGACATCGTTATTTTCAACGATGGCTACGGTGTGAAATCTGAGAAGA

TCGACAATGAAGAAGTGTTGATCATGTCCGAAAGCGACATTCTGGCAATTGTTGAAGCGTAATCCGCGCACG

ACACTGAACATACGAATTTAAGGAATAAAGATAATGGCAGCTAAAGACGTAAAATTCGGTAACGACGCTCGT

GTGAAAATGCTGCGCGGCGTAAACGTACTGGCAGATGCAGTGAAAGTTACCCTCGGTCCAAAAGGCCGTAA

CGTAGTTCTGGATAAATCTTTCGGTGCACCGACCATCACCAAAGATGGTGTTTCCGTTGCTCGTGAAATCGA
```

-continued

```
ACTGGAAGACAAGTTCGAAAATATGGGTGCGCAGATGGTGAAAGAAGTTGCCTCTAAAGCAAACGACGCTG
CAGGCGACGGTACCACCACTGCAACCGTACTGGCTCAGGCTATCATCACTGAAGGTCTGAAAGCTGTTGCT
GCGGGCATGAACCCGATGGACCTGAAACGTGGTATCGACAAAGCGGTTACCGCTGCAGTTGAAGAACTGAA
AGCGCTGTCCGTACCATGCTCTGACTCTAAAGCGATTGCTCAGGTTGGTACCATCTCCGCTAACTCCGACGA
AACCGTAGGTAAACTGATCGCTGAAGCGATGGACAAAGTCGGTAAAGAAGGCGTTATCACCGTTGAAGACG
GTACCGGTCTGCAGGACGAACTGGACGTGGTTGAAGGTATGCAGTTCGACCGTGGCTACCTGTCTCCTTAC
TTCATCAACAAGCCGGAAACTGGCGCAGTAGAACTGGAAAGCCCGTTCATCCTGCTGGCTGACAAGAAAAT
CTCCAACATCCGCGAAATGCTGCCGGTTCTGGAAGCTGTTGCCAAAGCAGGCAAACCGCTGCTGATCATCG
CTGAAGATGTAGAAGGCGAAGCGCTGGCAACTCTGGTTGTTAACACCATGCGTGGCATCGTGAAAGTCGCT
GCGGTTAAAGCACCGGGCTTCGGCGATCGTCGTAAAGCTATGCTGCAGGATATCGCAACCCTGACTGGCG
GTACCGTGATCTCTGAAGAGATCGGTATGGAGCTGGAAAAAGCAACCCTGGAAGACCTGGGTCAGGCTAAA
CGTGTTGTGATCAACAAAGACACCACCACTATCATCGATGGCGTGGGTGAAGAAGCTGCAATCCAGGGCCG
TGTTGCTCAGATCCGTCAGCAGATTGAAGAAGCAACTTCTGACTACGACCGTGAAAAACTGCAGGAACGCGT
AGCGAAACTGGCAGGCGGCGTTGCAGTTATCAAAGTGGGTGCTGCTACCGAAGTTGAAATGAAAGAGAAAA
AAGCACGCGTTGAAGATGCCCTGCACGCGACCCGTGCTGCGGTAGAAGAAGGCGTGGTTGCTGGTGGTGG
TGTTGCGCTGATCCGCGTAGCGTCTAAACTGGCTGACCTGCGTGGTCAGAACGAAGACCAGAACGTGGGTA
TCAAAGTTGCACTGCGTGCAATGGAAGCTCCGCTGCGTCAGATCGTATTGAACTGCGGCGAAGAACCGTCT
GTTGTTGCTAACACCGTTAAAGGCGGCGACGGCAACTACGGTTACAACGCAGCAACCGAAGAATACGGCAA
CATGATCGACATGGGTATCCTGGATCCAACCAAAGTAACTCGTTCTGCTCTGCAGTACGCAGCTTCTGTGGC
TGGCCTGATGATCACCACCGAATGCATGGTTACCGACCTGCCGAAAAACGATGCAGCTGACTTAGGCGCTG
CTGGCGGTATGGGCGGCATGGGTGGCATGGGCGGCATGATGTAACCCCCTAGCATAACCCCTTGGGGCCT
CTAAACGGGTCTTGAGGGGTTTTTTGCCCCTGAGACGCGTCAATCGAGTTCGTACCTAAGGGCGACACCCC
CTAATTAGCCCGGGCGAAAGGCCCAGTCTTTCGACTGAGCCTTTCGTTTTATTTGATGCCTGGCAGTTCCCT
ACTCTCGCATGGGGAGTCCCCACACTACCATCGGCGCTACGGCGTTTCACTTCTGAGTTCGGCATGGGGTC
AGGTGGGACCACCGCGCTACTGCCGCCAGGCAAACAAGGGGTGTTATGAGCCATATTCAGGTATAAATGGGC
TCGCGATAATGTTCAGAATTGGTTAATTGGTTGTAACACTGACCCCTATTTGTTTATTTTTCTAAATACATTC
AAATATGTATCCGCTCATGAGACAATAACCCTGATAAATGCTTCAATAATATTGAAAAAGGAAGAATATGAGC
CATATTCAACGGGAAACGTCGAGGCCGCGATTAAATTCCAACATGGATGCTGATTTATATGGGTATAAATGG
GCTCGCGATAATGTCGGGCAATCAGGTGCGACAATCTATCGCTTGTATGGGAAGCCCGATGCGCCAGAGTT
GTTTCTGAAACATGGCAAAGGTAGCGTTGCCAATGATGTTACAGATGAGATGGTCAGACTAAACTGGCTGAC
GGAATTTATGCCACTTCCGACCATCAAGCATTTTATCCGTACTCCTGATGATGCATGGTTACTCACCACTGCG
ATCCCCGGAAAAACAGCGTTCCAGGTATTAGAAGAATATCCTGATTCAGGTGAAAATATTGTTGATGCGCTG
GCAGTGTTCCTGCGCCGGTTGCACTCGATTCCTGTTTGTAATTGTCCTTTTAACAGCGATCGCGTATTTCGC
CTCGCTCAGGCGCAATCACGAATGAATAACGGTTTGGTTGATGCGAGTGATTTTGATGACGAGCGTAATGC
TGGCCTGTTGAACAAGTCTGGAAAGAAATGCATAAACTTTTGCCATTCTCACCGGATTCAGTCGTCACTCATG
GTGATTTCTCACTTGATAACCTTATTTTTGACGAGGGGAAATTAATAGGTTGTATTGATGTTGGACGAGTCGG
AATCGCAGACCGATACCAGGATCTTGCCATCCTATGGAACTGCCTCGGTGAGTTTTCTCCTTCATTACAGAA
ACGGCTTTTTCAAAAATATGGTATTGATAATCCTGATATGAATAAATTGCAGTTTCATTTGATGCTCGATGAG
TTTTTCTAAGCGGCGCGCCATCGAATGGCGCAAAACCTTTCGCGGTATGGCATGATAGCGCCCGGAAGAGAG
TCAATTCAGGGTGGTGAATATGAAACCAGTAACGTTATACGATGTCGCAGAGTATGCCGGTGTCTCTTATC
```

-continued

AGACCGTTTCCCGCGTGGTGAACCAGGCCAGCCACGTTTCTGCGAAAACGCGGGAAAAAGTGGAAGCGGCG
ATGGCGGAGCTGAATTACATTCCCAACCGCGTGGCACAACAACTGGCGGGCAAACAGTCGTTGCTGATTGG
CGTTGCCACCTCCAGTCTGGCCCTGCACGCGCCGTCGCAAATTGTCGCGGCGATTAAATCTCGCGCCGATC
AACTGGGTGCCAGCGTGGTGGTGTCGATGGTAGAACGAAGCGGCGTCGAAGCCTGTAAAGCGGCGGTGCA
CAATCTTCTCGCGCAACGCGTCAGTGGGCTGATCATTAACTATCCGCTGGATGACCAGGATGCCATTGCTGT
GGAAGCTGCCTGCACTAATGTTCCGGCGTTATTTCTTGATGTCTCTGACCAGACACCCATCAACAGTATTAT
TTTCTCCCATGAGGACGGTACGCGACTGGGCGTGGAGCATCTGGTCGCATTGGGTCACCAGCAAATCGCGC
TGTTAGCGGGCCCATTAAGTTCTGTCTCGGCGCGTCTGCGTCTGGCTGGCTGGCATAAATATCTCACTCGC
AATCAAATTCAGCCGATAGCGGAACGGGAAGGCGACTGGAGTGCCATGTCCGGTTTTCAACAAACCATGCA
AATGCTGAATGAGGGCATCGTTCCCACTGCGATGCTGGTTGCCAACGATCAGATGGCGCTGGGCGCAATGC
GCGCCATTACCGAGTCCGGGCTGCGCGTTGGTGCGGATATCTCGGTAGTGGGATACGACGATACCGAAGA
TAGCTCATGTTATATCCCGCCGTTAACCACCATCAAACAGGATTTTCGCCTGCTGGGGCAAACCAGCGTGGA
CCGCTTGCTGCAACTCTCTCAGGGCCAGGCGGTGAAGGGCAATCAGCTGTTGCCAGTCTCACTGGTGAAAA
GAAAAACCACCCTGGCGCCCAATACGCAAACCGCCTCTCCCCGCGCGTTGGCCGATTCATTAATGCAGCTG
GCACGACAGGTTTCCCGACTGGAAAGCGGGCAGTGA

SEQ ID NO: 18: Plasmid construct tac/+term
TTAATAAGATGATCTTCTTGAGATCGTTTTGGTCTGCGCGTAATCTCTTGCTCTGAAAACGAAAAAACCGCCT
TGCAGGGCGGTTTTTCGAAGGTTCTCTGAGCTACCAACTCTTTGAACCGAGGTAACTGGCTTGGAGGAGCG
CAGTCACCAAAACTTGTCCTTTCAGTTTAGCCTTAACCGGCGCATGACTTCAAGACTAACTCCTCTAAATCAA
TTACCAGTGGCTGCTGCCAGTGGTGCTTTTGCATGTCTTTCCGGGTTGGACTCAAGACGATAGTTACCGGAT
AAGGCGCAGCGGTCGGACTGAACGGGGGGTTCGTGCATACAGTCCAGCTTGGAGCGAACTGCCTACCCGG
AACTGAGTGTCAGGCGTGGAATGAGACAAACGCGGCCATAACAGCGGAATGACACCGGTAAACCGAAAGG
CAGGAACAGGAGAGCGCACGAGGGAGCCGCCAGGGGGAAACGCCTGGTATCTTTATAGTCCTGTCGGGTT
TCGCCACCACTGATTTGAGCGTCAGATTTCGTGATGCTTGTCAGGGGGGCGGAGCCTATGGAAAAACGGCT
TTGCCGCGGCCCTCTCACTTCCCTGTTAAGTATCTTCCTGGCATCTTCCAGGAAATCTCCGCCCCGTTCGTA
AGCCATTTCCGCTCGCCGCAGTCGAACGACCGAGCGTAGCGAGTCAGTGAGCGAGGAAGCGGAATATATC
CTGTATCACATATTCTGCTGACGCACCGGTGCAGCCTTTTTTCTCCTGCCACATGAAGCACTTCACTGACAC
CCTCATCAGTGCCAACATAGTAAGCCAGTATACACTCCGCTAGCGCTGAGGTCCCGCAGCCGAACGACCGA
GCGCAGCGAGTCAGTGAGCGAGGAAGCGGAAGGCGAGAGTAGGGAACTGCCAGGCATCAAACTAAGCAGA
AGGCCCCTGACGGATGCCTTTTTGCGTTTCTACAAACTCTTTCTGTGTTGTAAAACGACGGCCAGTCTTAA
GCTCGGGCCCCTGGGCGGTTCTGATAACGAGTAATCGTTAATCCGCAAATAACGTAAAAACCCGCTTCGG
CGGGTTTTTTTATGGGGGGAGTTTAGGGAAAGAGCATTTGTCAGAATATTTAAGGGCGCCTGTCACTTTGCT
TGATATATGAGAATTATTTAACCTTATAAATGAGAAAAAAGCAACGCACTTTAAATAAGATACGTTGCTTTTTC
GATTGATGAACACCTATAATTAAACTATTCATCTATTATTTATGATTTTTTGTATATACAATATTTCTAGTTTG
TTAAAGAGAATTAAGAAAATAAATCTCGAAAATAATAAAGGGAAAATCAGTTTTTGATATCAAAATTATACATG
TCAACGATAATACAAAATATAATACAAACTATAAGATGTTATCAGTATTTATTATGCATTTAGAATAAATTTTG
TGTCGCCCTTCCGCGAAATTAATACGACTCACTATAGGGGAATTGTGAGCGGATAACAATTCCCCTCTAGAAAT
AATTTTGTTTAACTTTTGAAGGAGATATACATATGGCAACGTTTGACCGCAATGATCCGCAGTTGGCAGGAACG
ATGTTCCCCACCCGAATAGAGGCGAATGTCTTTGACCTTGAAATTGAGGGCGAGATCCCACGTGCAATCAAC
GGGAGCTTCTTCCGCAACACCCCCGAACCTCAGGTCACCCCGCAACCTTTCCACACCTTCATCGATGGGGA
TGGTTTGGCGTCTGCTTTTCATTTCGAAGATGGCCATGTCGACTTTGTCAGCCGTTGGGTATGTACTCCTCG -continued

```
CTTTGAAGCTGAGCGGTCGGCTCGTAAATCACTCTTCGGTATGTACCGCAATCCGTTCACTGATGATCCATC

GGTAGAAGGTATTGATCGTACAGTCGCCAACACCAGTATCATCACTCATCACGGGAAAGTACTGGCCGCAAA

GGAAGATGGACTACCTTATGAGCTTGACCCCCAAACCCTGGAAACCCGAGGTCGTTATGATTACAAGGGGC

AGGTAACCAGCCATACACATACAGCGCACCCTAAGTTCGACCCCCAGACAGGTGAAATGTTACTCTTCGGCT

CCGCTGCTAAAGGCGAACGAACGCTTGATATGGCGTACTATATTGTTGATCGCTACGGCAAGGTGACACAT

GAGACCTGGTTTAAGCAGCCTTACGGTGCATTCATGCACGACTTTGCTGTCACGCGCAACTGGTCAATCTTT

CCGATCATGCCTGCGACAAATAGCCTTGAGCGTCTTAAAGCAAAGCAGCCCATTTACATGTGGGAGCCTGA

GCGAGGAAGCTATATAGGAGTACTTCCTCGTCGTGGTCAGGGCAAGGACATTCGTTGGTTCCGTGCCCCGG

CGTTGTGGGTTTTCCATGTCGTGAATGCTTGGGAGGAAGGGAATAGAATTCTGATTGACTTGATGGAAAGTG

AGATTTTGCCGTTCCCATTCCCGAACTCGCAGAACCTTCCATTTGATCCCTCCAAGGCTGTTCCGCGTCTAA

CCCGTTGGGAAATTGATCTCAATAGTGGTAACGATGAGATGAAACGTACGCAGCTACACGAATATTTTGCAG

AAATGCCTATCATGGATTTCCGTTTTGCGCTCCAGGATCATCGCTACGCCTACATGGGGGTTGACGATCCTC

GTCGCCCCTTAGCTCATCAGCAAGCTGAAAAAATCTTTGCCTACAATTCGTTAGGGGTTTGGGACAACCATC

GTAAAGATTATGAACTTTGGTTTACGGGAAAAATGTCTGCAGCGCAGGAACCGGCGTTTGTTCCTAGAAGCC

CAGATGCGCCTGAGGGCGATGGCTACCTACTCAGTGTAGTAGGGCGGCTCGATGAAAATCGTAGCGATCTA

GTTATCCTTGATACGCAATGTTTGGCAGCTGGGCCTGTGGCCACTGTCAAGCTTCCCTTCCGTCTCCGAGCA

GCGTTGCACGGTTGTTGGCAGTCTAAGAACTGACTAGCATAACCCCTTGGGGCCTCTAAACGGGTCTTGAG

GGGTTTTTTGGCATCCTGTCCATGACTCGGTGACAATTAATCATCGGCTCGTATAATGTGTGGAATTGTGAG

CGGATAACAATTCCCTCTAGAAATAATTTTGTTTAACTTTTAAAGGAGAGTTATCAATGAATATTCGTCCATTG

CATGATCGCGTGATCGTCAAGCGTAAAGAAGTTGAAACTAAATCTGCTGGCGGCATCGTTCTGACCGGCTCT

GCAGCGGCTAAATCCACCCGCGGCGAAGTGCTGGCTGTCGGCAATGGCCGTATCCTTGAAAATGGCGAAG

TGAAGCCGCTGGATGTGAAAGTTGGCGACATCGTTATTTTCAACGATGGCTACGGTGTGAAATCTGAGAAGA

TCGACAATGAAGAAGTGTTGATCATGTCCGAAAGCGACATTCTGGCAATTGTTGAAGCGTAATCCGCGCACG

ACACTGAACATACGAATTTAAGGAATAAAGATAATGGCAGCTAAAGACGTAAAATTCGGTAACGACGCTCGT

GTGAAAATGCTGCGCGCGTAAACGTACTGGCAGATGCAGTGAAAGTTACCCTCGGTCCAAAAGGCCGTAA

CGTAGTTCTGGATAAATCTTTCGGTGCACCGACCATCACCAAAGATGGTGTTTCCGTTGCTCGTGAAATCGA

ACTGGAAGACAAGTTCGAAAATATGGGTGCGCAGATGGTGAAAGAAGTTGCCTCTAAAGCAAACGACGCTG

CAGGCGACGGTACCACCACTGCAACCGTACTGGCTCAGGCTATCATCACTGAAGGTCTGAAAGCTGTTGCT

GCGGGCATGAACCCGATGGACCTGAAACGTGGTATCGACAAAGCGGTTACCGCTGCAGTTGAAGAACTGAA

AGCGCTGTCCGTACCATGCTCTGACTCTAAAGCGATTGCTCAGGTTGGTACCATCTCCGCTAACTCCGACGA

AACCGTAGGTAAACTGATCGCTGAAGCGATGGACAAAGTCGGTAAAGAAGGCGTTATCACCGTTGAAGACG

GTACCGGTCTGCAGGACGAACTGGACGTGGTTGAAGGTATGCAGTTCGACCGTGGCTACCTGTCTCCTTAC

TTCATCAACAAGCCGGAAACTGGCGCAGTAGAACTGGAAAGCCCGTTCATCCTGCTGGCTGACAAGAAAAT

CTCCAACATCCGCGAAATGCTGCCGGTTCTGGAAGCTGTTGCCAAAGCAGGCAAACCGCTGCTGATCATCG

CTGAAGATGTAGAAGGCGAAGCGCTGGCAACTCTGGTTGTTAACACCATGCGTGGCATCGTGAAAGTCGCT

GCGGTTAAAGCACCGGGCTTCGGCGATCGTCGTAAAGCTATGCTGCAGGATATCGCAACCCTGACTGGCG

GTACCGTGATCTCTGAAGAGATCGGTATGGAGCTGGAAAAAGCAACCCTGGAAGACCTGGGTCAGGCTAAA

CGTGTTGTGATCAACAAAGACACCACCACTATCATCGATGGCGTGGGTGAAGAAGCTGCAATCCAGGGCCG

TGTTGCTCAGATCCGTCAGCAGATTGAAGAAGCAACTTCTGACTACGACCGTGAAAAACTGCAGGAACGCGT

AGCGAAACTGGCAGGCGGCGTTGCAGTTATCAAAGTGGGTGCTGCTACCGAAGTTGAAATGAAAGAGAAA

AAGCACGCGTTGAAGATGCCCTGCACGCGACCCGTGCTGCGGTAGAAGAAGGCGTGGTTGCTGGTGGTGG
```

-continued

```
TGTTGCGCTGATCCGCGTAGCGTCTAAACTGGCTGACCTGCGTGGTCAGAACGAAGACCAGAACGTGGGTA
TCAAAGTTGCACTGCGTGCAATGGAAGCTCCGCTGCGTCAGATCGTATTGAACTGCGGCGAAGAACCGTCT
GTTGTTGCTAACACCGTTAAAGGCGGCGACGGCAACTACGGTTACAACGCAGCAACCGAAGAATACGGCAA
CATGATCGACATGGGTATCCTGGATCCAACCAAAGTAACTCGTTCTGCTCTGCAGTACGCAGCTTCTGTGGC
TGGCCTGATGATCACCACCGAATGCATGGTTACCGACCTGCCGAAAAACGATGCAGCTGACTTAGGCGCTG
CTGGCGGTATGGGCGGCATGGGTGGCATGGGCGGCATGATGTAACCCCCTAGCATAACCCCTTGGGGCCT
CTAAACGGGTCTTGAGGGGTTTTTTGCCCCTGAGACGCGTCAATCGAGTTCGTACCTAAGGGCGACACCCC
CTAATTAGCCCGGGCGAAAGGCCCAGTCTTTCGACTGAGCCTTTCGTTTTATTTGATGCCTGGCAGTTCCCT
ACTCTCGCATGGGGAGTCCCCACACTACCATCGGCGCTACGGCGTTTCACTTCTGAGTTCGGCATGGGGTC
AGGTGGGACCACCGCGCTACTGCCGCCAGGCAAACAAGGGGTGTTATGAGCCATATTCAGGTATAAATGGGC
TCGCGATAATGTTCAGAATTGGTTAATTGGTTGTAACACTGACCCCTATTTGTTTATTTTTCTAAATACATTC
AAATATGTATCCGCTCATGAGACAATAACCCTGATAAATGCTTCAATAATATTGAAAAAGGAAGAATATGAGC
CATATTCAACGGGAAACGTCGAGGCCGCGATTAAATTCCAACATGGATGCTGATTTATATGGGTATAAATGG
GCTCGCGATAATGTCGGGCAATCAGGTGCGACAATCTATCGCTTGTATGGGAAGCCCGATGCGCCAGAGTT
GTTTCTGAAACATGGCAAAGGTAGCGTTGCCAATGATGTTACAGATGAGATGGTCAGACTAAACTGGCTGAC
GGAATTTATGCCACTTCCGACCATCAAGCATTTTATCCGTACTCCTGATGATGCATGGTTACTCACCACTGCG
ATCCCCGGAAAAACAGCGTTCCAGGTATTAGAAGAATATCCTGATTCAGGTGAAAATATTGTTGATGCGCTG
GCAGTGTTCCTGCGCCGGTTGCACTCGATTCCTGTTTGTAATTGTCCTTTTAACAGCGATCGCGTATTTCGC
CTCGCTCAGGCGCAATCACGAATGAATAACGGTTTGGTTGATGCGAGTGATTTTGATGACGAGCGTAATGGC
TGGCCTGTTGAACAAGTCTGGAAAGAAATGCATAAACTTTTGCCATTCTCACCGGATTCAGTCGTCACTCATG
GTGATTTCTCACTTGATAACCTTATTTTTGACGAGGGGAAATTAATAGGTTGTATTGATGTTGGACGAGTCGG
AATCGCAGACCGATACCAGGATCTTGCCATCCTATGGAACTGCCTCGGTGAGTTTTCTCCTTCATTACAGAA
ACGGCTTTTTCAAAAATATGGTATTGATAATCCTGATATGAATAAATTGCAGTTTCATTTGATGCTCGATGAG
TTTTTCTAAGCGGCGCGCCATCGAATGGCGCAAAACCTTTCGCGGTATGGCATGATAGCGCCCGGAAGAGAG
TCAATTCAGGGTGGTGAATATGAAACCAGTAACGTTATACGATGTCGCAGAGTATGCCGGTGTCTCTTATCA
GACCGTTTCCCGCGTGGTGAACCAGGCCAGCCACGTTTCTGCGAAAACGCGGGAAAAAGTGGAAGCGGCG
ATGGCGGAGCTGAATTACATTCCCAACCGCGTGGCACAACAACTGGCGGGCAAACAGTCGTTGCTGATTGG
CGTTGCCACCTCCAGTCTGGCCCTGCACGCGCCGTCGCAAATTGTCGCGGCGATTAAATCTCGCGCCGATC
AACTGGGTGCCAGCGTGGTGGTGTCGATGGTAGAACGAAGCGGCGTCGAAGCCTGTAAAGCGGCGGTGCA
CAATCTTCTCGCGCAACGCGTCAGTGGGCTGATCATTAACTATCCGCTGGATGACCAGGATGCCATTGCTGT
GGAAGCTGCCTGCACTAATGTTCCGGCGTTATTTCTTGATGTCTCTGACCAGACACCCATCAACAGTATTAT
TTTCTCCCATGAGGACGGTACGCGACTGGGCGTGGAGCATCTGGTCGCATTGGGTCACCAGCAAATCGCGC
TGTTAGCGGGCCCATTAAGTTCTGTCTCGGCGCGTCTGCGTCTGGCTGGCTGGCATAAATATCTCACTCGC
AATCAAATTCAGCCGATAGCGGAACGGGAAGGCGACTGGAGTGCCATGTCCGGTTTTCAACAAACCATGCA
AATGCTGAATGAGGGCATCGTTCCCACTGCGATGCTGGTTGCCAACGATCAGATGGCGCTGGGCGCAATGC
GCGCCATTACCGAGTCCGGGCTGCGCGTTGGTGCGGATATCTCGGTAGTGGGATACGACGATACCGAAGA
TAGCTCATGTTATATCCCGCCGTTAACCACCATCAAACAGGATTTTCGCCTGCTGGGGCAAACCAGCGTGGA
CCGCTTGCTGCAACTCTCTCAGGGCCAGGCGGTGAAGGGCAATCAGCTGTTGCCAGTCTCACTGGTGAAAA
GAAAAACCACCCTGGCGCCCAATACGCAAACCGCCTCTCCCCGCGCGTTGGCCGATTCATTAATGCAGCTG
GCACGACAGGTTTCCCGACTGGAAAGCGGGCAGTGA
```

-continued

SEQ ID NO: 19: Plasmid construct T7/+term
TTAATAAGATGATCTTCTTGAGATCGTTTTGGTCTGCGCGTAATCTCTTGCTCTGAAAACGAAAAAACCGCCT

TGCAGGGCGGTTTTTCGAAGGTTCTCTGAGCTACCAACTCTTTGAACCGAGGTAACTGGCTTGGAGGAGCG

CAGTCACCAAAACTTGTCCTTTCAGTTTAGCCTTAACCGGCGCATGACTTCAAGACTAACTCCTCTAAATCAA

TTACCAGTGGCTGCTGCCAGTGGTGCTTTTGCATGTCTTTCCGGGTTGGACTCAAGACGATAGTTACCGGAT

AAGGCGCAGCGGTCGGACTGAACGGGGGGTTCGTGCATACAGTCCAGCTTGGAGCGAACTGCCTACCCGG

AACTGAGTGTCAGGCGTGGAATGAGACAAACGCGGCCATAACAGCGGAATGACACCGGTAAACCGAAAGG

CAGGAACAGGAGAGCGCACGAGGGAGCCGCCAGGGGGAAACGCCTGGTATCTTTATAGTCCTGTCGGGTT

TCGCCACCACTGATTTGAGCGTCAGATTTCGTGATGCTTGTCAGGGGGGCGGAGCCTATGGAAAAACGGCT

TTGCCGCGGCCCTCTCACTTCCCTGTTAAGTATCTTCCTGGCATCTTCCAGGAAATCTCCGCCCCGTTCGTA

AGCCATTTCCGCTCGCCGCAGTCGAACGACCGAGCGTAGCGAGTCAGTGAGCGAGGAAGCGGAATATATC

CTGTATCACATATTCTGCTGACGCACCGGTGCAGCCTTTTTTCTCCTGCCACATGAAGCACTTCACTGACAC

CCTCATCAGTGCCAACATAGTAAGCCAGTATACACTCCGCTAGCGCTGAGGTCCCGCAGCCGAACGACCGA

GCGCAGCGAGTCAGTGAGCGAGGAAGCGGAAGGCGAGAGTAGGGAACTGCCAGGCATCAAACTAAGCAGA

AGGCCCCTGACGGATGGCCTTTTTGCGTTTCTACAAACTCTTTCTGTGTTGTAAAACGACGGCCAGTCTTAA

GCTCGGGCCCCTGGGCGGTTCTGATAACGAGTAATCGTTAATCCGCAAATAACGTAAAAACCCGCTTCGG

CGGGTTTTTTATGGGGGGAGTTTAGGGAAAGAGCATTTGTCAGAATATTTAAGGGCGCCTGTCACTTTGCTTG

ATATATGAGAATTATTTAACCTTATAAATGAGAAAAAAGCAACGCACTTTAAATAAGATACGTTGCTTTTTCGA

TTGATGAACACCTATAATTAAACTATTCATCTATTATTTATGATTTTTTGTATATACAATATTTCTAGTTTGTT

AAAGAGAATTAAGAAAATAAATCTCGAAAATAATAAAGGGAAAATCAGTTTTTGATATCAAAATTATACATGTC

AACGATAATACAAAATATAATACAAACTATAAGATGTTATCAGTATTTATTATGCATTTAGAATAAATTTTGTG

TCGCCCTTCCGCGAAATTAATACGACTCACTATAGGGGAATTGTGAGCGGATAACAATTCCCCTCTAGAAATA

ATTTTGTTTAACTTTTGAAGGAGATATACATATGGCAACGTTTGACCGCAATGATCCGCAGTTGGCAGGAACG

ATGTTCCCCACCCGAATAGAGGCGAATGTCTTTGACCTTGAAATTGAGGGCGAGATCCCACGTGCAATCAAC

GGGAGCTTCTTCCGCAACACCCCCGAACCTCAGGTCACCCCGCAACCTTTCCACACCTTCATCGATGGGGA

TGGTTTGGCGTCTGCTTTTCATTTCGAAGATGGCCATGTCGACTTTGTCAGCCGTTGGGTATGTACTCCTCG

CTTTGAAGCTGAGCGGTCGGCTCGTAAATCACTCTTCGGTATGTACCGCAATCCGTTCACTGATGATCCATC

GGTAGAAGGTATTGATCGTACAGTCGCCAACACCAGTATCATCACTCATCACGGGAAAGTACTGGCCGCAAA

GGAAGATGGACTACCTTATGAGCTTGACCCCCAAACCCTGGAAACCCGAGGTCGTTATGATTACAAGGGGC

AGGTAACCAGCCATACACATACAGCGCACCCTAAGTTCGACCCCCAGACAGGTGAAATGTTACTCTTCGGCT

CCGCTGCTAAAGGCGAACGAACGCTTGATATGGCGTACTATATTGTTGATCGCTACGGCAAGGTGACACAT

GAGACCTGGTTTAAGCAGCCTTACGGTGCATTCATGCACGACTTTGCTGTCACGCGCAACTGGTCAATCTTT

CCGATCATGCCTGCGACAAATAGCCTTGAGCGTCTTAAAGCAAAGCAGCCCATTTACATGTGGGAGCCTGA

GCGAGGAAGCTATATAGGAGTACTTCCTCGTCGTGGTCAGGGCAAGGACATTCGTTGGTTCCGTGCCCCGG

CGTTGTGGGTTTTCCATGTCGTGAATGCTTGGGAGGAAGGGAATAGAATTCTGATTGACTTGATGGAAAGTG

AGATTTTGCCGTTCCCATTCCCGAACTCGCAGAACCTTCCATTTGATCCCTCCAAGGCTGTTCCGCGTCTAA

CCCGTTGGGAAATTGATCTCAATAGTGGTAACGATGAGATGAAACGTACGCAGCTACACGAATATTTTGCAG

AAATGCCTATCATGGATTTCCGTTTTGCGCTCCAGGATCATCGCTACGCCTACATGGGGGTTGACGATCCTC

GTCGCCCCTTAGCTCATCAGCAAGCTGAAAAAATCTTTGCCTACAATTCGTTAGGGGTTTGGGACAACCATC

GTAAAGATTATGAACTTTGGTTTACGGGAAAAATGTCTGCAGCGCAGGAACCGGCGTTTGTTCCTAGAAGCC

CAGATGCGCCTGAGGGCGATGGCTACCTACTCAGTGTAGTAGGGCGGCTCGATGAAAATCGTAGCGATCTA

-continued

```
GTTATCCTTGATACGCAATGTTTGGCAGCTGGGCCTGTGGCCACTGTCAAGCTTCCCTTCCGTCTCCGAGC
AGCGTTGCACGGTTGTTGGCAGTCTAAGAACTGACTAGCATAACCCCTTGGGGCCTCTAAACGGGTCTTGAG
GGGTTTTTTGGCATCCTGTCCATGACTCGGTAATACGACTCACTATAGGGGAATTGTGAGCGGATAACAATT
CCCTCTAGAAATAATTTTGTTTAACTTTTAAAGGAGAGTTATCAATGAATATTCGTCCATTGCATGATCGCG
TGATCGTCAAGCGTAAAGAAGTTGAAACTAAATCTGCTGGCGGCATCGTTCTGACCGGCTCTGCAGCGGCTA
AATCCACCCGCGGCGAAGTGCTGGCTGTCGGCAATGGCCGTATCCTTGAAAATGGCGAAGTGAAGCCGCTG
GATGTGAAAGTTGGCGACATCGTTATTTTCAACGATGGCTACGGTGTGAAATCTGAGAAGATCGACAATGAA
GAAGTGTTGATCATGTCCGAAAGCGACATTCTGGCAATTGTTGAAGCGTAATCCGCGCACGACACTGAACAT
ACGAATTTAAGGAATAAAGATAATGGCAGCTAAAGACGTAAAATTCGGTAACGACGCTCGTGTGAAAATGCT
GCGCGGCGTAAACGTACTGGCAGATGCAGTGAAAGTTACCCTCGGTCCAAAAGGCCGTAACGTAGTTCTGG
ATAAATCTTTCGGTGCACCGACCATCACCAAAGATGGTGTTTCCGTTGCTCGTGAAATCGAACTGGAAGACA
AGTTCGAAAATATGGGTGCGCAGATGGTGAAAGAAGTTGCCTCTAAAGCAAACGACGCTGCAGGCGACGGT
ACCACCACTGCAACCGTACTGGCTCAGGCTATCATCACTGAAGGTCTGAAAGCTGTTGCTGCGGGCATGAA
CCCGATGGACCTGAAACGTGGTATCGACAAAGCGGTTACCGCTGCAGTTGAAGAACTGAAAGCGCTGTCCG
TACCATGCTCTGACTCTAAAGCGATTGCTCAGGTTGGTACCATCTCCGCTAACTCCGACGAAACCGTAGGTA
AACTGATCGCTGAAGCGATGGACAAAGTCGGTAAAGAAGGCGTTATCACCGTTGAAGACGGTACCGGTCTG
CAGGACGAACTGGACGTGGTTGAAGGTATGCAGTTCGACCGTGGCTACCTGTCTCCTTACTTCATCAACAAG
CCGGAAACTGGCGCAGTAGAACTGGAAAGCCCGTTCATCCTGCTGGCTGACAAGAAAATCTCCAACATCCG
CGAAATGCTGCCGGTTCTGGAAGCTGTTGCCAAAGCAGGCAAACCGCTGCTGATCATCGCTGAAGATGTAG
AAGGCGAAGCGCTGGCAACTCTGGTTGTTAACACCATGCGTGGCATCGTGAAAGTCGCTGCGGTTAAAGCA
CCCGGGCTTCGGCGATCGTCGTAAAGCTATGCTGCAGGATATCGCAACCCTGACTGGCGGTACCGTGATCTC
TGAAGAGATCGGTATGGAGCTGGAAAAAGCAACCCTGGAAGACCTGGGTCAGGCTAAACGTGTTGTGATCA
ACAAAGACACCACCACTATCATCGATGGCGTGGGTGAAGAAGCTGCAATCCAGGGCCGTGTTGCTCAGATC
CGTCAGCAGATTGAAGAAGCAACTTCTGACTACGACCGTGAAAAACTGCAGGAACGCGTAGCGAAACTGGC
AGGCGGCGTTGCAGTTATCAAAGTGGGTGCTGCTACCGAAGTTGAAATGAAAGAGAAAAAAGCACGCGTTG
AAGATGCCCTGCACGCGACCCGTGCTGCGGTAGAAGAAGGCGTGGTTGCTGGTGGTGGTGTTGCGCTGAT
CCGCGTAGCGTCTAAACTGGCTGACCTGCGTGGTCAGAACGAAGACCAGAACGTGGGTATCAAAGTTGCAC
TGCGTGCAATGGAAGCTCCGCTGCGTCAGATCGTATTGAACTGCGGCGAAGAACCGTCTGTTGTTGCTAAC
ACCGTTAAAGGCGGCGACGGCAACTACGGTTACAACGCAGCAACCGAAGAATACGGCAACATGATCGACAT
GGGTATCCTGGATCCAACCAAAGTAACTCGTTCTGCTCTGCAGTACGCAGCTTCTGTGGCTGGCCTGATGAT
CACCACCGAATGCATGGTTACCGACCTGCCGAAAAACGATGCAGCTGACTTAGGCGCTGCTGGCGGTATGG
GCGGCATGGGTGGCATGGGCGGCATGATGTAACCCCCTAGCATAACCCCTTGGGGCCTCTAAACGGGTCT
TGAGGGGTTTTTTGCCCCTGAGACGCGTCAATCGAGTTCGTACCTAAGGGCGACACCCCCTAATTAGCCCG
GGCGAAAGGCCCAGTCTTTCGACTGAGCCTTTCGTTTTATTTGATGCCTGGCAGTTCCCTACTCTCGCATGG
GGAGTCCCCACACTACCATCGGCGCTACGGCGTTTCACTTCTGAGTTCGGCATGGGGTCAGGTGGGACCAC
CGCGCTACTGCCGCCAGGCAAACAAGGGGTGTTATGAGCCATATTCAGGTATAAATGGGCTCGCGATAATGT
TCAGAATTGGTTAATTGGTTGTAACACTGACCCCTATTTGTTTATTTTTCTAAATACATTCAAATATGTATCC
GCTCATGAGACAATAACCCTGATAAATGCTTCAATAATATTGAAAAAGGAAGAATATGAGCCATATTCAACG
GGAAACGTCGAGGCCGCGATTAAATTCCAACATGGATGCTGATTTATATGGGTATAAATGGGCTCGCGATAA
TGTCGGGCAATCAGGTGCGACAATCTATCGCTTGTATGGGAAGCCCGATGCGCCAGAGTTGTTTCTGAAACA
TGGCAAAGGTAGCGTTGCCAATGATGTTACAGATGAGATGGTCAGACTAAACTGGCTGACGGAATTTATGCC
```

ACTTCCGACCATCAAGCATTTTATCCGTACTCCTGATGATGCATGGTTACTCACCACTGCGATCCCCGGAAA

AACAGCGTTCCAGGTATTAGAAGAATATCCTGATTCAGGTGAAAATATTGTTGATGCGCTGGCAGTGTTCCT

GCGCCGGTTGCACTCGATTCCTGTTTGTAATTGTCCTTTTAACAGCGATCGCGTATTTCGCCTCGCTCAGGC

GCAATCACGAATGAATAACGGTTTGGTTGATGCGAGTGATTTTGATGACGAGCGTAATGGCTGGCCTGTTGA

ACAAGTCTGGAAAGAAATGCATAAACTTTTGCCATTCTCACCGGATTCAGTCGTCACTCATGGTGATTTCTCA

CTTGATAACCTTATTTTTGACGAGGGGAAATTAATAGGTTGTATTGATGTTGGACGAGTCGGAATCGCAGAC

CGATACCAGGATCTTGCCATCCTATGGAACTGCCTCGGTGAGTTTTCTCCTTCATTACAGAAACGGCTTTTTC

AAAAATATGGTATTGATAATCCTGATATGAATAAATTGCAGTTTCATTTGATGCTCGATGAGTTTTTCTAAG

CGGCGCGCCATCGAATGGCGCAAAACCTTTCGCGGTATGGCATGATAGCGCCCGAAGAGAGTCAATTCAGG

GTGGTGAATATGAAACCAGTAACGTTATACGATGTCGCAGAGTATGCCGGTGTCTCTTATCAGACCGTTTCC

CGCGTGGTGAACCAGGCCAGCCACGTTTCTGCGAAAACGCGGGAAAAAGTGGAAGCGGCGATGGCGGAG

CTGAATTACATTCCCAACCGCGTGGCACAACAACTGGCGGGCAAACAGTCGTTGCTGATTGGCGTTGCCAC

CTCCAGTCTGGCCCTGCACGCGCCGTCGCAAATTGTCGCGGCGATTAAATCTCGCGCCGATCAACTGGGTG

CCAGCGTGGTGGTGTCGATGGTAGAACGAAGCGGCGTCGAAGCCTGTAAAGCGGCGGTGCACAATCTTCT

CGCGCAACGCGTCAGTGGGCTGATCATTAACTATCCGCTGGATGACCAGGATGCCATTGCTGTGGAAGCTG

CCTGCACTAATGTTCCGGCGTTATTTCTTGATGTCTCTGACCAGACACCCATCAACAGTATTATTTTCTCC

CATGAGGACGGTACGCGACTGGGCGTGGAGCATCTGGTCGCATTGGGTCACCAGCAAATCGCGCTGTTAGCG

GGCCCATTAAGTTCTGTCTCGGCGCGTCTGCGTCTGGCTGGCTGGCATAAATATCTCACTCGCAATCAAAT

TCAGCCGATAGCGGAACGGGAAGGCGACTGGAGTGCCATGTCCGGTTTTCAACAAACCATGCAAATGCTGA

ATGAGGGCATCGTTCCCACTGCGATGCTGGTTGCCAACGATCAGATGGCGCTGGGCGCAATGCGCGCCATT

ACCGAGTCCGGGCTGCGCGTTGGTGCGGATATCTCGGTAGTGGGATACGACGATACCGAAGATAGCTCAT

GTTATATCCCGCCGTTAACCACCATCAAACAGGATTTTCGCCTGCTGGGGCAAACCAGCGTGGACCGCTTG

CTGCAACTCTCTCAGGGCCAGGCGGTGAAGGGCAATCAGCTGTTGCCAGTCTCACTGGTGAAAAGAAAAAC

CACCCTGGCGCCCAATACGCAAACCGCCTCTCCCCGCGCGTTGGCCGATTCATTAATGCAGCTGGCACGAC

AGGTTTCCCGACTGGAAAGCGGGCAGTGA

SEQ ID NO: 20: Plasmid construct T5/+term
TTAATAAGATGATCTTCTTGAGATCGTTTTGGTCTGCGCGTAATCTCTTGCTCTGAAAACGAAAAAACCGCCT

TGCAGGGCGGTTTTTCGAAGGTTCTCTGAGCTACCAACTCTTTGAACCGAGGTAACTGGCTTGGAGGAGCG

CAGTCACCAAAACTTGTCCTTTCAGTTTAGCCTTAACCGGCGCATGACTTCAAGACTAACTCCTCTAAATCAA

TTACCAGTGGCTGCTGCCAGTGGTGCTTTTGCATGTCTTTCCGGGTTGGACTCAAGACGATAGTTACCGGAT

AAGGCGCAGCGGTCGGACTGAACGGGGGGTTCGTGCATACAGTCCAGCTTGGAGCGAACTGCCTACCCGG

AACTGAGTGTCAGGCGTGGAATGAGACAAACGCGGCCATAACAGCGGAATGACACCGGTAAACCGAAAGG

CAGGAACAGGAGAGCGCACGAGGGAGCCGCCAGGGGGAAACGCCTGGTATCTTTATAGTCCTGTCGGGTT

TCGCCACCACTGATTTGAGCGTCAGATTTCGTGATGCTTGTCAGGGGGGCGGAGCCTATGGAAAAACGGCT

TTGCCGCGGCCCTCTCACTTCCCTGTTAAGTATCTTCCTGGCATCTTCCAGGAAATCTCCGCCCCGTTCGTA

AGCCATTTCCGCTCGCCGCAGTCGAACGACCGAGCGTAGCGAGTCAGTGAGCGAGGAAGCGGAATATATC

CTGTATCACATATTCTGCTGACGCACCGGTGCAGCCTTTTTTCTCCTGCCACATGAAGCACTTCACTGACAC

CCTCATCAGTGCCAACATAGTAAGCCAGTATACACTCCGCTAGCGCTGAGGTCCCGCAGCCGAACGACCGA

GCGCAGCGAGTCAGTGAGCGAGGAAGCGGAAGGCGAGAGTAGGGAACTGCCAGGCATCAAACTAAGCAGA

AGGCCCCTGACGGATGGCCTTTTTGCGTTTCTACAAACTCTTTCTGTGTTGTAAAACGACGGCCAGTCTTAA

GCTCGGGCCCCCTGGGCGGTTCTGATAACGAGTAATCGTTAATCCGCAAATAACGTAAAAACCCGCTTCGG

-continued

CGGGTTTTTTTATGGGGGGAGTTTAGGGAAAGAGCATTTGTCAGAATATTTAAGGGCGCCTGTCACTTTGCTTG
ATATATGAGAATTATTTAACCTTATAAATGAGAAAAAAGCAACGCACTTTAAATAAGATACGTTGCTTTTTCGA
TTGATGAACACCTATAATTAAACTATTCATCTATTATTTATGATTTTTTGTATATACAATATTTCTAGTTTGTT
AAAGAGAATTAAGAAAATAAATCTCGAAAATAATAAAGGGAAAATCAGTTTTTGATATCAAAATTATACATGTC
AACGATAATACAAAATATAATACAAACTATAAGATGTTATCAGTATTTATTATGCATTTAGAATAAATTTTGTG
TCGCCCTTCCGCGAAATTAATACGACTCACTATAGGGGAATTGTGAGCGGATAACAATTCCCCTCTAGAAATA
ATTTTGTTTAACTTTTGAAGGAGATATACATATGGCAACGTTTGACCGCAATGATCCGCAGTTGGCAGGAACG
ATGTTCCCCACCCGAATAGAGGCGAATGTCTTTGACCTTGAAATTGAGGGCGAGATCCCACGTGCAATCAAC
GGGAGCTTCTTCCGCAACACCCCCGAACCTCAGGTCACCCCGCAACCTTTCCACACCTTCATCGATGGGGA
TGGTTTGGCGTCTGCTTTTCATTTCGAAGATGGCCATGTCGACTTTGTCAGCCGTTGGGTATGTACTCCTCG
CTTTGAAGCTGAGCGGTCGGCTCGTAAATCACTCTTCGGTATGTACCGCAATCCGTTCACTGATGATCCATC
GGTAGAAGGTATTGATCGTACAGTCGCCAACACCAGTATCATCACTCATCACGGGAAAGTACTGGCCGCAAA
GGAAGATGGACTACCTTATGAGCTTGACCCCCAAACCCTGGAAACCCGAGGTCGTTATGATTACAAGGGGC
AGGTAACCAGCCATACACATACAGCGCACCCTAAGTTCGACCCCCAGACAGGTGAAATGTTACTCTTCGGCT
CCGCTGCTAAAGGCGAACGAACGCTTGATATGGCGTACTATATTGTTGATCGCTACGGCAAGGTGACACAT
GAGACCTGGTTTAAGCAGCCTTACGGTGCATTCATGCACGACTTTGCTGTCACGCGCAACTGGTCAATCTTT
CCGATCATGCCTGCGACAAATAGCCTTGAGCGTCTTAAAGCAAAGCAGCCCATTTACATGTGGGAGCCTGA
GCGAGGAAGCTATATAGGAGTACTTCCTCGTCGTGGTCAGGGCAAGGACATTCGTTGGTTCCGTGCCCCGG
CGTTGTGGGTTTTCCATGTCGTGAATGCTTGGGAGGAAGGGAATAGAATTCTGATTGACTTGATGGAAAGTG
AGATTTTGCCGTTCCCATTCCCGAACTCGCAGAACCTTCCATTTGATCCCTCCAAGGCTGTTCCGCGTCTAA
CCCGTTGGGAAATTGATCTCAATAGTGGTAACGATGAGATGAAACGTACGCAGCTACACGAATATTTTGCAG
AAATGCCTATCATGGATTTCCGTTTTGCGCTCCAGGATCATCGCTACGCCTACATGGGGGTTGACGATCCTC
GTCGCCCCTTAGCTCATCAGCAAGCTGAAAAAATCTTTGCCTACAATTCGTTAGGGGTTTGGGACAACCATC
GTAAAGATTATGAACTTTGGTTTACGGGAAAAATGTCTGCAGCGCAGGAACCGGCGTTTGTTCCTAGAAGCC
CAGATGCGCCTGAGGGCGATGGCTACCTACTCAGTGTAGTAGGGCGGCTCGATGAAAATCGTAGCGATCTA
GTTATCCTTGATACGCAATGTTTGGCAGCTGGGCCTGTGGCCACTGTCAAGCTTCCCTTCCGTCTCCGAGCA
GCGTTGCACGGTTGTTGGCAGTCTAAGAACTGACTAGCATAACCCCTTGGGGCCTCTAAACGGGTCTTGAG
GGGTTTTTTGGCATCCTGTCCATGACTCGGAAATCATAAAAAATTTATTTGCTTTGTGAGCGGATAACAATT
ATAATACCCTCTAGAAATAATTTTGTTTAACTTTTAAAGGAGAGTTATCAATGAATATTCGTCCATTGCATG
ATCGCGTGATCGTCAAGCGTAAAGAAGTTGAAACTAAATCTGCTGGCGGCATCGTTCTGACCGGCTCTGCAG
CGGCTAAATCCACCCGCGGCGAAGTGCTGGCTGTCGGCAATGGCCGTATCCTTGAAAATGGCGAAGTGAAGC
CGCTGGATGTGAAAGTTGGCGACATCGTTATTTTCAACGATGGCTACGGTGTGAAATCTGAGAAGATCGACA
ATGAAGAAGTGTTGATCATGTCCGAAAGCGACATTCTGGCAATTGTTGAAGCGTAATCCGCGCACGACACTG
AACATACGAATTTAAGGAATAAAGATAATGGCAGCTAAAGACGTAAAATTCGGTAACGACGCTCGTGTGAAAA
TGCTGCGCGGCGTAAACGTACTGGCAGATGCAGTGAAAGTTACCCTCGGTCCAAAAGGCCGTAACGTAGTTC
TGGATAAATCTTTCGGTGCACCGACCATCACCAAAGATGGTGTTTCCGTTGCTCGTGAAATCGAACTGGAAG
ACAAGTTCGAAAATATGGGTGCGCAGATGGTGAAAGAAGTTGCCTCTAAAGCAAACGACGCTGCAGGCGAC
GGTACCACCACTGCAACCGTACTGGCTCAGGCTATCATCACTGAAGGTCTGAAAGCTGTTGCTGCGGGCAT
GAACCCGATGGACCTGAAACGTGGTATCGACAAAGCGGTTACCGCTGCAGTTGAAGAACTGAAAGCGCTGT
CCGTACCATGCTCTGACTCTAAAGCGATTGCTCAGGTTGGTACCATCTCCGCTAACTCCGACGAAACCGTAG

-continued

```
GTAAACTGATCGCTGAAGCGATGGACAAAGTCGGTAAAGAAGGCGTTATCACCGTTGAAGACGGTACCGGT
CTGCAGGACGAACTGGACGTGGTTGAAGGTATGCAGTTCGACCGTGGCTACCGTGTCTCCTTACTTCATCAAC
AAGCCGGAAACTGGCGCAGTAGAACTGGAAAGCCCGTTCATCCTGCTGGCTGACAAGAAAATCTCCAACAT
CCGCGAAATGCTGCCGGTTCTGGAAGCTGTTTGCCAAAGCAGGCAAACCGCTGCTGATCATCGCTGAAGATG
TAGAAGGCGAAGCGCTGGCAACTCTGGTTGTTAACACCATGCGTGGCATCGTGAAAGTCGCTGCGGTTAAA
GCACCGGGCTTCGGCGATCGTCGTAAAGCTATGCTGCAGGATATCGCAACCCTGACTGGCGGTACCGTGAT
CTCTGAAGAGATCGGTATGGAGCTGGAAAAAGCAACCCTGGAAGACCTGGGTCAGGCTAAACGTGTTGTGA
TCAACAAAGACACCACCACTATCATCGATGGCGTGGGTGAAGAAGCTGCAATCCAGGGCCGTGTTGCTCAG
ATCCGTCAGCAGATTGAAGAAGCAACTTCTGACTACGACCGTGAAAAACTGCAGGAACGCGTAGCGAAACT
GGCAGGCGGCGTTGCAGTTATCAAAGTGGGTGCTGCTACCGAAGTTGAAATGAAAGAGAAAAAAGCACGCG
TTGAAGATGCCCTGCACGCGACCCGTGCTGCGGTAGAAGAAGGCGTGGTTGCTGGTGGTGGTGTTGCGCT
GATCCGCGTAGCGTCTAAACTGGCTGACCTGCGTGGTCAGAACGAAGACCAGAACGTGGGTATCAAAGTTG
CACTGCGTGCAATGGAAGCTCCGCTGCGTCAGATCGTATTGAACTGCGGCGAAGAACCGTCTGTTGTTGCT
AACACCGTTAAAGGCGGCGACGGCAACTACGGTTACAACGCAGCAACCGAAGAATACGGCAACATGATCGA
CATGGGTATCCTGGATCCAACCAAAGTAACTCGTTCTGCTCTGCAGTACGCAGCTTCTGTGGCTGGCCTGAT
GATCACCACCGAATGCATGGTTACCGACCTGCCGAAAAACGATGCAGCTGACTTAGGCGCTGCTGGCGGTA
TGGGCGGCATGGGTGGCATGGGCGGCATGATGTAACCCCCTAGCATAACCCCTTGGGGCCTCTAAACGGG
TCTTGAGGGGTTTTTTGCCCCTGAGACGCGTCAATCGAGTTCGTACCTAAGGGCGACACCCCCTAATTAGCC
CGGGCGAAAGGCCCAGTCTTTCGACTGAGCCTTTCGTTTTATTTGATGCCTGGCAGTTCCCTACTCTCGCAT
GGGGAGTCCCCACACTACCATCGGCGCTACGGCGTTTCACTTCTGAGTTCGGCATGGGGTCAGGTGGGACCA
CCGCGCTACTGCCGCCAGGCAAACAAGGGGTGTTATGAGCCATATTCAGGTATAAATGGGCTCGCGATAATG
TTCAGAATTGGTTAATTGGTTGTAACACTGACCCCTATTTGTTTATTTTTCTAAATACATTCAAATATGTAT
CCGCTCATGAGACAATAACCCTGATAAATGCTTCAATAATATTGAAAAAGGAAGAATATGAGCCATATTCAAC
GGGAAACGTCGAGGCCGCGATTAAATTCCAACATGGATGCTGATTTATATGGGTATAAATGGGCTCGCGATA
ATGTCGGGCAATCAGGTGCGACAATCTATCGCTTGTATGGGAAGCCCGATGCGCCAGAGTTGTTTCTGAAA
CATGGCAAAGGTAGCGTTGCCAATGATGTTACAGATGAGATGGTCAGACTAAACTGGCTGACGGAATTTATG
CCACTTCCGACCATCAAGCATTTTATCCGTACTCCTGATGATGCATGGTTACTCACCACTGCGATCCCCGGA
AAAACAGCGTTCCAGGTATTAGAAGAATATCCTGATTCAGGTGAAAATATTGTTGATGCGCTGGCAGTGTTC
CTGCGCCGGTTGCACTCGATTCCTGTTTGTAATTGTCCTTTTAACAGCGATCGCGTATTTCGCCTCGCTCAG
GCGCAATCACGAATGAATAACGGTTTGGTTGATGCGAGTGATTTTGATGACGAGCGTAATGGCTGGCCTGTT
GAACAAGTCTGGAAAGAAATGCATAAACTTTTGCCATTCTCACCGGATTCAGTCGTCACTCATGGTGATTTCT
CACTTGATAACCTTATTTTTGACGAGGGGAAATTAATAGGTTGTATTGATGTTGGACGAGTCGGAATCGCAGA
CCGATACCAGGATCTTGCCATCCTATGGAACTGCCTCGGTGAGTTTTCTCCTTCATTACAGAAACGGCTTTTT
CAAAAATATGGTATTGATAATCCTGATATGAATAAATTGCAGTTTCATTTGATGCTCGATGAGTTTTTCTAA
GCGGCGCGCCATCGAATGGCGCAAAACCTTTCGCGGTATGGCATGATAGCGCCCGGAAGAGAGTCAATTCAG
GGTGGTGAATATGAAACCAGTAACGTTATACGATGTCGCAGAGTATGCCGGTGTCTCTTATCAGACCGTTTC
CCGCGTGGTGAACCAGGCCAGCCACGTTTCTGCGAAAACGCGGGAAAAGTGGAAGCGGCGATGGCGGA
GCTGAATTACATTCCCAACCGCGTGGCACAACAACTGGCGGGCAAACAGTCGTTGCTGATTGGCGTTGCCA
CCTCCAGTCTGGCCCTGCACGCGCCGTCGCAAATTGTCGCGGCGATTAAATCTCGCGCCGATCAACTGGGT
GCCAGCGTGGTGGTGTCGATGGTAGAACGAAGCGGCGTCGAAGCCTGTAAAGCGGCGGTGCACAATCTTC
TCGCGCAACGCGTCAGTGGGCTGATCATTAACTATCCGCTGGATGACCAGGATGCCATTGCTGTGGAAGCT
```

```
GCCTGCACTAATGTTCCGGCGTTATTTCTTGATGTCTCTGACCAGACACCCATCAACAGTATTATTTTCTCCC

ATGAGGACGGTACGCGACTGGGCGTGGAGCATCTGGTCGCATTGGGTCACCAGCAAATCGCGCTGTTAGC

GGGCCCATTAAGTTCTGTCTCGGCGCGTCTGCGTCTGGCTGGCTGGCATAAATATCTCACTCGCAATCAAAT

TCAGCCGATAGCGGAACGGGAAGGCGACTGGAGTGCCATGTCCGGTTTTCAACAAACCATGCAAATGCTGA

ATGAGGGCATCGTTCCCACTGCGATGCTGGTTGCCAACGATCAGATGGCGCTGGGCGCAATGCGCGCCAT

TACCGAGTCCGGGCTGCGCGTTGGTGCGGATATCTCGGTAGTGGGATACGACGATACCGAAGATAGCTCAT

GTTATATCCCGCCGTTAACCACCATCAAACAGGATTTTCGCCTGCTGGGGCAAACCAGCGTGGACCGCTTG

CTGCAACTCTCTCAGGGCCAGGCGGTGAAGGGCAATCAGCTGTTGCCAGTCTCACTGGTGAAAAGAAAAAC

CACCCTGGCGCCCAATACGCAAACCGCCTCTCCCCGCGCGTTGGCCGATTCATTAATGCAGCTGGCACGAC

AGGTTTCCCGACTGGAAAGCGGGCAGTGA
```

SEQ ID NO: 21: Plasmid construct H10/+term
```
TTAATAAGATGATCTTCTTGAGATCGTTTTGGTCTGCGCGTAATCTCTTGCTCTGAAAACGAAAAAACCGCCT

TGCAGGGCGGTTTTTCGAAGGTTCTCTGAGCTACCAACTCTTTGAACCGAGGTAACTGGCTTGGAGGAGCG

CAGTCACCAAAACTTGTCCTTTCAGTTTAGCCTTAACCGGCGCATGACTTCAAGACTAACTCCTCTAAATCAA

TTACCAGTGGCTGCTGCCAGTGGTGCTTTTGCATGTCTTTCCGGGTTGGACTCAAGACGATAGTTACCGGAT

AAGGCGCAGCGGTCGGACTGAACGGGGGGTTCGTGCATACAGTCCAGCTTGGAGCGAACTGCCTACCCGG

AACTGAGTGTCAGGCGTGGAATGAGACAAACGCGGCCATAACAGCGGAATGACACCGGTAAACCGAAAGG

CAGGAACAGGAGAGCGCACGAGGGAGCCGCCAGGGGGAAACGCCTGGTATCTTTATAGTCCTGTCGGGTT

TCGCCACCACTGATTTGAGCGTCAGATTTCGTGATGCTTGTCAGGGGGCGGAGCCTATGGAAAAACGGCT

TTGCCGCGGCCCTCTCACTTCCCTGTTAAGTATCTTCCTGGCATCTTCCAGGAAATCTCCGCCCCGTTCGTA

AGCCATTTCCGCTCGCCGCAGTCGAACGACCGAGCGTAGCGAGTCAGTGAGCGAGGAAGCGGAATATATC

CTGTATCACATATTCTGCTGACGCACCGGTGCAGCCTTTTTTCTCCTGCCACATGAAGCACTTCACTGACAC

CCTCATCAGTGCCAACATAGTAAGCCAGTATACACTCCGCTAGCGCTGAGGTCCCGCAGCCGAACGACCGA

GCGCAGCGAGTCAGTGAGCGAGGAAGCGGAAGGCGAGAGTAGGGAACTGCCAGGCATCAAACTAAGCAGA

AGGCCCCTGACGGATGGCCTTTTTGCGTTTCTACAAACTCTTTCTGTGTTGTAAAACGACGGCCAGTCTTAA

GCTCGGGCCCCTGGGCGGTTCTGATAACGAGTAATCGTTAATCCGCAAATAACGTAAAAACCCGCTTCGG

CGGGTTTTTTTATGGGGGGAGTTTAGGGAAAGAGCATTTGTCAGAATATTTAAGGGCGCCTGTCACTTTGCT

TGATATATGAGAATTATTTAACCTTATAAATGAGAAAAAAGCAACGCACTTTAAATAAGATACGTTGCTTTTTC

GATTGATGAACACCTATAATTAAACTATTCATCTATTATTTATGATTTTTTGTATATACAATATTTCTAGTTTG

TTAAAGAGAATTAAGAAAATAAATCTCGAAAATAATAAAGGGAAAATCAGTTTTTGATATCAAAATTATACATG

TCAACGATAATACAAAATATAATACAAACTATAAGATGTTATCAGTATTTATTATGCATTTAGAATAAATTTTGT

GTCGCCCTTCCGCGAAATTAATACGACTCACTATAGGGGAATTGTGAGCGGATAACAATTCCCCTCTAGAAATA

ATTTTGTTTAACTTTTGAAGGAGATATACATATGGCAACGTTTGACCGCAATGATCCGCAGTTGGCAGGAACG

ATGTTCCCCACCCGAATAGAGGCGAATGTCTTTGACCTTGAAATTGAGGGCGAGATCCCACGTGCAATCAAC

GGGAGCTTCTTCCGCAACACCCCCGAACCTCAGGTCACCCCGCAACCTTTCCACACCTTCATCGATGGGGA

TGGTTTGGCGTCTGCTTTTCATTTCGAAGATGGCCATGTCGACTTTGTCAGCCGTTGGGTATGTACTCCTCG

CTTTGAAGCTGAGCGGTCGGCTCGTAAATCACTCTTCGGTATGTACCGCAATCCGTTCACTGATGATCCATC

GGTAGAAGGTATTGATCGTACAGTCGCCAACACCAGTATCATCACTCATCACGGGAAAGTACTGGCCGCAAA

GGAAGATGGACTACCTTATGAGCTTGACCCCCAAACCCTGGAAACCCGAGGTCGTTATGATTACAAGGGGC

AGGTAACCAGCCATACACATACAGCGCACCCTAAGTTCGACCCCCAGACAGGTGAAATGTTACTCTTCGGCT

CCGCTGCTAAAGGCGAACGAACGCTTGATATGGCGTACTATATTGTTGATCGCTACGGCAAGGTGACACAT
```

-continued

```
GAGACCTGGTTTAAGCAGCCTTACGGTGCATTCATGCACGACTTTGCTGTCACGCGCAACTGGTCAATCTTT

CCGATCATGCCTGCGACAAATAGCCTTGAGCGTCTTAAAGCAAAGCAGCCCATTTACATGTGGGAGCCTGA

GCGAGGAAGCTATATAGGAGTACTTCCTCGTCGTGGTCAGGGCAAGGACATTCGTTGGTTCCGTGCCCCGG

CGTTGTGGGTTTTCCATGTCGTGAATGCTGGGAGGAAGGGAATAGAATTCTGATTGACTTGATGGAAAGTG

AGATTTTGCCGTTCCCATTCCCGAACTCGCAGAACCTTCCATTTGATCCCTCCAAGGCTGTTCCGCGTCTAA

CCCGTTGGGAAATTGATCTCAATAGTGGTAACGATGAGATGAAACGTACGCAGCTACACGAATATTTTGCAG

AAATGCCTATCATGGATTTCCGTTTTGCGCTCCAGGATCATCGCTACGCCTACATGGGGGTTGACGATCCTC

GTCGCCCCTTAGCTCATCAGCAAGCTGAAAAAATCTTTGCCTACAATTCGTTAGGGGTTTGGGACAACCATC

GTAAAGATTATGAACTTTGGTTTACGGGAAAAATGTCTGCAGCGCAGGAACCGGCGTTTGTTCCTAGAAGCC

CAGATGCGCCTGAGGGCGATGGCTACCTACTCAGTGTAGTAGGGCGGCTCGATGAAAATCGTAGCGATCTA

GTTATCCTTGATACGCAATGTTTGGCAGCTGGGCCTGTGGCCACTGTCAAGCTTCCCTTCCGTCTCCGAGCA

GCGTTGCACGGTTGTTGGCAGTCTAAGAACTGACTAGCATAACCCCTTGGGGCCTCTAAACGGGTCTTGAG

GGGTTTTTTGGCATCCTGTCCATGACTCGGTAATACGACTCACTACGGAAGAATTGTGAGCGGATAACAATT

CCCTCTAGAAATAATTTTGTTTAACTTTTAAAGGAGAGTTATCAATGAATATTCGTCCATTGCATGATCGCGTG

ATCGTCAAGCGTAAAGAAGTTGAAACTAAATCTGCTGGCGGCATCGTTCTGACCGGCTCTGCAGCGGCTAA

ATCCACCCGCGGCGAAGTGCTGGCTGTCGGCAATGGCCGTATCCTTGAAAATGGCGAAGTGAAGCCGCTG

GATGTGAAAGTTGGCGACATCGTTATTTTCAACGATGGCTACGGTGTGAAATCTGAGAAGATCGACAATGAA

GAAGTGTTGATCATGTCCGAAAGCGACATTCTGGCAATTGTTGAAGCGTAATCCGCGCACGACACTGAACAT

ACGAATTTAAGGAATAAAGATAATGGCAGCTAAAGACGTAAAATTCGGTAACGACGCTCGTGTGAAAATGCT

GCGCGGCGTAAACGTACTGGCAGATGCAGTGAAAGTTACCCTCGGTCCAAAAGGCCGTAACGTAGTTCTGG

ATAAATCTTTCGGTGCACCGACCATCACCAAAGATGGTGTTTCCGTTGCTCGTGAAATCGAACTGGAAGACA

AGTTCGAAAATATGGGTGCGCAGATGGTGAAAGAAGTTGCCTCTAAAGCAAACGACGCTGCAGGCGACGGT

ACCACCACTGCAACCGTACTGGCTCAGGCTATCATCACTGAAGGTCTGAAAGCTGTTGCTGCGGGCATGAA

CCCGATGGACCTGAAACGTGGTATCGACAAAGCGGTTACCGCTGCAGTTGAAGAACTGAAAGCGCTGTCCG

TACCATGCTCTGACTCTAAAGCGATTGCTCAGGTTGGTACCATCTCCGCTAACTCCGACGAAACCGTAGGTA

AACTGATCGCTGAAGCGATGGACAAAGTCGGTAAAGAAGGCGTTATCACCGTTGAAGACGGGTACCGGTCTG

CAGGACGAACTGGACGTGGTTGAAGGTATGCAGTTCGACCGTGGCTACCTGTCTCCTTACTTCATCAACAAG

CCGGAAACTGGCGCAGTAGAACTGGAAAGCCCGTTCATCCTGCTGGCTGACAAGAAAATCTCCAACATCCG

CGAAATGCTGCCGGTTCTGGAAGCTGTTGCCAAAGCAGGCAAACCGCTGCTGATCATCGCTGAAGATGTAG

AAGGCGAAGCGCTGGCAACTCTGGTTGTTAACACCATGCGTGGCATCGTGAAAGTCGCTGCGGTTAAAGCA

CCGGGCTTCGGCGATCGTCGTAAAGCTATGCTGCAGGATATCGCAACCCTGACTGGCGGTACCGTGATCTC

TGAAGAGATCGGTATGGAGCTGGAAAAAGCAACCCTGGAAGACCTGGGTCAGGCTAAACGTGTTGTGATCA

ACAAAGACACCACCACTATCATCGATGGCGTGGGTGAAGAAGCTGCAATCCAGGGCCGTGTTGCTCAGATC

CGTCAGCAGATTGAAGAAGCAACTTCTGACTACGACCGTGAAAAACTGCAGGAACGCGTAGCGAAACTGGC

AGGCGGCGTTGCAGTTATCAAAGTGGGTGCTGCTACCGAAGTTGAAATGAAAGAGAAAAAAGCACGCGTTG

AAGATGCCCTGCACGCGACCCGTGCTGCGGTAGAAGAAGGCGTGGTTGCTGGTGGTGGTGTTGCGCTGAT

CCGCGTAGCGTCTAAACTGGCTGACCTGCGTGGTCAGAACGAAGACCAGAACGTGGGTATCAAAGTTGCAC

TGCGTGCAATGGAAGCTCCGCTGCGTCAGATCGTATTGAACTGCGGCGAAGAACCGTCTGTTGTTGCTAAC

ACCGTTAAAGGCGGCGACGGCAACTACGGTTACAACGCAGCAACCGAAGAATACGGCAACATGATCGACAT

GGGTATCCTGGATCCAACCAAAGTAACTCGTTCTGCTCTGCAGTACGCAGCTTCTGTGGCTGGCCTGATGAT
```

-continued

CACCACCGAATGCATGGTTACCGACCTGCCGAAAAACGATGCAGCTGACTTAGGCGCTGCTGGCGGTATGG
GCGGCATGGGTGGCATGGGCGGCATGATGTAACCCCCTAGCATAACCCCTTGGGGCCTCTAAACGGGTCT
TGAGGGGTTTTTTGCCCCTGAGACGCGTCAATCGAGTTCGTACCTAAGGGCGACACCCCCTAATTAGCCCG
GGCGAAAGGCCCAGTCTTTCGACTGAGCCTTTCGTTTTATTTGATGCCTGGCAGTTCCCTACTCTCGCATGG
GGAGTCCCCACACTACCATCGGCGCTACGGCGTTTCACTTCTGAGTTCGGCATGGGGTCAGGTGGGACCAC
CGCGCTACTGCCGCCAGGCAAACAAGGGGTGTTATGAGCCATATTCAGGTATAAATGGGCTCGCGATAATGT
TCAGAATTGGTTAATTGGTTGTAACACTGACCCCTATTTGTTTATTTTTCTAAATACATTCAAATATGTATCC
GCTCATGAGACAATAACCCTGATAAATGCTTCAATAATATTGAAAAAGGAAGAATATGAGCCATATTCAACGG
GAAACGTCGAGGCCGCGATTAAATTCCAACATGGATGCTGATTTATATGGGTATAAATGGGCTCGCGATAAT
GTCGGGCAATCAGGTGCGACAATCTATCGCTTGTATGGGAAGCCCGATGCGCCAGAGTTGTTTCTGAAACA
TGGCAAAGGTAGCGTTGCCAATGATGTTACAGATGAGATGGTCAGACTAAACTGGCTGACGGAATTTATGCC
ACTTCCGACCATCAAGCATTTTATCCGTACTCCTGATGATGCATGGTTACTCACCACTGCGATCCCCGGAAA
AACAGCGTTCCAGGTATTAGAAGAATATCCTGATTCAGGTGAAAATATTGTTGATGCGCTGGCAGTGTTCCT
GCGCCGGTTGCACTCGATTCCTGTTTGTAATTGTCCTTTTAACAGCGATCGCGTATTTCGCCTCGCTCAGGC
GCAATCACGAATGAATAACGGTTTGGTTGATGCGAGTGATTTTGATGACGAGCGTAATGGCTGGCCTGTTGA
ACAAGTCTGGAAAGAAATGCATAAACTTTTGCCATTCTCACCGGATTCAGTCGTCACTCATGGTGATTTCTCA
CTTGATAACCTTATTTTTGACGAGGGGAAATTAATAGGTTGTATTGATGTTGGACGAGTCGGAATCGCAGAC
CGATACCAGGATCTTGCCATCCTATGGAACTGCCTCGGTGAGTTTTCTCCTTCATTACAGAAACGGCTTTTTC
AAAAATATGGTATTGATAATCCTGATATGAATAAATTGCAGTTTCATTTGATGCTCGATGAGTTTTTCTAAGCG
GCGCGCCATCGAATGGCGCAAAACCTTTCGCGGTATGGCATGATAGCGCCCGGAAGAGAGTCAATTCAGG
GTGGTGAATATGAAACCAGTAACGTTATACGATGTCGCAGAGTATGCCGGTGTCTCTTATCAGACCGTTTCC
CGCGTGGTGAACCAGGCCAGCCACGTTTCTGCGAAAACGCGGGAAAAAGTGGAAGCGGCGATGGCGGAG
CTGAATTACATTCCCAACCGCGTGGCACAACAACTGGCGGGCAAACAGTCGTTGCTGATTGGCGTTGCCAC
CTCCAGTCTGGCCCTGCACGCGCCGTCGCAAATTGTCGCGGCGATTAAATCTCGCGCCGATCAACTGGGTG
CCAGCGTGGTGGTGTCGATGGTAGAACGAAGCGGCGTCGAAGCCTGTAAAGCGGCGGTGCACAATCTTCT
CGCGCAACGCGTCAGTGGGCTGATCATTAACTATCCGCTGGATGACCAGGATGCCATTGCTGTGGAAGCTG
CCTGCACTAATGTTCCGGCGTTATTTCTTGATGTCTCTGACCAGACACCCATCAACAGTATTATTTTCTCCC
ATGAGGACGGTACGCGACTGGGCGTGGAGCATCTGGTCGCATTGGGTCACCAGCAAATCGCGCTGTTAGCG
GGCCCATTAAGTTCTGTCTCGGCGCGTCTGCGTCTGGCTGGCTGGCATAAATATCTCACTCGCAATCAAATT
CAGCCGATAGCGGAACGGGAAGGCGACTGGAGTGCCATGTCCGGTTTTCAACAAACCATGCAAATGCTGAA
TGAGGGCATCGTTCCCACTGCGATGCTGGTTGCCAACGATCAGATGGCGCTGGGCGCAATGCGCGCCATT
ACCGAGTCCGGGCTGCGCGTTGGTGCGGATATCTCGGTAGTGGGATACGACGATACCGAAGATAGCTCAT
GTTATATCCCGCCGTTAACCACCATCAAACAGGATTTTCGCCTGCTGGGGCAAACCAGCGTGGACCGCTTG
CTGCAACTCTCTCAGGGCCAGGCGGTGAAGGGCAATCAGCTGTTGCCAGTCTCACTGGTGAAAAGAAAAAC
CACCCTGGCGCCCAATACGCAAACCGCCTCTCCCCGCGCGTTGGCCGATTCATTAATGCAGCTGGCACGAC
AGGTTTCCCGACTGGAAAGCGGGCAGTGA

SEQ ID NO: 22: Plasmid construct H9/+term
TTAATAAGATGATCTTCTTGAGATCGTTTGGTCTGCGCGTAATCTCTTGCTCTGAAAACGAAAAAACCGCCT
TGCAGGGCGGTTTTTCGAAGGTTCTCTGAGCTACCAACTCTTTGAACCGAGGTAACTGGCTTGGAGGAGCG
CAGTCACCAAAACTTGTCCTTTCAGTTTAGCCTTAACCGGCGCATGACTTCAAGACTAACTCCTCTAAATCAA
TTACCAGTGGCTGCTGCCAGTGGTGCTTTTGCATGTCTTTCCGGGTTGGACTCAAGACGATAGTTACCGGAT -continued

```
AAGGCGCAGCGGTCGGACTGAACGGGGGGTTCGTGCATACAGTCCAGCTTGGAGCGAACTGCCTACCCGG

AACTGAGTGTCAGGCGTGGAATGAGACAAACGCGGCCATAACAGCGGAATGACACCGGTAAACCGAAAGG

CAGGAACAGGAGAGCGCACGAGGGAGCCGCCAGGGGGAAACGCCTGGTATCTTTATAGTCCTGTCGGGTT

TCGCCACCACTGATTTGAGCGTCAGATTTCGTGATGCTTGTCAGGGGGGCGGAGCCTATGGAAAAACGGCT

TTGCCGCGGCCCTCTCACTTCCCTGTTAAGTATCTTCCTGGCATCTTCCAGGAAATCTCCGCCCCGTTCGTA

AGCCATTTCCGCTCGCCGCAGTCGAACGACCGAGCGTAGCGAGTCAGTGAGCGAGGAAGCGGAATATATC

CTGTATCACATATTCTGCTGACGCACCGGTGCAGCCTTTTTTCTCCTGCCACATGAAGCACTTCACTGACAC

CCTCATCAGTGCCAACATAGTAAGCCAGTATACACTCCGCTAGCGCTGAGGTCCCGCAGCCGAACGACCGA

GCGCAGCGAGTCAGTGAGCGAGGAAGCGGAAGGCGAGAGTAGGGAACTGCCAGGCATCAAACTAAGCAGA

AGGCCCCTGACGGATGGCCTTTTTGCGTTTCTACAAACTCTTTCTGTGTTGTAAAACGACGGCCAGTCTTAA

GCTCGGGCCCCTGGGCGGTTCTGATAACGAGTAATCGTTAATCCGCAAATAACGTAAAAACCCGCTTCGG

CGGGTTTTTTATGGGGGGAGTTTAGGGAAAGAGCATTTGTCAGAATATTTAAGGGCGCCTGTCACTTTGCT

TGATATATGAGAATTATTTAACCTTATAAATGAGAAAAAAGCAACGCACTTTAAATAAGATACGTTGCTTTTTC

GATTGATGAACACCTATAATTAAACTATTCATCTATTATTTATGATTTTTTGTATATACAATATTTCTAGTTTG

TTAAAGAGAATTAAGAAAATAAATCTCGAAAATAATAAAGGGAAAATCAGTTTTTGATATCAAAATTATACATG

TCAACGATAATACAAAATATAATACAAACTATAAGATGTTATCAGTATTTATTATGCATTTAGAATAAATTTTG

TGTCGCCCTTCCGCGAAATTAATACGACTCACTATAGGGGAATTGTGAGCGGATAACAATTCCCCTCTAGAAAT

AATTTTGTTTAACTTTTGAAGGAGATATACATATGGCAACGTTTGACCGCAATGATCCGCAGTTGGCAGGAACG

ATGTTCCCCACCCGAATAGAGGCGAATGTCTTTGACCTTGAAATTGAGGGCGAGATCCCACGTGCAATCAAC

GGGAGCTTCTTCCGCAACACCCCCGAACCTCAGGTCACCCCGCAACCTTTCCACACCTTCATCGATGGGGA

TGGTTTGGCGTCTGCTTTTCATTTCGAAGATGGCCATGTCGACTTTGTCAGCCGTTGGGTATGTACTCCTCG

CTTTGAAGCTGAGCGGTCGGCTCGTAAATCACTCTTCGGTATGTACCGCAATCCGTTCACTGATGATCCATC

GGTAGAAGGTATTGATCGTACAGTCGCCAACACCAGTATCATCACTCATCACGGGAAAGTACTGGCCGCAAA

GGAAGATGGACTACCTTATGAGCTTGACCCCCAAACCCTGGAAACCCGAGGTCGTTATGATTACAAGGGGC

AGGTAACCAGCCATACACATACAGCGCACCCTAAGTTCGACCCCCAGACAGGTGAAATGTTACTCTTCGGCT

CCGCTGCTAAAGGCGAACGAACGCTTGATATGGCGTACTATATTGTTGATCGCTACGGCAAGGTGACACAT

GAGACCTGGTTTAAGCAGCCTTACGGTGCATTCATGCACGACTTTGCTGTCACGCGCAACTGGTCAATCTTT

CCGATCATGCCTGCGACAAATAGCCTTGAGCGTCTTAAAGCAAAGCAGCCCATTTACATGTGGGAGCCTGA

GCGAGGAAGCTATATAGGAGTACTTCCTCGTCGTGGTCAGGGCAAGGACATTCGTTGGTTCCGTGCCCCGG

CGTTGTGGGTTTTCCATGTCGTGAATGCTTGGGAGGAAGGGAATAGAATTCTGATTGACTTGATGGAAAGTG

AGATTTGCCGTTCCCATTCCCGAACTCGCAGAACCTTCCATTTGATCCCTCCAAGGCTGTTCCGCGTCTAA

CCCGTTGGGAAATTGATCTCAATAGTGGTAACGATGAGATGAAACGTACGCAGCTACACGAATATTTTGCAG

AAATGCCTATCATGGATTTCCGTTTTGCGCTCCAGGATCATCGCTACGCCTACATGGGGGTTGACGATCCTC

GTCGCCCCTTAGCTCATCAGCAAGCTGAAAAAATCTTTGCCTACAATTCGTTAGGGGTTTGGGACAACCATC

GTAAAGATTATGAACTTTGGTTTACGGGAAAAATGTCTGCAGCGCAGGAACCGGCGTTTGTTCCTAGAAGCC

CAGATGCGCCTGAGGGCGATGGCTACCTACTCAGTGTAGTAGGGCGGCTCGATGAAAATCGTAGCGATCTA

GTTATCCTTGATACGCAATGTTTGGCAGCTGGGCCTGTGGCCACTGTCAAGCTTCCCTTCCGTCTCCGAGCA

GCGTTGCACGGTTGTTGGCAGTCTAAGAACTGACTAGCATAACCCCTTGGGGCCTCTAAACGGGTCTTGAG

GGGTTTTTTGGCATCCTGTCCATGACTCGGTAATACGACTCACTAATACTGAATTGTGAGCGGATAACAATTC

CCTCTAGAAATAATTTTGTTTAACTTTTAAAGGAGAGTTATCAATGAATATTCGTCCATTGCATGATCGCGTG

ATCGTCAAGCGTAAAGAAGTTGAAACTAAATCTGCTGGCGGCATCGTTCTGACCGGCTCTGCAGCGGCTAAAT
```

-continued

```
CCACCCGCGGCGAAGTGCTGGCTGTCGGCAATGGCCGTATCCTTGAAAATGGCGAAGTGAAGCCGCTGGA

TGTGAAAGTTGGCGACATCGTTATTTTCAACGATGGCTACGGTGTGAAATCTGAGAAGATCGACAATGAAGA

AGTGTTGATCATGTCCGAAAGCGACATTCTGGCAATTGTTGAAGCGTAATCCGCGCACGACACTGAACATAC

GAATTTAAGGAATAAAGATAATGGCAGCTAAAGACGTAAAATTCGGTAACGACGCTCGTGTGAAAATGCTGC

GCGGCGTAAACGTACTGGCAGATGCAGTGAAAGTTACCCTCGGTCCAAAAGGCCGTAACGTAGTTCTGGAT

AAATCTTTCGGTGCACCGACCATCACCAAAGATGGTGTTTCCGTTGCTCGTGAAATCGAACTGGAAGACAAG

TTCGAAAATATGGGTGCGCAGATGGTGAAAGAAGTTGCCTCTAAAGCAAACGACGCTGCAGGCGACGGTAC

CACCACTGCAACCGTACTGGCTCAGGCTATCATCACTGAAGGTCTGAAAGCTGTTGCTGCGGGCATGAACC

CGATGGACCTGAAACGTGGTATCGACAAAGCGGTTACCGCTGCAGTTGAAGAACTGAAAGCGCTGTCCGTA

CCATGCTCTGACTCTAAAGCGATTGCTCAGGTTGGTACCATCTCCGCTAACTCCGACGAAACCGTAGGTAAA

CTGATCGCTGAAGCGATGGACAAAGTCGGTAAAGAAGGCGTTATCACCGTTGAAGACGGTACCGGTCTGCA

GGACGAACTGGACGTGGTTGAAGGTATGCAGTTCGACCGTGGCTACCTGTCTCCTTACTTCATCAACAAGC

CGGAAACTGGCGCAGTAGAACTGGAAAGCCCGTTCATCCTGCTGGCTGACAAGAAAATCTCCAACATCCGC

GAAATGCTGCCGGTTCTGGAAGCTGTTGCCAAAGCAGGCAAACCGCTGCTGATCATCGCTGAAGATGTAGA

AGGCGAAGCGCTGGCAACTCTGGTTGTTAACACCATGCGTGGCATCGTGAAAGTCGCTGCGGTTAAAGCAC

CGGGCTTCGGCGATCGTCGTAAAGCTATGCTGCAGGATATCGCAACCCTGACTGGCGGTACCGTGATCTCT

GAAGAGATCGGTATGGAGCTGGAAAAAGCAACCCTGGAAGACCTGGGTCAGGCTAAACGTGTTGTGATCAA

CAAAGACACCACCACTATCATCGATGGCGTGGGTGAAGAAGCTGCAATCCAGGGCCGTGTTGCTCAGATCC

GTCAGCAGATTGAAGAAGCAACTTCTGACTACGACCGTGAAAAACTGCAGGAACGCGTAGCGAAACTGGCA

GGCGGCGTTGCAGTTATCAAAGTGGGTGCTGCTACCGAAGTTGAAATGAAAGAGAAAAAAGCACGCGTTGA

AGATGCCCTGCACGCGACCCGTGCTGCGGTAGAAGAAGGCGTGGTTGCTGGTGGTGGTGTTGCGCTGATC

CGCGTAGCGTCTAAACTGGCTGACCTGCGTGGTCAGAACGAAGACCAGAACGTGGGTATCAAAGTTGCACT

GCGTGCAATGGAAGCTCCGCTGCGTCAGATCGTATTGAACTGCGGCGAAGAACCGTCTGTTGTTGCTAACA

CCGTTAAAGGCGGCGACGGCAACTACGGTTACAACGCAGCAACCGAAGAATACGGCAACATGATCGACATG

GGTATCCTGGATCCAACCAAAGTAACTCGTTCTGCTCTGCAGTACGCAGCTTCTGTGGCTGGCCTGATGATC

ACCACCGAATGCATGGTTACCGACCTGCCGAAAAACGATGCAGCTGACTTAGGCGCTGCTGGCGGTATGGG

CGGCATGGGTGGCATGGGCGGCATGATGTAACCCCCTAGCATAACCCCTTGGGGCCTCTAAACGGGTCTT

GAGGGGTTTTTGCCCCTGAGACGCGTCAATCGAGTTCGTACCTAAGGGCGACACCCCTAATTAGCCCGG

GCGAAAGGCCCAGTCTTTCGACTGAGCCTTTCGTTTTATTTGATGCCTGGCAGTTCCCTACTCTCGCATGGG

GAGTCCCCACACTACCATCGGCGCTACGGCGTTTCACTTCTGAGTTCGGCATGGGGTCAGGTGGGACCACC

GCGCTACTGCCGCCAGGCAAACAAGGGGTGTTATGAGCCATATTCAGGTATAAATGGGCTCGCGATAATGT

TCAGAATTGGTTAATTGGTTGTAACACTGACCCCTATTTGTTTATTTTTCTAAATACATTCAAATATGTATCC

GCTCATGAGACAATAACCCTGATAAATGCTTCAATAATATTGAAAAAGGAAGAATATGAGCCATATTCAACGG

GAAACGTCGAGGCCGCGATTAAATTCCAACATGGATGCTGATTTATATGGGTATAAATGGGCTCGCGATAATG

TCGGGCAATCAGGTGCGACAATCTATCGCTTGTATGGGAAGCCCGATGCGCCAGAGTTGTTTCTGAAACATG

GCAAAGGTAGCGTTGCCAATGATGTTACAGATGAGATGGTCAGACTAAACTGGCTGACGGAATTTATGCCAC

TTCCGACCATCAAGCATTTTATCCGTACTCCTGATGATGCATGGTTACTCACCACTGCGATCCCCGGAAAAA

CAGCGTTCCAGGTATTAGAAGAATATCCTGATTCAGGTGAAAATATTGTTGATGCGCTGGCAGTGTTCCTGC

GCCGGTTGCACTCGATTCCTGTTTGTAATTGTCCTTTTAACAGCGATCGCGTATTTCGCCTCGCTCAGGCGC

AATCACGAATGAATAACGGTTTGGTTGATGCGAGTGATTTTGATGACGAGCGTAATGGCTGGCCTGTTGAAC
```

-continued

```
AAGTCTGGAAAGAAATGCATAAACTTTTGCCATTCTCACCGGATTCAGTCGTCACTCATGGTGATTTCTCACT
TGATAACCTTATTTTTGACGAGGGGAAATTAATAGGTTGTATTGATGTTGGACGAGTCGGAATCGCAGACCG
ATACCAGGATCTTGCCATCCTATGGAACTGCCTCGGTGAGTTTTCTCCTTCATTACAGAAACGGCTTTTTCAA
AAATATGGTATTGATAATCCTGATATGAATAAATTGCAGTTTCATTTGATGCTCGATGAGTTTTTCTAAGCGG
CGCGCCATCGAATGGCGCAAAACCTTTCGCGGTATGGCATGATAGCGCCCGGAAGAGAGTCAATTCAGGGTG
GTGAATATGAAACCAGTAACGTTATACGATGTCGCAGAGTATGCCGGTGTCTCTTATCAGACCGTTTCCCGC
GTGGTGAACCAGGCCAGCCACGTTTCTGCGAAAACGCGGGAAAAAGTGGAAGCGGCGATGGCGGAGCTGA
ATTACATTCCCAACCGCGTGGCACAACAACTGGCGGGCAAACAGTCGTTGCTGATTGGCGTTGCCACCTCC
AGTCTGGCCCTGCACGCGCCGTCGCAAATTGTCGCGGCGATTAAATCTCGCGCCGATCAACTGGGTGCCA
GCGTGGTGGTGTCGATGGTAGAACGAAGCGGCGTCGAAGCCTGTAAAGCGGCGGTGCACAATCTTCTCGC
GCAACGCGTCAGTGGGCTGATCATTAACTATCCGCTGGATGACCAGGATGCCATTGCTGTGGAAGCTGCCT
GCACTAATGTTCCGGCGTTATTTCTTGATGTCTCTGACCAGACACCCATCAACAGTATTATTTTCTCCCATG
AGGACGGTACGCGACTGGGCGTGGAGCATCTGGTCGCATTGGGTCACCAGCAAATCGCGCTGTTAGCGGGC
CCATTAAGTTCTGTCTCGGCGCGTCTGCGTCTGGCTGGCTGGCATAAATATCTCACTCGCAATCAAATTCAG
CCGATAGCGGAACGGGAAGGCGACTGGAGTGCCATGTCCGGTTTTCAACAAACCATGCAAATGCTGAATGA
GGGCATCGTTCCCACTGCGATGCTGGTTGCCAACGATCAGATGGCGCTGGGCGCAATGCGCGCCATTACC
GAGTCCGGGCTGCGCGTTGGTGCGGATATCTCGGTAGTGGGATACGACGATACCGAAGATAGCTCATGTTA
TATCCCGCCGTTAACCACCATCAAACAGGATTTTCGCCTGCTGGGGCAAACCAGCGTGGACCGCTTGCTGC
AACTCTCTCAGGGCCAGGCGGTGAAGGGCAATCAGCTGTTGCCAGTCTCACTGGTGAAAAGAAAAACCACC
CTGGCGCCCAATACGCAAACCGCCTCTCCCCGCGCGTTGGCCGATTCATTAATGCAGCTGGCACGACAGGT
TTCCCGACTGGAAAGCGGGCAGTGA
```

SEQ ID NO: 23: Plasmid construct G6/+term

```
TTAATAAGATGATCTTCTTGAGATCGTTTTGGTCTGCGCGTAATCTCTTGCTCTGAAAACGAAAAAACCGCCT
TGCAGGGCGGTTTTTCGAAGGTTCTCTGAGCTACCAACTCTTTGAACCGAGGTAACTGGCTTGGAGGAGCG
CAGTCACCAAAACTTGTCCTTTCAGTTTAGCCTTAACCGGCGCATGACTTCAAGACTAACTCCTCTAAATCAA
TTACCAGTGGCTGCTGCCAGTGGTGCTTTTGCATGTCTTTCCGGGTTGGACTCAAGACGATAGTTACCGGAT
AAGGCGCAGCGGTCGGACTGAACGGGGGGTTCGTGCATACAGTCCAGCTTGGAGCGAACTGCCTACCCGG
AACTGAGTGTCAGGCGTGGAATGAGACAAACGCGGCCATAACAGCGGAATGACACCGGTAAACCGAAAGG
CAGGAACAGGAGAGCGCACGAGGGAGCCGCCAGGGGGAAACGCCTGGTATCTTTATAGTCCTGTCGGGTT
TCGCCACCACTGATTTGAGCGTCAGATTTCGTGATGCTTGTCAGGGGGGCGGAGCCTATGGAAAAACGGCT
TTGCCGCGGCCCTCTCACTTCCCTGTTAAGTATCTTCCTGGCATCTTCCAGGAAATCTCCGCCCCGTTCGTA
AGCCATTTCCGCTCGCCGCAGTCGAACGACCGAGCGTAGCGAGTCAGTGAGCGAGGAAGCGGAATATATC
CTGTATCACATATTCTGCTGACGCACCGGTGCAGCCTTTTTTCTCCTGCCACATGAAGCACTTCACTGACAC
CCTCATCAGTGCCAACATAGTAAGCCAGTATACACTCCGCTAGCGCTGAGGTCCCGCAGCCGAACGACCGA
GCGCAGCGAGTCAGTGAGCGAGGAAGCGGAAGGCGAGAGTAGGGAACTGCCAGGCATCAAACTAAGCAGA
AGGCCCCTGACGGATGGCCTTTTTGCGTTTCTACAAACTCTTTCTGTGTTGTAAAACGACGGCCAGTCTTAA
GCTCGGGCCCCTGGGCGGTTCTGATAACGAGTAATCGTTAATCCGCAAATAACGTAAAAACCCGCTTCGG
CGGGTTTTTTATGGGGGGAGTTTAGGGAAAGAGCATTTGTCAGAATATTTAAGGGCGCCTGTCACTTTGCTTG
ATATATGAGAATTATTTAACCTTATAAATGAGAAAAAAGCAACGCACTTTAAATAAGATACGTTGCTTTTTCGA
TTGATGAACACCTATAATTAAACTATTCATCTATTATTTATGATTTTTTGTATATACAATATTTCTAGTTTGTT
AAAGAGAATTAAGAAAATAAATCTCGAAAATAATAAAGGGAAAATCAGTTTTTGATATCAAAATTATACATGTC
```

-continued

```
AACGATAATACAAAATATAATACAAACTATAAGATGTTATCAGTATTTATTATGCATTTAGAATAAATTTTGTG
TCGCCCTTCCGCGAAATTAATACGACTCACTATAGGGGAATTGTGAGCGGATAACAATTCCCCTCTAGAAATA
ATTTTGTTTAACTTTTGAAGGAGATATACATATGGCAACGTTTGACCGCAATGATCCGCAGTTGGCAGGAACG
ATGTTCCCCACCCGAATAGAGGCGAATGTCTTTGACCTTGAAATTGAGGGCGAGATCCCACGTGCAATCAAC
GGGAGCTTCTTCCGCAACACCCCCGAACCTCAGGTCACCCCGCAACCTTTCCACACCTTCATCGATGGGGA
TGGTTTGGCGTCTGCTTTTCATTTCGAAGATGGCCATGTCGACTTTGTCAGCCGTTGGGTATGTACTCCTCG
CTTTGAAGCTGAGCGGTCGGCTCGTAAATCACTCTTCGGTATGTACCGCAATCCGTTCACTGATGATCCATC
GGTAGAAGGTATTGATCGTACAGTCGCCAACACCAGTATCATCACTCATCACGGGAAAGTACTGGCCGCAAA
GGAAGATGGACTACCTTATGAGCTTGACCCCCAAACCCTGGAAACCCGAGGTCGTTATGATTACAAGGGGC
AGGTAACCAGCCATACACATACAGCGCACCCTAAGTTCGACCCCAGACAGGTGAAATGTTACTCTTCGGCT
CCGCTGCTAAAGGCGAACGAACGCTTGATATGGCGTACTATATTGTTGATCGCTACGGCAAGGTGACACAT
GAGACCTGGTTTAAGCAGCCTTACGGTGCATTCATGCACGACTTTGCTGTCACGCGCAACTGGTCAATCTTT
CCGATCATGCCTGCGACAAATAGCCTTGAGCGTCTTAAAGCAAAGCAGCCCATTTACATGTGGGAGCCTGA
GCGAGGAAGCTATATAGGAGTACTTCCTCGTCGTGGTCAGGGCAAGGACATTCGTTGGTTCCGTGCCCCGG
CGTTGTGGGTTTTCCATGTCGTGAATGCTTGGGAGGAAGGGAATAGAATTCTGATTGACTTGATGGAAAGTG
AGATTTTGCCGTTCCCATTCCCGAACTCGCAGAACCTTCCATTTGATCCCTCCAAGGCTGTTCCGCGTCTAA
CCCGTTGGGAAATTGATCTCAATAGTGGTAACGATGAGATGAAACGTACGCAGCTACACGAATATTTTGCAG
AAATGCCTATCATGGATTTCCGTTTTGCGCTCCAGGATCATCGCTACGCCTACATGGGGGTTGACGATCCTC
GTCGCCCCTTAGCTCATCAGCAAGCTGAAAAAATCTTTGCCTACAATTCGTTAGGGGTTTGGGACAACCATC
GTAAAGATTATGAACTTTGGTTTACGGGAAAAATGTCTGCAGCGCAGGAACCGGCGTTTGTTCCTAGAAGCC
CAGATGCGCCTGAGGGCGATGGCTACCTACTCAGTGTAGTAGGGCGGCTCGATGAAAATCGTAGCGATCTA
GTTATCCTTGATACGCAATGTTTGGCAGCTGGGCCTGTGGCCACTGTCAAGCTTCCCTTCCGTCTCCGAGCA
GCGTTGCACGGTTGTTGGCAGTCTAAGAACTGACTAGCATAACCCCTTGGGGCCTCTAAACGGGTCTTGAG
GGGTTTTTTGGCATCCCTGTCCATGACTCGGTAATACGACTCACTATTTCGGAATTGTGAGCGGATAACAATT
CCCTCTAGAAATAATTTTGTTTAACTTTTAAAGGAGAGTTATCAATGAATATTCGTCCATTGCATGATCGCGT
GATCGTCAAGCGTAAAGAAGTTGAAACTAAATCTGCTGGCGGCATCGTTCTGACCGGCTCTGCAGCGGCTAA
ATCCACCCGCGGCGAAGTGCTGGCTGTCGGCAATGGCCGTATCCTTGAAAATGGCGAAGTGAAGCCGCTG
GATGTGAAAGTTGGCGACATCGTTATTTTCAACGATGGCTACGGTGTGAAATCTGAGAAGATCGACAATGAA
GAAGTGTTGATCATGTCCGAAAGCGACATTCTGGCAATTGTTGAAGCGTAATCCGCGCACGACACTGAACAT
ACGAATTTAAGGAATAAAGATAATGGCAGCTAAAGACGTAAAATTCGGTAACGACGCTCGTGTGAAAATGCT
GCGCGGCGTAAACGTACTGGCAGATGCAGTGAAAGTTACCCTCGGTCCAAAAGGCCGTAACGTAGTTCTGG
ATAAATCTTTCGGTGCACCGACCATCACCAAAGATGGTGTTTCCGTTGCTCGTGAAATCGAACTGGAAGACA
AGTTCGAAAATATGGGTGCGCAGATGGTGAAAGAAGTTGCCTCTAAAGCAAACGACGCTGCAGGCGACGGT
ACCACCACTGCAACCGTACTGGCTCAGGCTATCATCACTGAAGGTCTGAAAGCTGTTGCTGCGGGCATGAA
CCCGATGGACCTGAAACGTGGTATCGACAAAGCGGTTACCGCTGCAGTTGAAGAACTGAAAGCGCTGTCCG
TACCATGCTCTGACTCTAAAGCGATTGCTCAGGTTGGTACCATCTCCGCTAACTCCGACGAAACCGTAGGTA
AACTGATCGCTGAAGCGATGGACAAAGTCGGTAAAGAAGGCGTTATCACCGTTGAAGACGGTACCGGTCTG
CAGGACGAACTGGACGTGGTTGAAGGTATGCAGTTCGACCGTGGCTACCTGTCTCCTTACTTCATCAACAAG
CCGGAAACTGGCGCAGTAGAACTGGAAAGCCCGTTCATCCTGCTGGCTGACAAGAAAATCTCCAACATCCG
CGAAATGCTGCCGGTTCTGGAAGCTGTTGCCAAAGCAGGCAAACCGCTGCTGATCATCGCTGAAGATGTAG
AAGGCGAAGCGCTGGCAACTCTGGTTGTTAACACCATGCGTGGCATCGTGAAAGTCGCTGCGGTTAAAGCA
```

-continued

```
CCGGGCTTCGGCGATCGTCGTAAAGCTATGCTGCAGGATATCGCAACCCTGACTGGCGGTACCGTGATCTC
TGAAGAGATCGGTATGGAGCTGGAAAAAGCAACCCTGGAAGACCTGGGTCAGGCTAAACGTGTTGTGATCA
ACAAAGACACCACCACTATCATCGATGGCGTGGGTGAAGAAGCTGCAATCCAGGGCCGTGTTGCTCAGATC
CGTCAGCAGATTGAAGAAGCAACTTCTGACTACGACCGTGAAAAACTGCAGGAACGCGTAGCGAAACTGGC
AGGCGGCGTTGCAGTTATCAAAGTGGGTGCTGCTACCGAAGTTGAAATGAAAGAGAAAAAAGCACGCGTTG
AAGATGCCCTGCACGCGACCCGTGCTGCGGTAGAAGAAGGCGTGGTTGCTGGTGGTGGTGTTGCGCTGAT
CCGCGTAGCGTCTAAACTGGCTGACCTGCGTGGTCAGAACGAAGACCAGAACGTGGGTATCAAAGTTGCAC
TGCGTGCAATGGAAGCTCCGCTGCGTCAGATCGTATTGAACTGCGGCGAAGAACCGTCTGTTGTTGCTAAC
ACCGTTAAAGGCGGCGACGGCAACTACGGTTACAACGCAGCAACCGAAGAATACGGCAACATGATCGACAT
GGGTATCCTGGATCCAACCAAAGTAACTCGTTCTGCTCTGCAGTACGCAGCTTCTGTGGCTGGCCTGATGAT
CACCACCGAATGCATGGTTACCGACCTGCCGAAAAACGATGCAGCTGACTTAGGCGCTGCTGGCGGTATGG
GCGGCATGGGTGGCATGGGCGGCATGATGTAACCCCCTAGCATAACCCCTTGGGCCTCTAAACGGGTCT
TGAGGGGTTTTTGCCCCTGAGACGCGTCAATCGAGTTCGTACCTAAGGGCGACACCCCCTAATTAGCCCG
GGCGAAAGGCCCAGTCTTTCGACTGAGCCTTTCGTTTTATTTGATGCCTGGCAGTTCCCTACTCTCGCATGG
GGAGTCCCCACACTACCATCGGCGCTACGGCGTTTCACTTCTGAGTTCGGCATGGGGTCAGGTGGGACCA
CCGCGCTACTGCCGCCAGGCAAACAAGGGGTGTTATGAGCCATATTCAGGTATAAATGGGCTCGCGATAATGT
TCAGAATTGGTTAATTGGTTGTAACACTGACCCCTATTTGTTTATTTTTCTAAATACATTCAAATATGTATCC
GCTCATGAGACAATAACCCTGATAAATGCTTCAATAATATTGAAAAAGGAAGAATATGAGCCATATTCAACGG
GAAACGTCGAGGCCGCGATTAAATTCCAACATGGATGCTGATTTATATGGGTATAAATGGGCTCGCGATAAT
GTCGGGCAATCAGGTGCGACAATCTATCGCTTGTATGGGAAGCCCGATGCGCCAGAGTTGTTTCTGAAACA
TGGCAAAGGTAGCGTTGCCAATGATGTTACAGATGAGATGGTCAGACTAAACTGGCTGACGGAATTTATGCC
ACTTCCGACCATCAAGCATTTTATCCGTACTCCTGATGATGCATGGTTACTCACCACTGCGATCCCCGGAAA
AACAGCGTTCCAGGTATTAGAAGAATATCCTGATTCAGGTGAAAATATTGTTGATGCGCTGGCAGTGTTCCT
GCGCCGGTTGCACTCGATTCCTGTTTGTAATTGTCCTTTTAACAGCGATCGCGTATTTCGCCTCGCTCAGGC
GCAATCACGAATGAATAACGGTTTGGTTGATGCGAGTGATTTTGATGACGAGCGTAATGGCTGGCCTGTTGA
ACAAGTCTGGAAAGAAATGCATAAACTTTTGCCATTCTCACCGGATTCAGTCGTCACTCATGGTGATTTCTCA
CTTGATAACCTTATTTTTGACGAGGGGAAATTAATAGGTTGTATTGATGTTGGACGAGTCGGAATCGCAGAC
CGATACCAGGATCTTGCCATCCTATGGAACTGCCTCGGTGAGTTTTCTCCTTCATTACAGAAACGGCTTTTTC
AAAAATATGGTATTGATAATCCTGATATGAATAAATTGCAGTTTCATTTGATGCTCGATGAGTTTTTCTAAGCG
GCGCGCCATCGAATGGCGCAAAACCTTTCGCGGTATGGCATGATAGCGCCCGGAAGAGAGTCAATTCAGG
GTGGTGAATATGAAACCAGTAACGTTATACGATGTCGCAGAGTATGCCGGTGTCTCTTATCAGACCGTTTCC
CGCGTGGTGAACCAGGCCAGCCACGTTTCTGCGAAAACGCGGGAAAAAGTGGAAGCGGCGATGGCGGAG
CTGAATTACATTCCCAACCGCGTGGCACAACAACTGGCGGGCAAACAGTCGTTGCTGATTGGCGTTGCCAC
CTCCAGTCTGGCCCTGCACGCGCCGTCGCAAATTGTCGCGGCGATTAAATCTCGCGCCGATCAACTGGGTG
CCAGCGTGGTGGTGTCGATGGTAGAACGAAGCGGCGTCGAAGCCTGTAAAGCGGCGGTGCACAATCTTCT
CGCGCAACGCGTCAGTGGGCTGATCATTAACTATCCGCTGGATGACCAGGATGCCATTGCTGTGGAAGCTG
CCTGCACTAATGTTCCGGCGTTATTTCTTGATGTCTCTGACCAGACACCCATCAACAGTATTATTTTCTCCCA
TGAGGACGGTACGCGACTGGGCGTGGAGCATCTGGTCGCATTGGGTCACCAGCAAATCGCGCTGTTAGCG
GGCCCATTAAGTTCTGTCTCGGCGCGTCTGCGTCTGGCTGGCTGGCATAAATATCTCACTCGCAATCAAATT
CAGCCGATAGCGGAACGGGAAGGCGACTGGAGTGCCATGTCCGGTTTTCAACAAACCATGCAAATGCTGAA
```

TGAGGGCATCGTTCCCACTGCGATGCTGGTTGCCAACGATCAGATGGCGCTGGGCGCAATGCGCGCCATT

ACCGAGTCCGGGCTGCGCGTTGGTGCGGATATCTCGGTAGTGGGATACGACGATACCGAAGATAGCTCAT

GTTATATCCCGCCGTTAACCACCATCAAACAGGATTTTCGCCTGCTGGGGCAAACCAGCGTGGACCGCTTG

CTGCAACTCTCTCAGGGCCAGGCGGTGAAGGGCAATCAGCTGTTGCCAGTCTCACTGGTGAAAAGAAAAAC

CACCCTGGCGCCCAATACGCAAACCGCCTCTCCCCGCGCGTTGGCCGATTCATTAATGCAGCTGGCACGAC

AGGTTTCCCGACTGGAAAGCGGGCAGTGA

SEQ ID NO: 24: Plasmid construct C4/+term
TTAATAAGATGATCTTCTTGAGATCGTTTTGGTCTGCGCGTAATCTCTTGCTCTGAAAACGAAAAAACCGCCT

TGCAGGGCGGTTTTTCGAAGGTTCTCTGAGCTACCAACTCTTTGAACCGAGGTAACTGGCTTGGAGGAGCG

CAGTCACCAAAACTTGTCCTTTCAGTTTAGCCTTAACCGGCGCATGACTTCAAGACTAACTCCTCTAAATCAA

TTACCAGTGGCTGCTGCCAGTGGTGCTTTTGCATGTCTTTCCGGGTTGGACTCAAGACGATAGTTACCGGAT

AAGGCGCAGCGGTCGGACTGAACGGGGGGTTCGTGCATACAGTCCAGCTTGGAGCGAACTGCCTACCCGG

AACTGAGTGTCAGGCGTGGAATGAGACAAACGCGGCCATAACAGCGGAATGACACCGGTAAACCGAAAGG

CAGGAACAGGAGAGCGCACGAGGGAGCCGCCAGGGGGAAACGCCTGGTATCTTTATAGTCCTGTCGGGTT

TCGCCACCACTGATTTGAGCGTCAGATTTCGTGATGCTTGTCAGGGGGGCGGAGCCTATGGAAAAACGGCT

TTGCCGCGGCCCTCTCACTTCCCTGTTAAGTATCTTCCTGGCATCTTCCAGGAAATCTCCGCCCCGTTCGTA

AGCCATTTCCGCTCGCCGCAGTCGAACGACCGAGCGTAGCGAGTCAGTGAGCGAGGAAGCGGAATATATC

CTGTATCACATATTCTGCTGACGCACCGGTGCAGCCTTTTTTCTCCTGCCACATGAAGCACTTCACTGACAC

CCTCATCAGTGCCAACATAGTAAGCCAGTATACACTCCGCTAGCGCTGAGGTCCCGCAGCCGAACGACCGA

GCGCAGCGAGTCAGTGAGCGAGGAAGCGGAAGGCGAGAGTAGGGAACTGCCAGGCATCAAACTAAGCAGA

AGGCCCCTGACGGATGGCCTTTTTGCGTTTCTACAAACTCTTTCTGTGTTGTAAAACGACGGCCAGTCTTAA

GCTCGGGCCCCTGGGCGGTTCTGATAACGAGTAATCGTTAATCCGCAAATAACGTAAAAACCCGCTTCGG

CGGGTTTTTTATGGGGGGAGTTTAGGGAAAGAGCATTTGTCAGAATATTTAAGGGCGCCTGTCACTTTGCTTG

ATATATGAGAATTATTTAACCTTATAAATGAGAAAAAAGCAACGCACTTTAAATAAGATACGTTGCTTTTTCGA

TTGATGAACACCTATAATTAAACTATTCATCTATTATTTATGATTTTTTGTATATACAATATTTCTAGTTTGTT

AAAGAGAATTAAGAAAATAAATCTCGAAAATAATAAAGGGAAAATCAGTTTTTGATATCAAAATTATACATGTC

AACGATAATACAAAATATAATACAAACTATAAGATGTTATCAGTATTTATTATGCATTTAGAATAAATTTTGT

GTCGCCCTTCCGCGAAATTAATACGACTCACTATAGGGGAATTGTGAGCGGATAACAATTCCCCTCTAGAAAT

AATTTTGTTTAACTTTTGAAGGAGATATACATATGGCAACGTTTGACCGCAATGATCCGCAGTTGGCAGGAAC

GATGTTCCCACCCGAATAGAGGCGAATGTCTTTGACCTTGAAATTGAGGGCGAGATCCCACGTGCAATCAAC

GGGAGCTTCTTCCGCAACACCCCCGAACCTCAGGTCACCCCGCAACCTTTCCACACCTTCATCGATGGGGA

TGGTTTGGCGTCTGCTTTTCATTTCGAAGATGGCCATGTCGACTTTGTCAGCCGTTGGGTATGTACTCCTCG

CTTTGAAGCTGAGCGGTCGGCTCGTAAATCACTCTTCGGTATGTACCGCAATCCGTTCACTGATGATCCATC

GGTAGAAGGTATTGATCGTACAGTCGCCAACACCAGTATCATCACTCATCACGGGAAAGTACTGGCCGCAAA

GGAAGATGGACTACCTTATGAGCTTGACCCCAAACCCTGGAAACCCGAGGTCGTTATGATTACAAGGGGC

AGGTAACCAGCCATACACATCAGCGCACCCTAAGTTCGACCCCAGACAGGTGAAATGTTACTCTTCGGCT

CCGCTGCTAAAGGCGAACGAACGCTTGATATGGCGTACTATATTGTTGATCGCTACGGCAAGGTGACACAT

GAGACCTGGTTTAAGCAGCCTTACGGTGCATTCATGCACGACTTTGCTGTCACGCGCAACTGGTCAATCTTT

CCGATCATGCCTGCGACAAATAGCCTTGAGCGTCTTAAAGCAAAGCAGCCCATTTACATGTGGGAGCCTGA

GCGAGGAAGCTATATAGGAGTACTTCCTCGTCGTGGTCAGGGCAAGGACATTCGTTGGTTCCGTGCCCCGG

CGTTGTGGGTTTTCCATGTCGTGAATGCTTGGGAGGAAGGGAATAGAATTCTGATTGACTTGATGGAAAGTG

-continued

```
AGATTTTGCCGTTCCCATTCCCGAACTCGCAGAACCTTCCATTTGATCCCTCCAAGGCTGTTCCGCGTCTAA

CCCGTTGGGAAATTGATCTCAATAGTGGTAACGATGAGATGAAACGTACGCAGCTACACGAATATTTTGCAG

AAATGCCTATCATGGATTTCCGTTTTGCGCTCCAGGATCATCGCTACGCCTACATGGGGGTTGACGATCCTC

GTCGCCCCTTAGCTCATCAGCAAGCTGAAAAAATCTTTGCCTACAATTCGTTAGGGGTTTGGGACAACCATC

GTAAAGATTATGAACTTTGGTTTACGGGAAAAATGTCTGCAGCGCAGGAACCGGCGTTTGTTCCTAGAAGCC

CAGATGCGCCTGAGGGCGATGGCTACCTACTCAGTGTAGTAGGGCGGCTCGATGAAAATCGTAGCGATCTA

GTTATCCTTGATACGCAATGTTTGGCAGCTGGGCCTGTGGCCACTGTCAAGCTTCCCTTCCGTCTCCGAGCA

GCGTTGCACGGTTGTTGGCAGTCTAAGAACTGACTAGCATAACCCCTTGGGGCCTCTAAACGGGTCTTGAG

GGGTTTTTTGGCATCCTGTCCATGACTCGGTAATACGACTCACTATCAAGGAATTGTGAGCGGATAACAATT

CCCTCTAGAAATAATTTTGTTTAACTTTTAAAGGAGAGTTATCAATGAATATTCGTCCATTGCATGATCGCGTG

ATCGTCAAGCGTAAAGAAGTTGAAACTAAATCTGCTGGCGGCATCGTTCTGACCGGCTCTGCAGCGGCTAA

ATCCACCCGCGGCGAAGTGCTGGCTGTCGGCAATGGCCGTATCCTTGAAAATGGCGAAGTGAAGCCGCTG

GATGTGAAAGTTGGCGACATCGTTATTTTCAACGATGGCTACGGTGTGAAATCTGAGAAGATCGACAATGAA

GAAGTGTTGATCATGTCCGAAAGCGACATTCTGGCAATTGTTGAAGCGTAATCCGCGCACGACACTGAACAT

ACGAATTTAAGGAATAAAGATAATGGCAGCTAAAGACGTAAAATTCGGTAACGACGCTCGTGTGAAAATGCT

GCGCGGCGTAAACGTACTGGCAGATGCAGTGAAAGTTACCCTCGGTCCAAAAGGCCGTAACGTAGTTCTGG

ATAAATCTTTCGGTGCACCGACCATCACCAAAGATGGTGTTTCCGTTGCTCGTGAAATCGAACTGGAAGACA

AGTTCGAAAATATGGGTGCGCAGATGGTGAAAGAAGTTGCCTCTAAAGCAAACGACGCTGCAGGCGACGGT

ACCACCACTGCAACCGTACTGGCTCAGGCTATCATCACTGAAGGTCTGAAAGCTGTTGCTGCGGGCATGAA

CCCGATGGACCTGAAACGTGGTATCGACAAAGCGGTTACCGCTGCAGTTGAAGAACTGAAAGCGCTGTCCG

TACCATGCTCTGACTCTAAAGCGATTGCTCAGGTTGGTACCATCTCCGCTAACTCCGACGAAACCGTAGGTA

AACTGATCGCTGAAGCGATGGACAAAGTCGGTAAAGAAGGCGTTATCACCGTTGAAGACGGTACCGGTCTG

CAGGACGAACTGGACGTGGTTGAAGGTATGCAGTTCGACCGTGGCTACCTGTCTCCTTACTTCATCAACAAG

CCGGAAACTGGCGCAGTAGAACTGGAAAGCCCGTTCATCCTGCTGGCTGACAAGAAAATCTCCAACATCCG

CGAAATGCTGCCGGTTCTGGAAGCTGTTGCCAAAGCAGGCAAACCGCTGCTGATCATCGCTGAAGATGTAG

AAGGCGAAGCGCTGGCAACTCTGGTTGTTAACACCATGCGTGGCATCGTGAAAGTCGCTGCGGTTAAAGCA

CCGGGCTTCGGCGATCGTCGTAAAGCTATGCTGCAGGATATCGCAACCCTGACTGGCGGTACCGTGATCTC

TGAAGAGATCGGTATGGAGCTGGAAAAAGCAACCCTGGAAGACCTGGGTCAGGCTAAACGTGTTGTGATCA

ACAAAGACACCACCACTATCATCGATGGCGTGGGTGAAGAAGCTGCAATCCAGGGCCGTGTTGCTCAGATC

CGTCAGCAGATTGAAGAAGCAACTTCTGACTACGACCGTGAAAAACTGCAGGAACGCGTAGCGAAACTGGC

AGGCGGCGTTGCAGTTATCAAAGTGGGTGCTGCTACCGAAGTTGAAATGAAAGAGAAAAAAGCACGCGTTG

AAGATGCCCTGCACGCGACCCGTGCTGCGGTAGAAGAAGGCGTGGTTGCTGGTGGTGGTGTTGCGCTGAT

CCGCGTAGCGTCTAAACTGGCTGACCTGCGTGGTCAGAACGAAGACCAGAACGTGGGTATCAAAGTTGCAC

TGCGTGCAATGGAAGCTCCGCTGCGTCAGATCGTATTGAACTGCGGCGAAGAACCGTCTGTTGTTGCTAAC

ACCGTTAAAGGCGGCGACGGCAACTACGGTTACAACGCAGCAACCGAAGAATACGGCAACATGATCGACAT

GGGTATCCTGGATCCAACCAAAGTAACTCGTTCTGCTCTGCAGTACGCAGCTTCTGTGGCTGGCCTGATGAT

CACCACCGAATGCATGGTTACCGACCTGCCGAAAAACGATGCAGCTGACTTAGGCGCTGCTGGCGGTATGG

GCGGCATGGGTGGCATGGGCGGCATGATGTAACCCCCTAGCATAACCCCTTGGGGCCTCTAAACGGGTCT

TGAGGGGTTTTTTGCCCCTGAGACGCGTCAATCGAGTTCGTACCTAAGGGCGACACCCCCTAATTAGCCCG

GGCGAAAGGCCCAGTCTTTCGACTGAGCCTTTCGTTTTATTTGATGCCTGGCAGTTCCCTACTCTCGCATGG

GGAGTCCCCACACTACCATCGGCGCTACGGCGTTTCACTTCTGAGTTCGGCATGGGGTCAGGTGGGACCAC
```

```
CGCGCTACTGCCGCCAGGCAAACAAGGGGTGTTATGAGCCATATTCAGGTATAAATGGGCTCGCGATAATGT
TCAGAATTGGTTAATTGGTTGTAACACTGACCCCTATTTGTTTATTTTTCTAAATACATTCAAATATGTATCC
GCTCATGAGACAATAACCCTGATAAATGCTTCAATAATATTGAAAAAGGAAGAATATGAGCCATATTCAACGG
GAAACGTCGAGGCCGCGATTAAATTCCAACATGGATGCTGATTTATATGGGTATAAATGGGCTCGCGATAAT
GTCGGGCAATCAGGTGCGACAATCTATCGCTTGTATGGGAAGCCCGATGCGCCAGAGTTGTTTCTGAAACA
TGGCAAAGGTAGCGTTGCCAATGATGTTACAGATGAGATGGTCAGACTAAACTGGCTGACGGAATTTATGCC
ACTTCCGACCATCAAGCATTTTATCCGTACTCCTGATGATGCATGGTTACTCACCACTGCGATCCCCGGAAA
AACAGCGTTCCAGGTATTAGAAGAATATCCTGATTCAGGTGAAAATATTGTTGATGCGCTGGCAGTGTTCCT
GCGCCGGTTGCACTCGATTCCTGTTTGTAATTGTCCTTTTAACAGCGATCGCGTATTTCGCCTCGCTCAGGC
GCAATCACGAATGAATAACGGTTTGGTTGATGCGAGTGATTTTGATGACGAGCGTAATGGCTGGCCTGTTGA
ACAAGTCTGGAAAGAAATGCATAAACTTTTGCCATTCTCACCGGATTCAGTCGTCACTCATGGTGATTTCTCA
CTTGATAACCTTATTTTTGACGAGGGGAAATTAATAGGTTGTATTGATGTTGGACGAGTCGGAATCGCAGAC
CGATACCAGGATCTTGCCATCCTATGGAACTGCCTCGGTGAGTTTTCTCCTTCATTACAGAAACGGCTTTTTC
AAAAATATGGTATTGATAATCCTGATATGAATAAATTGCAGTTTCATTTGATGCTCGATGAGTTTTTCTAAG
CGGCGCGCCATCGAATGGCGCAAAACCTTTCGCGGTATGGCATGATAGCGCCCGGAAGAGAGTCAATTCAGG
GTGGTGAATATGAAACCAGTAACGTTATACGATGTCGCAGAGTATGCCGGTGTCTCTTATCAGACCGTTTCC
CGCGTGGTGAACCAGGCCAGCCACGTTTCTGCGAAAACGCGGGAAAAAGTGGAAGCGGCGATGCGGAG
CTGAATTACATTCCCAACCGCGTGGCACAACAACTGGCGGGCAAACAGTCGTTGCTGATTGGCGTTGCCAC
CTCCAGTCTGGCCCTGCACGCGCCGTCGCAAATTGTCGCGGCGATTAAATCTCGCGCCGATCAACTGGGTG
CCAGCGTGGTGGTGTCGATGGTAGAACGAAGCGGCGTCGAAGCCTGTAAAGCGGCGGTGCACAATCTTCT
CGCGCAACGCGTCAGTGGGCTGATCATTAACTATCCGCTGGATGACCAGGATGCCATTGCTGTGGAAGCTG
CCTGCACTAATGTTCCGGCGTTATTTCTTGATGTCTCTGACCAGACACCCATCAACAGTATTATTTTCTCCC
ATGAGGACGGTACGCGACTGGGCGTGGAGCATCTGGTCGCATTGGGTCACCAGCAAATCGCGCTGTTAGCG
GGCCCATTAAGTTCTGTCTCGGCGCGTCTGCGTCTGGCTGGCTGGCATAAATATCTCACTCGCAATCAAATT
CAGCCGATAGCGGAACGGGAAGGCGACTGGAGTGCCATGTCCGGTTTTCAACAAACCATGCAAATGCTGAA
TGAGGGCATCGTTCCCACTGCGATGCTGGTTGCCAACGATCAGATGGCGCTGGGCGCAATGCGCGCCATT
ACCGAGTCCGGGCTGCGCGTTGGTGCGGATATCTCGGTAGTGGGATACGACGATACCGAAGATAGCTCAT
GTTATATCCCGCCGTTAACCACCATCAAACAGGATTTTCGCCTGCTGGGGCAAACCAGCGTGGACCGCTTG
CTGCAACTCTCTCAGGGCCAGGCGGTGAAGGGCAATCAGCTGTTGCCAGTCTCACTGGTGAAAGAAAAAC
CACCCTGGCGCCCAATACGCAAACCGCCTCTCCCCGCGCGTTGGCCGATTCATTAATGCAGCTGGCACGAC
AGGTTTCCCGACTGGAAAGCGGGCAGTGA
SEQ ID NO: 25: Plasmid construct PC1_triple
TTAATAAGATGATCTTCTTGAGATCGTTTTGGTCTGCGCGTAATCTCTTGCTCTGAAAACGAAAAAACCGCCT
TGCAGGGCGGTTTTTCGAAGGTTCTCTGAGCTACCAACTCTTTGAACCGAGGTAACTGGCTTGGAGGAGCG
CAGTCACCAAAACTTGTCCTTTCAGTTTAGCCTTAACCGGCGCATGACTTCAAGACTAACTCCTCTAAATCAA
TTACCAGTGGCTGCTGCCAGTGGTGCTTTTGCATGTCTTTCCGGGTTGGACTCAAGACGATAGTTACCGGAT
AAGGCGCAGCGGTCGGACTGAACGGGGGGTTCGTGCATACAGTCCAGCTTGGAGCGAACTGCCTACCCGG
AACTGAGTGTCAGGCGTGGAATGAGACAAACGCGGCCATAACAGCGGAATGACACCGGTAAACCGAAAGG
CAGGAACAGGAGAGCGCACGAGGGAGCCGCCAGGGGGAAACGCCTGGTATCTTTATAGTCCTGTCGGGTT
TCGCCACCACTGATTTGAGCGTCAGATTTCGTGATGCTTGTCAGGGGGGCGGAGCCTATGGAAAAACGGCT
TTGCCGCGGCCCTCTCACTTCCCTGTTAAGTATCTTCCTGGCATCTTCCAGGAAATCTCCGCCCCGTTCGTA
```

-continued

```
AGCCATTTCCGCTCGCCGCAGTCGAACGACCGAGCGTAGCGAGTCAGTGAGCGAGGAAGCGGAATATATC
CTGTATCACATATTCTGCTGACGCACCGGTGCAGCCTTTTTTCTCCTGCCACATGAAGCACTTCACTGACAC
CCTCATCAGTGCCAACATAGTAAGCCAGTATACACTCCGCTAGCGCTGAGGTCCCGCAGCCGAACGACCGA
GCGCAGCGAGTCAGTGAGCGAGGAAGCGGAAGGCGAGAGTAGGGAACTGCCAGGCATCAAACTAAGCAGA
AGGCCCCTGACGGATGGCCTTTTTGCGTTTCTACAAACTCTTTCTGTGTTGTAAAACGACGGCCAGTCTTAA
GCTCGGGCCCCTGGGCGGTTCTGATAACGAGTAATCGTTAATCCGCAAATAACGTAAAAACCCGCTTCGG
CGGGTTTTTTATGGGGGAGTTTAGGGAAAGAGCATTTGTCAGAATATTTAAGGGCGCCTGTCACTTTGCTTG
ATATATGAGAATTATTTAACCTTATAAATGAGAAAAAAGCAACGCACTTTAAATAAGATACGTTGCTTTTTCGA
TTGATGAACACCTATAATTAAACTATTCATCTATTATTTATGATTTTTTGTATATACAATATTTCTAGTTTGTT
AAAGAGAATTAAGAAAATAAATCTCGAAAATAATAAAGGGAAAATCAGTTTTTGATATCAAAATTATACATGTC
AACGATAATACAAAATATAATACAAACTATAAGATGTTATCAGTATTTATTATGCATTTAGAATAAATTTTGTG
TCGCCCTTCCGCGAAATTAATACGACTCACTATAGGGGAATTGTGAGCGGATAACAATTCCCCTCTAGAAATA
ATTTTGTTTAACTTTTGAAGGAGATATACATATGGCAACGTTTGACCGCAATGATCCGCAGTTGGCAGGAACG
ATGTTCCCCACCCGAATAGAGGCGAATGTCTTTGACCTTGAAATTGAGGGCGAGATCCCACGTGCAATCAAC
GGGAGCTTCTTCCGCAACACCCCCGAACCTCAGGTCACCCCGCAACCTTTCCACACCTTCATCGATGGGGA
TGGTTTGGCGTCTGCTTTTCATTTCGAAGATGGCCATGTCGACTTTGTCAGCCGTTGGGTATGTACTCCTCG
CTTTGAAGCTGAGCGGTCGGCTCGTAAATCACTCTTCGGTATGTACCGCAATCCGTTCACTGATGATCCATC
GGTAGAAGGTATTGATCGTACAGTCGCCAACACCAGTATCATCACTCATCACGGGAAAGTACTGGCCGCAAA
GGAAGATGGACTACCTTATGAGCTTGACCCCCAAACCCTGGAAACCCGAGGTCGTTATGATTACAAGGGGC
AGGTAACCAGCCATACACATACAGCGCACCCTAAGTTCGACCCCAGACAGGTGAAATGTTACTCTTCGGCT
CCGCTGCTAAAGGCGAACGAACGCTTGATATGGCGTACTATATTGTTGATCGCTACGGCAAGGTGACACAT
GAGACCTGGTTTAAGCAGCCTTACGGTGCATTCATGCACGACTTTGCTGTCACGCGCAACTGGTCAATCTTT
CCGATCATGCCTGCGACAAATAGCCTTGAGCGTCTTAAAGCAAAGCAGCCCATTTACATGTGGGAGCCTGA
GCGAGGAAGCTATATAGGAGTACTTCCTCGTCGTGGTCAGGGCAAGGACATTCGTTGGTTCCGTGCCCCGG
CGTTGTGGGTTTTCCATGTCGTGAATGCTTGGGAGGAAGGGAATAGAATTCTGATTGACTTGATGGAAAGTG
AGATTTTGCCGTTCCCATTCCCGAACTCGCAGAACCTTCCATTTGATCCCTCCAAGGCTGTTCCGCGTCTAA
CCCGTTGGGAAATTGATCTCAATAGTGGTAACGATGAGATGAAACGTACGCAGCTACACGAATATTTTGCAG
AAATGCCTATCATGGATTTCCGTTTTGCGCTCCAGGATCATCGCTACGCCTACATGGGGGTTGACGATCCTC
GTCGCCCCTTAGCTCATCAGCAAGCTGAAAAAATCTTTGCCTACAATTCGTTAGGGGTTTGGGACAACCATC
GTAAAGATTATGAACTTTGGTTTACGGGAAAAATGTCTGCAGCGCAGGAACCGGCGTTTGTTCCTAGAAGCC
CAGATGCGCCTGAGGGCGATGGCTACCTACTCAGTGTAGTAGGGCGGCTCGATGAAAATCGTAGCGATCTA
GTTATCCTTGATACGCAATGTTTGGCAGCTGGGCCTGTGGCCACTGTCAAGCTTCCCTTCCGTCTCCGAGCA
GCGTTGCACGGTTGTTGGCAGTCTAAGAACTGAGAAGGAGATATACATATGAATATTCGTCCATTGCATGAT
CGCGTGATCGTCAAGCGTAAAGAAGTTGAAACTAAATCTGCTGGCGGCATCGTTCTGACCGGCTCTGCAGC
GGCTAAATCCACCCGCGGCGAAGTGCTGGCTGTCGGCAATGGCCGTATCCTTGAAAATGGCGAAGTGAAG
CCGCTGGATGTGAAAGTTGGCGACATCGTTATTTTCAACGATGGCTACGGTGTGAAATCTGAGAAGATCGAC
AATGAAGAAGTGTTGATCATGTCCGAAAGCGACATTCTGGCAATTGTTGAAGCGTAATCCGCGCACGACACT
GAACATACGAATTTAAGGAATAAAGATAATGGCAGCTAAAGACGTAAAATTCGGTAACGACGCTCGTGTGAA
AATGCTGCGCGGCGTAAACGTACTGGCAGATGCAGTGAAAGTTACCCTCGGTCCAAAAGGCCGTAACGTAG
TTCTGGATAAATCTTTCGGTGCACCGACCATCACCAAAGATGGTGTTTCCGTTGCTCGTGAAATCGAACTGG
```

-continued

```
AAGACAAGTTCGAAAATATGGGTGCGCAGATGGTGAAAGAAGTTGCCTCTAAAGCAAACGACGCTGCAGGC
GACGGTACCACCACTGCAACCGTACTGGCTCAGGCTATCATCACTGAAGGTCTGAAAGCTGTTGCTGCGGG
CATGAACCCGATGGACCTGAAACGTGGTATCGACAAAGCGGTTACCGCTGCAGTTGAAGAACTGAAAGCGC
TGTCCGTACCATGCTCTGACTCTAAAGCGATTGCTCAGGTTGGTACCATCTCCGCTAACTCCGACGAAACCG
TAGGTAAACTGATCGCTGAAGCGATGGACAAAGTCGGTAAAGAAGGCGTTATCACCGTTGAAGACGGTACC
GGTCTGCAGGACGAACTGGACGTGGTTGAAGGTATGCAGTTCGACCGTGGCTACCTGTCTCCTTACTTCAT
CAACAAGCCGGAAACTGGCGCAGTAGAACTGGAAAGCCCGTTCATCCTGCTGGCTGACAAGAAAATCTCCA
ACATCCGCGAAATGCTGCCGGTTCTGGAAGCTGTTGCCAAAGCAGGCAAACCGCTGCTGATCATCGCTGAA
GATGTAGAAGGCGAAGCGCTGGCAACTCTGGTTGTTAACACCATGCGTGGCATCGTGAAAGTCGCTGCGGT
TAAAGCACCGGGCTTCGGCGATCGTCGTAAAGCTATGCTGCAGGATATCGCAACCCTGACTGGCGGTACCG
TGATCTCTGAAGAGATCGGTATGGAGCTGGAAAAAGCAACCCTGGAAGACCTGGGTCAGGCTAAACGTGTT
GTGATCAACAAAGACACCACCACTATCATCGATGGCGTGGGTGAAGAAGCTGCAATCCAGGGCCGTGTTGC
TCAGATCCGTCAGCAGATTGAAGAAGCAACTTCTGACTACGACCGTGAAAAACTGCAGGAACGCGTAGCGA
AACTGGCAGGCGGCGTTGCAGTTATCAAAGTGGGTGCTGCTACCGAAGTTGAAATGAAAGAGAAAAAAGCA
CGCGTTGAAGATGCCCTGCACGCGACCCGTGCTGCGGTAGAAGAAGGCGTGGTTGCTGGTGGTGGTGTTG
CGCTGATCCGCGTAGCGTCTAAACTGGCTGACCTGCGTGGTCAGAACGAAGACCAGAACGTGGGTATCAAA
GTTGCACTGCGTGCAATGGAAGCTCCGCTGCGTCAGATCGTATTGAACTGCGGCGAAGAACCGTCTGTTGT
TGCTAACACCGTTAAAGGCGGCGACGGCAACTACGGTTACAACGCAGCAACCGAAGAATACGGCAACATGA
TCGACATGGGTATCCTGGATCCAACCAAAGTAACTCGTTCTGCTCTGCAGTACGCAGCTTCTGTGGCTGGCC
TGATGATCACCACCGAATGCATGGTTACCGACCTGCCGAAAAACGATGCAGCTGACTTAGGCGCTGCTGGC
GGTATGGGCGGCATGGGTGGCATGGGCGGCATGATGTAACCCCCTAGCATAACCCCTTGGGGCCTCTAAA
CGGGTCTTGAGGGGTTTTTTGCCCCTGAGACGCGTCAATCGAGTTCGTACCTAAGGGCGACACCCCCTAAT
TAGCCCGGGCGAAAGGCCCAGTCTTTCGACTGAGCCTTTCGTTTTATTTGATGCCTGGCAGTTCCCTACTCT
CGCATGGGGAGTCCCCACACTACCATCGGCGCTACGGCGTTTCACTTCTGAGTTCGGCATGGGGTCAGGTG
GGACCACCGCGCTACTGCCGCCAGGCAAACAAGGGGTGTTATGAGCCATATTCAGGTATAAATGGGCTCGCG
ATAATGTTCAGAATTGGTTAATTGGTTGTAACACTGACCCCTATTTGTTTATTTTTCTAAATACATTCAAATA
TGTATCCGCTCATGAGACAATAACCCTGATAAATGCTTCAATAATATTGAAAAAGGAAGAATATGAGCCATAT
TCAACGGGAAACGTCGAGGCCGCGATTAAATTCCAACATGGATGCTGATTTATATGGGTATAAATGGGCTCG
CGATAATGTCGGGCAATCAGGTGCGACAATCTATCGCTTGTATGGGAAGCCCGATGCGCCAGAGTTGTTTC
TGAAACATGGCAAAGGTAGCGTTGCCAATGATGTTACAGATGAGATGGTCAGACTAAACTGGCTGACGGAAT
TTATGCCACTTCCGACCATCAAGCATTTTATCCGTACTCCTGATGATGCATGGTTACTCACCACTGCGATCCC
CGGAAAAACAGCGTTCCAGGTATTAGAAGAATATCCTGATTCAGGTGAAAATATTGTTGATGCGCTGGCAGT
GTTCCTGCGCCGGTTGCACTCGATTCCTGTTTGTAATTGTCCTTTTAACAGCGATCGCGTATTTCGCCTCGCT
CAGGCGCAATCACGAATGAATAACGGTTTGGTTGATGCGAGTGATTTTGATGACGAGCGTAATGGCTGGCC
TGTTGAACAAGTCTGGAAAGAAATGCATAAACTTTTGCCATTCTCACCGGATTCAGTCGTCACTCATGGTGAT
TTCTCACTTGATAACCTTATTTTTGACGAGGGGAAATTAATAGGTTGTATTGATGTTGGACGAGTCGGAATCG
CAGACCGATACCAGGATCTTGCCATCCTATGGAACTGCCTCGGTGAGTTTTCTCCTTCATTACAGAAACGGC
TTTTTCAAAAATATGGTATTGATAATCCTGATATGAATAAATTGCAGTTTCATTTGATGCTCGATGAGTTTTT
CTAAGCGGCGCGCCATCGAATGGCGCAAAACCTTTCGCGGTATGGCATGATAGCGCCCGGAAGAGAGTCAATT
CAGGGTGGTGAATATGAAACCAGTAACGTTATACGATGTCGCAGAGTATGCCGGTGTCTCTTATCAGACCGT
TTCCCGCGTGGTGAACCAGGCCAGCCACGTTTCTGCGAAAACGCGGGAAAAAGTGGAAGCGGCGATGGCG
```

-continued

```
GAGCTGAATTACATTCCCAACCGCGTGGCACAACAACTGGCGGGCAAACAGTCGTTGCTGATTGGCGTTGC
CACCTCCAGTCTGGCCCTGCACGCGCCGTCGCAAATTGTCGCGGCGATTAAATCTCGCGCCGATCAACTGG
GTGCCAGCGTGGTGGTGTCGATGGTAGAACGAAGCGGCGTCGAAGCCTGTAAAGCGGCGGTGCACAATCT
TCTCGCGCAACGCGTCAGTGGGCTGATCATTAACTATCCGCTGGATGACCAGGATGCCATTGCTGTGGAAG
CTGCCTGCACTAATGTTCCGGCGTTATTTCTTGATGTCTCTGACCAGACACCCATCAACAGTATTATTTTC
TCCCATGAGGACGGTACGCGACTGGGCGTGGAGCATCTGGTCGCATTGGGTCACCAGCAAATCGCGCTGTT
AGCGGGCCCATTAAGTTCTGTCTCGGCGCGTCTGCGTCTGGCTGGCTGGCATAAATATCTCACTCGCAATC
AAATTCAGCCGATAGCGGAACGGGAAGGCGACTGGAGTGCCATGTCCGGTTTTCAACAAACCATGCAAATG
CTGAATGAGGGCATCGTTCCCACTGCGATGCTGGTTGCCAACGATCAGATGGCGCTGGGCGCAATGCGCGC
CATTACCGAGTCCGGGCTGCGCGTTGGTGCGGATATCTCGGTAGTGGGATACGACGATACCGAAGATAGCT
CATGTTATATCCCGCCGTTAACCACCATCAAACAGGATTTTCGCCTGCTGGGGCAAACCAGCGTGGACCGC
TTGCTGCAACTCTCTCAGGGCCAGGCGGTGAAGGGCAATCAGCTGTTGCCAGTCTCACTGGTGAAAAGAAA
AACCACCCTGGCGCCCAATACGCAAACCGCCTCTCCCCGCGCGTTGGCCGATTCATTAATGCAGCTGGCAC
GACAGGTTTCCCGACTGGAAAGCGGGCAGTGA
```

---

The invention claimed is:

1. An expression system for a recombinant expression of a polypeptide having isoeugenol oxidizing activity, which expression system comprises a single nucleic acid construct carrying:
   a. a nucleotide sequence (A) encoding a polypeptide having enzymatic isoeugenol oxidizing activity, and
   b. at least one nucleotide sequence (B) encoding at least one helper polypeptide which alone or in cooperation assist in a functional expression of the polypeptide, encoded by said nucleotide sequence (A);
   wherein said expression system provides for a co-expression of said nucleotide sequences (A) and (B), and
   wherein said nucleotide sequence (A) comprises an amino acid sequence having at least 85% sequence identity to SEQ ID NO: 4 and comprising at least one mutation in an amino acid sequence position selected from T52, Q74, D440, and optionally at least one further mutation in an amino acid sequence position selected from N120, T121, F281, M298, and L470.

2. The expression system of claim 1, which is a single polycistronic nucleic acid construct.

3. The expression system of claim 1, wherein said at least nucleotide sequence (B) comprises nucleotide sequences (B1) and (B2), wherein
   a. (B1) encodes a polypeptide having chaperonin activity that comprises an amino acid sequence having at least 70% sequence identity to SEQ ID NO:8; and
   b. (B2) encodes a polypeptide having chaperonin activity that comprises an amino acid sequence having at least 70% sequence identity to SEQ ID NO:10.

4. An expression vector comprising:
   the single nucleic acid construct comprised by the recombinant expression system of claim 1 or a reverse complement thereof.

5. A non-human host organism or host cell comprising, optionally stably integrated into its genome, the expression vector of claim 4.

6. A non-human host organism or host cell comprising, optionally stably integrated into its genome,
   the single nucleic acid construct comprised by the recombinant expression system of claim 1.

7. A method for producing an isolated catalytically active polypeptide having isoeugenol oxidizing activity, the method comprising co-expressing said polypeptide having isoeugenol oxidizing activity and at least one helper polypeptide, each encoded by an expression system as defined in claim 1, in a host cell system; and optionally isolating said polypeptide having isoeugenol oxidizing activity.

8. A polypeptide having isoeugenol oxidizing activity that comprises an amino acid sequence having at least 95% sequence identity to SEQ ID NO: 4 and comprising at least one mutation in an amino acid sequence position selected from T52, Q74, D440 and optionally at least one further mutation in an amino acid sequence position selected from N120, T121, F281, M298, and L470.

9. The polypeptide of claim 8, wherein said-mutant the at least one mutation is selected from
   a. single mutants $T52X_1$, $Q74X_2$ and $D440X_3$;
   b. double mutants $T52X_1/Q74X_2$, $T52X_1/D440X_3$, $Q74X_2/D440X_3$; and
   c. triple mutant $T52X_1/Q74X_2/D440X_3$, wherein X₁ is P, M or K;

X₂ is H or A; and

X₃ is N, A, C, E, F, G, H, I, K, L, M, Q, R, S, T, V, W or Y.

10. A recombinant nucleic acid comprising a nucleotide sequence encoding a polypeptide of claim 8, wherein the nucleotide sequence has at least 85% sequence identity to SEQ ID NO: 5 and encodes a polypeptide having isoeugenol oxidizing activity.

11. A recombinant nucleic acid construct comprising the recombinant nucleic acid of claim 10, or a reverse complement thereof.

12. An expression vector comprising the recombinant nucleic acid construct of claim 11, or a reverse complement thereof.

13. A non-human host organism or host cell comprising, optionally stably integrated into its genome, the recombinant nucleic acid construct of claim 11.

14. An expression vector comprising the recombinant nucleic acid of claim 10, or a reverse complement thereof.

15. A non-human host organism or host cell comprising, optionally stably integrated into its genome, the recombinant nucleic acid of claim 10.

16. A method of producing vanillin, the method comprising:
   a. contacting isoeugenol with a polypeptide having isoeugenol oxidizing activity as defined in claim 8, in a presence of oxygen to produce vanillin; and
   b. optionally isolating the vanillin produced in step a.

17. The method of the claim 16, the method further comprising chemically or biochemically isomerizing eugenol to isoeugenol, and optionally isolating the isoeugenol.

* * * * *

SEQUENCE LISTING

<160> NUMBER OF SEQ ID NOS: 16

<210> SEQ ID NO 1
<211> LENGTH: 1437
<212> TYPE: DNA
<213> ORGANISM: Pseudomonas nitroreducens
<220> FEATURE:
<221> NAME/KEY: CDS
<222> LOCATION: (1)..(1437)
<220> FEATURE:
<221> NAME/KEY: misc_feature
<222> LOCATION: (1)..(1437)
<223> OTHER INFOORMATION: codon modified Iseougenol monooxygenase of p. nitroreducens Jin1

<400> SEQUENCE: 1

```
atg gca cgt ctg aac cgt aat gat ccg caa ctc gtc ggc acc ctg tta      48
Met Ala Arg Leu Asn Arg Asn Asp Pro Gln Leu Val Gly Thr Leu Leu
1               5                   10                  15 cca acc cgt att gag gct gac ctg ttc gac ctg gaa gtg gac ggc gaa      96
Pro Thr Arg Ile Glu Ala Asp Leu Phe Asp Leu Glu Val Asp Gly Glu
            20                  25                  30 att ccg aag tcc atc aac ggt acc ttc tac cgt aac acg ccg gag cct     144
Ile Pro Lys Ser Ile Asn Gly Thr Phe Tyr Arg Asn Thr Pro Glu Pro
        35                  40                  45 cag gtg acg ccg cag aaa ttc cac acc ttc atc gat ggt gac ggc atg     192
Gln Val Thr Pro Gln Lys Phe His Thr Phe Ile Asp Gly Asp Gly Met
    50                  55                  60 gcg tct gca ttt cat ttt gaa gat ggc cac gtg gac ttc atc agc cgc     240
Ala Ser Ala Phe His Phe Glu Asp Gly His Val Asp Phe Ile Ser Arg
65                  70                  75                  80 tgg gtt aaa acc gcg cgt ttc acg gcg gag aga ctg gca cgt aaa agc     288
Trp Val Lys Thr Ala Arg Phe Thr Ala Glu Arg Leu Ala Arg Lys Ser
                85                  90                  95 ctg ttc ggt atg tac cgt aat ccg tac acc gat gac acg tct gtg aag     336
Leu Phe Gly Met Tyr Arg Asn Pro Tyr Thr Asp Asp Thr Ser Val Lys
            100                 105                 110 ggt ctg gat cgt acc gtt gcc aac acg agc atc atc agc cat cac ggt     384
```

```
                Gly Leu Asp Arg Thr Val Ala Asn Thr Ser Ile Ile Ser His His Gly
                            115                 120                 125 aag gtt ctg gcg gtg aaa gaa gat ggc ttg ccg tac gag ctg gac cca         432
Lys Val Leu Ala Val Lys Glu Asp Gly Leu Pro Tyr Glu Leu Asp Pro
        130                 135                 140 cgc act ctg gaa acc cgt ggt cgc ttt gac tat gat ggc caa gtc acc         480
Arg Thr Leu Glu Thr Arg Gly Arg Phe Asp Tyr Asp Gly Gln Val Thr
145                 150                 155                 160 agc cag acg cac acc gcg cat ccg aag tat gac ccg gaa acc ggt gac         528
Ser Gln Thr His Thr Ala His Pro Lys Tyr Asp Pro Glu Thr Gly Asp
                165                 170                 175 ctg ttg ttc ttt ggc tcc gca gcc aag ggt gag gca acg cct gat atg         576
Leu Leu Phe Phe Gly Ser Ala Ala Lys Gly Glu Ala Thr Pro Asp Met
            180                 185                 190 gcc tat tac atc gtt gat aaa cat ggt aag gta acg cat gag act tgg         624
Ala Tyr Tyr Ile Val Asp Lys His Gly Lys Val Thr His Glu Thr Trp
        195                 200                 205 ttc gag caa ccg tat ggc gcc ttt atg cat gat ttt gct att acc cgc         672
Phe Glu Gln Pro Tyr Gly Ala Phe Met His Asp Phe Ala Ile Thr Arg
    210                 215                 220 aat tgg agc atc ttc ccg atc atg ccg gct acc aat tcg ttg agc cgc         720
Asn Trp Ser Ile Phe Pro Ile Met Pro Ala Thr Asn Ser Leu Ser Arg
225                 230                 235                 240 ctg aaa gcg aag cag ccg att tac atg tgg gag ccg gaa ctg ggt tcc         768
Leu Lys Ala Lys Gln Pro Ile Tyr Met Trp Glu Pro Glu Leu Gly Ser
                245                 250                 255 tat att ggt gtt ctg ccg cgt cgc ggt caa ggt agc cag atc cgc tgg         816
Tyr Ile Gly Val Leu Pro Arg Arg Gly Gln Gly Ser Gln Ile Arg Trp
            260                 265                 270 ctg aaa gca cca gcg ctg tgg gtc ttt cac gtc gtc aac gcc tgg gaa         864
Leu Lys Ala Pro Ala Leu Trp Val Phe His Val Val Asn Ala Trp Glu
        275                 280                 285 gtg ggc acc aaa atc tac att gac ctt atg gag agc gaa att ctg cca         912
Val Gly Thr Lys Ile Tyr Ile Asp Leu Met Glu Ser Glu Ile Leu Pro
    290                 295                 300 ttc ccg ttc ccg aat agc caa aat cag ccg ttc gct cct gag aaa gca         960
Phe Pro Phe Pro Asn Ser Gln Asn Gln Pro Phe Ala Pro Glu Lys Ala
305                 310                 315                 320 gtg ccg cgt ctg acc cgt tgg gag att gat ctg gat agc agc agc gat        1008
Val Pro Arg Leu Thr Arg Trp Glu Ile Asp Leu Asp Ser Ser Ser Asp
                325                 330                 335 gag att aag cgt acg cgt ctg cac gac ttc ttt gca gag atg ccg atc        1056
Glu Ile Lys Arg Thr Arg Leu His Asp Phe Phe Ala Glu Met Pro Ile
            340                 345                 350 atg gat ttt cgt ttt gcg ctg cag tgc aac cgc tac ggt ttt atg ggt        1104
Met Asp Phe Arg Phe Ala Leu Gln Cys Asn Arg Tyr Gly Phe Met Gly
        355                 360                 365 gtc gat gac ccg cgc aag ccg ctg gcg cac caa caa gcg gag aag att        1152
Val Asp Asp Pro Arg Lys Pro Leu Ala His Gln Gln Ala Glu Lys Ile
    370                 375                 380 ttt gcg tac aat agc ctg ggt atc tgg gac aac cac cgt ggt gat tat        1200
Phe Ala Tyr Asn Ser Leu Gly Ile Trp Asp Asn His Arg Gly Asp Tyr
385                 390                 395                 400 gat ttg tgg tac agc ggc gaa gcc tca gcg gcg caa gaa ccg gct ttc        1248
Asp Leu Trp Tyr Ser Gly Glu Ala Ser Ala Ala Gln Glu Pro Ala Phe
                405                 410                 415 gtt ccg cgt tct ccg act gca gcg gaa ggc gac ggt tat ctg ctg acc        1296
Val Pro Arg Ser Pro Thr Ala Ala Glu Gly Asp Gly Tyr Leu Leu Thr
            420                 425                 430
```

```
gtt gtg ggc cgt ttg gac gag aac cgc agc gac ctg gtc att ctg gac      1344
Val Val Gly Arg Leu Asp Glu Asn Arg Ser Asp Leu Val Ile Leu Asp
        435                 440                 445 acg cag gac atc cag agc ggt ccg gtt gcg acc att aaa ctg ccg ttt      1392
Thr Gln Asp Ile Gln Ser Gly Pro Val Ala Thr Ile Lys Leu Pro Phe
450                 455                 460 cgc ctg cgt gcg gcc ctg cac ggc tgt tgg gtt ccg cgt ccg taa          1437
Arg Leu Arg Ala Ala Leu His Gly Cys Trp Val Pro Arg Pro
465                 470                 475

<210> SEQ ID NO 2
<211> LENGTH: 478
<212> TYPE: PRT
<213> ORGANISM: Pseudomonas nitroreducens

<400> SEQUENCE: 2

Met Ala Arg Leu Asn Arg Asn Asp Pro Gln Leu Val Gly Thr Leu Leu
1               5                   10                  15

Pro Thr Arg Ile Glu Ala Asp Leu Phe Asp Leu Glu Val Asp Gly Glu
            20                  25                  30

Ile Pro Lys Ser Ile Asn Gly Thr Phe Tyr Arg Asn Thr Pro Glu Pro
        35                  40                  45

Gln Val Thr Pro Gln Lys Phe His Thr Phe Ile Asp Gly Asp Gly Met
    50                  55                  60

Ala Ser Ala Phe His Phe Glu Asp Gly His Val Asp Phe Ile Ser Arg
65                  70                  75                  80

Trp Val Lys Thr Ala Arg Phe Thr Ala Glu Arg Leu Ala Arg Lys Ser
                85                  90                  95

Leu Phe Gly Met Tyr Arg Asn Pro Tyr Thr Asp Asp Thr Ser Val Lys
            100                 105                 110

Gly Leu Asp Arg Thr Val Ala Asn Thr Ser Ile Ile Ser His His Gly
        115                 120                 125

Lys Val Leu Ala Val Lys Glu Asp Gly Leu Pro Tyr Glu Leu Asp Pro
    130                 135                 140

Arg Thr Leu Glu Thr Arg Gly Arg Phe Asp Tyr Asp Gly Gln Val Thr
145                 150                 155                 160

Ser Gln Thr His Thr Ala His Pro Lys Tyr Asp Pro Glu Thr Gly Asp
                165                 170                 175

Leu Leu Phe Phe Gly Ser Ala Ala Lys Gly Glu Ala Thr Pro Asp Met
            180                 185                 190

Ala Tyr Tyr Ile Val Asp Lys His Gly Lys Val Thr His Glu Thr Trp
        195                 200                 205

Phe Glu Gln Pro Tyr Gly Ala Phe Met His Asp Phe Ala Ile Thr Arg
    210                 215                 220

Asn Trp Ser Ile Phe Pro Ile Met Pro Ala Thr Asn Ser Leu Ser Arg
225                 230                 235                 240

Leu Lys Ala Lys Gln Pro Ile Tyr Met Trp Glu Pro Glu Leu Gly Ser
                245                 250                 255

Tyr Ile Gly Val Leu Pro Arg Arg Gly Gln Gly Ser Gln Ile Arg Trp
            260                 265                 270

Leu Lys Ala Pro Ala Leu Trp Val Phe His Val Asn Ala Trp Glu
        275                 280                 285

Val Gly Thr Lys Ile Tyr Ile Asp Leu Met Glu Ser Glu Ile Leu Pro
    290                 295                 300

Phe Pro Phe Pro Asn Ser Gln Asn Gln Pro Phe Ala Pro Glu Lys Ala
305                 310                 315                 320
```

```
Val Pro Arg Leu Thr Arg Trp Glu Ile Asp Leu Asp Ser Ser Ser Asp
            325                 330                 335

Glu Ile Lys Arg Thr Arg Leu His Asp Phe Ala Glu Met Pro Ile
            340                 345                 350

Met Asp Phe Arg Phe Ala Leu Gln Cys Asn Arg Tyr Gly Phe Met Gly
            355                 360                 365

Val Asp Asp Pro Arg Lys Pro Leu Ala His Gln Gln Ala Glu Lys Ile
            370                 375                 380

Phe Ala Tyr Asn Ser Leu Gly Ile Trp Asp Asn His Arg Gly Asp Tyr
385                 390                 395                 400

Asp Leu Trp Tyr Ser Gly Glu Ala Ser Ala Gln Glu Pro Ala Phe
            405                 410                 415

Val Pro Arg Ser Pro Thr Ala Ala Glu Gly Asp Gly Tyr Leu Leu Thr
            420                 425                 430

Val Val Gly Arg Leu Asp Glu Asn Arg Ser Asp Leu Val Ile Leu Asp
            435                 440                 445

Thr Gln Asp Ile Gln Ser Gly Pro Val Ala Thr Ile Lys Leu Pro Phe
            450                 455                 460

Arg Leu Arg Ala Ala Leu His Gly Cys Trp Val Pro Arg Pro
465                 470                 475
```

<210> SEQ ID NO 3
<211> LENGTH: 1437
<212> TYPE: DNA
<213> ORGANISM: Pseudomonas putida
<220> FEATURE:
<221> NAME/KEY: misc_feature
<223> OTHER INFORMATION: Isoeugenol monooxygenase of p. putida IE27 at
      GenBank Accession AB291707
<220> FEATURE:
<221> NAME/KEY: CDS
<222> LOCATION: (1)..(1437)

<400> SEQUENCE: 3

```
atg gca acg ttt gac cgc aat gat ccg cag ttg gca gga acg atg ttc      48
Met Ala Thr Phe Asp Arg Asn Asp Pro Gln Leu Ala Gly Thr Met Phe
1               5                   10                  15 ccc acc cga ata gag gcg aat gtc ttt gac ctt gaa att gag ggc gag      96
Pro Thr Arg Ile Glu Ala Asn Val Phe Asp Leu Glu Ile Glu Gly Glu
                20                  25                  30 atc cca cgt gca atc aac ggg agc ttc ttc cgc aac acc ccc gaa cct     144
Ile Pro Arg Ala Ile Asn Gly Ser Phe Phe Arg Asn Thr Pro Glu Pro
            35                  40                  45 cag gtc acc acg caa cct ttc cac acc ttc atc gat ggg gat ggt ttg     192
Gln Val Thr Thr Gln Pro Phe His Thr Phe Ile Asp Gly Asp Gly Leu
        50                  55                  60 gcg tct gct ttt cat ttc gaa gat ggc cag gtc gac ttt gtc agc cgt     240
Ala Ser Ala Phe His Phe Glu Asp Gly Gln Val Asp Phe Val Ser Arg
65                  70                  75                  80 tgg gta tgt act cct cgc ttt gaa gct gag cgg tcg gct cgt aaa tca     288
Trp Val Cys Thr Pro Arg Phe Glu Ala Glu Arg Ser Ala Arg Lys Ser
                85                  90                  95 ctc ttc ggt atg tac cgc aat ccg ttc act gat gat cca tcg gta gaa     336
Leu Phe Gly Met Tyr Arg Asn Pro Phe Thr Asp Asp Pro Ser Val Glu
                100                 105                 110 ggt att gat cgt aca gtc gcc aac acc agt atc atc act cat cac ggg     384
Gly Ile Asp Arg Thr Val Ala Asn Thr Ser Ile Ile Thr His His Gly
            115                 120                 125 aaa gta ctg gcc gca aag gaa gat gga cta cct tat gag ctt gac ccc     432
```

```
                Lys Val Leu Ala Ala Lys Glu Asp Gly Leu Pro Tyr Glu Leu Asp Pro
                    130                 135                 140 caa acc ctg gaa acc cga ggt cgt tat gat tac aag ggg cag gta acc       480
Gln Thr Leu Glu Thr Arg Gly Arg Tyr Asp Tyr Lys Gly Gln Val Thr
145                 150                 155                 160 agc cat aca cat aca gcg cac cct aag ttc gac ccc cag aca ggt gaa       528
Ser His Thr His Thr Ala His Pro Lys Phe Asp Pro Gln Thr Gly Glu
                    165                 170                 175 atg tta ctc ttc ggc tcc gct gct aaa ggc gaa cga acg ctt gat atg       576
Met Leu Leu Phe Gly Ser Ala Ala Lys Gly Glu Arg Thr Leu Asp Met
                180                 185                 190 gcg tac tat att gtt gat cgc tac ggc aag gtg aca cat gag acc tgg       624
Ala Tyr Tyr Ile Val Asp Arg Tyr Gly Lys Val Thr His Glu Thr Trp
            195                 200                 205 ttt aag cag cct tac ggt gca ttc atg cac gac ttt gct gtc acg cgc       672
Phe Lys Gln Pro Tyr Gly Ala Phe Met His Asp Phe Ala Val Thr Arg
        210                 215                 220 aac tgg tca atc ttt ccg atc atg cct gcg aca aat agc ctt gag cgt       720
Asn Trp Ser Ile Phe Pro Ile Met Pro Ala Thr Asn Ser Leu Glu Arg
225                 230                 235                 240 ctt aaa gca aag cag ccc att tac atg tgg gag cct gag cga gga agc       768
Leu Lys Ala Lys Gln Pro Ile Tyr Met Trp Glu Pro Glu Arg Gly Ser
                245                 250                 255 tat ata gga gta ctt cct cgt cgt ggt cag ggc aag gac att cgt tgg       816
Tyr Ile Gly Val Leu Pro Arg Arg Gly Gln Gly Lys Asp Ile Arg Trp
            260                 265                 270 ttc cgt gcc ccg gcg ttg tgg gtt ttc cat gtc gtg aat gct tgg gag       864
Phe Arg Ala Pro Ala Leu Trp Val Phe His Val Val Asn Ala Trp Glu
        275                 280                 285 gaa ggg aat aga att ctg att gac ttg atg gaa agt gag att ttg ccg       912
Glu Gly Asn Arg Ile Leu Ile Asp Leu Met Glu Ser Glu Ile Leu Pro
290                 295                 300 ttc cca ttc ccg aac tcg cag aac ctt cca ttt gat ccc tcc aag gct       960
Phe Pro Phe Pro Asn Ser Gln Asn Leu Pro Phe Asp Pro Ser Lys Ala
                305                 310                 315                 320 gtt ccg cgt cta acc cgt tgg gaa att gat ctc aat agt ggt aac gat      1008
Val Pro Arg Leu Thr Arg Trp Glu Ile Asp Leu Asn Ser Gly Asn Asp
            325                 330                 335 gag atg aaa cgt acg cag cta cac gaa tat ttt gca gaa atg cct atc      1056
Glu Met Lys Arg Thr Gln Leu His Glu Tyr Phe Ala Glu Met Pro Ile
        340                 345                 350 atg gat ttc cgt ttt gcg ctc cag gat cat cgc tac gcc tac atg ggg      1104
Met Asp Phe Arg Phe Ala Leu Gln Asp His Arg Tyr Ala Tyr Met Gly
                355                 360                 365 gtt gac gat cct cgt cgc ccc tta gct cat cag caa gct gaa aaa atc      1152
Val Asp Asp Pro Arg Arg Pro Leu Ala His Gln Gln Ala Glu Lys Ile
370                 375                 380 ttt gcc tac aat tcg tta ggg gtt tgg gac aac cat cgt aaa gat tat      1200
Phe Ala Tyr Asn Ser Leu Gly Val Trp Asp Asn His Arg Lys Asp Tyr
                385                 390                 395                 400 gaa ctt tgg ttt acg gga aaa atg tct gca gcg cag gaa ccg gcg ttt      1248
Glu Leu Trp Phe Thr Gly Lys Met Ser Ala Ala Gln Glu Pro Ala Phe
            405                 410                 415 gtt cct aga agc cca gat gcg cct gag ggc gat ggc tac cta ctc agt      1296
Val Pro Arg Ser Pro Asp Ala Pro Glu Gly Asp Gly Tyr Leu Leu Ser
        420                 425                 430 gta gta ggg cgg ctc gat gaa gat cgt agc gat cta gtt atc ctt gat      1344
Val Val Gly Arg Leu Asp Glu Asp Arg Ser Asp Leu Val Ile Leu Asp
                435                 440                 445
```

```
acg caa tgt ttg gca gct ggg cct gtg gcc act gtc aag ctt ccc ttc   1392
Thr Gln Cys Leu Ala Ala Gly Pro Val Ala Thr Val Lys Leu Pro Phe
450             455                 460 cgt ctc cga gca gcg ttg cac ggt tgt tgg cag tct aag aac tga       1437
Arg Leu Arg Ala Ala Leu His Gly Cys Trp Gln Ser Lys Asn
465             470                 475
```

<210> SEQ ID NO 4
<211> LENGTH: 478
<212> TYPE: PRT
<213> ORGANISM: Pseudomonas putida

<400> SEQUENCE: 4

```
Met Ala Thr Phe Asp Arg Asn Asp Pro Gln Leu Ala Gly Thr Met Phe
1               5                   10                  15

Pro Thr Arg Ile Glu Ala Asn Val Phe Asp Leu Glu Ile Glu Gly Glu
                20                  25                  30

Ile Pro Arg Ala Ile Asn Gly Ser Phe Phe Arg Asn Thr Pro Glu Pro
            35                  40                  45

Gln Val Thr Thr Gln Pro Phe His Thr Phe Ile Asp Gly Asp Gly Leu
        50                  55                  60

Ala Ser Ala Phe His Phe Glu Asp Gly Gln Val Asp Phe Val Ser Arg
65                  70                  75                  80

Trp Val Cys Thr Pro Arg Phe Glu Ala Glu Arg Ser Ala Arg Lys Ser
                85                  90                  95

Leu Phe Gly Met Tyr Arg Asn Pro Phe Thr Asp Asp Pro Ser Val Glu
                100                 105                 110

Gly Ile Asp Arg Thr Val Ala Asn Thr Ser Ile Ile Thr His His Gly
            115                 120                 125

Lys Val Leu Ala Ala Lys Glu Asp Gly Leu Pro Tyr Glu Leu Asp Pro
130                 135                 140

Gln Thr Leu Glu Thr Arg Gly Arg Tyr Asp Tyr Lys Gly Gln Val Thr
145                 150                 155                 160

Ser His Thr His Thr Ala His Pro Lys Phe Asp Pro Gln Thr Gly Glu
                165                 170                 175

Met Leu Leu Phe Gly Ser Ala Ala Lys Gly Glu Arg Thr Leu Asp Met
                180                 185                 190

Ala Tyr Tyr Ile Val Asp Arg Tyr Gly Lys Val Thr His Glu Thr Trp
            195                 200                 205

Phe Lys Gln Pro Tyr Gly Ala Phe Met His Asp Phe Ala Val Thr Arg
210                 215                 220

Asn Trp Ser Ile Phe Pro Ile Met Pro Ala Thr Asn Ser Leu Glu Arg
225                 230                 235                 240

Leu Lys Ala Lys Gln Pro Ile Tyr Met Trp Glu Pro Glu Arg Gly Ser
                245                 250                 255

Tyr Ile Gly Val Leu Pro Arg Arg Gly Gln Gly Lys Asp Ile Arg Trp
                260                 265                 270

Phe Arg Ala Pro Ala Leu Trp Val Phe His Val Val Asn Ala Trp Glu
            275                 280                 285

Glu Gly Asn Arg Ile Leu Ile Asp Leu Met Ser Glu Ile Leu Pro
290                 295                 300

Phe Pro Phe Pro Asn Ser Gln Asn Leu Pro Phe Asp Pro Ser Lys Ala
305                 310                 315                 320

Val Pro Arg Leu Thr Arg Trp Glu Ile Asp Leu Asn Ser Gly Asn Asp
                325                 330                 335
```

```
Glu Met Lys Arg Thr Gln Leu His Glu Tyr Phe Ala Glu Met Pro Ile
            340                 345                 350

Met Asp Phe Arg Phe Ala Leu Gln Asp His Arg Tyr Ala Tyr Met Gly
            355                 360                 365

Val Asp Asp Pro Arg Arg Pro Leu Ala His Gln Gln Ala Glu Lys Ile
    370                 375                 380

Phe Ala Tyr Asn Ser Leu Gly Val Trp Asp Asn His Arg Lys Asp Tyr
385                 390                 395                 400

Glu Leu Trp Phe Thr Gly Lys Met Ser Ala Ala Gln Glu Pro Ala Phe
                405                 410                 415

Val Pro Arg Ser Pro Asp Ala Pro Glu Gly Asp Gly Tyr Leu Leu Ser
            420                 425                 430

Val Val Gly Arg Leu Asp Glu Asp Arg Ser Asp Leu Val Ile Leu Asp
            435                 440                 445

Thr Gln Cys Leu Ala Ala Gly Pro Val Ala Thr Val Lys Leu Pro Phe
    450                 455                 460

Arg Leu Arg Ala Ala Leu His Gly Cys Trp Gln Ser Lys Asn
465                 470                 475

<210> SEQ ID NO 5
<211> LENGTH: 1437
<212> TYPE: DNA
<213> ORGANISM: Pseudomonas putida
<220> FEATURE:
<221> NAME/KEY: misc_feature
<223> OTHER INFORMATION: codon modified Isoeugenol monoxygenase of p.
      putida IE27
<220> FEATURE:
<221> NAME/KEY: CDS
<222> LOCATION: (1)..(1437)

<400> SEQUENCE: 5 atg gcc act ttt gac cgc aat gac ccg caa ctg gca ggc acc atg ttc      48
Met Ala Thr Phe Asp Arg Asn Asp Pro Gln Leu Ala Gly Thr Met Phe
1               5                   10                  15 ccg acg cgc atc gaa gcg aat gtt ttt gat ctg gag att gaa ggt gag      96
Pro Thr Arg Ile Glu Ala Asn Val Phe Asp Leu Glu Ile Glu Gly Glu
                20                  25                  30 att ccg cgt gcg atc aac ggt agc ttt ttc cgc aac acg cca gag ccg     144
Ile Pro Arg Ala Ile Asn Gly Ser Phe Phe Arg Asn Thr Pro Glu Pro
            35                  40                  45 caa gtc acc acg cag ccg ttt cat act ttc atc gac ggc gac ggc ctg     192
Gln Val Thr Thr Gln Pro Phe His Thr Phe Ile Asp Gly Asp Gly Leu
        50                  55                  60 gcg tca gcg ttc cac ttc gaa gat ggc cag gtc gac ttt gtg agc cgc     240
Ala Ser Ala Phe His Phe Glu Asp Gly Gln Val Asp Phe Val Ser Arg
65                  70                  75                  80 tgg gtc tgc acc ccg cgt ttc gag gca gag cgc agc gcg cgt aaa agc     288
Trp Val Cys Thr Pro Arg Phe Glu Ala Glu Arg Ser Ala Arg Lys Ser
                85                  90                  95 ctg ttt ggt atg tat cgc aat ccg ttt acg gat gac ccg agc gtt gaa     336
Leu Phe Gly Met Tyr Arg Asn Pro Phe Thr Asp Asp Pro Ser Val Glu
                100                 105                 110 ggc att gac cgt acc gtg gcg aat acc tcg atc att acc cac cac ggt     384
Gly Ile Asp Arg Thr Val Ala Asn Thr Ser Ile Ile Thr His His Gly
            115                 120                 125 aag gtc ctg gca gca aaa gaa gat ggc ttg ccg tac gag tta gat ccg     432
Lys Val Leu Ala Ala Lys Glu Asp Gly Leu Pro Tyr Glu Leu Asp Pro
        130                 135                 140 cag acc ctg gaa acg cgt ggt cgc tat gac tac aag ggc cag gtt acc     480
```

```
             Gln Thr Leu Glu Thr Arg Gly Arg Tyr Asp Tyr Lys Gly Gln Val Thr
             145                 150                 155                 160 agc cat acc cac acg gct cac cct aag ttt gat ccg caa acg ggt gag        528
Ser His Thr His Thr Ala His Pro Lys Phe Asp Pro Gln Thr Gly Glu
                165                 170                 175 atg ctg ctg ttc ggc agc gcg gca aag ggt gag cgt acc ctg gac atg        576
Met Leu Leu Phe Gly Ser Ala Ala Lys Gly Glu Arg Thr Leu Asp Met
            180                 185                 190 gcg tac tat atc gtt gac cgt tac ggt aaa gtg acc cat gaa acc tgg        624
Ala Tyr Tyr Ile Val Asp Arg Tyr Gly Lys Val Thr His Glu Thr Trp
            195                 200                 205 ttc aag caa ccg tac ggc gcc ttt atg cac gac ttc gca gtc acg cgc        672
Phe Lys Gln Pro Tyr Gly Ala Phe Met His Asp Phe Ala Val Thr Arg
    210                 215                 220 aac tgg tct atc ttt ccg att atg ccg gcc acc aat agc ctg gag cgt        720
Asn Trp Ser Ile Phe Pro Ile Met Pro Ala Thr Asn Ser Leu Glu Arg
225                 230                 235                 240 ctg aaa gct aag caa ccg att tac atg tgg gaa ccg gag cgt ggt tcc        768
Leu Lys Ala Lys Gln Pro Ile Tyr Met Trp Glu Pro Glu Arg Gly Ser
                245                 250                 255 tac atc ggc gtg ctg ccg cgt cgt ggt cag ggt aaa gat atc cgc tgg        816
Tyr Ile Gly Val Leu Pro Arg Arg Gly Gln Gly Lys Asp Ile Arg Trp
            260                 265                 270 ttc cgt gcg cct gcc ctc tgg gtg ttc cac gtt gtg aac gca tgg gaa        864
Phe Arg Ala Pro Ala Leu Trp Val Phe His Val Val Asn Ala Trp Glu
            275                 280                 285 gag ggc aat cgt att ctg atc gat ctg atg gag agc gaa atc ctg cca        912
Glu Gly Asn Arg Ile Leu Ile Asp Leu Met Glu Ser Glu Ile Leu Pro
            290                 295                 300 ttc ccg ttt ccg aac tct cag aat ctg ccg ttc gat ccg agc aaa gcc        960
Phe Pro Phe Pro Asn Ser Gln Asn Leu Pro Phe Asp Pro Ser Lys Ala
305                 310                 315                 320 gta ccg cgc ttg acc cgt tgg gag att gat ttg aac agc ggt aat gac       1008
Val Pro Arg Leu Thr Arg Trp Glu Ile Asp Leu Asn Ser Gly Asn Asp
                325                 330                 335 gag atg aag cgt act cag ctg cac gaa tac ttc gct gag atg ccg att       1056
Glu Met Lys Arg Thr Gln Leu His Glu Tyr Phe Ala Glu Met Pro Ile
            340                 345                 350 atg gac ttt cgt ttc gcg ctg caa gat cac cgt tac gcg tat atg ggt       1104
Met Asp Phe Arg Phe Ala Leu Gln Asp His Arg Tyr Ala Tyr Met Gly
            355                 360                 365 gtt gat gat cca cgc cgt cca ttg gcg cat caa caa gcg gaa aag att       1152
Val Asp Asp Pro Arg Arg Pro Leu Ala His Gln Gln Ala Glu Lys Ile
            370                 375                 380 ttt gcg tat aac agc ctg ggt gtt tgg gac aac cat cgt aaa gac tat       1200
Phe Ala Tyr Asn Ser Leu Gly Val Trp Asp Asn His Arg Lys Asp Tyr
385                 390                 395                 400 gag ctg tgg ttt acg ggt aaa atg tcc gcg gct cag gaa ccg gcc ttc       1248
Glu Leu Trp Phe Thr Gly Lys Met Ser Ala Ala Gln Glu Pro Ala Phe
                405                 410                 415 gtg ccg cgc agc ccg gac gcc cct gag ggt gat ggt tat ttg ctg tcc       1296
Val Pro Arg Ser Pro Asp Ala Pro Glu Gly Asp Gly Tyr Leu Leu Ser
            420                 425                 430 gtc gtg ggt cgc ctg gat gaa gat cgt agc gac ctg gtt atc ctg gac       1344
Val Val Gly Arg Leu Asp Glu Asp Arg Ser Asp Leu Val Ile Leu Asp
            435                 440                 445 acc cag tgc ctt gcg gca ggc ccg gtt gcg acc gtc aag ctg ccg ttc       1392
Thr Gln Cys Leu Ala Ala Gly Pro Val Ala Thr Val Lys Leu Pro Phe
            450                 455                 460
```

```
                                                      -continued cgt ctg cgt gca gct ctg cat ggt tgt tgg cag agc aaa aac taa        1437
Arg Leu Arg Ala Ala Leu His Gly Cys Trp Gln Ser Lys Asn
465                 470                 475

<210> SEQ ID NO 6
<211> LENGTH: 478
<212> TYPE: PRT
<213> ORGANISM: Pseudomonas putida

<400> SEQUENCE: 6

Met Ala Thr Phe Asp Arg Asn Asp Pro Gln Leu Ala Gly Thr Met Phe
1               5                   10                  15

Pro Thr Arg Ile Glu Ala Asn Val Phe Asp Leu Glu Ile Glu Gly Glu
            20                  25                  30

Ile Pro Arg Ala Ile Asn Gly Ser Phe Phe Arg Asn Thr Pro Glu Pro
        35                  40                  45

Gln Val Thr Thr Gln Pro Phe His Thr Phe Ile Asp Gly Asp Gly Leu
    50                  55                  60

Ala Ser Ala Phe His Phe Glu Asp Gly Gln Val Asp Phe Val Ser Arg
65                  70                  75                  80

Trp Val Cys Thr Pro Arg Phe Glu Ala Glu Arg Ser Ala Arg Lys Ser
                85                  90                  95

Leu Phe Gly Met Tyr Arg Asn Pro Phe Thr Asp Asp Pro Ser Val Glu
            100                 105                 110

Gly Ile Asp Arg Thr Val Ala Asn Thr Ser Ile Ile Thr His His Gly
        115                 120                 125

Lys Val Leu Ala Ala Lys Glu Asp Gly Leu Pro Tyr Glu Leu Asp Pro
130                 135                 140

Gln Thr Leu Glu Thr Arg Gly Arg Tyr Asp Tyr Lys Gly Gln Val Thr
145                 150                 155                 160

Ser His Thr His Thr Ala His Pro Lys Phe Asp Pro Gln Thr Gly Glu
                165                 170                 175

Met Leu Leu Phe Gly Ser Ala Ala Lys Gly Glu Arg Thr Leu Asp Met
            180                 185                 190

Ala Tyr Tyr Ile Val Asp Arg Tyr Gly Lys Val Thr His Glu Thr Trp
        195                 200                 205

Phe Lys Gln Pro Tyr Gly Ala Phe Met His Asp Phe Ala Val Thr Arg
    210                 215                 220

Asn Trp Ser Ile Phe Pro Ile Met Pro Ala Thr Asn Ser Leu Glu Arg
225                 230                 235                 240

Leu Lys Ala Lys Gln Pro Ile Tyr Met Trp Glu Pro Glu Arg Gly Ser
                245                 250                 255

Tyr Ile Gly Val Leu Pro Arg Gly Gln Gly Lys Asp Ile Arg Trp
            260                 265                 270

Phe Arg Ala Pro Ala Leu Trp Val Phe His Val Val Asn Ala Trp Glu
        275                 280                 285

Glu Gly Asn Arg Ile Leu Ile Asp Leu Met Glu Ser Glu Ile Leu Pro
    290                 295                 300

Phe Pro Phe Pro Asn Ser Gln Asn Leu Pro Phe Asp Pro Ser Lys Ala
305                 310                 315                 320

Val Pro Arg Leu Thr Arg Trp Glu Ile Asp Leu Asn Ser Gly Asn Asp
                325                 330                 335

Glu Met Lys Arg Thr Gln Leu His Glu Tyr Phe Ala Glu Met Pro Ile
            340                 345                 350

Met Asp Phe Arg Phe Ala Leu Gln Asp His Arg Tyr Ala Tyr Met Gly
```

```
              355                 360                 365
Val Asp Asp Pro Arg Arg Pro Leu Ala His Gln Gln Ala Glu Lys Ile
        370                 375                 380

Phe Ala Tyr Asn Ser Leu Gly Val Trp Asp Asn His Arg Lys Asp Tyr
385                 390                 395                 400

Glu Leu Trp Phe Thr Gly Lys Met Ser Ala Ala Gln Glu Pro Ala Phe
                405                 410                 415

Val Pro Arg Ser Pro Asp Ala Pro Glu Gly Asp Gly Tyr Leu Leu Ser
                420                 425                 430

Val Val Gly Arg Leu Asp Glu Asp Arg Ser Asp Leu Val Ile Leu Asp
                435                 440                 445

Thr Gln Cys Leu Ala Ala Gly Pro Val Ala Thr Val Lys Leu Pro Phe
        450                 455                 460

Arg Leu Arg Ala Ala Leu His Gly Cys Trp Gln Ser Lys Asn
465                 470                 475

<210> SEQ ID NO 7
<211> LENGTH: 1647
<212> TYPE: DNA
<213> ORGANISM: Escherichia coli
<220> FEATURE:
<221> NAME/KEY: misc_feature
<223> OTHER INFORMATION: chaperonin GroEL of e. coli at GenBank
      Accession CP009685.1 in region 3964433 to 3966079
<220> FEATURE:
<221> NAME/KEY: CDS
<222> LOCATION: (1)..(1647)

<400> SEQUENCE: 7 atg gca gct aaa gac gta aaa ttc ggt aac gac gct cgt gtg aaa atg        48
Met Ala Ala Lys Asp Val Lys Phe Gly Asn Asp Ala Arg Val Lys Met
1               5                   10                  15 ctg cgc ggc gta aac gta ctg gca gat gca gtg aaa gtt acc ctc ggt        96
Leu Arg Gly Val Asn Val Leu Ala Asp Ala Val Lys Val Thr Leu Gly
            20                  25                  30 cca aaa ggc cgt aac gta gtt ctg gat aaa tct ttc ggt gca ccg acc       144
Pro Lys Gly Arg Asn Val Val Leu Asp Lys Ser Phe Gly Ala Pro Thr
        35                  40                  45 atc acc aaa gat ggt gtt tcc gtt gct cgt gaa atc gaa ctg gaa gac       192
Ile Thr Lys Asp Gly Val Ser Val Ala Arg Glu Ile Glu Leu Glu Asp
    50                  55                  60 aag ttc gaa aat atg ggt gcg cag atg gtg aaa gaa gtt gcc tct aaa       240
Lys Phe Glu Asn Met Gly Ala Gln Met Val Lys Glu Val Ala Ser Lys
65                  70                  75                  80 gca aac gac gct gca ggc gac ggt acc acc act gca acc gta ctg gct       288
Ala Asn Asp Ala Ala Gly Asp Gly Thr Thr Thr Ala Thr Val Leu Ala
                85                  90                  95 cag gct atc atc act gaa ggt ctg aaa gct gtt gct gcg ggc atg aac       336
Gln Ala Ile Ile Thr Glu Gly Leu Lys Ala Val Ala Ala Gly Met Asn
            100                 105                 110 ccg atg gac ctg aaa cgt ggt atc gac aaa gcg gtt acc gct gca gtt       384
Pro Met Asp Leu Lys Arg Gly Ile Asp Lys Ala Val Thr Ala Ala Val
        115                 120                 125 gaa gaa ctg aaa gcg ctg tcc gta cca tgc tct gac tct aaa gcg att       432
Glu Glu Leu Lys Ala Leu Ser Val Pro Cys Ser Asp Ser Lys Ala Ile
    130                 135                 140 gct cag gtt ggt acc atc tcc gct aac tcc gac gaa acc gta ggt aaa       480
Ala Gln Val Gly Thr Ile Ser Ala Asn Ser Asp Glu Thr Val Gly Lys
145                 150                 155                 160 ctg atc gct gaa gcg atg gac aaa gtc ggt aaa gaa ggc gtt atc acc       528
```

| | | | | | | | | | | | | |
|---|---|---|---|---|---|---|---|---|---|---|---|---|
| Leu | Ile | Ala | Glu | Ala | Met | Asp | Lys | Val | Gly | Lys | Glu | Gly | Val | Ile | Thr |
| | | | 165 | | | | 170 | | | | | 175 | | | |

| gtt | gaa | gac | ggt | acc | ggt | ctg | cag | gac | gaa | ctg | gac | gtg | gtt | gaa | ggt | 576 |
|---|---|---|---|---|---|---|---|---|---|---|---|---|---|---|---|---|
| Val | Glu | Asp | Gly | Thr | Gly | Leu | Gln | Asp | Glu | Leu | Asp | Val | Val | Glu | Gly | |
| | | | 180 | | | | | 185 | | | | | 190 | | | |

| atg | cag | ttc | gac | cgt | ggc | tac | ctg | tct | cct | tac | ttc | atc | aac | aag | ccg | 624 |
|---|---|---|---|---|---|---|---|---|---|---|---|---|---|---|---|---|
| Met | Gln | Phe | Asp | Arg | Gly | Tyr | Leu | Ser | Pro | Tyr | Phe | Ile | Asn | Lys | Pro | |
| | | | 195 | | | | | 200 | | | | | 205 | | | |

| gaa | act | ggc | gca | gta | gaa | ctg | gaa | agc | ccg | ttc | atc | ctg | ctg | gct | gac | 672 |
|---|---|---|---|---|---|---|---|---|---|---|---|---|---|---|---|---|
| Glu | Thr | Gly | Ala | Val | Glu | Leu | Glu | Ser | Pro | Phe | Ile | Leu | Leu | Ala | Asp | |
| | 210 | | | | | 215 | | | | | 220 | | | | | |

| aag | aaa | atc | tcc | aac | atc | cgc | gaa | atg | ctg | ccg | gtt | ctg | gaa | gct | gtt | 720 |
|---|---|---|---|---|---|---|---|---|---|---|---|---|---|---|---|---|
| Lys | Lys | Ile | Ser | Asn | Ile | Arg | Glu | Met | Leu | Pro | Val | Leu | Glu | Ala | Val | |
| 225 | | | | | 230 | | | | | 235 | | | | | 240 | |

| gcc | aaa | gca | ggc | aaa | ccg | ctg | ctg | atc | atc | gct | gaa | gat | gta | gaa | ggc | 768 |
|---|---|---|---|---|---|---|---|---|---|---|---|---|---|---|---|---|
| Ala | Lys | Ala | Gly | Lys | Pro | Leu | Leu | Ile | Ile | Ala | Glu | Asp | Val | Glu | Gly | |
| | | | | 245 | | | | | 250 | | | | | 255 | | |

| gaa | gcg | ctg | gca | act | ctg | gtt | gtt | aac | acc | atg | cgt | ggc | atc | gtg | aaa | 816 |
|---|---|---|---|---|---|---|---|---|---|---|---|---|---|---|---|---|
| Glu | Ala | Leu | Ala | Thr | Leu | Val | Val | Asn | Thr | Met | Arg | Gly | Ile | Val | Lys | |
| | | 260 | | | | | 265 | | | | | 270 | | | | |

| gtc | gct | gcg | gtt | aaa | gca | ccg | ggc | ttc | ggc | gat | cgt | cgt | aaa | gct | atg | 864 |
|---|---|---|---|---|---|---|---|---|---|---|---|---|---|---|---|---|
| Val | Ala | Ala | Val | Lys | Ala | Pro | Gly | Phe | Gly | Asp | Arg | Arg | Lys | Ala | Met | |
| | 275 | | | | | 280 | | | | | 285 | | | | | |

| ctg | cag | gat | atc | gca | acc | ctg | act | ggc | ggt | acc | gtg | atc | tct | gaa | gag | 912 |
|---|---|---|---|---|---|---|---|---|---|---|---|---|---|---|---|---|
| Leu | Gln | Asp | Ile | Ala | Thr | Leu | Thr | Gly | Gly | Thr | Val | Ile | Ser | Glu | Glu | |
| | 290 | | | | | 295 | | | | | 300 | | | | | |

| atc | ggt | atg | gag | ctg | gaa | aaa | gca | acc | ctg | gaa | gac | ctg | ggt | cag | gct | 960 |
|---|---|---|---|---|---|---|---|---|---|---|---|---|---|---|---|---|
| Ile | Gly | Met | Glu | Leu | Glu | Lys | Ala | Thr | Leu | Glu | Asp | Leu | Gly | Gln | Ala | |
| 305 | | | | | 310 | | | | | 315 | | | | | 320 | |

| aaa | cgt | gtt | gtg | atc | aac | aaa | gac | acc | acc | act | atc | atc | gat | ggc | gtg | 1008 |
|---|---|---|---|---|---|---|---|---|---|---|---|---|---|---|---|---|
| Lys | Arg | Val | Val | Ile | Asn | Lys | Asp | Thr | Thr | Thr | Ile | Ile | Asp | Gly | Val | |
| | | | | 325 | | | | | 330 | | | | | 335 | | |

| ggt | gaa | gaa | gct | gca | atc | cag | ggc | cgt | gtt | gct | cag | atc | cgt | cag | cag | 1056 |
|---|---|---|---|---|---|---|---|---|---|---|---|---|---|---|---|---|
| Gly | Glu | Glu | Ala | Ala | Ile | Gln | Gly | Arg | Val | Ala | Gln | Ile | Arg | Gln | Gln | |
| | | | 340 | | | | | 345 | | | | | 350 | | | |

| att | gaa | gaa | gca | act | tct | gac | tac | gac | cgt | gaa | aaa | ctg | cag | gaa | cgc | 1104 |
|---|---|---|---|---|---|---|---|---|---|---|---|---|---|---|---|---|
| Ile | Glu | Glu | Ala | Thr | Ser | Asp | Tyr | Asp | Arg | Glu | Lys | Leu | Gln | Glu | Arg | |
| | | | | 355 | | | | | 360 | | | | | 365 | | |

| gta | gcg | aaa | ctg | gca | ggc | ggc | gtt | gca | gtt | atc | aaa | gtg | ggt | gct | gct | 1152 |
|---|---|---|---|---|---|---|---|---|---|---|---|---|---|---|---|---|
| Val | Ala | Lys | Leu | Ala | Gly | Gly | Val | Ala | Val | Ile | Lys | Val | Gly | Ala | Ala | |
| | 370 | | | | | 375 | | | | | 380 | | | | | |

| acc | gaa | gtt | gaa | atg | aaa | gag | aaa | aaa | gca | cgc | gtt | gaa | gat | gcc | ctg | 1200 |
|---|---|---|---|---|---|---|---|---|---|---|---|---|---|---|---|---|
| Thr | Glu | Val | Glu | Met | Lys | Glu | Lys | Lys | Ala | Arg | Val | Glu | Asp | Ala | Leu | |
| 385 | | | | | 390 | | | | | 395 | | | | | 400 | |

| cac | gcg | acc | cgt | gct | gcg | gta | gaa | gaa | ggc | gtg | gtt | gct | ggt | ggt | ggt | 1248 |
|---|---|---|---|---|---|---|---|---|---|---|---|---|---|---|---|---|
| His | Ala | Thr | Arg | Ala | Ala | Val | Glu | Glu | Gly | Val | Val | Ala | Gly | Gly | Gly | |
| | | | 405 | | | | | 410 | | | | | 415 | | | |

| gtt | gcg | ctg | atc | cgc | gta | gcg | tct | aaa | ctg | gct | gac | ctg | cgt | ggt | cag | 1296 |
|---|---|---|---|---|---|---|---|---|---|---|---|---|---|---|---|---|
| Val | Ala | Leu | Ile | Arg | Val | Ala | Ser | Lys | Leu | Ala | Asp | Leu | Arg | Gly | Gln | |
| | | 420 | | | | | 425 | | | | | 430 | | | | |

| aac | gaa | gac | cag | aac | gtg | ggt | atc | aaa | gtt | gca | ctg | cgt | gca | atg | gaa | 1344 |
|---|---|---|---|---|---|---|---|---|---|---|---|---|---|---|---|---|
| Asn | Glu | Asp | Gln | Asn | Val | Gly | Ile | Lys | Val | Ala | Leu | Arg | Ala | Met | Glu | |
| | | | 435 | | | | | 440 | | | | | 445 | | | |

| gct | ccg | ctg | cgt | cag | atc | gta | ttg | aac | tgc | ggc | gaa | gaa | ccg | tct | gtt | 1392 |
|---|---|---|---|---|---|---|---|---|---|---|---|---|---|---|---|---|
| Ala | Pro | Leu | Arg | Gln | Ile | Val | Leu | Asn | Cys | Gly | Glu | Glu | Pro | Ser | Val | |
| | | | | 450 | | | | | 455 | | | | | 460 | | |

| gtt | gct | aac | acc | gtt | aaa | ggc | ggc | gac | ggc | aac | tac | ggt | tac | aac | gca | 1440 |
|---|---|---|---|---|---|---|---|---|---|---|---|---|---|---|---|---|
| Val | Ala | Asn | Thr | Val | Lys | Gly | Gly | Asp | Gly | Asn | Tyr | Gly | Tyr | Asn | Ala | |
| 465 | | | | | 470 | | | | | 475 | | | | | 480 | |

-continued

| | | |
|---|---|---|
| gca acc gaa gaa tac ggc aac atg atc gac atg ggt atc ctg gat cca<br>Ala Thr Glu Glu Tyr Gly Asn Met Ile Asp Met Gly Ile Leu Asp Pro<br>                485                      490                    495 | 1488 |
| acc aaa gta act cgt tct gct ctg cag tac gca gct tct gtg gct ggc<br>Thr Lys Val Thr Arg Ser Ala Leu Gln Tyr Ala Ala Ser Val Ala Gly<br>        500                      505                      510 | 1536 |
| ctg atg atc acc acc gaa tgc atg gtt acc gac ctg ccg aaa aac gat<br>Leu Met Ile Thr Thr Glu Cys Met Val Thr Asp Leu Pro Lys Asn Asp<br>            515                      520                    525 | 1584 |
| gca gct gac tta ggc gct gct ggt ggt atg ggc atg ggt ggc atg<br>Ala Ala Asp Leu Gly Ala Ala Gly Gly Met Gly Met Gly Gly Met<br>530                      535                      540 | 1632 |
| ggc ggc atg atg taa<br>Gly Gly Met Met<br>545 | 1647 |

<210> SEQ ID NO 8
<211> LENGTH: 548
<212> TYPE: PRT
<213> ORGANISM: Escherichia coli

<400> SEQUENCE: 8

Met Ala Ala Lys Asp Val Lys Phe Gly Asn Asp Ala Arg Val Lys Met
1               5                   10                  15

Leu Arg Gly Val Asn Val Leu Ala Asp Ala Val Lys Val Thr Leu Gly
                20                  25                  30

Pro Lys Gly Arg Asn Val Val Leu Asp Lys Ser Phe Gly Ala Pro Thr
            35                  40                  45

Ile Thr Lys Asp Gly Val Ser Val Ala Arg Glu Ile Glu Leu Glu Asp
        50                  55                  60

Lys Phe Glu Asn Met Gly Ala Gln Met Val Lys Glu Val Ala Ser Lys
65                  70                  75                  80

Ala Asn Asp Ala Ala Gly Asp Gly Thr Thr Thr Ala Thr Val Leu Ala
                85                  90                  95

Gln Ala Ile Ile Thr Glu Gly Leu Lys Ala Val Ala Ala Gly Met Asn
            100                 105                 110

Pro Met Asp Leu Lys Arg Gly Ile Asp Lys Ala Val Thr Ala Ala Val
        115                 120                 125

Glu Glu Leu Lys Ala Leu Ser Val Pro Cys Ser Asp Ser Lys Ala Ile
130                 135                 140

Ala Gln Val Gly Thr Ile Ser Ala Asn Ser Asp Glu Thr Val Gly Lys
145                 150                 155                 160

Leu Ile Ala Glu Ala Met Asp Lys Val Gly Lys Glu Gly Val Ile Thr
                165                 170                 175

Val Glu Asp Gly Thr Gly Leu Gln Asp Glu Leu Asp Val Val Glu Gly
            180                 185                 190

Met Gln Phe Asp Arg Gly Tyr Leu Ser Pro Tyr Phe Ile Asn Lys Pro
        195                 200                 205

Glu Thr Gly Ala Val Glu Leu Glu Ser Pro Phe Ile Leu Leu Ala Asp
    210                 215                 220

Lys Lys Ile Ser Asn Ile Arg Glu Met Leu Pro Val Leu Glu Ala Val
225                 230                 235                 240

Ala Lys Ala Gly Lys Pro Leu Leu Ile Ile Ala Glu Asp Val Glu Gly
                245                 250                 255

Glu Ala Leu Ala Thr Leu Val Val Asn Thr Met Arg Gly Ile Val Lys
            260                 265                 270

```
Val Ala Ala Val Lys Ala Pro Gly Phe Gly Asp Arg Arg Lys Ala Met
            275                 280                 285

Leu Gln Asp Ile Ala Thr Leu Thr Gly Gly Thr Val Ile Ser Glu Glu
        290                 295                 300

Ile Gly Met Glu Leu Glu Lys Ala Thr Leu Glu Asp Leu Gly Gln Ala
305                 310                 315                 320

Lys Arg Val Val Ile Asn Lys Asp Thr Thr Thr Ile Ile Asp Gly Val
                325                 330                 335

Gly Glu Glu Ala Ala Ile Gln Gly Arg Val Ala Gln Ile Arg Gln Gln
            340                 345                 350

Ile Glu Glu Ala Thr Ser Asp Tyr Asp Arg Glu Lys Leu Gln Glu Arg
        355                 360                 365

Val Ala Lys Leu Ala Gly Gly Val Ala Val Ile Lys Val Gly Ala Ala
    370                 375                 380

Thr Glu Val Glu Met Lys Glu Lys Lys Ala Arg Val Glu Asp Ala Leu
385                 390                 395                 400

His Ala Thr Arg Ala Ala Val Glu Glu Gly Val Val Ala Gly Gly Gly
                405                 410                 415

Val Ala Leu Ile Arg Val Ala Ser Lys Leu Ala Asp Leu Arg Gly Gln
            420                 425                 430

Asn Glu Asp Gln Asn Val Gly Ile Lys Val Ala Leu Arg Ala Met Glu
        435                 440                 445

Ala Pro Leu Arg Gln Ile Val Leu Asn Cys Gly Glu Glu Pro Ser Val
    450                 455                 460

Val Ala Asn Thr Val Lys Gly Gly Asp Gly Asn Tyr Gly Tyr Asn Ala
465                 470                 475                 480

Ala Thr Glu Glu Tyr Gly Asn Met Ile Asp Met Gly Ile Leu Asp Pro
                485                 490                 495

Thr Lys Val Thr Arg Ser Ala Leu Gln Tyr Ala Ala Ser Val Ala Gly
            500                 505                 510

Leu Met Ile Thr Thr Glu Cys Met Val Thr Asp Leu Pro Lys Asn Asp
        515                 520                 525

Ala Ala Asp Leu Gly Ala Ala Gly Gly Met Gly Gly Met Gly Gly Met
    530                 535                 540

Gly Gly Met Met
545

<210> SEQ ID NO 9
<211> LENGTH: 294
<212> TYPE: DNA
<213> ORGANISM: Escherichia coli
<220> FEATURE:
<221> NAME/KEY: misc_feature
<223> OTHER INFORMATION: chaperonin GroES of e. coli at GenBank
      Accession CP009685.1 in region 3966123 to 3966416
<220> FEATURE:
<221> NAME/KEY: CDS
<222> LOCATION: (1)..(294)

<400> SEQUENCE: 9 atg aat att cgt cca ttg cat gat cgc gtg atc gtc aag cgt aaa gaa     48
Met Asn Ile Arg Pro Leu His Asp Arg Val Ile Val Lys Arg Lys Glu
1               5                   10                  15 gtt gaa act aaa tct gct ggc ggc atc gtt ctg acc ggc tct gca gcg     96
Val Glu Thr Lys Ser Ala Gly Gly Ile Val Leu Thr Gly Ser Ala Ala
            20                  25                  30 gct aaa tcc acc cgc ggc gaa gtg ctg gct gtc ggc aat ggc cgt atc    144
Ala Lys Ser Thr Arg Gly Glu Val Leu Ala Val Gly Asn Gly Arg Ile
```

-continued

```
                     35                  40                  45
ctt gaa aat ggc gaa gtg aag ccg ctg gat gtg aaa gtt ggc gac atc      192
Leu Glu Asn Gly Glu Val Lys Pro Leu Asp Val Lys Val Gly Asp Ile
         50                  55                  60 gtt att ttc aac gat ggc tac ggt gtg aaa tct gag aag atc gac aat      240
Val Ile Phe Asn Asp Gly Tyr Gly Val Lys Ser Glu Lys Ile Asp Asn
 65                  70                  75                  80 gaa gaa gtg ttg atc atg tcc gaa agc gac att ctg gca att gtt gaa      288
Glu Glu Val Leu Ile Met Ser Glu Ser Asp Ile Leu Ala Ile Val Glu
                 85                  90                  95 gcg taa                                                              294
Ala

<210> SEQ ID NO 10
<211> LENGTH: 97
<212> TYPE: PRT
<213> ORGANISM: Escherichia coli

<400> SEQUENCE: 10

Met Asn Ile Arg Pro Leu His Asp Arg Val Ile Val Lys Arg Lys Glu
 1               5                  10                  15

Val Glu Thr Lys Ser Ala Gly Gly Ile Val Leu Thr Gly Ser Ala Ala
             20                  25                  30

Ala Lys Ser Thr Arg Gly Glu Val Leu Ala Val Gly Asn Gly Arg Ile
         35                  40                  45

Leu Glu Asn Gly Glu Val Lys Pro Leu Asp Val Lys Val Gly Asp Ile
     50                  55                  60

Val Ile Phe Asn Asp Gly Tyr Gly Val Lys Ser Glu Lys Ile Asp Asn
 65                  70                  75                  80

Glu Glu Val Leu Ile Met Ser Glu Ser Asp Ile Leu Ala Ile Val Glu
                 85                  90                  95

Ala

<210> SEQ ID NO 11
<211> LENGTH: 3451
<212> TYPE: DNA
<213> ORGANISM: Artificial Sequence
<220> FEATURE:
<223> OTHER INFORMATION: Polycistroncic construct containing codon
      modified isoeugenol monooxygenase of p. nitroreducens Jin1, GroES,
      GroEL

<400> SEQUENCE: 11
gaaggagata tacatatggc acgtctgaac cgtaatgatc cgcaactcgt cggcaccctg       60
ttaccaaccc gtattgaggc tgacctgttc gacctggaag tggacggcga aattccgaag      120
tccatcaacg gtaccttcta ccgtaacacg ccggagcctc aggtgacgcc gcagaaattc      180
cacaccttca tcgatggtga cggcatggcg tctgcatttc attttgaaga tggccacgtg      240
gacttcatca gccgctgggt taaaaccgcg cgtttcacgg cggagagact ggcacgtaaa      300
agcctgttcg gtatgtaccg taatccgtac accgatgaca cgtctgtgaa gggtctggat      360
cgtaccgttg ccaacacgag catcatcagc catcacggta aggttctggc ggtgaaagaa      420
gatggcttgc cgtacgagct ggacccacgc actctgaaa cccgtggtcg ctttgactat      480
gatggccaag tcaccagcca gacgcacacc gcgcatccga agtatgaccc ggaaaccggt      540
gacctgttgt cctttggctc cgcagccaag ggtgaggcaa cgcctgatat ggcctattac      600
atcgttgata acatggtaa ggtaacgcat gagacttggt tcgagcaacc gtatggcgcc      660
```

| | |
|---|---|
| tttatgcatg attttgctat tacccgcaat tggagcatct tcccgatcat gccggctacc | 720 |
| aattcgttga gccgcctgaa agcgaagcag ccgatttaca tgtgggagcc ggaactgggt | 780 |
| tcctatattg gtgttctgcc gcgtcgcggt caaggtagcc agatccgctg gctgaaagca | 840 |
| ccagcgctgt gggtctttca cgtcgtcaac gcctgggaag tgggcaccaa aatctacatt | 900 |
| gaccttatgg agagcgaaat tctgccattc ccgttcccga atagccaaaa tcagccgttc | 960 |
| gctcctgaga aagcagtgcc gcgtctgacc cgttgggaga ttgatctgga tagcagcagc | 1020 |
| gatgagatta agcgtacgcg tctgcacgac ttctttgcag agatgccgat catggatttt | 1080 |
| cgttttgcgc tgcagtgcaa ccgctacggt tttatgggtg tcgatgaccc gcgcaagccg | 1140 |
| ctggcgcacc aacaagcgga gaagattttt gcgtacaata gcctgggtat ctgggacaac | 1200 |
| caccgtggtg attatgattt tgtggtacag cggcgaagcct cagcggcgca agaaccggct | 1260 |
| ttcgttccgc gttctccgac tgcagcggaa ggcgacggtt atctgctgac cgttgtgggc | 1320 |
| cgtttggacg agaaccgcag cgacctggtc attctggaca cgcaggacat ccagagcggt | 1380 |
| ccggttgcga ccattaaact gccgtttcgc ctgcgtgcgg ccctgcacgg ctgttgggtt | 1440 |
| ccgcgtccgt aagaaggaga tatacatatg aatattcgtc cattgcatga tcgcgtgatc | 1500 |
| gtcaagcgta aagaagttga aactaaatct gctggcggca tcgttctgac cggctctgca | 1560 |
| gcggctaaat ccacccgcgg cgaagtgctg gctgtcggca atggccgtat ccttgaaaat | 1620 |
| ggcgaagtga agccgctgga tgtgaaagtt ggcgacatcg ttatttcaa cgatggctac | 1680 |
| ggtgtgaaat ctgagaagat cgacaatgaa gaagtgttga tcatgtccga aagcgacatt | 1740 |
| ctggcaattg ttgaagcgta atccgcgcac gacactgaac atacgaattt aaggaataaa | 1800 |
| gataatggca gctaaagacg taaaattcgg taacgacgct cgtgtgaaaa tgctgcgcgg | 1860 |
| cgtaaacgta ctggcagatg cagtgaaagt taccctcggt ccaaaaggcc gtaacgtagt | 1920 |
| tctggataaa tctttcggtg caccgaccat caccaaagat ggtgtttccg ttgctcgtga | 1980 |
| aatcgaactg gaagacaagt tcgaaaatat gggtgcgcag atggtgaaag aagttgcctc | 2040 |
| taaagcaaac gacgctgcag gcgacggtac caccactgca accgtactgg ctcaggctat | 2100 |
| catcactgaa ggtctgaaag ctgttgctgc gggcatgaac ccgatggacc tgaaacgtgg | 2160 |
| tatcgacaaa gcggttaccg ctgcagttga agaactgaaa gcgctgtccg taccatgctc | 2220 |
| tgactctaaa gcgattgctc aggttggtac catctccgct aactccgacg aaaccgtagg | 2280 |
| taaactgatc gctgaagcga tggacaaagt cggtaaagaa ggcgttatca ccgttgaaga | 2340 |
| cggtaccggt ctgcaggacg aactggacgt ggttgaaggt atgcagttcg accgtggcta | 2400 |
| cctgtctcct tacttcatca acaagccgga aactggcgca gtagaactgg aaagcccgtt | 2460 |
| catcctgctg gctgacaaga aaatctccaa catccgcgaa atgctgccgg ttctggaagc | 2520 |
| tgttgccaaa gcaggcaaac cgctgctgat catcgctgaa gatgtagaag gcgaagcgct | 2580 |
| ggcaactctg gttgttaaca ccatgcgtgg catcgtgaaa gtcgctgcgg ttaaagcacc | 2640 |
| gggcttcggc gatcgtcgta agctatgct gcaggatatc gcaaccctga ctggcggtac | 2700 |
| cgtgatctct gaagagatcg gtatggagct ggaaaaagca ccctggaag acctgggtca | 2760 |
| ggctaaacgt gttgtgatca acaaagacac caccactatc atcgatggcg tgggtgaaga | 2820 |
| agctgcaatc cagggccgtg ttgctcagat ccgtcagcag attgaagaag caacttctga | 2880 |
| ctacgaccgt gaaaaactgc aggaacgcgt agcgaaactg gcaggcggcg ttgcagttat | 2940 |
| caaagtgggt gctgctaccg aagttgaaat gaaagagaaa aaagcacgcg ttgaagatgc | 3000 |
| cctgcacgcg acccgtgctg cggtagaaga aggcgtggtt gctggtggtg gtgttgcgct | 3060 |

-continued

```
gatccgcgta gcgtctaaac tggctgacct gcgtggtcag aacgaagacc agaacgtggg    3120
tatcaaagtt gcactgcgtg caatggaagc tccgctgcgt cagatcgtat tgaactgcgg    3180
cgaagaaccg tctgttgttg ctaacaccgt taaaggcggc gacggcaact acggttacaa    3240
cgcagcaacc gaagaatacg gcaacatgat cgacatgggt atcctggatc caaccaaagt    3300
aactcgttct gctctgcagt acgcagcttc tgtggctggc ctgatgatca ccaccgaatg    3360
catggttacc gacctgccga aaaacgatgc agctgactta ggcgctgctg gcggtatggg    3420
cggcatgggt ggcatgggcg gcatgatgta a                                   3451
```

<210> SEQ ID NO 12
<211> LENGTH: 3475
<212> TYPE: DNA
<213> ORGANISM: Artificial Sequence
<220> FEATURE:
<223> OTHER INFORMATION: Polycistroncic construct containing codon
      modified isoeugenol monooxygenase of p. nitroreducens Jin1, GroES,
      GroEL

<400> SEQUENCE: 12

```
gaaggagata tacatatggc acgtctgaac cgtaatgatc cgcaactcgt cggcaccctg     60
ttaccaaccc gtattgaggc tgacctgttc gacctggaag tggacggcga aattccgaag    120
tccatcaacg gtaccttcta ccgtaacacg ccggagcctc aggtgacgcc gcagaaattc    180
cacaccttca tcgatggtga cggcatggcg tctgcatttc attttgaaga tggccacgtg    240
gacttcatca gccgctgggt taaaaccgcg cgtttcacgg cggagagact ggcacgtaaa    300
agcctgttcg gtatgtaccg taatccgtac accgatgaca cgtctgtgaa gggtctggat    360
cgtaccgttg ccaacacgag catcatcagc catcacggta aggttctggc ggtgaaagaa    420
gatggcttgc cgtacgagct ggacccacgc actctggaaa cccgtggtcg ctttgactat    480
gatggccaag tcaccagcca gacgcacacc gcgcatccga agtatgaccc ggaaaccggt    540
gacctgttgt tctttggctc cgcagccaag ggtgaggcaa cgcctgatat ggcctattac    600
atcgttgata acatggtaa ggtaacgcat gagacttggt tcgagcaacc gtatggcgcc    660
tttatgcatg attttgctat tacccgcaat tggagcatct tcccgatcat gccggctacc    720
aattcgttga ccgcctgaa agcgaagcag ccgatttaca tgtgggagcc ggaactgggt    780
tcctatattg gtgttctgcc gcgtcgcggt caaggtagcc agatccgctg gctgaaagca    840
ccagcgctgt gggtctttca cgtcgtcaac gcctgggaag tgggcaccaa aatctacatt    900
gaccttatgg agagcgaaat tctgccattc ccgttcccga atagccaaaa tcagccgttc    960
gctcctgaga aagcagtgcc gcgtctgacc cgttgggaga ttgatctgga tagcagcagc   1020
gatgagatta agcgtacgcg tctgcacgac ttctttgcag agatgccgat catggatttt   1080
cgttttgcgc tgcagtgcaa ccgctacggt tttatgggtg tcgatgaccc gcgcaagccg   1140
ctggcgcacc aacaagcgga gaagatttt gcgtacaata gcctgggtat ctgggacaac   1200
caccgtggtg attatgattt gtggtacagc ggcgaagcct cagcggcgca agaaccggct   1260
ttcgttccgc gttctccgac tgcagcggaa ggcgacggtt atctgctgac cgttgtgggc   1320
cgtttggacg agaaccgcag cgacctggtc attctggaca cgcaggacat ccagagcggt   1380
ccggttgcga ccattaaact gccgtttcgc ctgcgtgcgg ccctgcacgg ctgttgggtt   1440
ccgcgtccgt aatccgcgca cgacactgaa catacggaag gagatataca tatgaatatt   1500
cgtccattgc atgatcgcgt gatcgtcaag cgtaaagaag ttgaaactaa atctgctggc   1560
```

| | |
|---|---|
| ggcatcgttc tgaccggctc tgcagcggct aaatccaccc gcggcgaagt gctggctgtc | 1620 |
| ggcaatggcc gtatccttga aaatggcgaa gtgaagccgc tggatgtgaa agttggcgac | 1680 |
| atcgttattt tcaacgatgg ctacggtgtg aaatctgaga agatcgacaa tgaagaagtg | 1740 |
| ttgatcatgt ccgaaagcga cattctggca attgttgaag cgtaatccgc gcacgacact | 1800 |
| gaacatacga atttaaggaa taaagataat ggcagctaaa gacgtaaaat tcggtaacga | 1860 |
| cgctcgtgtg aaaatgctgc gcggcgtaaa cgtactggca gatgcagtga agttaccct | 1920 |
| cggtccaaaa ggccgtaacg tagttctgga taaatctttc ggtgcaccga ccatcaccaa | 1980 |
| agatggtgtt ccgttgctc gtgaaatcga actggaagac aagttcgaaa atatgggtgc | 2040 |
| gcagatggtg aaagaagttg cctctaaagc aaacgacgct gcaggcgacg gtaccaccac | 2100 |
| tgcaaccgta ctggctcagg ctatcatcac tgaaggtctg aaagctgttg ctgcgggcat | 2160 |
| gaacccgatg gacctgaaac gtggtatcga caaagcggtt accgctgcag ttgaagaact | 2220 |
| gaaagcgctg tccgtaccat gctctgactc taaagcgatt gctcaggttg gtaccatctc | 2280 |
| cgctaactcc gacgaaaccg taggtaaact gatcgctgaa gcgatggaca aagtcggtaa | 2340 |
| agaaggcgtt atcaccgttg aagacggtac cggtctgcag gacgaactgg acgtggttga | 2400 |
| aggtatgcag ttcgaccgtg gctacctgtc tccttacttc atcaacaagc cggaaactgg | 2460 |
| cgcagtagaa ctggaaagcc cgttcatcct gctggctgac aagaaaatct ccaacatccg | 2520 |
| cgaaatgctg ccggttctgg aagctgttgc caaagcaggc aaaccgctgc tgatcatcgc | 2580 |
| tgaagatgta gaaggcgaag cgctggcaac tctggttgtt aacaccatgc gtggcatcgt | 2640 |
| gaaagtcgct gcggttaaag caccgggctt cggcgatcgt cgtaaagcta tgctgcagga | 2700 |
| tatcgcaacc ctgactggcg gtaccgtgat ctctgaagag atcggtatgg agctggaaaa | 2760 |
| agcaaccctg gaagacctgg gtcaggctaa acgtgttgtg atcaacaaag acaccaccac | 2820 |
| tatcatcgat ggcgtgggtg aagaagctgc aatccagggc cgtgttgctc agatccgtca | 2880 |
| gcagattgaa gaagcaactt ctgactacga ccgtgaaaaa ctgcaggaac gcgtagcgaa | 2940 |
| actggcaggc ggcgttgcag ttatcaaagt gggtgctgct accgaagttg aaatgaaaga | 3000 |
| gaaaaaagca cgcgttgaag atgccctgca cgcgacccgt gctgcggtag aagaaggcgt | 3060 |
| ggttgctggt ggtggtgttg cgctgatccg cgtagcgtct aaactggctg acctgcgtgg | 3120 |
| tcagaacgaa gaccagaacg tgggtatcaa agttgcactg cgtgcaatgg aagctccgct | 3180 |
| gcgtcagatc gtattgaact gcggcgaaga accgtctgtt gttgctaaca ccgttaaagg | 3240 |
| cggcgacggc aactacggtt acaacgcagc aaccgaagaa tacggcaaca tgatcgacat | 3300 |
| gggtatcctg gatccaacca agtaactcg ttctgctctg cagtacgcag cttctgtggc | 3360 |
| tggcctgatg atcaccaccg aatgcatggt taccgacctg ccgaaaaacg atgcagctga | 3420 |
| cttaggcgct gctggcggta tgggcggcat gggtggcatg ggcggcatga tgtaa | 3475 |

<210> SEQ ID NO 13
<211> LENGTH: 3456
<212> TYPE: DNA
<213> ORGANISM: Artificial Sequence
<220> FEATURE:
<223> OTHER INFORMATION: Polycistroncic construct containing codon
    modified isoeugenol monooxygenase of p. nitroreducens Jin1, GroES,
    GroEL

<400> SEQUENCE: 13

| | |
|---|---|
| gaaggagata tacatatggc acgtctgaac cgtaatgatc cgcaactcgt cggcaccctg | 60 |
| ttaccaaccc gtattgaggc tgacctgttc gacctggaag tggacggcga aattccgaag | 120 |

```
tccatcaacg gtaccttcta ccgtaacacg ccggagcctc aggtgacgcc gcagaaattc      180
cacaccttca tcgatggtga cggcatggcg tctgcatttc attttgaaga tggccacgtg      240
gacttcatca gccgctgggt taaaaccgcg cgtttcacgg cggagagact ggcacgtaaa      300
agcctgttcg gtatgtaccg taatccgtac accgatgaca cgtctgtgaa gggtctggat      360
cgtaccgttg ccaacacgag catcatcagc catcacggta aggttctggc ggtgaaagaa      420
gatggcttgc cgtacgagct ggacccacgc actctggaaa cccgtggtcg ctttgactat      480
gatggccaag tcaccagcca gacgcacacc gcgcatccga agtatgaccc ggaaaccggt      540
gacctgttgt tctttggctc cgcagccaag ggtgaggcaa cgcctgatat ggcctattac      600
atcgttgata acatggtaa ggtaacgcat gagacttggt tcgagcaacc gtatggcgcc      660
tttatgcatg attttgctat tacccgcaat tggagcatct cccgatcat gccggctacc       720 aattcgttga gccgcctgaa agcgaagcag ccgatttaca tgtgggagcc ggaactgggt      780
tcctatattg gtgttctgcc gcgtcgcggt caaggtagcc agatccgctg gctgaaagca      840
ccagcgctgt gggtctttca cgtcgtcaac gcctgggaag tgggcaccaa aatctacatt      900
gaccttatgg agagcgaaat tctgccattc ccgttcccga atagccaaaa tcagccgttc      960
gctcctgaga aagcagtgcc gcgtctgacc cgttgggaga ttgatctgga tagcagcagc     1020
gatgagatta agcgtacgcg tctgcacgac ttctttgcag agatgccgat catggatttt     1080
cgttttgcgc tgcagtgcaa ccgctacggt tttatgggtg tcgatgaccc cgcaagccg     1140 ctggcgcacc aacaagcgga gaagattttt gcgtacaata gcctgggtat ctgggacaac     1200
caccgtggtg attatgattt tgtggtacagc ggcgaagcct cagcggcgca agaaccggct    1260
ttcgttccgc gttctccgac tgcagcggaa ggcgacggtt atctgctgac cgttgtgggc     1320
cgtttggacg agaaccgcag cgacctggtc attctggaca cgcaggacat ccagagcggt     1380
ccggttgcga ccattaaact gccgtttcgc ctgcgtgcgg ccctgcacgg ctgttgggtt     1440
ccgcgtccgt aaaattaggt aaaaaataaa aaatgaatat tcgtccattg catgatcgcg     1500
tgatcgtcaa gcgtaaagaa gttgaaacta atctgctgg cggcatcgtt ctgaccggct      1560
ctgcagcggc taaatccacc cgcggcgaag tgctggctgt cggcaatggc cgtatccttg     1620
aaaatggcga agtgaagccg ctggatgtga agttggcga catcgttatt ttcaacgatg      1680
gctacggtgt gaaatctgag aagatcgaca atgaagaagt gttgatcatg tccgaaagcg     1740
acattctggc aattgttgaa gcgtaatccg cgcacgacac tgaacatacg aatttaagga     1800
ataaagataa tggcagctaa agacgtaaaa ttcggtaacg acgctcgtgt gaaaatgctg     1860
cgcggcgtaa acgtactggc agatgcagtg aaagttaccc tcggtccaaa aggccgtaac     1920
gtagttctgg ataaatcttt cggtgcaccg accatcacca agatggtgt ttccgttgct     1980 cgtgaaatcg aactggaaga caagttcgaa aatatgggtg cgcagatggt gaaagaagtt     2040
gcctctaaag caaacgacgc tgcaggcgac ggtaccacca ctgcaaccgt actggctcag     2100
gctatcatca ctgaaggtct gaaagctgtt gctgcgggca tgaacccgat ggacctgaaa     2160
cgtggtatcg acaaagcggt taccgctgca gttgaagaac tgaaagcgct gtccgtacca     2220
tgctctgact ctaaagcgat tgctcaggtt ggtaccatct ccgctaactc cgacgaaacc     2280
gtaggtaaac tgatcgctga agcgatggac aaagtcggta agaaggcgt tatcaccgtt     2340 gaagacggta ccggtctgca ggacgaactg gacgtggttg aaggtatgca gttcgaccgt     2400
ggctacctgt ctccttactt catcaacaag ccggaaactg gcgcagtaga actggaaagc     2460
```

| | |
|---|---|
| ccgttcatcc tgctggctga caagaaaatc tccaacatcc gcgaaatgct gccggttctg | 2520 |
| gaagctgttg ccaaagcagg caaaccgctg ctgatcatcg ctgaagatgt agaaggcgaa | 2580 |
| gcgctggcaa ctctggttgt taacaccatg cgtggcatcg tgaaagtcgc tgcggttaaa | 2640 |
| gcaccgggct tcggcgatcg tcgtaaagct atgctgcagg atatcgcaac cctgactggc | 2700 |
| ggtaccgtga tctctgaaga tcggtatg gagctggaaa aagcaaccct ggaagacctg | 2760 |
| ggtcaggcta acgtgttgt gatcaacaaa gacaccacca ctatcatcga tggcgtgggt | 2820 |
| gaagaagctg caatccaggg ccgtgttgct cagatccgtc agcagattga agaagcaact | 2880 |
| tctgactacg accgtgaaaa actgcaggaa cgcgtagcga actggcagg cggcgttgca | 2940 |
| gttatcaaag tgggtgctgc taccgaagtt gaaatgaaag agaaaaaagc acgcgttgaa | 3000 |
| gatgccctgc acgcgacccg tgctgcggta gaagaaggcg tggttgctgg tggtggtgtt | 3060 |
| gcgctgatcc gcgtagcgtc taaactggct gacctgcgtg gtcagaacga agaccagaac | 3120 |
| gtgggtatca agttgcact gcgtgcaatg gaagctccgc tgcgtcagat cgtattgaac | 3180 |
| tgcggcgaag aaccgtctgt tgttgctaac accgttaaag cggcgacgg caactacggt | 3240 |
| tacaacgcag caaccgaaga atacggcaac atgatcgaca tgggtatcct ggatccaacc | 3300 |
| aaagtaactc gttctgctct gcagtacgca gcttctgtgg ctggcctgat gatcaccacc | 3360 |
| gaatgcatgg ttaccgacct gccgaaaaac gatgcagctg acttaggcgc tgctggcggt | 3420 |
| atgggcggca tgggtggcat gggcggcatg atgtaa | 3456 |

<210> SEQ ID NO 14
<211> LENGTH: 3423
<212> TYPE: DNA
<213> ORGANISM: Artificial Sequence
<220> FEATURE:
<223> OTHER INFORMATION: Polycistroncic construct containing codon modified isoeugenol monooxygenase of p. nitroreducens Jin1, GroES, GroEL

<400> SEQUENCE: 14

| | |
|---|---|
| gaaggagata tacatatggc acgtctgaac cgtaatgatc gcaactcgt cggcaccctg | 60 |
| ttaccaaccc gtattgaggc tgacctgttc gacctggaag tggacggcga aattccgaag | 120 |
| tccatcaacg gtaccttcta ccgtaacacg ccggagcctc aggtgacgcc gcagaaattc | 180 |
| cacaccttca tcgatggtga cggcatggcg tctgcatttc attttgaaga tggccacgtg | 240 |
| gacttcatca gccgctgggt taaaaccgcg cgtttcacgg cggagagact ggcacgtaaa | 300 |
| agcctgttcg gtatgtaccg taatccgtac accgatgaca cgtctgtgaa gggtctggat | 360 |
| cgtaccgttg ccaacacgag catcatcagc catcacggta aggttctggc ggtgaaagaa | 420 |
| gatggcttgc cgtacgagct ggacccacgc actctggaaa cccgtggtcg ctttgactat | 480 |
| gatggccaag tcaccagcca gacgcacacc gcgcatccga agtatgaccc ggaaaccggt | 540 |
| gacctgttgt tctttggctc cgcagccaag ggtgaggcaa cgcctgatat ggcctattac | 600 |
| atcgttgata acatggtaa ggtaacgcat gagacttggt tcgagcaacc gtatggcgcc | 660 |
| tttatgcatg atttttgctat taccgcaat tggagcatct tcccgatcat gccggctacc | 720 |
| aattcgttga gcgcctgaa agcgaagcag ccgatttaca tgtgggagcc ggaactgggt | 780 |
| tcctatattg gtgttctgcc gcgtcgcggt caaggtagcc agatccgctg gctgaaagca | 840 |
| ccagcgctgt gggtctttca cgtcgtcaac gcctgggaag tggcaccaa aatctacatt | 900 |
| gaccttatgg agagcgaaat tctgccattc ccgttcccga atagccaaaa tcagccgttc | 960 |
| gctcctgaga aagcagtgcc gcgtctgacc cgttgggaga ttgatctgga tagcagcagc | 1020 |

```
gatgagatta agcgtacgcg tctgcacgac ttctttgcag agatgccgat catggatttt    1080
cgttttgcgc tgcagtgcaa ccgctacggt tttatgggtg tcgatgaccc gcgcaagccg    1140
ctggcgcacc aacaagcgga gaagattttt gcgtacaata gcctgggtat ctgggacaac    1200
caccgtggtg attatgattt gtggtacagc ggcgaagcct cagcggcgca agaaccggct    1260
ttcgttccgc gttctccgac tgcagcggaa ggcgacggtt atctgctgac cgttgtgggc    1320
cgtttggacg agaaccgcag cgacctggtc attctggaca cgcaggacat ccagagcggt    1380
ccggttgcga ccattaaact gccgtttcgc ctgcgtgcgg ccctgcacgg ctgttgggtt    1440
ccgcgtccgt aagaaggaga tatacatatg aatattcgtc cattgcatga tcgcgtgatc    1500
gtcaagcgta aagaagttga aactaaatct gctggcggca tcgttctgac cggctctgca    1560
gcggctaaat ccacccgcgg cgaagtgctg gctgtcggca tggccgtat ccttgaaaat    1620 ggcgaagtga agccgctgga tgtgaaagtt ggcgacatcg ttattttcaa cgatggctac    1680
ggtgtgaaat ctgagaagat cgacaatgaa gaagtgttga tcatgtccga agcgacatt    1740 ctggcaattg ttgaagcgta agaaggagat atacatatgg cagctaaaga cgtaaaattc    1800
ggtaacgacg ctcgtgtgaa aatgctgcgc ggcgtaaacg tactggcaga tgcagtgaaa    1860
gttaccctcg gtccaaaagg ccgtaacgta gttctggata aatctttcgg tgcaccgacc    1920
atcaccaaag atggtgtttc cgttgctcgt gaaatcgaac tggaagacaa gttcgaaaat    1980
atgggtgcgc agatggtgaa agaagttgcc tctaaagcaa cgacgctgc aggcgacggt    2040 accaccactg caaccgtact ggctcaggct atcatcactg aaggtctgaa agctgttgct    2100
gcgggcatga acccgatgga cctgaaacgt ggtatcgaca aagcggttac cgctgcagtt    2160
gaagaactga aagcgctgtc cgtaccatgc tctgactcta aagcgattgc tcaggttggt    2220
accatctccg ctaactccga cgaaaccgta ggtaaactga tcgctgaagc gatggacaaa    2280
gtcggtaaag aaggcgttat caccgttgaa gacggtaccg gtctgcagga cgaactggac    2340
gtggttgaag gtatgcagtt cgaccgtggc tacctgtctc cttacttcat caacaagccg    2400
gaaactggcg cagtagaact ggaaagcccc ttcatcctgc tggctgacaa gaaaatctcc    2460
aacatccgcg aaatgctgcc ggttctggaa gctgttgcca agcaggcaa accgctgctg    2520 atcatcgctg aagatgtaga aggcgaagcg ctggcaactc tggttgttaa caccatgcgt    2580
ggcatcgtga aagtcgctgc ggttaaagca ccgggcttcg gcgatcgtcg taagctatg    2640 ctgcaggata tcgcaaccct gactggcggt accgtgatct ctgaagagat cggtatggag    2700
ctggaaaaag caaccctgga agacctgggt caggctaaac gtgttgtgat caacaaagac    2760
accaccacta tcatcgatgg cgtgggtgaa gaagctgcaa tccagggccg tgttgctcag    2820
atccgtcagc agattgaaga agcaacttct gactacgacc gtgaaaaact gcaggaacgc    2880
gtagcgaaac tggcaggcgg cgttgcagtt atcaaagtgg gtgctgctac cgaagttgaa    2940
atgaaagaga aaaaagcacg cgttgaagat gccctgcacg cgacccgtgc tgcggtagaa    3000
gaaggcgtgg ttgctggtgg tggtgttgcg ctgatccgcg tagcgtctaa actggctgac    3060
ctgcgtggtc agaacgaaga ccagaacgtg ggtatcaaag ttgcactgcg tgcaatggaa    3120
gctccgctgc gtcagatcgt attgaactgc ggcgaagaac cgtctgttgt tgctaacacc    3180
gttaaaggcg cgacggcaa ctacggttac aacgcagcaa ccgaagaata cggcaacatg    3240
atcgacatgg gtatcctgga tccaaccaaa gtaactcgtt ctgctctgca gtacgcagct    3300
tctgtggctg gcctgatgat caccaccgaa tgcatggtta ccgacctgcc gaaaaacgat    3360
```

```
gcagctgact taggcgctgc tggcggtatg ggcggcatgg gtggcatggg cggcatgatg    3420
taa                                                                  3423

<210> SEQ ID NO 15
<211> LENGTH: 3456
<212> TYPE: DNA
<213> ORGANISM: Artificial Sequence
<220> FEATURE:
<223> OTHER INFORMATION: Polycistroncic construct containing codon
      modified isoeugenol monooxygenase of p. nitroreducens Jin1, GroES,
      GroEL

<400> SEQUENCE: 15
gaaggagata tacatatggc acgtctgaac cgtaatgatc gcaactcgt cggcaccctg      60 ttaccaaccc gtattgaggc tgacctgttc gacctggaag tggacggcga aattccgaag    120
tccatcaacg gtaccttcta ccgtaacacg ccggagcctc aggtgacgcc gcagaaattc    180
cacaccttca tcgatggtga cggcatggcg tctgcatttc attttgaaga tggccacgtg    240
gacttcatca gccgctgggt taaaaccgcg cgtttcacgg cggagagact ggcacgtaaa    300
agcctgttcg gtatgtaccg taatccgtac accgatgaca cgtctgtgaa gggtctggat    360
cgtaccgttg ccaacacgag catcatcagc catcacggta aggttctggc ggtgaaagaa    420
gatggcttgc cgtacgagct ggacccacgc actctggaaa cccgtggtcg ctttgactat    480
gatggccaag tcaccagcca gacgcacacc gcgcatccga gtatgaccc ggaaaccggt     540 gacctgttgt tctttggctc gcagccaag ggtgaggcaa cgcctgatat ggcctattac     600
atcgttgata acatggtaa ggtaacgcat gagacttggt tcgagcaacc gtatggcgcc     660
tttatgcatg attttgctat tacccgcaat tggagcatct tcccgatcat gccggctacc    720
aattcgttga gccgcctgaa agcgaagcag ccgatttaca tgtgggagcc ggaactgggt    780
tcctatattg gtgttctgcc gcgtcgcggt caaggtagcc agatccgctg gctgaaagca    840
ccagcgctgt gggtctttca cgtcgtcaac gcctgggaag tgggcaccaa aatctacatt    900
gaccttatgg agagcgaaat tctgccattc ccgttcccga atagccaaaa tcagccgttc    960
gctcctgaga aagcagtgcc gcgtctgacc cgttgggaga ttgatctgga tagcagcagc   1020
gatgagatta agcgtacgcg tctgcacgac ttctttgcag agatgccgat catggatttt   1080
cgttttgcgc tgcagtgcaa ccgctacggt tttatgggtg tcgatgaccc gcgcaagccg   1140
ctggcgcacc aacaagcgga gaagatttt gcgtacaata gcctgggtat ctgggacaac   1200
caccgtggtg attatgattt gtggtacagc ggcgaagcct cagcggcgca agaaccggct   1260
ttcgttccgc gttctccgac tgcagcggaa ggcgacggtt atctgctgac cgttgtgggc   1320
cgtttggacg agaaccgcag cgacctggtc attctggaca cgcaggacat ccagagcggt   1380
ccggttgcga ccattaaact gccgtttcgc ctgcgtgcgg ccctgcacgg ctgttgggtt   1440
ccgcgtccgt aaaagatagc aaaaataaa aatgaatat cgtccattg catgatcgcg     1500 tgatcgtcaa gcgtaaagaa gttgaaacta atctgctgg cggcatcgtt ctgaccggct    1560
ctgcagcggc taaatccacc cgcggcgaag tgctggctgt cggcaatggc cgtatccttg   1620
aaaatggcga agtgaagccg ctggatgtga agttggcga catcgttatt ttcaacgatg    1680
gctacggtgt gaaatctgag aagatcgaca tgaagaagt gttgatcatg tccgaaagcg    1740
acattctggc aattgttgaa gcgtaatccg cgcacgacac tgaacatacg aatttaagga   1800
ataaagataa tggcagctaa agacgtaaaa ttcggtaacg acgtcgtgt gaaaatgctg   1860 cgcggcgtaa acgtactggc agatgcagtg aaagttaccc tcggtccaaa aggccgtaac   1920
```

```
gtagttctgg ataaatcttt cggtgcaccg accatcacca aagatggtgt ttccgttgct    1980
cgtgaaatcg aactggaaga caagttcgaa aatatgggtg cgcagatggt gaaagaagtt    2040
gcctctaaag caaacgacgc tgcaggcgac ggtaccacca ctgcaaccgt actggctcag    2100
gctatcatca ctgaaggtct gaaagctgtt gctgcgggca tgaacccgat ggacctgaaa    2160
cgtggtatcg acaaagcggt taccgctgca gttgaagaac tgaaagcgct gtccgtacca    2220
tgctctgact ctaaagcgat tgctcaggtt ggtaccatct ccgctaactc cgacgaaacc    2280
gtaggtaaac tgatcgctga agcgatggac aaagtcggta agaaggcgt tatcaccgtt    2340 gaagacggta ccggtctgca ggacgaactg gacgtggttg aaggtatgca gttcgaccgt    2400
ggctacctgt ctccttactt catcaacaag ccggaaactg gcgcagtaga actggaaagc    2460
ccgttcatcc tgctggctga caagaaaatc tccaacatcc gcgaaatgct gccggttctg    2520
gaagctgttg ccaaagcagg caaaccgctg ctgatcatcg ctgaagatgt agaaggcgaa    2580
gcgctggcaa ctctggttgt taacaccatg cgtggcatcg tgaaagtcgc tgcggttaaa    2640
gcaccgggct tcggcgatcg tcgtaaagct atgctgcagg atatcgcaac cctgactggc    2700
ggtaccgtga tctctgaaga gatcggtatg gagctggaaa aagcaacccct ggaagacctg    2760 ggtcaggcta aacgtgttgt gatcaacaaa gacaccacca ctatcatcga tggcgtgggt    2820
gaagaagctg caatccaggg ccgtgttgct cagatccgtc agcagattga agaagcaact    2880
tctgactacg accgtgaaaa actgcaggaa cgcgtagcga aactggcagg cggcgttgca    2940
gttatcaaag tgggtgctgc taccgaagtt gaaatgaaag agaaaaaagc acgcgttgaa    3000
gatgccctgc acgcgacccg tgctgcggta gaagaaggcg tggttgctgg tggtggtgtt    3060
gcgctgatcc gcgtagcgtc taaactggct gacctgcgtg gtcagaacga agaccagaac    3120
gtgggtatca aagttgcact gcgtgcaatg gaagctccgc tgcgtcagat cgtattgaac    3180
tgcggcgaag aaccgtctgt tgttgctaac accgttaaag gcggcgacgg caactacggt    3240
tacaacgcag caaccgaaga atacggcaac atgatcgaca tgggtatcct ggatccaacc    3300
aaagtaactc gttctgctct gcagtacgca gcttctgtgg ctggcctgat gatcaccacc    3360
gaatgcatgg ttaccgacct gccgaaaaac gatgcagctg acttaggcgc tgctggcggt    3420
atgggcggca tgggtggcat gggcggcatg atgtaa                             3456
```

<210> SEQ ID NO 16
<211> LENGTH: 5424
<212> TYPE: DNA
<213> ORGANISM: Artificial Sequence
<220> FEATURE:
<223> OTHER INFORMATION: e.coli modified with plasmids
      pIEM2_c154_t222_a1318
<220> FEATURE:
<221> NAME/KEY: Ori_p15a
<222> LOCATION: (1)..(827)
<220> FEATURE:
<221> NAME/KEY: Term_rpoC
<222> LOCATION: (1009)..(1128)
<220> FEATURE:
<221> NAME/KEY: Term_bla
<222> LOCATION: (1129)..(1429)
<220> FEATURE:
<221> NAME/KEY: P_T7_Inducible
<222> LOCATION: (1456)..(1497)
<220> FEATURE:
<221> NAME/KEY: LacO1
<222> LOCATION: (1477)..(1497)
<220> FEATURE:
<221> NAME/KEY: IEM_C154_T222_A1318
<222> LOCATION: (1528)..(2997)

```
<220> FEATURE:
<221> NAME/KEY: Term_T7
<222> LOCATION: (3002)..(3049)
<220> FEATURE:
<221> NAME/KEY: P_Amp
<222> LOCATION: (3322)..(3439)
<220> FEATURE:
<221> NAME/KEY: Kanamycin-r
<222> LOCATION: (3450)..(4259)
<220> FEATURE:
<221> NAME/KEY: P_lacI
<222> LOCATION: (4260)..(4341)
<220> FEATURE:
<221> NAME/KEY: lacI
<222> LOCATION: (4342)..(5424)

<400> SEQUENCE: 16
```

| | | | | | |
|---|---|---|---|---|---|
| ttaataagat | gatcttcttg | agatcgtttt | ggtctgcgcg | taatctcttg | ctctgaaaac | 60 |
| gaaaaaaccg | ccttgcaggg | cggttttttcg | aaggttctct | gagctaccaa | ctctttgaac | 120 |
| cgaggtaact | ggcttggagg | agcgcagtca | ccaaaacttg | tcctttcagt | ttagccttaa | 180 |
| ccggcgcatg | acttcaagac | taactcctct | aaatcaatta | ccagtggctg | ctgccagtgg | 240 |
| tgcttttgca | tgtctttccg | ggttggactc | aagacgatag | ttaccggata | aggcgcagcg | 300 |
| gtcggactga | acgggggggtt | cgtgcataca | gtccagcttg | gagcgaactg | cctacccgga | 360 |
| actgagtgtc | aggcgtggaa | tgagacaaac | gcggccataa | cagcggaatg | acaccggtaa | 420 |
| accgaaaggc | aggaacagga | gagcgcacga | gggagccgcc | aggggggaaac | gcctggtatc | 480 |
| tttatagtcc | tgtcgggttt | cgccaccact | gatttgagcg | tcagatttcg | tgatgcttgt | 540 |
| caggggggcg | gagcctatgg | aaaaacggct | ttgccgcggc | cctctcactt | ccctgttaag | 600 |
| tatcttcctg | gcatcttcca | ggaaatctcc | gccccgttcg | taagccattt | ccgctcgccg | 660 |
| cagtcgaacg | accgagcgta | gcgagtcagt | gagcgaggaa | gcggaatata | tcctgtatca | 720 |
| catattctgc | tgacgcaccg | gtgcagcctt | ttttctcctg | ccacatgaag | cacttcactg | 780 |
| acaccctcat | cagtgccaac | atagtaagcc | agtatacact | ccgctagcgc | tgaggtcccg | 840 |
| cagccgaacg | accgagcgca | gcgagtcagt | gagcgaggaa | gcggaaggcg | agagtaggga | 900 |
| actgccaggc | atcaaactaa | gcagaaggcc | cctgacggat | ggcctttttg | cgtttctaca | 960 |
| aactctttct | gtgttgtaaa | acgacggcca | gtcttaagct | cgggcccccct | gggcggttct | 1020 |
| gataacgagt | aatcgttaat | ccgcaaataa | cgtaaaaacc | cgcttcggcg | gttttttta | 1080 |
| tgggggagt | ttagggaaag | agcatttgtc | agaatattta | agggcgcctg | tcactttgct | 1140 |
| tgatatatga | gaattattta | accttataaa | tgagaaaaaa | gcaacgcact | ttaaataaga | 1200 |
| tacgttgctt | tttcgattga | tgaacaccta | taattaaact | attcatctat | tatttatgat | 1260 |
| tttttgtata | tacaatattt | ctagtttgtt | aaagagaatt | aagaaaataa | atctcgaaaa | 1320 |
| taataaaggg | aaaatcagtt | tttgatatca | aaattataca | tgtcaacgat | aatacaaaat | 1380 |
| ataatacaaa | ctataagatg | ttatcagtat | ttattatgca | tttagaataa | attttgtgtc | 1440 |
| gcccttccgc | gaaattaata | cgactcacta | tagggggaatt | gtgagcggat | aacaattccc | 1500 |
| ctctagaaat | aattttgttt | aacttttgaa | ggagatatac | atatggcaac | gtttgaccgc | 1560 |
| aatgatccgc | agtggcagg | aacgatgttc | cccacccgaa | tagaggcgaa | tgtctttgac | 1620 |
| cttgaaattg | agggcgagat | cccacgtgca | atcaacggga | gcttcttccg | caacaccccc | 1680 |
| gaacctcagg | tcacccccgca | acctttccac | accttcatcg | atgggggatgg | tttggcgtct | 1740 |
| gcttttcatt | tcgaagatgg | ccatgtcgac | tttgtcagcc | gttgggtatg | tactcctcgc | 1800 |
| tttgaagctg | agcggtcggc | tcgtaaatca | ctcttcggta | tgtaccgcaa | tccgttcact | 1860 |

```
gatgatccat cggtagaagg tattgatcgt acagtcgcca acaccagtat catcactcat    1920
cacgggaaag tactggccgc aaaggaagat ggactacctt atgagcttga cccccaaacc    1980
ctggaaaccc gaggtcgtta tgattacaag gggcaggtaa ccagccatac acatacagcg    2040
cacccctaagt tcgaccccca gacaggtgaa atgttactct tcggctccgc tgctaaaggc   2100
gaacgaacgc ttgatatggc gtactatatt gttgatcgct acggcaaggt gacacatgag    2160
acctggttta agcagcctta cggtgcattc atgcacgact ttgctgtcac gcgcaactgg    2220
tcaatctttc cgatcatgcc tgcgacaaat agccttgagc gtcttaaagc aaagcagccc    2280
atttacatgt gggagcctga gcgaggaagc tatataggag tacttcctcg tcgtggtcag    2340
ggcaaggaca ttcgttggtt ccgtgccccg gcgttgtggg ttttccatgt cgtgaatgct    2400
tgggaggaag ggaatagaat tctgattgac ttgatggaaa gtgagatttt gccgttccca    2460
ttcccgaact cgcagaacct tccatttgat ccctccaagg ctgttccgcg tctaacccgt    2520
tgggaaattg atctcaatag tggtaacgat gagatgaaac gtacgcagct acacgaatat    2580
tttgcagaaa tgcctatcat ggatttccgt tttgcgctcc aggatcatcg ctacgcctac    2640
atggggttg acgatcctcg tcgcccctta gctcatcagc aagctgaaaa aatctttgcc     2700
tacaattcgt taggggtttg ggacaaccat cgtaaagatt atgaactttg gtttacggga    2760
aaaatgtctg cagcgcagga accggcgttt gttcctagaa gcccagatgc gcctgagggc    2820
gatggctacc tactcagtgt agtagggcgg ctcgatgaaa atcgtagcga tctagttatc    2880
cttgatacgc aatgtttggc agctgggcct gtggccactg tcaagcttcc cttccgtctc    2940
cgagcagcgt tgcacggttg ttggcagtct aagaactgag gatccgaatt cgagctcccc    3000
cctagcataa cccccttgggg cctctaaacg ggtcttgagg ggtttttgc ccctgagacg     3060
cgtcaatcga gttcgtacct aagggcgaca ccccctaatt agcccgggcg aaaggcccag    3120
tctttcgact gagcctttcg ttttatttga tgcctggcag ttccctactc tcgcatgggg    3180
agtccccaca ctaccatcgg cgctacggcg tttcacttct gagttcggca tggggtcagg    3240
tgggaccacc gcgctactgc cgccaggcaa acaaggggtg ttatgagcca tattcaggta    3300
taaatgggct cgcgataatg ttcagaattg gttaattggt tgtaacactg acccctattt    3360
gtttattttt ctaaatacat tcaaatatgt atccgctcat gagacaataa ccctgataaa    3420
tgcttcaata atattgaaaa aggaagaata tgagccatat tcaacgggaa acgtcgaggc    3480
cgcgattaaa ttccaacatg gatgctgatt tatatgggta taaatgggct cgcgataatg    3540
tcgggcaatc aggtgcgaca atctatcgct tgtatgggaa gcccgatgcg ccagagttgt    3600
ttctgaaaca tggcaaaggt agcgttgcca atgatgttac agatgagatg gtcagactaa    3660
actggctgac ggaatttatg ccacttccga ccatcaagca ttttatccgt actcctgatg    3720
atgcatggtt actcaccact gcgatccccg gaaaaacagc gttccaggta ttagaagaat    3780
atcctgattc aggtgaaaat attgttgatg cgctggcagt gttcctgcgc cggttgcact    3840
cgattcctgt ttgtaattgt cctttttaaca gcgatcgcgt atttcgcctc gctcaggcgc    3900
aatcacgaat gaataacggt ttggttgatg cgagtgattt tgatgacgag cgtaatggct    3960
ggcctgttga acaagtctgg aaagaaatgc ataaactttt gccattctca ccggattcag    4020
tcgtcactca tggtgatttc tcacttgata accttatttt tgacgagggg aaattaatag    4080
gttgtattga tgttggacga gtcggaatcg cagaccgata ccaggatctt gccatcctat    4140
ggaactgcct cggtgagttt tctccttcat tacagaaacg ctttttcaa aaatatggta    4200
```

-continued

```
ttgataatcc tgatatgaat aaattgcagt ttcatttgat gctcgatgag tttttctaag    4260
cggcgcgcca tcgaatggcg caaaaccttt cgcggtatgg catgatagcg cccggaagag    4320
agtcaattca gggtggtgaa tatgaaacca gtaacgttat acgatgtcgc agagtatgcc    4380
ggtgtctctt atcagaccgt ttcccgcgtg gtgaaccagg ccagccacgt ttctgcgaaa    4440
acgcgggaaa aagtggaagc ggcgatggcg gagctgaatt acattccaa ccgcgtggca     4500 caacaactgg cgggcaaaca gtcgttgctg attggcgttg ccacctccag tctggccctg    4560
cacgcgccgt cgcaaattgt cgcggcgatt aaatctcgcg ccgatcaact gggtgccagc    4620
gtggtggtgt cgatggtaga acgaagcggc gtcgaagcct gtaaagcggc ggtgcacaat    4680
cttctcgcgc aacgcgtcag tgggctgatc attaactatc cgctggatga ccaggatgcc    4740
attgctgtgg aagctgcctg cactaatgtt ccggcgttat ttcttgatgt ctctgaccag    4800
acacccatca acagtattat tttctcccat gaggacggta cgcgactggg cgtggagcat    4860
ctggtcgcat tgggtcacca gcaaatcgcg ctgttagcgg gcccattaag ttctgtctcg    4920
gcgcgtctgc gtctggctgg ctggcataaa tatctcactc gcaatcaaat tcagccgata    4980
gcggaacggg aaggcgactg gagtgccatg tccggttttc aacaaaccat gcaaatgctg    5040
aatgagggca tcgttcccac tgcgatgctg gttgccaacg atcagatggc gctgggcgca    5100
atgcgcgcca ttaccgagtc cgggctgcgc gttggtgcgg atatctcggt agtgggatac    5160
gacgataccg aagatagctc atgttatatc ccgccgttaa ccaccatcaa acaggatttt    5220
cgcctgctgg ggcaaaccag cgtggaccgc ttgctgcaac tctctcaggg ccaggcggtg    5280
aagggcaatc agctgttgcc agtctcactg gtgaaaagaa aaaccaccct ggcgcccaat    5340
acgcaaaccg cctctcccg cgcgttggcc gattcattaa tgcagctggc acgacaggtt     5400
tcccgactgg aaagcgggca gtga                                           5424
```